US009694107B2

(12) United States Patent
Nakamura et al.

(10) Patent No.: US 9,694,107 B2
(45) Date of Patent: Jul. 4, 2017

(54) SCAFFOLD-FREE SELF-ORGANIZED 3D SYNTHETIC TISSUE

(71) Applicant: TWO CELLS, CO., LTD., Hiroshima (JP)

(72) Inventors: Norimasa Nakamura, Nishinomiya (JP); Hideki Yoshikawa, Toyonaka (JP); Wataru Ando, Ibaraki (JP)

(73) Assignee: Two Cells, Co., Ltd., Hiroshima (JP)

( * ) Notice: Subject to any disclaimer, the term of this patent is extended or adjusted under 35 U.S.C. 154(b) by 0 days.

(21) Appl. No.: 15/166,059

(22) Filed: May 26, 2016

(65) Prior Publication Data

US 2016/0256608 A1    Sep. 8, 2016

Related U.S. Application Data

(60) Division of application No. 11/676,172, filed on Feb. 16, 2007, now Pat. No. 9,370,606, which is a continuation of application No. 10/566,845, filed as application No. PCT/JP2004/011401 on Aug. 2, 2004, now abandoned.

(30) Foreign Application Priority Data

Aug. 1, 2003  (JP) .................................. 2003-285475
Mar. 2, 2004  (JP) .................................. 2004-058285

(51) Int. Cl.
| | |
|---|---|
| C12N 5/00 | (2006.01) |
| A61L 27/36 | (2006.01) |
| A61L 27/38 | (2006.01) |
| C07K 14/47 | (2006.01) |
| C12N 5/077 | (2010.01) |
| A61L 27/24 | (2006.01) |
| A61L 27/50 | (2006.01) |
| A61K 35/12 | (2015.01) |

(52) U.S. Cl.
CPC .......... *A61L 27/3612* (2013.01); *A61L 27/24* (2013.01); *A61L 27/3633* (2013.01); *A61L 27/3817* (2013.01); *A61L 27/3852* (2013.01); *A61L 27/3895* (2013.01); *A61L 27/50* (2013.01); *C07K 14/47* (2013.01); *C12N 5/0654* (2013.01); *C12N 5/0655* (2013.01); *A61K 35/12* (2013.01); *A61L 2430/06* (2013.01); *C12N 2500/25* (2013.01); *C12N 2500/38* (2013.01); *C12N 2501/135* (2013.01); *C12N 2501/15* (2013.01); *C12N 2501/155* (2013.01); *C12N 2501/20* (2013.01); *C12N 2501/33* (2013.01); *C12N 2501/39* (2013.01); *C12N 2501/999* (2013.01); *C12N 2502/1311* (2013.01); *C12N 2506/1384* (2013.01)

(58) Field of Classification Search
CPC ... A61L 27/3633; A61L 27/3843; C12N 5/00; C12N 5/0655
See application file for complete search history.

(56) References Cited

U.S. PATENT DOCUMENTS

| | | | |
|---|---|---|---|
| 5,723,331 | A | 3/1998 | Tubo et al. |
| 5,855,610 | A | 1/1999 | Vacanti et al. |
| 6,413,538 | B1 | 7/2002 | Garcia et al. |
| 6,541,024 | B1 | 4/2003 | Kadiyala et al. |
| 2002/0122790 | A1 | 9/2002 | Hunziker |
| 2002/0182241 | A1 | 12/2002 | Borenstein et al. |
| 2003/0091979 | A1 | 5/2003 | Eschenhagen |
| 2004/0018621 | A1 | 1/2004 | Reid et al. |

FOREIGN PATENT DOCUMENTS

| | | |
|---|---|---|
| JP | 10-511847 A | 11/1998 |
| WO | 95/30742 A1 | 11/1995 |
| WO | 95/33821 A1 | 12/1995 |
| WO | 96/21003 A1 | 7/1996 |
| WO | 00/51527 A1 | 9/2000 |
| WO | 03/024463 A1 | 3/2003 |

OTHER PUBLICATIONS

Brent et al., "A Somitic Compartment of Tendon Progenitors," *Cell* 113:235-248, 2003.
Bukhari et al., "Time to First Occurrence of Erosions in Inflammatory Polyarthritis," *Arthritis & Rheumatism* 44(6):1248-1253, 2001.
De Bari et al., "Multipotent Mesenchymal Stem Cells From Adult Human Synovial Membrane," *Arthritis & Rheumatism* 44(8):1928-1942, 2001.
Dreyer et al., "Lmx1b expression during joint and tendon formation: localization and evaluation of potential downstream targets," *Gene Expression Patterns* 4:397-405, 2004.
Grogan et al., "A static, closed and scaffold-free bioreactor system that permits chondrogenesis in vitro," *OsteoArthritis and Cartilage* 11:403-411, 2003.

(Continued)

*Primary Examiner* — Ruth Davis
(74) *Attorney, Agent, or Firm* — Seed IP Law Group LLP

(57) ABSTRACT

The present invention can be used for actual implantation surgery without a scaffold. The present invention provides a synthetic tissue or complex which can be produced by culture and has a high level of differentiation ability. The present invention also provides a therapy and medicament for repairing and/or regenerating tissue using replacement and covering. By culturing cells under specific culture conditions such that medium contains an extracellular matrix synthesis promoting agent, the cells are organized and are easily detached from a culture dish. The present invention was achieved by finding such a phenomenon. In addition, the self contraction of the tissue can be regulated by culturing the tissue in a suspended manner. Therefore, it is possible to regulate the three-dimensional shape of the tissue. The present invention also provides a method for producing an implantable synthetic tissue which does not require a plurality of monolayer cell sheets assembled to form a three-dimensionally structured synthetic tissue. The present invention is characterized by richness in adhesion molecules, nonnecessity of additional fixation at an implantation site, and good biological integration.

9 Claims, 46 Drawing Sheets

(56) References Cited

OTHER PUBLICATIONS

Hata et al., "$_L$-Ascorbic Acid 2-Phosphate Stimulates Collagen Accumulation, Cell Proliferation, and Formation of a Three-Dimensional Tissuelike Substance by Skin Fibroblasts," *Journal of Cellular Physiology* 138:8-16, 1989.

Havenith et al., "Muscle fiber typing in routinely processed skeletal muscle with monoclonal antibodies," *Histochemistry* 93:497-499, 1990.

Heart Transplant—Lung Transplant, Technical and ethical framework and practice, $3^{rd}$ Edition, Aug. 31, 1997, 130 pages.

Histopathological Diagnosis of the Rejection of Human Grafted Organs, The Japan Society for Transplantation, The Japanese Society of Pathology, The $2^{nd}$ edition, Mar. 2, 2009, 63 pages.

Jankowski et al., "Muscle-derived stem cells," *Gene Therapy* 9:642-647, 2002. (7 pages).

Kale et al., "Three-dimensional cellular development is essential for ex vivo formation of human bone," *Nature Biotechnology* 18:954-958, 2000. (6 pages).

Kulyk et al., "Sox9 Expression during Chondrogenesis in Micromass Cultures of Embryonic Limb Mesenchyme," *Experimental Cell Research* 255: 327-332, 2000.

Kushida et al., "Decrease in culture temperature releases monolayer endothelial cell sheets together with deposited fibronectin matrix from temperature-responsive culture surfaces," *Journal of Biomedical Materials Research* 45:355-362, 1999.

Lee et al., "Isolation of multipotent mesenchymal stem cells from umbilical cord blood," *Blood* 103:1669-1675, 2004. (8 pages).

Life Science, Report No. 19, Decision Making in Modern Medicine, Chapter 12, Organ Transplant, Jun. 30, 1989, 227 pages.

Mainil-Varlet et al., "Articular cartilage repair using a tissue-engineered cartilage-like Implant: an animal study," *OsteoArthritis and Cartilage* 9(Supplement A): S6-S15, 2001.

Masuda et al., "A novel two step method for the formation of tissue-engineered cartilage by mature bovine chondrocytes: the alginate-recovered-chondrocyte (ARC) method," *Journal of Orthopaedic Research* 21:139-148, 2003.

Pittinger et al., "Multilineage Potential of Adult Human Mesenchymal Stem Cells," *Science* 284:143-147, 1999. (6 pages).

Riederer-Henderson et al., "Attachment and extracellular matrix differences between tendon and synovial fibroblastic cells," In Vitro 19(2):127-133, 1983.

Salingcarnboriboon et al., "Establishment of tendon-derived cell lines exhibiting pluripotent mesenchymal stem cell-like property," *Experimental Cell Research* 287:289-300, 2003.

Shimizu et al., "Fabrication of Pulsatile Cardiac Tissue Grafts Using a Novel 3-Dimension Cell Sheet Manipulation Technique and Temperature-Responsive Cell Culture Surfaces," *Circulation Research* 90(3):e40-e48, 2002. (16 pages).

Takenawa et al., "Wasp and Wave family proteins: key molecules for rapid rearrangement of cortical actin filaments and cell movement," *Journal of Cell Science* 114(10):1801-1809, 2001.

Webster et al., "Isolation of Human Myoblasts with the Fluorescence-Activated Cell Sorter," *Experimental Cell Research* 174:252-265, 1988.

Wickham et al., "Multipotent Stromal Cells Derived From the Infrapatellar Fat Pad of the Knee," *Clinical Orthopaedics and Related Research* 412:196-212, 2003.

Wolfman et al., "Ectopic Induction of Tendon and Ligament in Rats by Growth and Differentiation Factors 5, 6, and 7, Members of the TGF-β Gene Family," *Journal of Clinical Investigation* 100(2):321-330, 1997.

Yamato, "Reconstruction of three-dimensional tissue structures by cell sheet engineering," *Journal of Clinical and Experimental Medicine* 195(3):193-197, 2000. (6 pages) (with partial English translation).

Young et al., "The Relationship between SMN, the Spinal Muscular Atrophy Protein, and Nuclear Coiled Bodies in Differentiated Tissues and Cultured Cells," *Experimental Cell Research* 256:365-374, 2000.

FIG.3
Day 3　　Day 7
Day 14　　Day 21
($1\times10^6$cell/ cm² Asc-2P 1mM)
Day 1　It is difficult to detach cell sheet FIG.5
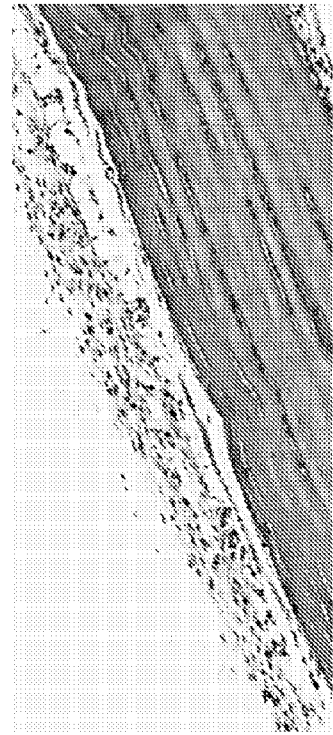
Normal tendon tissue
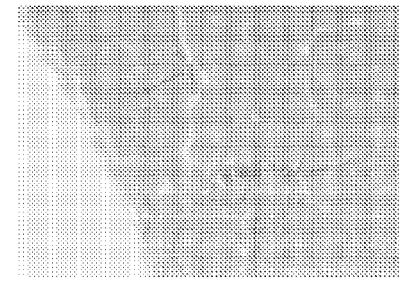
Normal meniscus tissue
Normal cartilage tissue
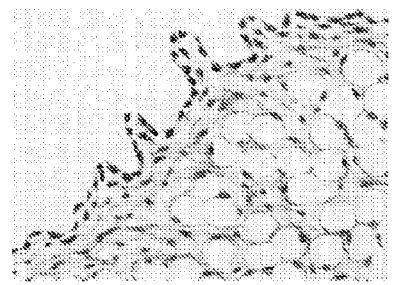
Normal synovial membrane tissue
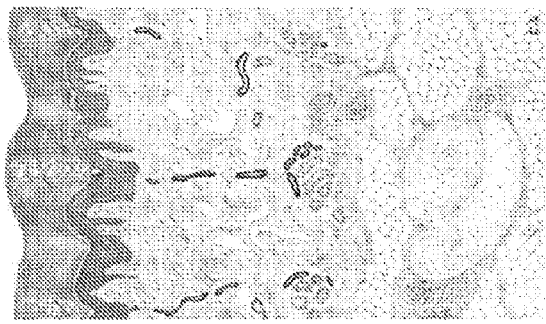
Normal skin FIG.23
remove superficial zone
digested with
chondroitinase ABC
(Hunziker EB. JBJS 1996)
Cultured for
7 days
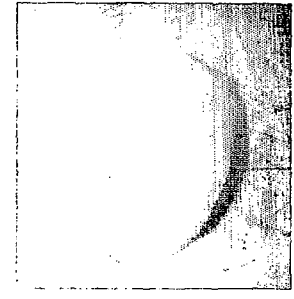
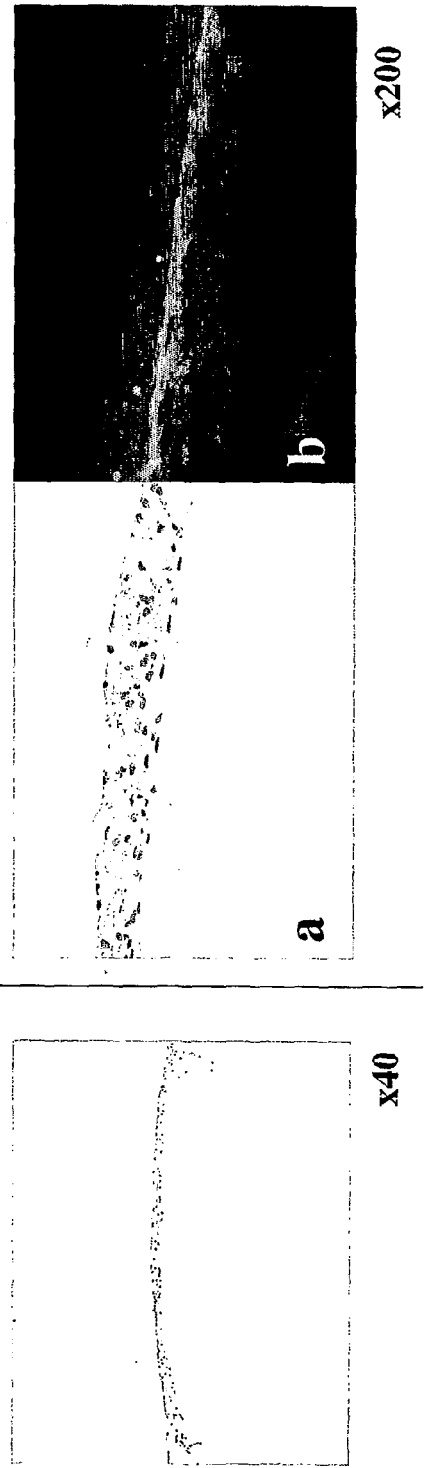
HE staining — Fibronectin
a
b ×200
×40

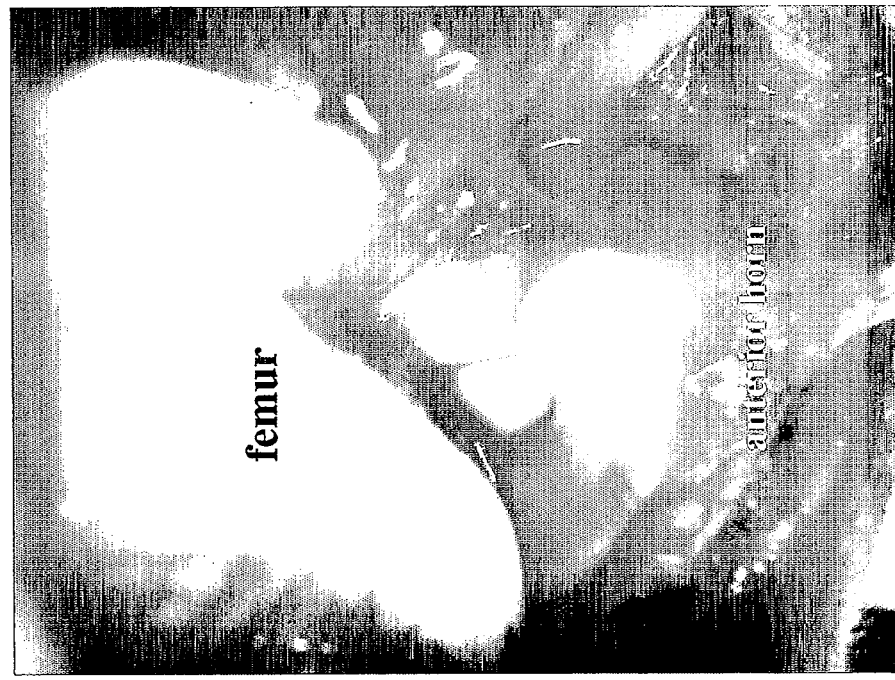
FIG.29

FIG. 30
membrana synovialis derived artificial tissue

FIG.33  Vitronectin  Fibronectin  HE staining $$H = \frac{F}{A} = \frac{F}{k_1 h_p^2}$$

$$E = \left[\frac{dF}{dh}\right]_{F_{max}} \frac{1-\nu^2}{2 \cdot k_2 \cdot h_{pmax}}$$

$$h_p = h_r + 0.25(h_{max} - h_r)$$

F: load
A: contact projection area
hp: contact depth
k1k2: shape conflict
Fmax: Maximum load
hmax: Maximum displacement
hr: point at which tangential line intersects
dF/dh: Gradient of tangential line of load removal curve
$\nu$ : Poisson's ratio

SEQUENCE LISTING

```
<160> NUMBER OF SEQ ID NOS: 30

<210> SEQ ID NO 1
<211> LENGTH: 6085
<212> TYPE: DNA
<213> ORGANISM: Homo sapiens
<220> FEATURE:
<221> NAME/KEY: CDS
<222> LOCATION: (115)..(5940)

<400> SEQUENCE: 1
tacggctgcg agaagacgac agaaggggt cctgctttaa aaagctccaa gaactgtctc      60
actcccaggc tacatcttct cacttgctaa caaggacctc tgagttcagc agcc atg     117
                                                              Met
                                                               1 agt tca gac tca gaa ttg gct gtt ttt ggg gag gct gct cct ttc ctc     165
Ser Ser Asp Ser Glu Leu Ala Val Phe Gly Glu Ala Ala Pro Phe Leu
          5                  10                  15 cga aag tct gaa agg gag cgc att gag gcc cag aat agg ccc ttt gat     213
Arg Lys Ser Glu Arg Glu Arg Ile Glu Ala Gln Asn Arg Pro Phe Asp
     20                  25                  30 gcc aaa aca tct gtc ttt gtg gcg gag ccc aaa gaa tcc ttt gtc aaa     261
Ala Lys Thr Ser Val Phe Val Ala Glu Pro Lys Glu Ser Phe Val Lys
 35                  40                  45 ggg acc atc cag agc aga gaa gga gga aaa gtg acg gtg aag act gag     309
Gly Thr Ile Gln Ser Arg Glu Gly Gly Lys Val Thr Val Lys Thr Glu
 50                  55                  60                  65 gga gga gcg act ctg aca gtg aag gat gat cag gtc ttc ccc atg aac     357
Gly Gly Ala Thr Leu Thr Val Lys Asp Asp Gln Val Phe Pro Met Asn
                 70                  75                  80 cct ccc aaa tat gac aag atc gag gat atg gcc atg atg act cat ctg     405
Pro Pro Lys Tyr Asp Lys Ile Glu Asp Met Ala Met Met Thr His Leu
             85                  90                  95 cat gag cct gct gtg ctg tac aac ctc aaa gaa cgt tat gca gcc tgg     453
His Glu Pro Ala Val Leu Tyr Asn Leu Lys Glu Arg Tyr Ala Ala Trp
        100                 105                 110 atg atc tac acc tat tca ggt ctc ttc tgt gtc act gtc aac ccc tac     501
Met Ile Tyr Thr Tyr Ser Gly Leu Phe Cys Val Thr Val Asn Pro Tyr
    115                 120                 125
```

-continued

| | |
|---|---|
| aag tgg ctg cct gtg tat aag ccc gag gtg gtg aca gcc tac cga ggc<br>Lys Trp Leu Pro Val Tyr Lys Pro Glu Val Val Thr Ala Tyr Arg Gly<br>130                  135                    140                  145 | 549 |
| aaa aag cgc cag ggg gcc ccg ccc cac atc ttc tcc atc tct gac aac<br>Lys Lys Arg Gln Gly Ala Pro Pro His Ile Phe Ser Ile Ser Asp Asn<br>              150                    155                    160 | 597 |
| gcc tat cag ttc atg ctg act gac cga gag aat cag tca atc ctg atc<br>Ala Tyr Gln Phe Met Leu Thr Asp Arg Glu Asn Gln Ser Ile Leu Ile<br>                  165                    170                    175 | 645 |
| act gga gaa tct ggt gca ggg aag act gtg aac acc aag cgt gtc atc<br>Thr Gly Glu Ser Gly Ala Gly Lys Thr Val Asn Thr Lys Arg Val Ile<br>180                  185                    190 | 693 |
| cag tac ttt gca aca att gca gtt act ggt gag aag aag gaa gaa<br>Gln Tyr Phe Ala Thr Ile Ala Val Thr Gly Glu Lys Lys Glu Glu<br>195                  200                  205 | 741 |
| att act tct ggc aaa ata cag ggg act ctg gaa gat caa atc atc agt<br>Ile Thr Ser Gly Lys Ile Gln Gly Thr Leu Glu Asp Gln Ile Ile Ser<br>210                  215                    220                    225 | 789 |
| gcc aac ccc cta ctg gag gcc ttt ggc aac gcc aag acc gtg agg aat<br>Ala Asn Pro Leu Leu Glu Ala Phe Gly Asn Ala Lys Thr Val Arg Asn<br>              230                    235                    240 | 837 |
| gac aac tcc tct cgc ttt ggt aaa ttc atc aga atc cac ttt ggc act<br>Asp Asn Ser Ser Arg Phe Gly Lys Phe Ile Arg Ile His Phe Gly Thr<br>                  245                    250                    255 | 885 |
| act gga aaa ctg gca tct gct gat att gaa aca tat ctg cta gag aag<br>Thr Gly Lys Leu Ala Ser Ala Asp Ile Glu Thr Tyr Leu Leu Glu Lys<br>260                  265                    270 | 933 |
| tct aga gtt gtt ttc cag ctt aag gct gag aga agt tat cat att ttt<br>Ser Arg Val Val Phe Gln Leu Lys Ala Glu Arg Ser Tyr His Ile Phe<br>275                  280                    285 | 981 |
| tac cag att aca tcg aat aag aaa cca gaa ctt att gaa atg ctt ctg<br>Tyr Gln Ile Thr Ser Asn Lys Lys Pro Glu Leu Ile Glu Met Leu Leu<br>290                  295                    300                    305 | 1029 |
| att acc acg aac cca tat gat tac cca ttt gtc agt caa ggg gag atc<br>Ile Thr Thr Asn Pro Tyr Asp Tyr Pro Phe Val Ser Gln Gly Glu Ile<br>              310                    315                    320 | 1077 |
| agt gtg gcc agc atc gat gat cag gaa gaa ctg atg gcc aca gat agt<br>Ser Val Ala Ser Ile Asp Asp Gln Glu Glu Leu Met Ala Thr Asp Ser<br>                  325                    330                    335 | 1125 |
| gct att gat att ttg ggc ttt act aat gaa gaa aag gtc tcc att tac<br>Ala Ile Asp Ile Leu Gly Phe Thr Asn Glu Glu Lys Val Ser Ile Tyr<br>340                  345                    350 | 1173 |
| aag ctc acg ggg gct gtg atg cat tat ggg aac cta aaa ttt aag caa<br>Lys Leu Thr Gly Ala Val Met His Tyr Gly Asn Leu Lys Phe Lys Gln<br>355                  360                    365 | 1221 |
| aag cag cgt gag gag caa gca gag cca gat ggc aca gaa gtt gct gac<br>Lys Gln Arg Glu Glu Gln Ala Glu Pro Asp Gly Thr Glu Val Ala Asp<br>370                  375                    380                    385 | 1269 |
| aag gcg gcc tac ctc cag agt ctg aac tct gca gat ctg ctc aaa gct<br>Lys Ala Ala Tyr Leu Gln Ser Leu Asn Ser Ala Asp Leu Leu Lys Ala<br>                  390                    395                    400 | 1317 |
| ctc tgc tac ccc agg gtc aag gtc ggc aat gag tat gtc acc aaa ggc<br>Leu Cys Tyr Pro Arg Val Lys Val Gly Asn Glu Tyr Val Thr Lys Gly<br>                  405                    410                    415 | 1365 |
| cag act gta gaa cag gtg tcc aac gca gta ggt gct ctg gcc aaa gcc<br>Gln Thr Val Glu Gln Val Ser Asn Ala Val Gly Ala Leu Ala Lys Ala<br>              420                    425                    430 | 1413 |
| gtc tac gag aag atg ttc ctg tgg atg gtt gcc cgc atc aac cag cag<br>Val Tyr Glu Lys Met Phe Leu Trp Met Val Ala Arg Ile Asn Gln Gln<br>435                  440                    445 | 1461 |

```
ctg gac acc aag cag ccc agg cag tac ttc atc ggg gtc ttg gac att    1509
Leu Asp Thr Lys Gln Pro Arg Gln Tyr Phe Ile Gly Val Leu Asp Ile
450                 455                 460                 465 gct ggt ttt gag att ttt gat ttc aac agc ctg gag cag ctg tgc atc    1557
Ala Gly Phe Glu Ile Phe Asp Phe Asn Ser Leu Glu Gln Leu Cys Ile
                470                 475                 480 aac ttc acc aat gag aaa ctg caa cag ttt ttc aac cac cac atg ttc    1605
Asn Phe Thr Asn Glu Lys Leu Gln Gln Phe Phe Asn His His Met Phe
            485                 490                 495 gtg ctg gag cag gag gag tac aag aag gaa ggc atc gag tgg acg ttc    1653
Val Leu Glu Gln Glu Glu Tyr Lys Lys Glu Gly Ile Glu Trp Thr Phe
        500                 505                 510 atc gac ttc ggg atg gac ctg gct gcc tgc atc gag ctc atc gag aag    1701
Ile Asp Phe Gly Met Asp Leu Ala Ala Cys Ile Glu Leu Ile Glu Lys
    515                 520                 525 cct atg ggc atc ttc tcc atc ctg gaa gag gag tgc atg ttc cct aag    1749
Pro Met Gly Ile Phe Ser Ile Leu Glu Glu Glu Cys Met Phe Pro Lys
530                 535                 540                 545 gca aca gac acc tcc ttc aag aac aag ctg tat gac cag cac ctg ggc    1797
Ala Thr Asp Thr Ser Phe Lys Asn Lys Leu Tyr Asp Gln His Leu Gly
                550                 555                 560 aag tct gcc aac ttc cag aag ccc aag gtg gtc aaa ggc aag gcc gag    1845
Lys Ser Ala Asn Phe Gln Lys Pro Lys Val Val Lys Gly Lys Ala Glu
            565                 570                 575 gcc cac ttc gct ctg att cac tat gct ggt gtt gtg gac tac aac att    1893
Ala His Phe Ala Leu Ile His Tyr Ala Gly Val Val Asp Tyr Asn Ile
        580                 585                 590 act ggc tgg ctg gag aag aac aag gac ccc ctg aat gag acc gtg gtt    1941
Thr Gly Trp Leu Glu Lys Asn Lys Asp Pro Leu Asn Glu Thr Val Val
    595                 600                 605 gga ctg tac cag aag tct gca atg aaa act cta gct cag ctc ttc tct    1989
Gly Leu Tyr Gln Lys Ser Ala Met Lys Thr Leu Ala Gln Leu Phe Ser
610                 615                 620                 625 ggg gct caa act gct gaa gga gag gga gct ggc gga ggg gcc aag aaa    2037
Gly Ala Gln Thr Ala Glu Gly Glu Gly Ala Gly Gly Gly Ala Lys Lys
                630                 635                 640 ggt ggt aag aag aag ggc tct tct ttc cag aca gtg tct gcc ctt ttc    2085
Gly Gly Lys Lys Lys Gly Ser Ser Phe Gln Thr Val Ser Ala Leu Phe
            645                 650                 655 aga gag aat ttg aac aag ctg atg acc aac ctc agg agt acc cat cct    2133
Arg Glu Asn Leu Asn Lys Leu Met Thr Asn Leu Arg Ser Thr His Pro
        660                 665                 670 cac ttt gtg agg tgt atc atc ccc aat gag aca aaa act cct ggt gcc    2181
His Phe Val Arg Cys Ile Ile Pro Asn Glu Thr Lys Thr Pro Gly Ala
    675                 680                 685 atg gag cat gag ctt gtc ctc cac cag ctg agg tgt aac ggt gtg ctg    2229
Met Glu His Glu Leu Val Leu His Gln Leu Arg Cys Asn Gly Val Leu
690                 695                 700                 705 gaa ggc atc cgc atc tgt agg aaa gga ttt cca agc aga atc ctt tat    2277
Glu Gly Ile Arg Ile Cys Arg Lys Gly Phe Pro Ser Arg Ile Leu Tyr
                710                 715                 720 gca gac ttc aaa cag aga tac aag gta tta aat gca agt gca atc cct    2325
Ala Asp Phe Lys Gln Arg Tyr Lys Val Leu Asn Ala Ser Ala Ile Pro
            725                 730                 735 gaa ggg caa ttc att gat agc aag aag gcc tct gag aag ctc ctt gca    2373
Glu Gly Gln Phe Ile Asp Ser Lys Lys Ala Ser Glu Lys Leu Leu Ala
        740                 745                 750 tcc atc gac att gac cac acc cag tat aaa ttt ggg cac acc aag gtc    2421
Ser Ile Asp Ile Asp His Thr Gln Tyr Lys Phe Gly His Thr Lys Val
```

|  |  |
|---|---|
| ttt ttc aaa gct ggt ctt ctg ggg ctc cta gag gag atg cga gat gac<br>Phe Phe Lys Ala Gly Leu Leu Gly Leu Leu Glu Glu Met Arg Asp Asp<br>770               775                 780               785 | 2469 |
| aag ctg gcc cag ctg att acc cga acc cag gcc agg tgc aga ggg ttc<br>Lys Leu Ala Gln Leu Ile Thr Arg Thr Gln Ala Arg Cys Arg Gly Phe<br>               790                 795                 800 | 2517 |
| ttg gca aga gtg gag tac cag agg atg gtg gag aga agg gag gcc atc<br>Leu Ala Arg Val Glu Tyr Gln Arg Met Val Glu Arg Arg Glu Ala Ile<br>          805                 810                 815 | 2565 |
| ttc tgt atc cag tac aat atc aga tcc ttc atg aat gtc aag cac tgg<br>Phe Cys Ile Gln Tyr Asn Ile Arg Ser Phe Met Asn Val Lys His Trp<br>          820                 825                 830 | 2613 |
| ccc tgg atg aaa ctc ttc ttc aag atc aag cct ctg ttg aag agt gca<br>Pro Trp Met Lys Leu Phe Phe Lys Ile Lys Pro Leu Leu Lys Ser Ala<br>835               840                 845 | 2661 |
| gaa act gag aag gag atg gcc acc atg aag gaa gaa ttt cag aaa att<br>Glu Thr Glu Lys Glu Met Ala Thr Met Lys Glu Glu Phe Gln Lys Ile<br>850               855               860               865 | 2709 |
| aaa gac gaa ctt gcc aag tca gag gca aaa agg aag gaa ctg gaa gaa<br>Lys Asp Glu Leu Ala Lys Ser Glu Ala Lys Arg Lys Glu Leu Glu Glu<br>          870                 875                 880 | 2757 |
| aag atg gtg acg ctg ttg aaa gaa aaa aat gac ttg cag ctc caa gtt<br>Lys Met Val Thr Leu Leu Lys Glu Lys Asn Asp Leu Gln Leu Gln Val<br>               885                 890                 895 | 2805 |
| cag gct gaa gcc gaa ggc ttg gct gat gca gag gaa agg tgt gac cag<br>Gln Ala Glu Ala Glu Gly Leu Ala Asp Ala Glu Glu Arg Cys Asp Gln<br>          900                 905                 910 | 2853 |
| cta atc aaa acc aaa atc cag cta gaa gcc aaa atc aaa gag gtg act<br>Leu Ile Lys Thr Lys Ile Gln Leu Glu Ala Lys Ile Lys Glu Val Thr<br>          915                 920                 925 | 2901 |
| gag aga gct gag gat gag gaa gag atc aat gct gag ctg aca gcc aag<br>Glu Arg Ala Glu Asp Glu Glu Glu Ile Asn Ala Glu Leu Thr Ala Lys<br>930               935                 940               945 | 2949 |
| aag agg aaa ctg gag gat gaa tgt tca gaa ctc aag aaa gac att gat<br>Lys Arg Lys Leu Glu Asp Glu Cys Ser Glu Leu Lys Lys Asp Ile Asp<br>          950                 955                 960 | 2997 |
| gac ctt gag ctg aca ctg gcc aag gtt gag aag gag aaa cat gcc aca<br>Asp Leu Glu Leu Thr Leu Ala Lys Val Glu Lys Glu Lys His Ala Thr<br>          965                 970                 975 | 3045 |
| gaa aac aag gtg aaa aac ctc aca gaa gag atg gca ggt ctg gat gaa<br>Glu Asn Lys Val Lys Asn Leu Thr Glu Glu Met Ala Gly Leu Asp Glu<br>          980                 985                 990 | 3093 |
| acc att gct aag ctg acc aag gag aag aag gct ctc cag gag gcc cac<br>Thr Ile Ala Lys Leu Thr Lys Glu Lys Lys Ala Leu Gln Glu Ala His<br>          995                1000               1005 | 3141 |
| cag  cag acc ctg gat gac  ctg cag gca gag gag  gac aaa gtc aac<br>Gln  Gln Thr Leu Asp Asp  Leu Gln Ala Glu Glu  Asp Lys Val Asn<br>1010              1015                1020 | 3186 |
| acc  ctg acc aaa gct aaa  atc aaa ctt gaa caa  caa gtg gat gat<br>Thr  Leu Thr Lys Ala Lys  Ile Lys Leu Glu Gln  Gln Val Asp Asp<br>1025              1030                1035 | 3231 |
| ctt  gaa ggg tcc ttg gag  caa gaa aag aaa ctt  cgc atg gac cta<br>Leu  Glu Gly Ser Leu Glu  Gln Glu Lys Lys Leu  Arg Met Asp Leu<br>1040              1045                1050 | 3276 |
| gaa  agg gct aag agg aaa  ctt gag ggt gac ttg  aag ttg gcc caa<br>Glu  Arg Ala Lys Arg Lys  Leu Glu Gly Asp Leu  Lys Leu Ala Gln<br>1055              1060                1065 | 3321 |
| gaa  tcc ata atg gac att  gaa aat gag aaa cag  caa ctt gat gaa | 3366 |

|     |     |     |     |     |     |     |     |     |     |     |     |      |
|-----|-----|-----|-----|-----|-----|-----|-----|-----|-----|-----|-----|------|
| Glu | Ser | Ile | Met | Asp | Ile | Glu | Asn | Glu | Lys | Gln | Gln | Leu Asp Glu |
| 1070 |    |     |     | 1075|     |     |     | 1080|     |     |     |      |

```
aag ctc aaa aag aaa gag ttt gaa atc agc aat ctg caa agc aag    3411
Lys Leu Lys Lys Lys Glu Phe Glu Ile Ser Asn Leu Gln Ser Lys
1085            1090            1095 att gaa gat gaa cag gca ctt ggc att caa ttg cag aag aaa att    3456
Ile Glu Asp Glu Gln Ala Leu Gly Ile Gln Leu Gln Lys Lys Ile
1100            1105            1110 aaa gaa ttg caa gcc cgc att gag gag ctg gag gag gaa atc gag    3501
Lys Glu Leu Gln Ala Arg Ile Glu Glu Leu Glu Glu Glu Ile Glu
1115            1120            1125 gca gag cgg gcc tcc cgg gcc aaa gca gag aag cag cgc tct gac    3546
Ala Glu Arg Ala Ser Arg Ala Lys Ala Glu Lys Gln Arg Ser Asp
1130            1135            1140 ctc tcc cgg gag ctg gag gag atc agc gag agg ctg gaa gaa gcc    3591
Leu Ser Arg Glu Leu Glu Glu Ile Ser Glu Arg Leu Glu Glu Ala
1145            1150            1155 ggt ggg gcc act tca gcc cag att gag atg aac aag aag cgg gag    3636
Gly Gly Ala Thr Ser Ala Gln Ile Glu Met Asn Lys Lys Arg Glu
1160            1165            1170 gct gag ttc cag aaa atg cgc agg gac ctg gag gag gcc acc cta    3681
Ala Glu Phe Gln Lys Met Arg Arg Asp Leu Glu Glu Ala Thr Leu
1175            1180            1185 cag cat gaa gcc aca gcg gcc acc ctg agg aag aag cat gca gat    3726
Gln His Glu Ala Thr Ala Ala Thr Leu Arg Lys Lys His Ala Asp
1190            1195            1200 agt gtg gcc gag ctt ggg gag cag att gac aac ctg cag cga gtg    3771
Ser Val Ala Glu Leu Gly Glu Gln Ile Asp Asn Leu Gln Arg Val
1205            1210            1215 aag cag aag ctg gag aag gag aag agt gag atg aag atg gag att    3816
Lys Gln Lys Leu Glu Lys Glu Lys Ser Glu Met Lys Met Glu Ile
1220            1225            1230 gat gac ctt gct agt aat gta gaa acg gtc tcc aaa gcc aag gga    3861
Asp Asp Leu Ala Ser Asn Val Glu Thr Val Ser Lys Ala Lys Gly
1235            1240            1245 aac cta gag aaa atg tgc cgg act cta gag gac caa ctg agt gaa    3906
Asn Leu Glu Lys Met Cys Arg Thr Leu Glu Asp Gln Leu Ser Glu
1250            1255            1260 ctg aaa tca aag gaa gag gag cag cag cgg ctg atc aat gac ctg    3951
Leu Lys Ser Lys Glu Glu Glu Gln Gln Arg Leu Ile Asn Asp Leu
1265            1270            1275 act gcg cag agg ggg cgc ctg cag act gaa tct ggt gag ttt tca    3996
Thr Ala Gln Arg Gly Arg Leu Gln Thr Glu Ser Gly Glu Phe Ser
1280            1285            1290 cgc cag ctt gat gaa aag gaa gct ctg gtg tct cag tta tca aga    4041
Arg Gln Leu Asp Glu Lys Glu Ala Leu Val Ser Gln Leu Ser Arg
1295            1300            1305 ggc aaa caa gcc ttt act caa cag att gaa gaa tta aag agg caa    4086
Gly Lys Gln Ala Phe Thr Gln Gln Ile Glu Glu Leu Lys Arg Gln
1310            1315            1320 ctt gaa gag gag ata aaa gcc aag aac gcc ctg gcg cat gcc ctg    4131
Leu Glu Glu Glu Ile Lys Ala Lys Asn Ala Leu Ala His Ala Leu
1325            1330            1335 cag tct tcc cgc cac gac tgt gac ctg ctg cgg gaa cag tat gag    4176
Gln Ser Ser Arg His Asp Cys Asp Leu Leu Arg Glu Gln Tyr Glu
1340            1345            1350 gag gag cag gaa tcc aag gcc gag ctg cag aga gca ctg tcc aag    4221
Glu Glu Gln Glu Ser Lys Ala Glu Leu Gln Arg Ala Leu Ser Lys
1355            1360            1365
```

```
                                               -continued gcc aac acc gag gtt gcc caa tgg agg acc aaa tac gag acg gac       4266
Ala Asn Thr Glu Val Ala Gln Trp Arg Thr Lys Tyr Glu Thr Asp
1370            1375                1380 gcc atc cag cgc aca gag gag ctg gag gag gcc aag aag aag ctg       4311
Ala Ile Gln Arg Thr Glu Glu Leu Glu Glu Ala Lys Lys Lys Leu
1385            1390                1395 gcc cag cgg ctg cag gca gct gag gaa cat gta gaa gct gtg aac       4356
Ala Gln Arg Leu Gln Ala Ala Glu Glu His Val Glu Ala Val Asn
1400            1405                1410 gcc aaa tgt gct tcc ctc gaa aag acg aag cag cgg ctg cag aat       4401
Ala Lys Cys Ala Ser Leu Glu Lys Thr Lys Gln Arg Leu Gln Asn
1415            1420                1425 gag gtc gag gac ctc atg ctt gat gtg gag agg aca aat gcc gcc       4446
Glu Val Glu Asp Leu Met Leu Asp Val Glu Arg Thr Asn Ala Ala
1430            1435                1440 tgt gcc gcc ctt gac aaa aag caa agg aac ttc gat aag atc ctg       4491
Cys Ala Ala Leu Asp Lys Lys Gln Arg Asn Phe Asp Lys Ile Leu
1445            1450                1455 gca gaa tgg aaa cag aaa tgt gag gaa acg cat gct gag ctt gag       4536
Ala Glu Trp Lys Gln Lys Cys Glu Glu Thr His Ala Glu Leu Glu
1460            1465                1470 gcc tcc cag aag gag gcc cgt tcc ctt ggc act gag ctg ttc aag       4581
Ala Ser Gln Lys Glu Ala Arg Ser Leu Gly Thr Glu Leu Phe Lys
1475            1480                1485 ata aag aat gcc tat gag gaa tct ttg gat cag cta gaa acc ctg       4626
Ile Lys Asn Ala Tyr Glu Glu Ser Leu Asp Gln Leu Glu Thr Leu
1490            1495                1500 aag cga gag aac aaa aac tta cag cag gag att tct gac ctc acg       4671
Lys Arg Glu Asn Lys Asn Leu Gln Gln Glu Ile Ser Asp Leu Thr
1505            1510                1515 gaa cag att gca gaa gga ggg aaa cgt atc cat gaa ctg gag aaa       4716
Glu Gln Ile Ala Glu Gly Gly Lys Arg Ile His Glu Leu Glu Lys
1520            1525                1530 ata aag aaa caa gtg gaa caa gaa aag tgt gaa ctt cag gct gct       4761
Ile Lys Lys Gln Val Glu Gln Glu Lys Cys Glu Leu Gln Ala Ala
1535            1540                1545 tta gaa gaa gca gag gca tct ctt gaa cat gaa gag gga aag atc       4806
Leu Glu Glu Ala Glu Ala Ser Leu Glu His Glu Glu Gly Lys Ile
1550            1555                1560 ctg cgc atc cag ctt gag ttg aac caa gtc aag tct gag gtt gat       4851
Leu Arg Ile Gln Leu Glu Leu Asn Gln Val Lys Ser Glu Val Asp
1565            1570                1575 agg aaa att gct gaa aaa gat gag gaa att gac cag ctg aag aga       4896
Arg Lys Ile Ala Glu Lys Asp Glu Glu Ile Asp Gln Leu Lys Arg
1580            1585                1590 aac cac att aga atc gtg gag tcc atg cag agc acg ctg gat gct       4941
Asn His Ile Arg Ile Val Glu Ser Met Gln Ser Thr Leu Asp Ala
1595            1600                1605 gag atc agg agt agg aat gat gcc att agg ctc aag aag aag atg       4986
Glu Ile Arg Ser Arg Asn Asp Ala Ile Arg Leu Lys Lys Lys Met
1610            1615                1620 gag gga gac ctc aat gaa atg gaa atc cag ctg aac cat gcc aac       5031
Glu Gly Asp Leu Asn Glu Met Glu Ile Gln Leu Asn His Ala Asn
1625            1630                1635 cgc atg gct gct gag gcc ctg agg aac tac agg aac acc caa ggc       5076
Arg Met Ala Ala Glu Ala Leu Arg Asn Tyr Arg Asn Thr Gln Gly
1640            1645                1650 atc ctc aag gat acc cag atc cac ctg gat gat gct ctc cgg agc       5121
Ile Leu Lys Asp Thr Gln Ile His Leu Asp Asp Ala Leu Arg Ser
1655            1660                1665
```

| | | | | | | | | | | |
|---|---|---|---|---|---|---|---|---|---|---|
| cag | gag | gac | ctg | aag | gaa | cag | ctg | gcc | atg | gtg | gag | cgc | aga | gcc | 5166 |
| Gln | Glu | Asp | Leu | Lys | Glu | Gln | Leu | Ala | Met | Val | Glu | Arg | Arg | Ala | |
| 1670 | | | | 1675 | | | | | 1680 | | | | | | | aac ctg ctg cag gct gag atc gag gag ctg cgg gcc act ctg gaa     5211
Asn Leu Leu Gln Ala Glu Ile Glu Glu Leu Arg Ala Thr Leu Glu
1685              1690                1695 cag aca gag agg agc aga aaa atc gca gaa cag gag ctc ctg gat     5256
Gln Thr Glu Arg Ser Arg Lys Ile Ala Glu Gln Glu Leu Leu Asp
1700              1705                1710 gcc agt gag cgt gtt cag cta ctg cac acc cag aac acc agc ctg     5301
Ala Ser Glu Arg Val Gln Leu Leu His Thr Gln Asn Thr Ser Leu
1715              1720                1725 atc aac acc aag aag aag ctg gag aca gat att tcc caa atg caa     5346
Ile Asn Thr Lys Lys Lys Leu Glu Thr Asp Ile Ser Gln Met Gln
1730              1735                1740 gga gag atg gag gac att ctc cag gaa gcc cgc aat gca gaa gaa     5391
Gly Glu Met Glu Asp Ile Leu Gln Glu Ala Arg Asn Ala Glu Glu
1745              1750                1755 aag gcc aag aag gcc atc act gat gcc gcc atg atg gct gag gag     5436
Lys Ala Lys Lys Ala Ile Thr Asp Ala Ala Met Met Ala Glu Glu
1760              1765                1770 ctg aag aag gag cag gac acc agc gcc cac ctg gag cgg atg aag     5481
Leu Lys Lys Glu Gln Asp Thr Ser Ala His Leu Glu Arg Met Lys
1775              1780                1785 aag aac atg gag cag acc gtg aag gat ctg cag ctc cgt ctg gat     5526
Lys Asn Met Glu Gln Thr Val Lys Asp Leu Gln Leu Arg Leu Asp
1790              1795                1800 gag gct gag cag ctg gcc ctg aag ggt ggg aag aag cag atc cag     5571
Glu Ala Glu Gln Leu Ala Leu Lys Gly Gly Lys Lys Gln Ile Gln
1805              1810                1815 aaa ctg gag gcc agg gta cgg gag ctg gaa gga gag gtt gag agt     5616
Lys Leu Glu Ala Arg Val Arg Glu Leu Glu Gly Glu Val Glu Ser
1820              1825                1830 gag caa aag cgt aat gct gag gct gtc aaa ggt ctg cgc aaa cat     5661
Glu Gln Lys Arg Asn Ala Glu Ala Val Lys Gly Leu Arg Lys His
1835              1840                1845 gag agg cga gtg aag gaa ctc act tac cag acg gaa gaa gat aga     5706
Glu Arg Arg Val Lys Glu Leu Thr Tyr Gln Thr Glu Glu Asp Arg
1850              1855                1860 aag aat att ctc agg ctt caa gat ttg gta gat aaa ctt cag gca     5751
Lys Asn Ile Leu Arg Leu Gln Asp Leu Val Asp Lys Leu Gln Ala
1865              1870                1875 aaa gtg aaa tct tat aag aga caa gct gag gag gct gag gaa caa     5796
Lys Val Lys Ser Tyr Lys Arg Gln Ala Glu Glu Ala Glu Glu Gln
1880              1885                1890 tcc aac acc aat cta gct aaa ttc cgc aag ctc cag cat gag ctg     5841
Ser Asn Thr Asn Leu Ala Lys Phe Arg Lys Leu Gln His Glu Leu
1895              1900                1905 gag gag gcc gag gaa cgg gct gac att gct gag tcc cag gtg aac     5886
Glu Glu Ala Glu Glu Arg Ala Asp Ile Ala Glu Ser Gln Val Asn
1910              1915                1920 aaa ctg cgg gtg aag agc cgg gag gtt cac aca aaa gtc ata agt     5931
Lys Leu Arg Val Lys Ser Arg Glu Val His Thr Lys Val Ile Ser
1925              1930                1935 gaa gag tga tcatgtcctg atgccatgga atgactgaag acaggcacaa         5980
Glu Glu
1940 aatgtgacat ctttggtcat ttccctctgt aattattgtg tattctaccc tgttgcaaag  6040 gaaataaagc atagggtagt ttgcaaacaa aaaaaaaaaa aaaaa                          6085

<210> SEQ ID NO 2
<211> LENGTH: 1941
<212> TYPE: PRT
<213> ORGANISM: Homo sapiens

<400> SEQUENCE: 2

Met Ser Ser Asp Ser Glu Leu Ala Val Phe Gly Glu Ala Ala Pro Phe
1               5                   10                  15

Leu Arg Lys Ser Glu Arg Glu Arg Ile Glu Ala Gln Asn Arg Pro Phe
            20                  25                  30

Asp Ala Lys Thr Ser Val Phe Val Ala Glu Pro Lys Glu Ser Phe Val
        35                  40                  45

Lys Gly Thr Ile Gln Ser Arg Glu Gly Gly Lys Val Thr Val Lys Thr
    50                  55                  60

Glu Gly Gly Ala Thr Leu Thr Val Lys Asp Asp Gln Val Phe Pro Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Lys Pro Glu Val Val Thr Ala Tyr Arg
    130                 135                 140

Gly Lys Lys Arg Gln Gly Ala Pro Pro His Ile Phe Ser Ile Ser Asp
145                 150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
        195                 200                 205

Glu Ile Thr Ser Gly Lys Ile Gln Gly Thr Leu Glu Asp Gln Ile Ile
    210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Thr Thr Gly Lys Leu Ala Ser Ala Asp Ile Glu Thr Tyr Leu Leu Glu
            260                 265                 270

Lys Ser Arg Val Val Phe Gln Leu Lys Ala Glu Arg Ser Tyr His Ile
        275                 280                 285

Phe Tyr Gln Ile Thr Ser Asn Lys Lys Pro Glu Leu Ile Glu Met Leu
    290                 295                 300

Leu Ile Thr Thr Asn Pro Tyr Asp Tyr Pro Phe Val Ser Gln Gly Glu
305                 310                 315                 320

Ile Ser Val Ala Ser Ile Asp Asp Gln Glu Glu Leu Met Ala Thr Asp
                325                 330                 335

Ser Ala Ile Asp Ile Leu Gly Phe Thr Asn Glu Glu Lys Val Ser Ile
            340                 345                 350

Tyr Lys Leu Thr Gly Ala Val Met His Tyr Gly Asn Leu Lys Phe Lys
        355                 360                 365

```
Gln Lys Gln Arg Glu Glu Gln Ala Glu Pro Asp Gly Thr Glu Val Ala
    370                 375                 380

Asp Lys Ala Ala Tyr Leu Gln Ser Leu Asn Ser Ala Asp Leu Leu Lys
385                 390                 395                 400

Ala Leu Cys Tyr Pro Arg Val Lys Val Gly Asn Glu Tyr Val Thr Lys
                405                 410                 415

Gly Gln Thr Val Glu Gln Val Ser Asn Ala Val Gly Ala Leu Ala Lys
            420                 425                 430

Ala Val Tyr Glu Lys Met Phe Leu Trp Met Val Ala Arg Ile Asn Gln
            435                 440                 445

Gln Leu Asp Thr Lys Gln Pro Arg Gln Tyr Phe Ile Gly Val Leu Asp
    450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Thr
                500                 505                 510

Phe Ile Asp Phe Gly Met Asp Leu Ala Ala Cys Ile Glu Leu Ile Glu
                515                 520                 525

Lys Pro Met Gly Ile Phe Ser Ile Leu Glu Glu Cys Met Phe Pro
    530                 535                 540

Lys Ala Thr Asp Thr Ser Phe Lys Asn Lys Leu Tyr Asp Gln His Leu
545                 550                 555                 560

Gly Lys Ser Ala Asn Phe Gln Lys Pro Lys Val Val Lys Gly Lys Ala
                565                 570                 575

Glu Ala His Phe Ala Leu Ile His Tyr Ala Gly Val Val Asp Tyr Asn
            580                 585                 590

Ile Thr Gly Trp Leu Glu Lys Asn Lys Asp Pro Leu Asn Glu Thr Val
        595                 600                 605

Val Gly Leu Tyr Gln Lys Ser Ala Met Lys Thr Leu Ala Gln Leu Phe
    610                 615                 620

Ser Gly Ala Gln Thr Ala Glu Gly Glu Gly Ala Gly Gly Ala Lys
625                 630                 635                 640

Lys Gly Gly Lys Lys Lys Gly Ser Ser Phe Gln Thr Val Ser Ala Leu
                645                 650                 655

Phe Arg Glu Asn Leu Asn Lys Leu Met Thr Asn Leu Arg Ser Thr His
                660                 665                 670

Pro His Phe Val Arg Cys Ile Ile Pro Asn Glu Thr Lys Thr Pro Gly
            675                 680                 685

Ala Met Glu His Glu Leu Val Leu His Gln Leu Arg Cys Asn Gly Val
690                 695                 700

Leu Glu Gly Ile Arg Ile Cys Arg Lys Gly Phe Pro Ser Arg Ile Leu
705                 710                 715                 720

Tyr Ala Asp Phe Lys Gln Arg Tyr Lys Val Leu Asn Ala Ser Ala Ile
                725                 730                 735

Pro Glu Gly Gln Phe Ile Asp Ser Lys Lys Ala Ser Glu Lys Leu Leu
            740                 745                 750

Ala Ser Ile Asp Ile Asp His Thr Gln Tyr Lys Phe Gly His Thr Lys
            755                 760                 765

Val Phe Phe Lys Ala Gly Leu Leu Gly Leu Leu Glu Glu Met Arg Asp
    770                 775                 780

Asp Lys Leu Ala Gln Leu Ile Thr Arg Thr Gln Ala Arg Cys Arg Gly
```

-continued

```
            785                 790                 795                 800
        Phe Leu Ala Arg Val Glu Tyr Gln Arg Met Val Glu Arg Glu Ala
                        805                 810                 815
        Ile Phe Cys Ile Gln Tyr Asn Ile Arg Ser Phe Met Asn Val Lys His
                        820                 825                 830
        Trp Pro Trp Met Lys Leu Phe Phe Lys Ile Lys Pro Leu Leu Lys Ser
                        835                 840                 845
        Ala Glu Thr Glu Lys Glu Met Ala Thr Met Lys Glu Glu Phe Gln Lys
                850                 855                 860
        Ile Lys Asp Glu Leu Ala Lys Ser Glu Ala Lys Arg Lys Glu Leu Glu
        865                 870                 875                 880
        Glu Lys Met Val Thr Leu Leu Lys Glu Lys Asn Asp Leu Gln Leu Gln
                            885                 890                 895
        Val Gln Ala Glu Ala Glu Gly Leu Ala Asp Ala Glu Glu Arg Cys Asp
                        900                 905                 910
        Gln Leu Ile Lys Thr Lys Ile Gln Leu Glu Ala Lys Ile Lys Glu Val
                        915                 920                 925
        Thr Glu Arg Ala Glu Asp Glu Glu Ile Asn Ala Glu Leu Thr Ala
                930                 935                 940
        Lys Lys Arg Lys Leu Glu Asp Glu Cys Ser Glu Leu Lys Lys Asp Ile
        945                 950                 955                 960
        Asp Asp Leu Glu Leu Thr Leu Ala Lys Val Glu Lys Glu Lys His Ala
                        965                 970                 975
        Thr Glu Asn Lys Val Lys Asn Leu Thr Glu Glu Met Ala Gly Leu Asp
                        980                 985                 990
        Glu Thr Ile Ala Lys Leu Thr Lys Glu Lys Lys Ala Leu Gln Glu Ala
                        995                 1000                1005
        His Gln Gln Thr Leu Asp Asp Leu Gln Ala Glu Glu Asp Lys Val
                    1010                1015                1020
        Asn Thr Leu Thr Lys Ala Lys Ile Lys Leu Glu Gln Gln Val Asp
                    1025                1030                1035
        Asp Leu Glu Gly Ser Leu Glu Gln Glu Lys Lys Leu Arg Met Asp
                    1040                1045                1050
        Leu Glu Arg Ala Lys Arg Lys Leu Glu Gly Asp Leu Lys Leu Ala
                    1055                1060                1065
        Gln Glu Ser Ile Met Asp Ile Glu Asn Glu Lys Gln Gln Leu Asp
                    1070                1075                1080
        Glu Lys Leu Lys Lys Lys Glu Phe Glu Ile Ser Asn Leu Gln Ser
                    1085                1090                1095
        Lys Ile Glu Asp Glu Gln Ala Leu Gly Ile Gln Leu Gln Lys Lys
                    1100                1105                1110
        Ile Lys Glu Leu Gln Ala Arg Ile Glu Glu Leu Glu Glu Ile
                    1115                1120                1125
        Glu Ala Glu Arg Ala Ser Arg Ala Lys Ala Glu Lys Gln Arg Ser
                    1130                1135                1140
        Asp Leu Ser Arg Glu Leu Glu Glu Ile Ser Glu Arg Leu Glu Glu
                    1145                1150                1155
        Ala Gly Gly Ala Thr Ser Ala Gln Ile Glu Met Asn Lys Lys Arg
                    1160                1165                1170
        Glu Ala Glu Phe Gln Lys Met Arg Arg Asp Leu Glu Glu Ala Thr
                    1175                1180                1185
        Leu Gln His Glu Ala Thr Ala Ala Thr Leu Arg Lys Lys His Ala
                    1190                1195                1200
```

```
Asp Ser Val Ala Glu Leu Gly Glu Gln Ile Asp Asn Leu Gln Arg
    1205                1210                1215
Val Lys Gln Lys Leu Glu Lys Glu Lys Ser Glu Met Lys Met Glu
    1220                1225                1230
Ile Asp Asp Leu Ala Ser Asn Val Glu Thr Val Ser Lys Ala Lys
    1235                1240                1245
Gly Asn Leu Glu Lys Met Cys Arg Thr Leu Glu Asp Gln Leu Ser
    1250                1255                1260
Glu Leu Lys Ser Lys Glu Glu Gln Gln Arg Leu Ile Asn Asp
    1265                1270                1275
Leu Thr Ala Gln Arg Gly Arg Leu Gln Thr Glu Ser Gly Glu Phe
    1280                1285                1290
Ser Arg Gln Leu Asp Glu Lys Glu Ala Leu Val Ser Gln Leu Ser
    1295                1300                1305
Arg Gly Lys Gln Ala Phe Thr Gln Gln Ile Glu Glu Leu Lys Arg
    1310                1315                1320
Gln Leu Glu Glu Glu Ile Lys Ala Lys Asn Ala Leu Ala His Ala
    1325                1330                1335
Leu Gln Ser Ser Arg His Asp Cys Asp Leu Leu Arg Glu Gln Tyr
    1340                1345                1350
Glu Glu Glu Gln Glu Ser Lys Ala Glu Leu Gln Arg Ala Leu Ser
    1355                1360                1365
Lys Ala Asn Thr Glu Val Ala Gln Trp Arg Thr Lys Tyr Glu Thr
    1370                1375                1380
Asp Ala Ile Gln Arg Thr Glu Glu Leu Glu Glu Ala Lys Lys Lys
    1385                1390                1395
Leu Ala Gln Arg Leu Gln Ala Ala Glu Glu His Val Glu Ala Val
    1400                1405                1410
Asn Ala Lys Cys Ala Ser Leu Glu Lys Thr Lys Gln Arg Leu Gln
    1415                1420                1425
Asn Glu Val Glu Asp Leu Met Leu Asp Val Glu Arg Thr Asn Ala
    1430                1435                1440
Ala Cys Ala Ala Leu Asp Lys Lys Gln Arg Asn Phe Asp Lys Ile
    1445                1450                1455
Leu Ala Glu Trp Lys Gln Lys Cys Glu Glu Thr His Ala Glu Leu
    1460                1465                1470
Glu Ala Ser Gln Lys Glu Ala Arg Ser Leu Gly Thr Glu Leu Phe
    1475                1480                1485
Lys Ile Lys Asn Ala Tyr Glu Glu Ser Leu Asp Gln Leu Glu Thr
    1490                1495                1500
Leu Lys Arg Glu Asn Lys Asn Leu Gln Gln Glu Ile Ser Asp Leu
    1505                1510                1515
Thr Glu Gln Ile Ala Glu Gly Gly Lys Arg Ile His Glu Leu Glu
    1520                1525                1530
Lys Ile Lys Lys Gln Val Glu Gln Glu Lys Cys Glu Leu Gln Ala
    1535                1540                1545
Ala Leu Glu Glu Ala Glu Ala Ser Leu Glu His Glu Glu Gly Lys
    1550                1555                1560
Ile Leu Arg Ile Gln Leu Glu Leu Asn Gln Val Lys Ser Glu Val
    1565                1570                1575
Asp Arg Lys Ile Ala Glu Lys Asp Glu Glu Ile Asp Gln Leu Lys
    1580                1585                1590
```

Arg Asn His Ile Arg Ile Val Glu Ser Met Gln Ser Thr Leu Asp
    1595                1600                1605

Ala Glu Ile Arg Ser Arg Asn Asp Ala Ile Arg Leu Lys Lys Lys
    1610                1615                1620

Met Glu Gly Asp Leu Asn Glu Met Glu Ile Gln Leu Asn His Ala
    1625                1630                1635

Asn Arg Met Ala Ala Glu Ala Leu Arg Asn Tyr Arg Asn Thr Gln
    1640                1645                1650

Gly Ile Leu Lys Asp Thr Gln Ile His Leu Asp Asp Ala Leu Arg
    1655                1660                1665

Ser Gln Glu Asp Leu Lys Glu Gln Leu Ala Met Val Glu Arg Arg
    1670                1675                1680

Ala Asn Leu Leu Gln Ala Glu Ile Glu Glu Leu Arg Ala Thr Leu
    1685                1690                1695

Glu Gln Thr Glu Arg Ser Arg Lys Ile Ala Glu Gln Glu Leu Leu
    1700                1705                1710

Asp Ala Ser Glu Arg Val Gln Leu Leu His Thr Gln Asn Thr Ser
    1715                1720                1725

Leu Ile Asn Thr Lys Lys Lys Leu Glu Thr Asp Ile Ser Gln Met
    1730                1735                1740

Gln Gly Glu Met Glu Asp Ile Leu Gln Glu Ala Arg Asn Ala Glu
    1745                1750                1755

Glu Lys Ala Lys Lys Ala Ile Thr Asp Ala Ala Met Met Ala Glu
    1760                1765                1770

Glu Leu Lys Lys Glu Gln Asp Thr Ser Ala His Leu Glu Arg Met
    1775                1780                1785

Lys Lys Asn Met Glu Gln Thr Val Lys Asp Leu Gln Leu Arg Leu
    1790                1795                1800

Asp Glu Ala Glu Gln Leu Ala Leu Lys Gly Gly Lys Lys Gln Ile
    1805                1810                1815

Gln Lys Leu Glu Ala Arg Val Arg Glu Leu Glu Gly Glu Val Glu
    1820                1825                1830

Ser Glu Gln Lys Arg Asn Ala Glu Ala Val Lys Gly Leu Arg Lys
    1835                1840                1845

His Glu Arg Arg Val Lys Glu Leu Thr Tyr Gln Thr Glu Glu Asp
    1850                1855                1860

Arg Lys Asn Ile Leu Arg Leu Gln Asp Leu Val Asp Lys Leu Gln
    1865                1870                1875

Ala Lys Val Lys Ser Tyr Lys Arg Gln Ala Glu Glu Ala Glu Glu
    1880                1885                1890

Gln Ser Asn Thr Asn Leu Ala Lys Phe Arg Lys Leu Gln His Glu
    1895                1900                1905

Leu Glu Glu Ala Glu Glu Arg Ala Asp Ile Ala Glu Ser Gln Val
    1910                1915                1920

Asn Lys Leu Arg Val Lys Ser Arg Glu Val His Thr Lys Val Ile
    1925                1930                1935

Ser Glu Glu
    1940

<210> SEQ ID NO 3
<211> LENGTH: 6016
<212> TYPE: DNA
<213> ORGANISM: Homo sapiens
<220> FEATURE:
<221> NAME/KEY: CDS

<222> LOCATION: (112)..(5931)

<400> SEQUENCE: 3

| | |
|---|---|
| atccttcctc aaaattcttg aagtagttgt ctgctttgag cctgccacct tcttcatctg | 60 |
| ataatacaag aggtatacct agtccagcac tgccatcaat aacctgcagc c atg agt<br>                                        Met Ser<br>                                         1 | 117 |
| tct gac tct gag atg gcc att ttt ggg gag gct gct cct ttc ctc cga<br>Ser Asp Ser Glu Met Ala Ile Phe Gly Glu Ala Ala Pro Phe Leu Arg<br>   5          10          15 | 165 |
| aag tct gaa aag gag cga att gaa gct cag aac aag cct ttt gat gcc<br>Lys Ser Glu Lys Glu Arg Ile Glu Ala Gln Asn Lys Pro Phe Asp Ala<br>20          25          30 | 213 |
| aag aca tca gtc ttt gtg gtg gac cct aag gag tcc tac gtg aaa gca<br>Lys Thr Ser Val Phe Val Val Asp Pro Lys Glu Ser Tyr Val Lys Ala<br>35        40          45         50 | 261 |
| ata gtg cag agc agg gaa ggg ggg aag gtg aca gcc aag acc gaa gct<br>Ile Val Gln Ser Arg Glu Gly Gly Lys Val Thr Ala Lys Thr Glu Ala<br>         55          60          65 | 309 |
| gga gct act gta act gtg aaa gaa gac caa gtc ttc tcc atg aac cct<br>Gly Ala Thr Val Thr Val Lys Glu Asp Gln Val Phe Ser Met Asn Pro<br>     70          75         80 | 357 |
| ccc aaa tat gac aag atc gag gac atg gcc atg atg act cac ctg cat<br>Pro Lys Tyr Asp Lys Ile Glu Asp Met Ala Met Met Thr His Leu His<br>       85          90         95 | 405 |
| gag cct gct gtg ctg tat aac ctc aaa gag cgt tac gca gcc tgg atg<br>Glu Pro Ala Val Leu Tyr Asn Leu Lys Glu Arg Tyr Ala Ala Trp Met<br>100          105          110 | 453 |
| atc tac acc tac tcg ggc ctc ttc tgt gtc acc gtc aac ccc tac aag<br>Ile Tyr Thr Tyr Ser Gly Leu Phe Cys Val Thr Val Asn Pro Tyr Lys<br>115         120          125         130 | 501 |
| tgg ctg ccg gtg tac aac cct gag gtg gtg aca gcc tac cga ggc aaa<br>Trp Leu Pro Val Tyr Asn Pro Glu Val Val Thr Ala Tyr Arg Gly Lys<br>            135          140         145 | 549 |
| aag cgc cag gag gcc cca ccc cat atc ttc tcc atc tct gac aat gcc<br>Lys Arg Gln Glu Ala Pro Pro His Ile Phe Ser Ile Ser Asp Asn Ala<br>            150         155         160 | 597 |
| tat cag ttc atg cta act gat cgt gaa aac cag tca atc ttg att act<br>Tyr Gln Phe Met Leu Thr Asp Arg Glu Asn Gln Ser Ile Leu Ile Thr<br>        165         170         175 | 645 |
| gga gaa tct ggt gca ggg aag act gtg aac acg aag cgt gtc atc cag<br>Gly Glu Ser Gly Ala Gly Lys Thr Val Asn Thr Lys Arg Val Ile Gln<br>180         185          190 | 693 |
| tac ttt gca aca att gca gtt act gga gag aag aaa aaa gag gaa cct<br>Tyr Phe Ala Thr Ile Ala Val Thr Gly Glu Lys Lys Lys Glu Glu Pro<br>195         200          205         210 | 741 |
| gcc tct ggc aaa atg cag ggg acc ctt gaa gat caa atc atc agt gct<br>Ala Ser Gly Lys Met Gln Gly Thr Leu Glu Asp Gln Ile Ile Ser Ala<br>            215         220         225 | 789 |
| aac ccc cta ctg gaa gcc ttc ggc aat gcc aag acc gtg agg aat gac<br>Asn Pro Leu Leu Glu Ala Phe Gly Asn Ala Lys Thr Val Arg Asn Asp<br>        230          235         240 | 837 |
| aac tcc tct cgc ttt ggt aaa ttc atc agg atc cat ttt ggt gcc aca<br>Asn Ser Ser Arg Phe Gly Lys Phe Ile Arg Ile His Phe Gly Ala Thr<br>        245         250         255 | 885 |
| ggc aaa ctg gct tct gca gat att gaa aca tat ctg cta gag aag tcc<br>Gly Lys Leu Ala Ser Ala Asp Ile Glu Thr Tyr Leu Leu Glu Lys Ser<br>    260          265         270 | 933 |
| cga gtt act ttt cag cta aag gct gaa aga agc tac cac ata ttt tat<br> | 981 |

```
                Arg Val Thr Phe Gln Leu Lys Ala Glu Arg Ser Tyr His Ile Phe Tyr
                275                 280                 285                 290 caa atc ctg tcc aat aag aaa cca gag ctc att gaa atg ctt ctg atc         1029
Gln Ile Leu Ser Asn Lys Lys Pro Glu Leu Ile Glu Met Leu Leu Ile
                        295                 300                 305 acc acc aac cca tat gac ttc gca ttt gtc agc caa ggg gaa att act         1077
Thr Thr Asn Pro Tyr Asp Phe Ala Phe Val Ser Gln Gly Glu Ile Thr
                    310                 315                 320 gtg ccc agc att gat gac cag gaa gag ctg atg gcc aca gat agt gct         1125
Val Pro Ser Ile Asp Asp Gln Glu Glu Leu Met Ala Thr Asp Ser Ala
                325                 330                 335 gtg gac atc ctg ggt ttc act gct gat gaa aag gtg gcc att tac aag         1173
Val Asp Ile Leu Gly Phe Thr Ala Asp Glu Lys Val Ala Ile Tyr Lys
            340                 345                 350 ctc act gga gcc gtg atg cat tat ggg aac atg aaa ttc aag caa aag         1221
Leu Thr Gly Ala Val Met His Tyr Gly Asn Met Lys Phe Lys Gln Lys
355                 360                 365                 370 caa agg gaa gag cag gca gag cca gat ggc acg gaa gtt gct gac aaa         1269
Gln Arg Glu Glu Gln Ala Glu Pro Asp Gly Thr Glu Val Ala Asp Lys
                        375                 380                 385 gct gct tat ctg aca agt ctg aac tct gct gac ctg ctc aaa tct ctc         1317
Ala Ala Tyr Leu Thr Ser Leu Asn Ser Ala Asp Leu Leu Lys Ser Leu
                    390                 395                 400 tgc tat ccc aga gtc aag gtc ggc aat gag ttc gta acc aaa ggc cag         1365
Cys Tyr Pro Arg Val Lys Val Gly Asn Glu Phe Val Thr Lys Gly Gln
                405                 410                 415 act gtg cag cag gtg tac aac gca gtg ggt gct ctg gcc aaa gcc atc         1413
Thr Val Gln Gln Val Tyr Asn Ala Val Gly Ala Leu Ala Lys Ala Ile
420                 425                 430 tac gag aag atg ttc ctg tgg atg gtc acc cgc atc aac cag cag ctg         1461
Tyr Glu Lys Met Phe Leu Trp Met Val Thr Arg Ile Asn Gln Gln Leu
435                 440                 445                 450 gac acc aag cag ccc agg cag tac ttc atc ggg gtc ttg gac att gct         1509
Asp Thr Lys Gln Pro Arg Gln Tyr Phe Ile Gly Val Leu Asp Ile Ala
                455                 460                 465 ggc ttt gag atc ttt gat ttc aac agc ctg gag cag ctg tgc atc aac         1557
Gly Phe Glu Ile Phe Asp Phe Asn Ser Leu Glu Gln Leu Cys Ile Asn
            470                 475                 480 ttc acc aac gag aaa ctg caa cag ttt ttc aac cac cac atg ttc gtg         1605
Phe Thr Asn Glu Lys Leu Gln Gln Phe Phe Asn His His Met Phe Val
            485                 490                 495 ctg gag cag gaa gag tac aag aag gaa ggc atc gag tgg gag ttc att         1653
Leu Glu Gln Glu Glu Tyr Lys Lys Glu Gly Ile Glu Trp Glu Phe Ile
500                 505                 510 gac ttc ggg atg gac ctg gct gcc tgc atc gag ctc atc gag aag cct         1701
Asp Phe Gly Met Asp Leu Ala Ala Cys Ile Glu Leu Ile Glu Lys Pro
515                 520                 525                 530 atg ggc atc ttc tcc atc cta gaa gag gag tgc atg ttc ccc aag gca         1749
Met Gly Ile Phe Ser Ile Leu Glu Glu Glu Cys Met Phe Pro Lys Ala
                535                 540                 545 aca gac acc tcc ttc aag aac aag ctg tat gaa caa cat ctt gga aaa         1797
Thr Asp Thr Ser Phe Lys Asn Lys Leu Tyr Glu Gln His Leu Gly Lys
                550                 555                 560 tcc aac aac ttc cag aag ccc aag cct gcc aaa ggc aag cct gag gct         1845
Ser Asn Asn Phe Gln Lys Pro Lys Pro Ala Lys Gly Lys Pro Glu Ala
                565                 570                 575 cac ttc tca ctg gtg cac tat gcc ggc acc gtg gac tac aac atc gcc         1893
His Phe Ser Leu Val His Tyr Ala Gly Thr Val Asp Tyr Asn Ile Ala
            580                 585                 590
```

| | | |
|---|---|---|
| ggc tgg ctg gac aaa aac aag gac ccc ctg aat gag act gtg gtg ggg<br>Gly Trp Leu Asp Lys Asn Lys Asp Pro Leu Asn Glu Thr Val Val Gly<br>595                      600                  605                  610 | 1941 |
| ctg tac cag aag tct gca atg aag act ctg gct ttc ctc ttc tct ggg<br>Leu Tyr Gln Lys Ser Ala Met Lys Thr Leu Ala Phe Leu Phe Ser Gly<br>                  615                  620                  625 | 1989 |
| gca caa act gct gaa gca gag ggt ggt ggt gga aag aaa ggt ggc aaa<br>Ala Gln Thr Ala Glu Ala Glu Gly Gly Gly Gly Lys Lys Gly Gly Lys<br>                  630                  635                  640 | 2037 |
| aag aag ggt tct tct ttc cag aca gtg tca gct ctt ttc agg gag aat<br>Lys Lys Gly Ser Ser Phe Gln Thr Val Ser Ala Leu Phe Arg Glu Asn<br>                  645                  650                  655 | 2085 |
| ttg aat aag ctg atg acc aac ttg agg agc act cac ccc cac ttt gtg<br>Leu Asn Lys Leu Met Thr Asn Leu Arg Ser Thr His Pro His Phe Val<br>660                      665                  670 | 2133 |
| cgg tgc atc atc ccc aat gaa act aaa act cct ggt gcc atg gag cat<br>Arg Cys Ile Ile Pro Asn Glu Thr Lys Thr Pro Gly Ala Met Glu His<br>675                      680                  685                  690 | 2181 |
| gag ctt gtc ctg cat cag ctg agg tgt aac ggt gtg ctg gaa ggc atc<br>Glu Leu Val Leu His Gln Leu Arg Cys Asn Gly Val Leu Glu Gly Ile<br>                  695                  700                  705 | 2229 |
| cgc atc tgc agg aaa ggc ttc cca agc aga atc ctt tat gca gac ttc<br>Arg Ile Cys Arg Lys Gly Phe Pro Ser Arg Ile Leu Tyr Ala Asp Phe<br>710                      715                  720 | 2277 |
| aaa cag aga tac aag gtt cta aat gcg agt gct atc cca gag ggt cag<br>Lys Gln Arg Tyr Lys Val Leu Asn Ala Ser Ala Ile Pro Glu Gly Gln<br>                  725                  730                  735 | 2325 |
| ttc att gac agc aag aag gct tct gag aaa ctt cta ggg tct att gaa<br>Phe Ile Asp Ser Lys Lys Ala Ser Glu Lys Leu Leu Gly Ser Ile Glu<br>740                      745                  750 | 2373 |
| att gac cac acc cag tac aaa ttc ggt cat acc aag gtt ttc ttc aaa<br>Ile Asp His Thr Gln Tyr Lys Phe Gly His Thr Lys Val Phe Phe Lys<br>755                      760                  765                  770 | 2421 |
| gct ggc ctg ctg gga act cta gaa gaa atg cga gat gaa aag cta gct<br>Ala Gly Leu Leu Gly Thr Leu Glu Glu Met Arg Asp Glu Lys Leu Ala<br>                  775                  780                  785 | 2469 |
| caa ctc atc acg cgc act caa gcc ata tgc agg ggg ttc ctg atg aga<br>Gln Leu Ile Thr Arg Thr Gln Ala Ile Cys Arg Gly Phe Leu Met Arg<br>                  790                  795                  800 | 2517 |
| gtg gag ttc aga aag atg atg gag agg aga gag tcc atc ttc tgc att<br>Val Glu Phe Arg Lys Met Met Glu Arg Arg Glu Ser Ile Phe Cys Ile<br>805                      810                  815 | 2565 |
| cag tac aac atc cgt gct ttc atg aat gtg aag cac tgg ccc tgg atg<br>Gln Tyr Asn Ile Arg Ala Phe Met Asn Val Lys His Trp Pro Trp Met<br>820                      825                  830 | 2613 |
| aag ctg tat ttc aag atc aag ccc ctc ctc aag agt gca gag aca gag<br>Lys Leu Tyr Phe Lys Ile Lys Pro Leu Leu Lys Ser Ala Glu Thr Glu<br>835                      840                  845                  850 | 2661 |
| aag gag atg gcc aac atg aag gaa gaa ttt gag aaa acc aaa gaa gag<br>Lys Glu Met Ala Asn Met Lys Glu Glu Phe Glu Lys Thr Lys Glu Glu<br>                  855                  860                  865 | 2709 |
| ctg gct aag aca gag gca aaa agg aaa gaa cta gaa gaa aag atg gtg<br>Leu Ala Lys Thr Glu Ala Lys Arg Lys Glu Leu Glu Glu Lys Met Val<br>                  870                  875                  880 | 2757 |
| acg cta atg caa gag aaa aat gac tta caa ctc caa gtt caa gct gaa<br>Thr Leu Met Gln Glu Lys Asn Asp Leu Gln Leu Gln Val Gln Ala Glu<br>                  885                  890                  895 | 2805 |
| gca gat gcc ttg gct gat gca gag gaa aga tgt gat cag ttg att aaa<br>Ala Asp Ala Leu Ala Asp Ala Glu Glu Arg Cys Asp Gln Leu Ile Lys<br>900                      905                  910 | 2853 |

-continued

| | |
|---|---|
| acc aaa atc caa ctt gag gcc aaa atc aaa gag gta act gaa aga gct<br>Thr Lys Ile Gln Leu Glu Ala Lys Ile Lys Glu Val Thr Glu Arg Ala<br>915                    920                925              930 | 2901 |
| gag gat gag gaa gag atc aat gct gag ctg aca gcc aag aag agg aaa<br>Glu Asp Glu Glu Glu Ile Asn Ala Glu Leu Thr Ala Lys Lys Arg Lys<br>               935                  940               945 | 2949 |
| ctg gag gat gaa tgt tca gag ctc aag aaa gac att gat gac ctt gag<br>Leu Glu Asp Glu Cys Ser Glu Leu Lys Lys Asp Ile Asp Asp Leu Glu<br>           950                  955               960 | 2997 |
| ctg aca ctg gcc aag gtt gag aag gag aaa cat gcc aca gag aac aag<br>Leu Thr Leu Ala Lys Val Glu Lys Glu Lys His Ala Thr Glu Asn Lys<br>965                    970                975 | 3045 |
| gtg aaa aac ctc aca gaa gag atg gca ggt ctg gat gaa acc att gct<br>Val Lys Asn Leu Thr Glu Glu Met Ala Gly Leu Asp Glu Thr Ile Ala<br>           980                  985               990 | 3093 |
| aag ctg acc aag gag aag aag gct ctc cag gag gcc cac cag cag<br>Lys Leu Thr Lys Glu Lys Lys Ala Leu Gln Glu Ala His Gln Gln<br>995                   1000              1005 | 3138 |
| acc ctg gat gac ctg cag atg gag gag gac aaa gtc aac acc ctg<br>Thr Leu Asp Asp Leu Gln Met Glu Glu Asp Lys Val Asn Thr Leu<br>1010                1015               1020 | 3183 |
| acc aaa gct aaa acc aag cta gaa cag caa gtg gac gat ctt gaa<br>Thr Lys Ala Lys Thr Lys Leu Glu Gln Gln Val Asp Asp Leu Glu<br>1025                1030               1035 | 3228 |
| gga tct ctg gaa caa gaa aag aaa ctt tgc atg gac tta gaa aga<br>Gly Ser Leu Glu Gln Glu Lys Lys Leu Cys Met Asp Leu Glu Arg<br>1040                1045               1050 | 3273 |
| gcc aag aga aaa ctg gag ggt gac cta aaa ttg gcc caa gaa tcc<br>Ala Lys Arg Lys Leu Glu Gly Asp Leu Lys Leu Ala Gln Glu Ser<br>1055                1060               1065 | 3318 |
| aca atg gat aca gaa aat gac aaa cag caa ctt aat gag aaa ctc<br>Thr Met Asp Thr Glu Asn Asp Lys Gln Gln Leu Asn Glu Lys Leu<br>1070                1075               1080 | 3363 |
| aaa aag aaa gag ttt gaa atg agc aat ctg caa ggc aag att gaa<br>Lys Lys Lys Glu Phe Glu Met Ser Asn Leu Gln Gly Lys Ile Glu<br>1085                1090               1095 | 3408 |
| gat gaa caa gcc ctt gca atg cag cta caa aag aag atc aaa gaa<br>Asp Glu Gln Ala Leu Ala Met Gln Leu Gln Lys Lys Ile Lys Glu<br>1100                1105               1110 | 3453 |
| tta cag gcc cgc att gag gag ctg gag gag gaa atc gag gca gag<br>Leu Gln Ala Arg Ile Glu Glu Leu Glu Glu Glu Ile Glu Ala Glu<br>1115                1120               1125 | 3498 |
| cgg gcc tcc cgg gcc aaa gca gaa aag cag cgc tct gac ctc tcc<br>Arg Ala Ser Arg Ala Lys Ala Glu Lys Gln Arg Ser Asp Leu Ser<br>1130                1135               1140 | 3543 |
| cgg gag ctg gag gag atc agt gag agg ctg gaa gaa gcc ggt ggg<br>Arg Glu Leu Glu Glu Ile Ser Glu Arg Leu Glu Glu Ala Gly Gly<br>1145                1150               1155 | 3588 |
| gcc act tca gcc cag att gag ttg aac aag aag cgg gag gct gag<br>Ala Thr Ser Ala Gln Ile Glu Leu Asn Lys Lys Arg Glu Ala Glu<br>1160                1165               1170 | 3633 |
| ttc cag aaa atg cgc agg gac ctg gaa gag tcc acc ctg cag cac<br>Phe Gln Lys Met Arg Arg Asp Leu Glu Glu Ser Thr Leu Gln His<br>1175                1180               1185 | 3678 |
| gaa gcc acg gca gct gct ctt cgg aag aag cac gca gat agt gtg<br>Glu Ala Thr Ala Ala Ala Leu Arg Lys Lys His Ala Asp Ser Val<br>1190                1195               1200 | 3723 |
| gct gag ctt ggg aag cag atc gac agc ctt cag cgg gtc aag cag<br>Ala Glu Leu Gly Lys Gln Ile Asp Ser Leu Gln Arg Val Lys Gln | 3768 |

|  |  |  |  |  |  |  |  |  |  |  |  |  |  |  |  |
|---|---|---|---|---|---|---|---|---|---|---|---|---|---|---|---|
| 1205 |  |  |  | 1210 |  |  |  | 1215 |  |  |  |  |  |  |  |
| aag | ctg | gag | aag | gaa | aag | agt | gag | ctg | aag | atg | gag | atc | aat | gac | 3813 |
| Lys | Leu | Glu | Lys | Glu | Lys | Ser | Glu | Leu | Lys | Met | Glu | Ile | Asn | Asp |  |
| 1220 |  |  |  |  | 1225 |  |  |  |  | 1230 |  |  |  |  |  |
| ctt | gct | agt | aac | atg | gag | act | gtc | tcc | aaa | gcc | aag | gca | aac | ttt | 3858 |
| Leu | Ala | Ser | Asn | Met | Glu | Thr | Val | Ser | Lys | Ala | Lys | Ala | Asn | Phe |  |
| 1235 |  |  |  |  | 1240 |  |  |  |  | 1245 |  |  |  |  |  |
| gag | aaa | atg | tgc | cgc | acc | cta | gag | gac | cag | ctt | agt | gaa | ata | aaa | 3903 |
| Glu | Lys | Met | Cys | Arg | Thr | Leu | Glu | Asp | Gln | Leu | Ser | Glu | Ile | Lys |  |
| 1250 |  |  |  |  | 1255 |  |  |  |  | 1260 |  |  |  |  |  |
| aca | aag | gaa | gaa | gag | cag | caa | cgc | tta | ata | aat | gag | ttg | tca | gcc | 3948 |
| Thr | Lys | Glu | Glu | Glu | Gln | Gln | Arg | Leu | Ile | Asn | Glu | Leu | Ser | Ala |  |
| 1265 |  |  |  |  | 1270 |  |  |  |  | 1275 |  |  |  |  |  |
| cag | aag | gca | cgt | tta | cac | aca | gaa | tca | ggt | gag | ttt | tca | cga | cag | 3993 |
| Gln | Lys | Ala | Arg | Leu | His | Thr | Glu | Ser | Gly | Glu | Phe | Ser | Arg | Gln |  |
| 1280 |  |  |  |  | 1285 |  |  |  |  | 1290 |  |  |  |  |  |
| cta | gat | gaa | aaa | gat | gct | atg | gtt | tct | cag | cta | tcc | cga | ggc | aaa | 4038 |
| Leu | Asp | Glu | Lys | Asp | Ala | Met | Val | Ser | Gln | Leu | Ser | Arg | Gly | Lys |  |
| 1295 |  |  |  |  | 1300 |  |  |  |  | 1305 |  |  |  |  |  |
| caa | gca | ttt | aca | caa | cag | att | gaa | gaa | tta | aag | agg | cag | cta | gaa | 4083 |
| Gln | Ala | Phe | Thr | Gln | Gln | Ile | Glu | Glu | Leu | Lys | Arg | Gln | Leu | Glu |  |
| 1310 |  |  |  |  | 1315 |  |  |  |  | 1320 |  |  |  |  |  |
| gag | gag | act | aag | gcc | aag | agc | act | ctg | gcc | cat | gcc | ctg | cag | tca | 4128 |
| Glu | Glu | Thr | Lys | Ala | Lys | Ser | Thr | Leu | Ala | His | Ala | Leu | Gln | Ser |  |
| 1325 |  |  |  |  | 1330 |  |  |  |  | 1335 |  |  |  |  |  |
| gcc | cgc | cat | gac | tgt | gac | ctg | ctg | cgg | gaa | cag | tat | gag | gag | gag | 4173 |
| Ala | Arg | His | Asp | Cys | Asp | Leu | Leu | Arg | Glu | Gln | Tyr | Glu | Glu | Glu |  |
| 1340 |  |  |  |  | 1345 |  |  |  |  | 1350 |  |  |  |  |  |
| cag | gaa | gcc | aag | gct | gag | ctg | cag | agg | gga | atg | tcc | aag | gcc | aac | 4218 |
| Gln | Glu | Ala | Lys | Ala | Glu | Leu | Gln | Arg | Gly | Met | Ser | Lys | Ala | Asn |  |
| 1355 |  |  |  |  | 1360 |  |  |  |  | 1365 |  |  |  |  |  |
| agt | gag | gtt | gcc | cag | tgg | agg | acc | aag | tac | gag | acg | gac | gcc | atc | 4263 |
| Ser | Glu | Val | Ala | Gln | Trp | Arg | Thr | Lys | Tyr | Glu | Thr | Asp | Ala | Ile |  |
| 1370 |  |  |  |  | 1375 |  |  |  |  | 1380 |  |  |  |  |  |
| cag | cgc | aca | gag | gag | ctg | gag | gag | gcc | aag | aag | aag | cta | gcc | cag | 4308 |
| Gln | Arg | Thr | Glu | Glu | Leu | Glu | Glu | Ala | Lys | Lys | Lys | Leu | Ala | Gln |  |
| 1385 |  |  |  |  | 1390 |  |  |  |  | 1395 |  |  |  |  |  |
| cgt | ctg | cag | gat | gca | gaa | gaa | cat | gta | gaa | gct | gtg | aat | tcc | aaa | 4353 |
| Arg | Leu | Gln | Asp | Ala | Glu | Glu | His | Val | Glu | Ala | Val | Asn | Ser | Lys |  |
| 1400 |  |  |  |  | 1405 |  |  |  |  | 1410 |  |  |  |  |  |
| tgt | gct | tct | ctt | gaa | aag | aca | aag | cag | agg | cta | cag | aat | gaa | gta | 4398 |
| Cys | Ala | Ser | Leu | Glu | Lys | Thr | Lys | Gln | Arg | Leu | Gln | Asn | Glu | Val |  |
| 1415 |  |  |  |  | 1420 |  |  |  |  | 1425 |  |  |  |  |  |
| gag | gac | ctc | atg | att | gat | gtg | gaa | cga | tct | aat | gct | gcc | tgc | ata | 4443 |
| Glu | Asp | Leu | Met | Ile | Asp | Val | Glu | Arg | Ser | Asn | Ala | Ala | Cys | Ile |  |
| 1430 |  |  |  |  | 1435 |  |  |  |  | 1440 |  |  |  |  |  |
| gct | ctc | gat | aag | aag | caa | aga | aac | ttt | gac | aag | gtt | ctg | gca | gaa | 4488 |
| Ala | Leu | Asp | Lys | Lys | Gln | Arg | Asn | Phe | Asp | Lys | Val | Leu | Ala | Glu |  |
| 1445 |  |  |  |  | 1450 |  |  |  |  | 1455 |  |  |  |  |  |
| tgg | aaa | cag | aag | tat | gag | gaa | act | cag | gct | gaa | ctt | gag | gcc | tcc | 4533 |
| Trp | Lys | Gln | Lys | Tyr | Glu | Glu | Thr | Gln | Ala | Glu | Leu | Glu | Ala | Ser |  |
| 1460 |  |  |  |  | 1465 |  |  |  |  | 1470 |  |  |  |  |  |
| cag | aag | gag | tcg | cgt | tct | ctc | agc | act | gag | ctg | ttc | aag | gtg | aag | 4578 |
| Gln | Lys | Glu | Ser | Arg | Ser | Leu | Ser | Thr | Glu | Leu | Phe | Lys | Val | Lys |  |
| 1475 |  |  |  |  | 1480 |  |  |  |  | 1485 |  |  |  |  |  |
| aat | gcc | tac | gag | gaa | tcc | ctg | gat | cat | ctt | gaa | act | cta | aag | cga | 4623 |
| Asn | Ala | Tyr | Glu | Glu | Ser | Leu | Asp | His | Leu | Glu | Thr | Leu | Lys | Arg |  |
| 1490 |  |  |  |  | 1495 |  |  |  |  | 1500 |  |  |  |  |  |
| gag | aat | aag | aac | tta | caa | cag | gag | att | tct | gac | ctg | aca | gag | caa | 4668 |

-continued

| | | |
|---|---|---|
| Glu Asn Lys Asn Leu Gln Gln Glu Ile Ser Asp Leu Thr Glu Gln<br>1505                           1510                         1515 | | |
| att gca gag ggt gga aag cat atc cat gaa ctg gag aaa gta aag<br>Ile Ala Glu Gly Gly Lys His Ile His Glu Leu Glu Lys Val Lys<br>1520                         1525                        1530 | | 4713 |
| aaa caa ctt gat cat gag aag agt gaa cta cag act tcc cta gag<br>Lys Gln Leu Asp His Glu Lys Ser Glu Leu Gln Thr Ser Leu Glu<br>1535                         1540                        1545 | | 4758 |
| gaa gca gag gca tct ctt gag cat gaa gaa ggc aaa att ctt cgc<br>Glu Ala Glu Ala Ser Leu Glu His Glu Glu Gly Lys Ile Leu Arg<br>1550                         1555                        1560 | | 4803 |
| att caa ctt gag cta aat cag gtg aaa tct gag att gac cga aaa<br>Ile Gln Leu Glu Leu Asn Gln Val Lys Ser Glu Ile Asp Arg Lys<br>1565                         1570                        1575 | | 4848 |
| att gct gaa aaa gat gaa gaa ctc gat cag cta aag agg aac cat<br>Ile Ala Glu Lys Asp Glu Glu Leu Asp Gln Leu Lys Arg Asn His<br>1580                         1585                        1590 | | 4893 |
| ctc aga gtt gtg gag tca atg cag agt aca ctg gat gct gag atc<br>Leu Arg Val Val Glu Ser Met Gln Ser Thr Leu Asp Ala Glu Ile<br>1595                         1600                        1605 | | 4938 |
| agg agc aga aat gat gct ctg agg atc aag aag aag atg gag gga<br>Arg Ser Arg Asn Asp Ala Leu Arg Ile Lys Lys Lys Met Glu Gly<br>1610                         1615                        1620 | | 4983 |
| gat ctt aat gaa atg gaa atc cag ctg aac cat gcc aac cgc cag<br>Asp Leu Asn Glu Met Glu Ile Gln Leu Asn His Ala Asn Arg Gln<br>1625                         1630                        1635 | | 5028 |
| gct gct gag gca cta agg aat ctt aga aac aca caa gga ata ctg<br>Ala Ala Glu Ala Leu Arg Asn Leu Arg Asn Thr Gln Gly Ile Leu<br>1640                         1645                        1650 | | 5073 |
| aag gac act cag cta cat ttg gat gat gcc atc aga ggc caa gat<br>Lys Asp Thr Gln Leu His Leu Asp Asp Ala Ile Arg Gly Gln Asp<br>1655                         1660                        1665 | | 5118 |
| gac ctt aag gaa caa ttg gca atg gtt gag cgc aga gct aac ctg<br>Asp Leu Lys Glu Gln Leu Ala Met Val Glu Arg Arg Ala Asn Leu<br>1670                         1675                        1680 | | 5163 |
| atg cag gct gaa gtt gaa gag ctc agg gca tcc ctg gaa cgg act<br>Met Gln Ala Glu Val Glu Glu Leu Arg Ala Ser Leu Glu Arg Thr<br>1685                         1690                        1695 | | 5208 |
| gag aga ggc agg aaa atg gca gag caa gag ctt ctg gat gcc agt<br>Glu Arg Gly Arg Lys Met Ala Glu Gln Glu Leu Leu Asp Ala Ser<br>1700                         1705                        1710 | | 5253 |
| gaa cgt gtg caa ctt ctg cac act cag aac acc agc ctg atc aac<br>Glu Arg Val Gln Leu Leu His Thr Gln Asn Thr Ser Leu Ile Asn<br>1715                         1720                        1725 | | 5298 |
| acc aag aag aag ctg gaa aca gac att tcc caa atc cag gga gag<br>Thr Lys Lys Lys Leu Glu Thr Asp Ile Ser Gln Ile Gln Gly Glu<br>1730                         1735                        1740 | | 5343 |
| atg gag gac atc gtc cag gaa gcc cgc aat gca gag gag aag gcc<br>Met Glu Asp Ile Val Gln Glu Ala Arg Asn Ala Glu Glu Lys Ala<br>1745                         1750                        1755 | | 5388 |
| aag aag gcc atc act gat gct gcc atg atg gct gag gag ctg aag<br>Lys Lys Ala Ile Thr Asp Ala Ala Met Met Ala Glu Glu Leu Lys<br>1760                         1765                        1770 | | 5433 |
| aag gaa cag gac acc agc gcc cac ctg gag cgg atg aag aag aac<br>Lys Glu Gln Asp Thr Ser Ala His Leu Glu Arg Met Lys Lys Asn<br>1775                         1780                        1785 | | 5478 |
| atg gag cag acc gtg aag gat ctg cag ctc cgt ctg ggt gag gct<br>Met Glu Gln Thr Val Lys Asp Leu Gln Leu Arg Leu Gly Glu Ala<br>1790                         1795                        1800 | | 5523 |

-continued

| | | | | | | | | | | | | | | |
|---|---|---|---|---|---|---|---|---|---|---|---|---|---|---|
| gag | cag | ctg | gcg | ctg | aag | ggt | ggg | aag | aag | cag | atc | cag | aaa | ctg | 5568 |
| Glu | Gln | Leu | Ala | Leu | Lys | Gly | Gly | Lys | Lys | Gln | Ile | Gln | Lys | Leu | |
| 1805 | | | | 1810 | | | | | 1815 | | | | | | |
| gag | gcc | agg | gtg | aga | gag | ctt | gaa | agt | gag | gtg | gaa | agt | gaa | cag | 5613 |
| Glu | Ala | Arg | Val | Arg | Glu | Leu | Glu | Ser | Glu | Val | Glu | Ser | Glu | Gln | |
| 1820 | | | | 1825 | | | | | 1830 | | | | | | |
| aag | cac | aat | gtt | gag | gct | gtc | aag | ggt | ctt | cgc | aaa | cat | gag | aga | 5658 |
| Lys | His | Asn | Val | Glu | Ala | Val | Lys | Gly | Leu | Arg | Lys | His | Glu | Arg | |
| 1835 | | | | 1840 | | | | | 1845 | | | | | | |
| aga | gtg | aag | gaa | ctc | act | tac | cag | act | gag | gag | gac | cgc | aag | aat | 5703 |
| Arg | Val | Lys | Glu | Leu | Thr | Tyr | Gln | Thr | Glu | Glu | Asp | Arg | Lys | Asn | |
| 1850 | | | | 1855 | | | | | 1860 | | | | | | |
| att | ctc | agg | ctg | cag | gac | ttg | gtg | gac | aaa | ttg | caa | acc | aaa | gtc | 5748 |
| Ile | Leu | Arg | Leu | Gln | Asp | Leu | Val | Asp | Lys | Leu | Gln | Thr | Lys | Val | |
| 1865 | | | | 1870 | | | | | 1875 | | | | | | |
| aaa | gct | tac | aag | aga | caa | gct | gaa | gag | gct | gag | gaa | caa | tcc | aat | 5793 |
| Lys | Ala | Tyr | Lys | Arg | Gln | Ala | Glu | Glu | Ala | Glu | Glu | Gln | Ser | Asn | |
| 1880 | | | | 1885 | | | | | 1890 | | | | | | |
| gtc | aac | ctt | gcc | aag | ttc | cgc | aag | ctc | cag | cac | gag | ctg | gag | gag | 5838 |
| Val | Asn | Leu | Ala | Lys | Phe | Arg | Lys | Leu | Gln | His | Glu | Leu | Glu | Glu | |
| 1895 | | | | 1900 | | | | | 1905 | | | | | | |
| gcc | gag | gaa | cgg | gct | gac | att | gct | gag | tcc | caa | gtc | aac | aag | ctg | 5883 |
| Ala | Glu | Glu | Arg | Ala | Asp | Ile | Ala | Glu | Ser | Gln | Val | Asn | Lys | Leu | |
| 1910 | | | | 1915 | | | | | 1920 | | | | | | |
| aga | gtg | aag | agt | cgg | gag | gtt | cac | aca | aaa | gtc | ata | agt | gaa | gag | 5928 |
| Arg | Val | Lys | Ser | Arg | Glu | Val | His | Thr | Lys | Val | Ile | Ser | Glu | Glu | |
| 1925 | | | | 1930 | | | | | 1935 | | | | | | | taa ttcattctaa tgaaagaaaa tgtgaccaaa gaatgcacg aaatgtgaag                                      5981 ttctttgtca ctgtcctgta tatcaaggaa ataaa                                                         6016

<210> SEQ ID NO 4
<211> LENGTH: 1939
<212> TYPE: PRT
<213> ORGANISM: Homo sapiens

<400> SEQUENCE: 4

Met Ser Ser Asp Ser Glu Met Ala Ile Phe Gly Glu Ala Ala Pro Phe
1               5                   10                  15

Leu Arg Lys Ser Glu Lys Glu Arg Ile Glu Ala Gln Asn Lys Pro Phe
            20                  25                  30

Asp Ala Lys Thr Ser Val Phe Val Val Asp Pro Lys Glu Ser Tyr Val
        35                  40                  45

Lys Ala Ile Val Gln Ser Arg Glu Gly Gly Lys Val Thr Ala Lys Thr
    50                  55                  60

Glu Ala Gly Ala Thr Val Thr Val Lys Glu Asp Gln Val Phe Ser Met
65                  70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Asn Pro Glu Val Val Thr Ala Tyr Arg
    130                 135                 140

Gly Lys Lys Arg Gln Glu Ala Pro Pro His Ile Phe Ser Ile Ser Asp
145                 150                 155                 160

Asn Ala Tyr Gln Phe Met Leu Thr Asp Arg Glu Asn Gln Ser Ile Leu

```
            165                 170                 175
Ile Thr Gly Glu Ser Gly Ala Gly Lys Thr Val Asn Thr Lys Arg Val
            180                 185                 190

Ile Gln Tyr Phe Ala Thr Ile Ala Val Thr Gly Glu Lys Lys Lys Glu
            195                 200                 205

Glu Pro Ala Ser Gly Lys Met Gln Gly Thr Leu Glu Asp Gln Ile Ile
            210                 215                 220

Ser Ala Asn Pro Leu Leu Glu Ala Phe Gly Asn Ala Lys Thr Val Arg
225                 230                 235                 240

Asn Asp Asn Ser Ser Arg Phe Gly Lys Phe Ile Arg Ile His Phe Gly
                245                 250                 255

Ala Thr Gly Lys Leu Ala Ser Ala Asp Ile Glu Thr Tyr Leu Leu Glu
                260                 265                 270

Lys Ser Arg Val Thr Phe Gln Leu Lys Ala Glu Arg Ser Tyr His Ile
                275                 280                 285

Phe Tyr Gln Ile Leu Ser Asn Lys Lys Pro Glu Leu Ile Glu Met Leu
            290                 295                 300

Leu Ile Thr Thr Asn Pro Tyr Asp Phe Ala Phe Val Ser Gln Gly Glu
305                 310                 315                 320

Ile Thr Val Pro Ser Ile Asp Asp Gln Glu Glu Leu Met Ala Thr Asp
                325                 330                 335

Ser Ala Val Asp Ile Leu Gly Phe Thr Ala Asp Glu Lys Val Ala Ile
                340                 345                 350

Tyr Lys Leu Thr Gly Ala Val Met His Tyr Gly Asn Met Lys Phe Lys
                355                 360                 365

Gln Lys Gln Arg Glu Glu Gln Ala Glu Pro Asp Gly Thr Glu Val Ala
            370                 375                 380

Asp Lys Ala Ala Tyr Leu Thr Ser Leu Asn Ser Ala Asp Leu Leu Lys
385                 390                 395                 400

Ser Leu Cys Tyr Pro Arg Val Lys Val Gly Asn Glu Phe Val Thr Lys
                405                 410                 415

Gly Gln Thr Val Gln Gln Val Tyr Asn Ala Val Gly Ala Leu Ala Lys
                420                 425                 430

Ala Ile Tyr Glu Lys Met Phe Leu Trp Met Val Thr Arg Ile Asn Gln
                435                 440                 445

Gln Leu Asp Thr Lys Gln Pro Arg Gln Tyr Phe Ile Gly Val Leu Asp
            450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Phe Asn His His Met
                485                 490                 495

Phe Val Leu Glu Gln Glu Glu Tyr Lys Lys Glu Gly Ile Glu Trp Glu
                500                 505                 510

Phe Ile Asp Phe Gly Met Asp Leu Ala Ala Cys Ile Glu Leu Ile Glu
                515                 520                 525

Lys Pro Met Gly Ile Phe Ser Ile Leu Glu Glu Glu Cys Met Phe Pro
            530                 535                 540

Lys Ala Thr Asp Thr Ser Phe Lys Asn Lys Leu Tyr Glu Gln His Leu
545                 550                 555                 560

Gly Lys Ser Asn Asn Phe Gln Lys Pro Lys Pro Ala Lys Gly Lys Pro
                565                 570                 575

Glu Ala His Phe Ser Leu Val His Tyr Ala Gly Thr Val Asp Tyr Asn
                580                 585                 590
```

-continued

```
Ile Ala Gly Trp Leu Asp Lys Asn Lys Asp Pro Leu Asn Glu Thr Val
        595                 600                 605

Val Gly Leu Tyr Gln Lys Ser Ala Met Lys Thr Leu Ala Phe Leu Phe
        610                 615                 620

Ser Gly Ala Gln Thr Ala Glu Ala Glu Gly Gly Gly Lys Lys Gly
625                 630                 635                 640

Gly Lys Lys Gly Ser Ser Phe Gln Thr Val Ser Ala Leu Phe Arg
                645                 650                 655

Glu Asn Leu Asn Lys Leu Met Thr Asn Leu Arg Ser Thr His Pro His
                660                 665                 670

Phe Val Arg Cys Ile Ile Pro Asn Glu Thr Lys Thr Pro Gly Ala Met
                675                 680                 685

Glu His Glu Leu Val Leu His Gln Leu Arg Cys Asn Gly Val Leu Glu
                690                 695                 700

Gly Ile Arg Ile Cys Arg Lys Gly Phe Pro Ser Arg Ile Leu Tyr Ala
705                 710                 715                 720

Asp Phe Lys Gln Arg Tyr Lys Val Leu Asn Ala Ser Ala Ile Pro Glu
                725                 730                 735

Gly Gln Phe Ile Asp Ser Lys Lys Ala Ser Glu Lys Leu Leu Gly Ser
                740                 745                 750

Ile Glu Ile Asp His Thr Gln Tyr Lys Phe Gly His Thr Lys Val Phe
                755                 760                 765

Phe Lys Ala Gly Leu Leu Gly Thr Leu Glu Glu Met Arg Asp Glu Lys
                770                 775                 780

Leu Ala Gln Leu Ile Thr Arg Thr Gln Ala Ile Cys Arg Gly Phe Leu
785                 790                 795                 800

Met Arg Val Glu Phe Arg Lys Met Met Glu Arg Arg Glu Ser Ile Phe
                805                 810                 815

Cys Ile Gln Tyr Asn Ile Arg Ala Phe Met Asn Val Lys His Trp Pro
                820                 825                 830

Trp Met Lys Leu Tyr Phe Lys Ile Lys Pro Leu Leu Lys Ser Ala Glu
                835                 840                 845

Thr Glu Lys Glu Met Ala Asn Met Lys Glu Glu Phe Glu Lys Thr Lys
        850                 855                 860

Glu Glu Leu Ala Lys Thr Glu Ala Lys Arg Lys Glu Leu Glu Glu Lys
865                 870                 875                 880

Met Val Thr Leu Met Gln Glu Lys Asn Asp Leu Gln Leu Gln Val Gln
                885                 890                 895

Ala Glu Ala Asp Ala Leu Ala Asp Ala Glu Glu Arg Cys Asp Gln Leu
                900                 905                 910

Ile Lys Thr Lys Ile Gln Leu Glu Ala Lys Ile Lys Glu Val Thr Glu
                915                 920                 925

Arg Ala Glu Asp Glu Glu Glu Ile Asn Ala Glu Leu Thr Ala Lys Lys
        930                 935                 940

Arg Lys Leu Glu Asp Glu Cys Ser Glu Leu Lys Lys Asp Ile Asp Asp
945                 950                 955                 960

Leu Glu Leu Thr Leu Ala Lys Val Glu Lys Glu Lys His Ala Thr Glu
                965                 970                 975

Asn Lys Val Lys Asn Leu Thr Glu Glu Met Ala Gly Leu Asp Glu Thr
                980                 985                 990

Ile Ala Lys Leu Thr Lys Glu Lys Lys Ala Leu Gln Glu Ala His Gln
                995                 1000                1005
```

```
Gln Thr Leu Asp Asp Leu Gln Met Glu Glu Asp Lys Val Asn Thr
    1010                1015                1020

Leu Thr Lys Ala Lys Thr Lys Leu Glu Gln Gln Val Asp Asp Leu
    1025                1030                1035

Glu Gly Ser Leu Glu Gln Glu Lys Lys Leu Cys Met Asp Leu Glu
    1040                1045                1050

Arg Ala Lys Arg Lys Leu Glu Gly Asp Leu Lys Leu Ala Gln Glu
    1055                1060                1065

Ser Thr Met Asp Thr Glu Asn Asp Lys Gln Gln Leu Asn Glu Lys
    1070                1075                1080

Leu Lys Lys Lys Glu Phe Glu Met Ser Asn Leu Gln Gly Lys Ile
    1085                1090                1095

Glu Asp Glu Gln Ala Leu Ala Met Gln Leu Gln Lys Lys Ile Lys
    1100                1105                1110

Glu Leu Gln Ala Arg Ile Glu Glu Leu Glu Glu Ile Glu Ala
    1115                1120                1125

Glu Arg Ala Ser Arg Ala Lys Ala Glu Lys Gln Arg Ser Asp Leu
    1130                1135                1140

Ser Arg Glu Leu Glu Glu Ile Ser Glu Arg Leu Glu Glu Ala Gly
    1145                1150                1155

Gly Ala Thr Ser Ala Gln Ile Glu Leu Asn Lys Lys Arg Glu Ala
    1160                1165                1170

Glu Phe Gln Lys Met Arg Arg Asp Leu Glu Glu Ser Thr Leu Gln
    1175                1180                1185

His Glu Ala Thr Ala Ala Ala Leu Arg Lys Lys His Ala Asp Ser
    1190                1195                1200

Val Ala Glu Leu Gly Lys Gln Ile Asp Ser Leu Gln Arg Val Lys
    1205                1210                1215

Gln Lys Leu Glu Lys Glu Lys Ser Glu Leu Lys Met Glu Ile Asn
    1220                1225                1230

Asp Leu Ala Ser Asn Met Glu Thr Val Ser Lys Ala Lys Ala Asn
    1235                1240                1245

Phe Glu Lys Met Cys Arg Thr Leu Glu Asp Gln Leu Ser Glu Ile
    1250                1255                1260

Lys Thr Lys Glu Glu Glu Gln Gln Arg Leu Ile Asn Glu Leu Ser
    1265                1270                1275

Ala Gln Lys Ala Arg Leu His Thr Glu Ser Gly Glu Phe Ser Arg
    1280                1285                1290

Gln Leu Asp Glu Lys Asp Ala Met Val Ser Gln Leu Ser Arg Gly
    1295                1300                1305

Lys Gln Ala Phe Thr Gln Gln Ile Glu Glu Leu Lys Arg Gln Leu
    1310                1315                1320

Glu Glu Glu Thr Lys Ala Lys Ser Thr Leu Ala His Ala Leu Gln
    1325                1330                1335

Ser Ala Arg His Asp Cys Asp Leu Leu Arg Glu Gln Tyr Glu Glu
    1340                1345                1350

Glu Gln Glu Ala Lys Ala Glu Leu Gln Arg Gly Met Ser Lys Ala
    1355                1360                1365

Asn Ser Glu Val Ala Gln Trp Arg Thr Lys Tyr Glu Thr Asp Ala
    1370                1375                1380

Ile Gln Arg Thr Glu Glu Leu Glu Glu Ala Lys Lys Lys Leu Ala
    1385                1390                1395

Gln Arg Leu Gln Asp Ala Glu Glu His Val Glu Ala Val Asn Ser
```

-continued

```
            1400              1405              1410
Lys Cys Ala Ser Leu Glu Lys Thr Lys Gln Arg Leu Gln Asn Glu
    1415              1420              1425

Val Glu Asp Leu Met Ile Asp Val Glu Arg Ser Asn Ala Ala Cys
    1430              1435              1440

Ile Ala Leu Asp Lys Lys Gln Arg Asn Phe Asp Lys Val Leu Ala
    1445              1450              1455

Glu Trp Lys Gln Lys Tyr Glu Glu Thr Gln Ala Glu Leu Glu Ala
    1460              1465              1470

Ser Gln Lys Glu Ser Arg Ser Leu Ser Thr Glu Leu Phe Lys Val
    1475              1480              1485

Lys Asn Ala Tyr Glu Glu Ser Leu Asp His Leu Glu Thr Leu Lys
    1490              1495              1500

Arg Glu Asn Lys Asn Leu Gln Gln Glu Ile Ser Asp Leu Thr Glu
    1505              1510              1515

Gln Ile Ala Glu Gly Gly Lys His Ile His Glu Leu Glu Lys Val
    1520              1525              1530

Lys Lys Gln Leu Asp His Glu Lys Ser Glu Leu Gln Thr Ser Leu
    1535              1540              1545

Glu Glu Ala Glu Ala Ser Leu Glu His Glu Glu Gly Lys Ile Leu
    1550              1555              1560

Arg Ile Gln Leu Glu Leu Asn Gln Val Lys Ser Glu Ile Asp Arg
    1565              1570              1575

Lys Ile Ala Glu Lys Asp Glu Glu Leu Asp Gln Leu Lys Arg Asn
    1580              1585              1590

His Leu Arg Val Val Glu Ser Met Gln Ser Thr Leu Asp Ala Glu
    1595              1600              1605

Ile Arg Ser Arg Asn Asp Ala Leu Arg Ile Lys Lys Lys Met Glu
    1610              1615              1620

Gly Asp Leu Asn Glu Met Glu Ile Gln Leu Asn His Ala Asn Arg
    1625              1630              1635

Gln Ala Ala Glu Ala Leu Arg Asn Leu Arg Asn Thr Gln Gly Ile
    1640              1645              1650

Leu Lys Asp Thr Gln Leu His Leu Asp Asp Ala Ile Arg Gly Gln
    1655              1660              1665

Asp Asp Leu Lys Glu Gln Leu Ala Met Val Glu Arg Arg Ala Asn
    1670              1675              1680

Leu Met Gln Ala Glu Val Glu Glu Leu Arg Ala Ser Leu Glu Arg
    1685              1690              1695

Thr Glu Arg Gly Arg Lys Met Ala Glu Gln Glu Leu Leu Asp Ala
    1700              1705              1710

Ser Glu Arg Val Gln Leu Leu His Thr Gln Asn Thr Ser Leu Ile
    1715              1720              1725

Asn Thr Lys Lys Lys Leu Glu Thr Asp Ile Ser Gln Ile Gln Gly
    1730              1735              1740

Glu Met Glu Asp Ile Val Gln Glu Ala Arg Asn Ala Glu Glu Lys
    1745              1750              1755

Ala Lys Lys Ala Ile Thr Asp Ala Ala Met Met Ala Glu Glu Leu
    1760              1765              1770

Lys Lys Glu Gln Asp Thr Ser Ala His Leu Glu Arg Met Lys Lys
    1775              1780              1785

Asn Met Glu Gln Thr Val Lys Asp Leu Gln Leu Arg Leu Gly Glu
    1790              1795              1800
```

| Ala | Glu | Gln | Leu | Ala | Leu | Lys | Gly | Gly | Lys | Lys | Gln | Ile | Gln | Lys |
|-----|-----|-----|-----|-----|-----|-----|-----|-----|-----|-----|-----|-----|-----|-----|
| 1805 | | | | 1810 | | | | | 1815 | | | | | |

| Leu | Glu | Ala | Arg | Val | Arg | Glu | Leu | Glu | Ser | Glu | Val | Glu | Ser | Glu |
|-----|-----|-----|-----|-----|-----|-----|-----|-----|-----|-----|-----|-----|-----|-----|
| 1820 | | | | | 1825 | | | | | 1830 | | | | |

| Gln | Lys | His | Asn | Val | Glu | Ala | Val | Lys | Gly | Leu | Arg | Lys | His | Glu |
|-----|-----|-----|-----|-----|-----|-----|-----|-----|-----|-----|-----|-----|-----|-----|
| 1835 | | | | | 1840 | | | | | 1845 | | | | |

| Arg | Arg | Val | Lys | Glu | Leu | Thr | Tyr | Gln | Thr | Glu | Glu | Asp | Arg | Lys |
|-----|-----|-----|-----|-----|-----|-----|-----|-----|-----|-----|-----|-----|-----|-----|
| 1850 | | | | | 1855 | | | | | 1860 | | | | |

| Asn | Ile | Leu | Arg | Leu | Gln | Asp | Leu | Val | Asp | Lys | Leu | Gln | Thr | Lys |
|-----|-----|-----|-----|-----|-----|-----|-----|-----|-----|-----|-----|-----|-----|-----|
| 1865 | | | | | 1870 | | | | | 1875 | | | | |

| Val | Lys | Ala | Tyr | Lys | Arg | Gln | Ala | Glu | Glu | Ala | Glu | Glu | Gln | Ser |
|-----|-----|-----|-----|-----|-----|-----|-----|-----|-----|-----|-----|-----|-----|-----|
| 1880 | | | | | 1885 | | | | | 1890 | | | | |

| Asn | Val | Asn | Leu | Ala | Lys | Phe | Arg | Lys | Leu | Gln | His | Glu | Leu | Glu |
|-----|-----|-----|-----|-----|-----|-----|-----|-----|-----|-----|-----|-----|-----|-----|
| 1895 | | | | | 1900 | | | | | 1905 | | | | |

| Glu | Ala | Glu | Glu | Arg | Ala | Asp | Ile | Ala | Glu | Ser | Gln | Val | Asn | Lys |
|-----|-----|-----|-----|-----|-----|-----|-----|-----|-----|-----|-----|-----|-----|-----|
| 1910 | | | | | 1915 | | | | | 1920 | | | | |

| Leu | Arg | Val | Lys | Ser | Arg | Glu | Val | His | Thr | Lys | Val | Ile | Ser | Glu |
|-----|-----|-----|-----|-----|-----|-----|-----|-----|-----|-----|-----|-----|-----|-----|
| 1925 | | | | | 1930 | | | | | 1935 | | | | |

Glu

<210> SEQ ID NO 5
<211> LENGTH: 5925
<212> TYPE: DNA
<213> ORGANISM: Homo sapiens
<220> FEATURE:
<221> NAME/KEY: CDS
<222> LOCATION: (1)..(5820)

<400> SEQUENCE: 5

| atg | agt | tct | gac | tct | gag | atg | gcc | att | ttt | ggg | gag | gct | gct | cct | ttc | 48 |
|-----|-----|-----|-----|-----|-----|-----|-----|-----|-----|-----|-----|-----|-----|-----|-----|----|
| Met | Ser | Ser | Asp | Ser | Glu | Met | Ala | Ile | Phe | Gly | Glu | Ala | Ala | Pro | Phe | |
| 1 | | | | 5 | | | | | 10 | | | | | 15 | | |

| ctc | cga | aag | tct | gaa | agg | gag | cga | att | gaa | gcc | cag | aac | aag | cct | ttt | 96 |
|-----|-----|-----|-----|-----|-----|-----|-----|-----|-----|-----|-----|-----|-----|-----|-----|----|
| Leu | Arg | Lys | Ser | Glu | Arg | Glu | Arg | Ile | Glu | Ala | Gln | Asn | Lys | Pro | Phe | |
| | | | 20 | | | | | 25 | | | | | 30 | | | |

| gat | gcc | aag | aca | tca | gtc | ttt | gtg | gtg | gac | cct | aag | gag | tcc | ttt | gtg | 144 |
|-----|-----|-----|-----|-----|-----|-----|-----|-----|-----|-----|-----|-----|-----|-----|-----|-----|
| Asp | Ala | Lys | Thr | Ser | Val | Phe | Val | Val | Asp | Pro | Lys | Glu | Ser | Phe | Val | |
| | | | | 35 | | | | | 40 | | | | | 45 | | |

| aaa | gca | aca | gtg | cag | agc | agg | gaa | ggg | ggg | aag | gtg | aca | gct | aag | acc | 192 |
|-----|-----|-----|-----|-----|-----|-----|-----|-----|-----|-----|-----|-----|-----|-----|-----|-----|
| Lys | Ala | Thr | Val | Gln | Ser | Arg | Glu | Gly | Gly | Lys | Val | Thr | Ala | Lys | Thr | |
| | 50 | | | | | 55 | | | | | 60 | | | | | |

| gaa | gct | gga | gct | act | gta | aca | gtg | aaa | gat | gac | caa | gtc | ttc | ccc | atg | 240 |
|-----|-----|-----|-----|-----|-----|-----|-----|-----|-----|-----|-----|-----|-----|-----|-----|-----|
| Glu | Ala | Gly | Ala | Thr | Val | Thr | Val | Lys | Asp | Asp | Gln | Val | Phe | Pro | Met | |
| 65 | | | | | 70 | | | | | 75 | | | | | 80 | |

| aac | cct | ccc | aaa | tat | gac | aag | atc | gag | gac | atg | gcc | atg | atg | act | cat | 288 |
|-----|-----|-----|-----|-----|-----|-----|-----|-----|-----|-----|-----|-----|-----|-----|-----|-----|
| Asn | Pro | Pro | Lys | Tyr | Asp | Lys | Ile | Glu | Asp | Met | Ala | Met | Met | Thr | His | |
| | | | | 85 | | | | | 90 | | | | | 95 | | |

| cta | cac | gag | cct | gct | gtg | ctg | tac | aac | ctc | aaa | gag | cgc | tac | gca | gcc | 336 |
|-----|-----|-----|-----|-----|-----|-----|-----|-----|-----|-----|-----|-----|-----|-----|-----|-----|
| Leu | His | Glu | Pro | Ala | Val | Leu | Tyr | Asn | Leu | Lys | Glu | Arg | Tyr | Ala | Ala | |
| | | | | 100 | | | | | 105 | | | | | 110 | | |

| tgg | atg | atc | tac | acc | tac | tca | ggc | ttg | ttc | tgt | gtc | act | gtc | aac | ccc | 384 |
|-----|-----|-----|-----|-----|-----|-----|-----|-----|-----|-----|-----|-----|-----|-----|-----|-----|
| Trp | Met | Ile | Tyr | Thr | Tyr | Ser | Gly | Leu | Phe | Cys | Val | Thr | Val | Asn | Pro | |
| | | | 115 | | | | | 120 | | | | | 125 | | | |

| tac | aag | tgg | ttg | cca | gtg | tat | aat | gca | gaa | gtg | gtg | aca | gcc | tac | cga | 432 |
|-----|-----|-----|-----|-----|-----|-----|-----|-----|-----|-----|-----|-----|-----|-----|-----|-----|
| Tyr | Lys | Trp | Leu | Pro | Val | Tyr | Asn | Ala | Glu | Val | Val | Thr | Ala | Tyr | Arg | |
| | | | 130 | | | | | 135 | | | | | 140 | | | |

| ggc | aaa | aag | cgc | cag | gaa | gcc | cca | ccc | cac | atc | ttc | tcc | atc | tct | gac | 480 |
|-----|-----|-----|-----|-----|-----|-----|-----|-----|-----|-----|-----|-----|-----|-----|-----|-----|
| Gly | Lys | Lys | Arg | Gln | Glu | Ala | Pro | Pro | His | Ile | Phe | Ser | Ile | Ser | Asp | |

-continued

| | |
|---|---|
| aat gcc tat cag ttc atg ctg act gat cgg gag aat cag tct atc ttg<br>Asn Ala Tyr Gln Phe Met Leu Thr Asp Arg Glu Asn Gln Ser Ile Leu<br>                165                      170                    175 | 528 |
| atc acc gga gaa tct ggc gca ggg aag act gtg aac acc aag cgt gtc<br>Ile Thr Gly Glu Ser Gly Ala Gly Lys Thr Val Asn Thr Lys Arg Val<br>         180                      185                      190 | 576 |
| atc cag tac ttt gca aca att gca gtt act ggg gag aag aag aag gaa<br>Ile Gln Tyr Phe Ala Thr Ile Ala Val Thr Gly Glu Lys Lys Lys Glu<br>              195                      200                    205 | 624 |
| gaa gtt act tct ggc aaa atg cag ggg act ctg gaa gat caa atc atc<br>Glu Val Thr Ser Gly Lys Met Gln Gly Thr Leu Glu Asp Gln Ile Ile<br>210                      215                      220 | 672 |
| agt gcc aac ccc cta ctg gag gcc ttt ggc aac gcc aag acc gtg agg<br>Ser Ala Asn Pro Leu Leu Glu Ala Phe Gly Asn Ala Lys Thr Val Arg<br>225                      230                      235                    240 | 720 |
| aat gac aac tcc tct cgc ttt ggt aaa ttc atc agg atc cac ttc ggt<br>Asn Asp Asn Ser Ser Arg Phe Gly Lys Phe Ile Arg Ile His Phe Gly<br>                    245                      250                    255 | 768 |
| acc aca ggg aaa ctg gct tct gct gat att gaa aca tat ctt ctg gag<br>Thr Thr Gly Lys Leu Ala Ser Ala Asp Ile Glu Thr Tyr Leu Leu Glu<br>         260                      265                      270 | 816 |
| aag tct aga gtt act ttc cag cta aag gct gaa aga agc tat cat att<br>Lys Ser Arg Val Thr Phe Gln Leu Lys Ala Glu Arg Ser Tyr His Ile<br>275                      280                      285 | 864 |
| ttt tat cag atc atg tct aac aag aag cca gat cta att gaa atg ctc<br>Phe Tyr Gln Ile Met Ser Asn Lys Lys Pro Asp Leu Ile Glu Met Leu<br>         290                      295                    300 | 912 |
| ctg atc acc acc aac cca tac gat tat gcc ttc gtc agt caa ggg gag<br>Leu Ile Thr Thr Asn Pro Tyr Asp Tyr Ala Phe Val Ser Gln Gly Glu<br>305                      310                      315                    320 | 960 |
| atc aca gtg ccc agc att gat gac caa gaa gag ttg atg gct aca gat<br>Ile Thr Val Pro Ser Ile Asp Asp Gln Glu Glu Leu Met Ala Thr Asp<br>                    325                      330                    335 | 1008 |
| agt gcc att gaa att ctg ggc ttt act tca gat gaa aga gtg tcc atc<br>Ser Ala Ile Glu Ile Leu Gly Phe Thr Ser Asp Glu Arg Val Ser Ile<br>                  340                      345                    350 | 1056 |
| tat aag ctc aca ggg gct gtg atg cat tat ggg aac atg aaa ttc aag<br>Tyr Lys Leu Thr Gly Ala Val Met His Tyr Gly Asn Met Lys Phe Lys<br>              355                      360                    365 | 1104 |
| caa aag cag cgt gag gag caa gct gag cca gat ggc act gaa gtt gct<br>Gln Lys Gln Arg Glu Glu Gln Ala Glu Pro Asp Gly Thr Glu Val Ala<br>370                      375                      380 | 1152 |
| gac aag gca gcc tat ctc caa aat ctg aac tct gca gat ctg ctc aaa<br>Asp Lys Ala Ala Tyr Leu Gln Asn Leu Asn Ser Ala Asp Leu Leu Lys<br>385                      390                      395                    400 | 1200 |
| gcc ctc tgc tac cct agg gtc aag gtc ggc aat gag tat gtc acc aaa<br>Ala Leu Cys Tyr Pro Arg Val Lys Val Gly Asn Glu Tyr Val Thr Lys<br>                  405                      410                    415 | 1248 |
| ggt caa act gtg cag cag gtg tac aat gca gtg ggt gct ctg gcc aaa<br>Gly Gln Thr Val Gln Gln Val Tyr Asn Ala Val Gly Ala Leu Ala Lys<br>              420                      425                    430 | 1296 |
| gct gtc tac gat aag atg ttc ttg tgg atg gtc acc cgc atc aac cag<br>Ala Val Tyr Asp Lys Met Phe Leu Trp Met Val Thr Arg Ile Asn Gln<br>         435                      440                    445 | 1344 |
| cag ctg gac acc aag cag ccc agg cag tac ttc att ggg gtc ttg gac<br>Gln Leu Asp Thr Lys Gln Pro Arg Gln Tyr Phe Ile Gly Val Leu Asp<br>         450                      455                    460 | 1392 |
| att gct ggc ttt gag atc ttt gat ttc aac agc ctg gag cag ctg tgc | 1440 |

```
Ile Ala Gly Phe Glu Ile Phe Asp Phe Asn Ser Leu Glu Gln Leu Cys
465                 470                 475                 480 atc aac ttc acc aat gag aaa ctg caa cag ttt ttc aac cac cac atg      1488
Ile Asn Phe Thr Asn Glu Lys Leu Gln Gln Phe Phe Asn His His Met
                485                 490                 495 ttc gtg ctg gag cag gag gag tac aag aag gaa ggc att gag tgg acg      1536
Phe Val Leu Glu Gln Glu Glu Tyr Lys Lys Glu Gly Ile Glu Trp Thr
            500                 505                 510 ttc att gac ttt ggg atg gac ctg gct gcc tgc atc gag ctc atc gag      1584
Phe Ile Asp Phe Gly Met Asp Leu Ala Ala Cys Ile Glu Leu Ile Glu
            515                 520                 525 aag cct atg ggc atc ttc tcc atc ctg gaa gag gag tgc atg ttc ccc      1632
Lys Pro Met Gly Ile Phe Ser Ile Leu Glu Glu Glu Cys Met Phe Pro
530                 535                 540 aag gcg aca gac acc tcc ttc aag aac aag ctg tat gaa caa cat ctt      1680
Lys Ala Thr Asp Thr Ser Phe Lys Asn Lys Leu Tyr Glu Gln His Leu
545                 550                 555                 560 gga aaa tcc aat aac ttc cag aag ccc aag cct gcc aaa ggc aag cct      1728
Gly Lys Ser Asn Asn Phe Gln Lys Pro Lys Pro Ala Lys Gly Lys Pro
                565                 570                 575 gag gcc cac ttc tct ttg att cac tat gct ggc acc gtg gac tac aac      1776
Glu Ala His Phe Ser Leu Ile His Tyr Ala Gly Thr Val Asp Tyr Asn
            580                 585                 590 att gcc ggc tgg ctt gac aag aac aag gac ccc ctg aat gag act gtg      1824
Ile Ala Gly Trp Leu Asp Lys Asn Lys Asp Pro Leu Asn Glu Thr Val
            595                 600                 605 gtg ggg ctg tac cag aag tct gca atg aag act ctg gct ctc ctc ttt      1872
Val Gly Leu Tyr Gln Lys Ser Ala Met Lys Thr Leu Ala Leu Leu Phe
            610                 615                 620 gtt ggg gca acg gga gcg gaa gca gag gct ggc ggt gga aag aaa ggt      1920
Val Gly Ala Thr Gly Ala Glu Ala Glu Ala Gly Gly Gly Lys Lys Gly
625                 630                 635                 640 ggt aag aag aag ggt tct tct ttc cag act gtg tcg gct ctc ttc agg      1968
Gly Lys Lys Lys Gly Ser Ser Phe Gln Thr Val Ser Ala Leu Phe Arg
                645                 650                 655 gag aat ttg aat aag ctg atg acc aac ttg agg agc act cac ccc cac      2016
Glu Asn Leu Asn Lys Leu Met Thr Asn Leu Arg Ser Thr His Pro His
            660                 665                 670 ttt gtg cgg tgc atc atc ccc aat gaa act aaa act cct ggt gcc atg      2064
Phe Val Arg Cys Ile Ile Pro Asn Glu Thr Lys Thr Pro Gly Ala Met
            675                 680                 685 gag cat gag ctt gtc ctg cat cag ctg agg tgt aac ggt gtg ctg gaa      2112
Glu His Glu Leu Val Leu His Gln Leu Arg Cys Asn Gly Val Leu Glu
            690                 695                 700 ggc atc cgc atc tgc agg aaa ggc ttc cca agc aga atc ctt tat gca      2160
Gly Ile Arg Ile Cys Arg Lys Gly Phe Pro Ser Arg Ile Leu Tyr Ala
705                 710                 715                 720 gac ttc aaa cag aga tac aag gtg tta aat gca agt gct atc cct gaa      2208
Asp Phe Lys Gln Arg Tyr Lys Val Leu Asn Ala Ser Ala Ile Pro Glu
                725                 730                 735 gga caa ttc atc gat agc aag aag gct tca gag aag ctc ctg ggg tcc      2256
Gly Gln Phe Ile Asp Ser Lys Lys Ala Ser Glu Lys Leu Leu Gly Ser
            740                 745                 750 att gac att gac cac acc cag tat aaa ttt ggt cac acc aag gtc ttc      2304
Ile Asp Ile Asp His Thr Gln Tyr Lys Phe Gly His Thr Lys Val Phe
            755                 760                 765 ttc aaa gct ggt ctt ctg ggg ctc cta gag gag atg cga gat gag aag      2352
Phe Lys Ala Gly Leu Leu Gly Leu Leu Glu Glu Met Arg Asp Glu Lys
770                 775                 780
```

```
                                      -continued
ctg gcc cag ctg att acc cga acc cag gcc atg tgc aga ggg ttc ttg    2400
Leu Ala Gln Leu Ile Thr Arg Thr Gln Ala Met Cys Arg Gly Phe Leu
785                 790                 795                 800 gca aga gtg gag tac cag aaa atg gtg gaa aga aga gag tcc atc ttc    2448
Ala Arg Val Glu Tyr Gln Lys Met Val Glu Arg Arg Glu Ser Ile Phe
                805                 810                 815 tgc atc cag tac aat gtc cgt gcc ttc atg aat gtc aag cac tgg ccc    2496
Cys Ile Gln Tyr Asn Val Arg Ala Phe Met Asn Val Lys His Trp Pro
            820                 825                 830 tgg atg aag ctg tat ttc aag atc aaa ccc ctc ctc aaa agt gca gag    2544
Trp Met Lys Leu Tyr Phe Lys Ile Lys Pro Leu Leu Lys Ser Ala Glu
        835                 840                 845 aca gag aag gag atg gcc aac atg aag gaa gaa ttt gag aaa acc aaa    2592
Thr Glu Lys Glu Met Ala Asn Met Lys Glu Glu Phe Glu Lys Thr Lys
850                 855                 860 gaa gag ctg gct aag acc gag gca aaa agg aaa gag ctg gaa gaa aaa    2640
Glu Glu Leu Ala Lys Thr Glu Ala Lys Arg Lys Glu Leu Glu Glu Lys
865                 870                 875                 880 atg gtg act ctg atg caa gaa aaa aat gac ttg caa ctc cag gtt caa    2688
Met Val Thr Leu Met Gln Glu Lys Asn Asp Leu Gln Leu Gln Val Gln
                885                 890                 895 gct gaa gct gac agc ttg gct gat gca gag gaa agg tgt gac cag cta    2736
Ala Glu Ala Asp Ser Leu Ala Asp Ala Glu Glu Arg Cys Asp Gln Leu
            900                 905                 910 atc aaa acc aaa atc cag cta gaa gcc aaa atc aaa gag gtg act gag    2784
Ile Lys Thr Lys Ile Gln Leu Glu Ala Lys Ile Lys Glu Val Thr Glu
        915                 920                 925 aga gct gag gat gag gaa gag atc aat gct gag ctg aca gcc aag aag    2832
Arg Ala Glu Asp Glu Glu Glu Ile Asn Ala Glu Leu Thr Ala Lys Lys
930                 935                 940 agg aaa ctg gag gat gaa tgt tca gaa ctc aag aaa gac att gat gac    2880
Arg Lys Leu Glu Asp Glu Cys Ser Glu Leu Lys Lys Asp Ile Asp Asp
945                 950                 955                 960 ctt gag ctg aca ctg gcc aag gtt gag aag gag aaa cat gcc aca gaa    2928
Leu Glu Leu Thr Leu Ala Lys Val Glu Lys Glu Lys His Ala Thr Glu
                965                 970                 975 aac aag gtg aaa aac ctc aca gaa gag atg gcg ggt ctg gat gaa acc    2976
Asn Lys Val Lys Asn Leu Thr Glu Glu Met Ala Gly Leu Asp Glu Thr
            980                 985                 990 att gct aag ctg acc aag gag aag  aag gct ctc cag gag  gcc cac cag   3024
Ile Ala Lys Leu Thr Lys Glu Lys  Lys Ala Leu Gln Glu  Ala His Gln
        995                 1000                1005 cag acc ctg gat gac ctg cag  gca gag gag gac aaa  gtc aac acc       3069
Gln Thr Leu Asp Asp Leu Gln  Ala Glu Glu Asp Lys  Val Asn Thr
1010                1015                     1020 ctg acc aaa gct aaa atc aaa  ctt gaa caa caa gtg  gat gat ctt       3114
Leu Thr Lys Ala Lys Ile Lys  Leu Glu Gln Gln Val  Asp Asp Leu
1025                1030                     1035 gaa gga tct ttg gaa caa gaa  aag aaa atc cgg atg  gat cta gaa       3159
Glu Gly Ser Leu Glu Gln Glu  Lys Lys Ile Arg Met  Asp Leu Glu
1040                1045                     1050 aga gca aag aga aaa cta gag  gga gac cta aaa ttg  gct caa gaa       3204
Arg Ala Lys Arg Lys Leu Glu  Gly Asp Leu Lys Leu  Ala Gln Glu
1055                1060                     1065 tcc gca atg gat ata gaa aat  gac aaa caa caa ctt  gat gaa aag       3249
Ser Ala Met Asp Ile Glu Asn  Asp Lys Gln Gln Leu  Asp Glu Lys
1070                1075                     1080 ctt aaa aag aaa gag ttt gaa  atg agc ggt ctg caa  agc aag att       3294
Leu Lys Lys Lys Glu Phe Glu  Met Ser Gly Leu Gln  Ser Lys Ile
1085                1090                     1095
```

```
gaa gat gaa caa gcc ctt ggt atg cag ctg cag aag aaa atc aag      3339
Glu Asp Glu Gln Ala Leu Gly Met Gln Leu Gln Lys Lys Ile Lys
    1100                1105                1110 gag tta caa gcc cgc att gag gag ctg gag gag gaa atc gag gca      3384
Glu Leu Gln Ala Arg Ile Glu Glu Leu Glu Glu Glu Ile Glu Ala
        1115                1120                1125 gag cgg gcc tcc cgg gcc aaa gca gag aag cag cgc tct gat ctc      3429
Glu Arg Ala Ser Arg Ala Lys Ala Glu Lys Gln Arg Ser Asp Leu
            1130                1135                1140 tcc cgg gag ctg gag gag atc agt gag agg ctg gaa gaa gcc ggt      3474
Ser Arg Glu Leu Glu Glu Ile Ser Glu Arg Leu Glu Glu Ala Gly
    1145                1150                1155 ggg gcc acc tcg gcc cag att gag atg aac aag aag cgg gaa gct      3519
Gly Ala Thr Ser Ala Gln Ile Glu Met Asn Lys Lys Arg Glu Ala
        1160                1165                1170 gag ttc cag aaa atg cgc agg gac ctg gag gag gcc acc cta cag      3564
Glu Phe Gln Lys Met Arg Arg Asp Leu Glu Glu Ala Thr Leu Gln
            1175                1180                1185 cat gag gcc acg gcg gcc acc ctg agg aag aag cat gca gat agt      3609
His Glu Ala Thr Ala Ala Thr Leu Arg Lys Lys His Ala Asp Ser
    1190                1195                1200 gtg gcc gag ctt ggg gag cag att gac aac ctg cag cga gtg aag      3654
Val Ala Glu Leu Gly Glu Gln Ile Asp Asn Leu Gln Arg Val Lys
        1205                1210                1215 cag aag ctg gag aag gag aag agt gag atg aag atg gag atc gat      3699
Gln Lys Leu Glu Lys Glu Lys Ser Glu Met Lys Met Glu Ile Asp
            1220                1225                1230 gac ctt gct agt aac atg gag act gtc tcc aaa gcc aag gga aac      3744
Asp Leu Ala Ser Asn Met Glu Thr Val Ser Lys Ala Lys Gly Asn
    1235                1240                1245 ctt gaa aag atg tgc cgc gct cta gaa gat caa ctg agt gaa att      3789
Leu Glu Lys Met Cys Arg Ala Leu Glu Asp Gln Leu Ser Glu Ile
        1250                1255                1260 aag acc aag gaa gag gag cag cag cgg ctg atc aat gac ctc aca      3834
Lys Thr Lys Glu Glu Glu Gln Gln Arg Leu Ile Asn Asp Leu Thr
            1265                1270                1275 gca cag aga gcg cgc ctg caa aca gaa tca ggt gaa tat tca cgc      3879
Ala Gln Arg Ala Arg Leu Gln Thr Glu Ser Gly Glu Tyr Ser Arg
    1280                1285                1290 cag cta gat gaa aag gac aca cta gtt tca cag ctc tcg agg ggc      3924
Gln Leu Asp Glu Lys Asp Thr Leu Val Ser Gln Leu Ser Arg Gly
        1295                1300                1305 aaa caa gcc ttt act caa cag att gag gaa ctg aaa agg caa ctt      3969
Lys Gln Ala Phe Thr Gln Gln Ile Glu Glu Leu Lys Arg Gln Leu
            1310                1315                1320 gaa gag gag ata aag gcc aag agt gcc ctg gca cat gcc ctg cag      4014
Glu Glu Glu Ile Lys Ala Lys Ser Ala Leu Ala His Ala Leu Gln
    1325                1330                1335 tcc tcc cgc cat gac tgt gac ctg ctg cgg gaa cag tat gag gag      4059
Ser Ser Arg His Asp Cys Asp Leu Leu Arg Glu Gln Tyr Glu Glu
        1340                1345                1350 gag cag gaa gcc aag gcc gag cta cag aga gca atg tcc aag gcc      4104
Glu Gln Glu Ala Lys Ala Glu Leu Gln Arg Ala Met Ser Lys Ala
            1355                1360                1365 aac agt gag gtt gcc cag tgg agg acc aaa tat gag aca gat gcc      4149
Asn Ser Glu Val Ala Gln Trp Arg Thr Lys Tyr Glu Thr Asp Ala
    1370                1375                1380 atc cag cgc aca gag gag ctg gag gag gcc aag aag aag ctg gct      4194
Ile Gln Arg Thr Glu Glu Leu Glu Glu Ala Lys Lys Lys Leu Ala
```

```
                1385                1390                1395
cag cgt ctg cag gat gct gag gaa cat gta gaa gct gtg aat gcc       4239
Gln Arg Leu Gln Asp Ala Glu Glu His Val Glu Ala Val Asn Ala
        1400                1405                1410 aaa tgt gct tcc ctt gag aag acg aag cag agg ctc cag aat gaa       4284
Lys Cys Ala Ser Leu Glu Lys Thr Lys Gln Arg Leu Gln Asn Glu
    1415                1420                1425 gtt gag gac ctc atg att gat gtt gag agg aca aat gct gcc tgt       4329
Val Glu Asp Leu Met Ile Asp Val Glu Arg Thr Asn Ala Ala Cys
1430                1435                1440 gcc gcc ctg gac aaa aag caa agg aac ttt gat aag atc ctg gca       4374
Ala Ala Leu Asp Lys Lys Gln Arg Asn Phe Asp Lys Ile Leu Ala
        1445                1450                1455 gaa tgg aaa cag aag tgt gaa gaa act cat gct gaa ctt gaa gct       4419
Glu Trp Lys Gln Lys Cys Glu Glu Thr His Ala Glu Leu Glu Ala
    1460                1465                1470 tct caa aag gaa tcc cgc tca ctc agc aca gaa cta ttt aag att       4464
Ser Gln Lys Glu Ser Arg Ser Leu Ser Thr Glu Leu Phe Lys Ile
1475                1480                1485 aag aat gct tat gag gaa tct tta gac caa ctt gaa acc ttg aaa       4509
Lys Asn Ala Tyr Glu Glu Ser Leu Asp Gln Leu Glu Thr Leu Lys
        1490                1495                1500 cgg gaa aat aag aat ctg cag cag gag att tct gat ctc act gaa       4554
Arg Glu Asn Lys Asn Leu Gln Gln Glu Ile Ser Asp Leu Thr Glu
    1505                1510                1515 cag att gca gaa gga gga aag cgc atc cat gaa ctg gaa aaa ata       4599
Gln Ile Ala Glu Gly Gly Lys Arg Ile His Glu Leu Glu Lys Ile
1520                1525                1530 aag aag caa gtt gag caa gaa aag tct gaa ctt cag gct gcc tta       4644
Lys Lys Gln Val Glu Gln Glu Lys Ser Glu Leu Gln Ala Ala Leu
        1535                1540                1545 gag gag gca gag gca tct ctt gaa cat gaa gag gga aag atc ctg       4689
Glu Glu Ala Glu Ala Ser Leu Glu His Glu Glu Gly Lys Ile Leu
    1550                1555                1560 cgc atc cag ctt gag ttg aac caa gtc aag tct gag gtt gat agg       4734
Arg Ile Gln Leu Glu Leu Asn Gln Val Lys Ser Glu Val Asp Arg
1565                1570                1575 aaa att gct gaa aaa gat gag gaa att gac cag atg aag aga aac       4779
Lys Ile Ala Glu Lys Asp Glu Glu Ile Asp Gln Met Lys Arg Asn
        1580                1585                1590 cac att aga atc gtg gag tcc atg cag agc aca ctg gat gct gag       4824
His Ile Arg Ile Val Glu Ser Met Gln Ser Thr Leu Asp Ala Glu
    1595                1600                1605 atc agg agc agg aat gat gcc att agg ctc aag aag aag atg gag       4869
Ile Arg Ser Arg Asn Asp Ala Ile Arg Leu Lys Lys Lys Met Glu
1610                1615                1620 gga gac ctc aat gaa atg gaa atc cag ctg aac cat gcc aac cgc       4914
Gly Asp Leu Asn Glu Met Glu Ile Gln Leu Asn His Ala Asn Arg
        1625                1630                1635 atg gct gct gag gcc ctg agg aac tat agg aac acc caa gcc atc       4959
Met Ala Ala Glu Ala Leu Arg Asn Tyr Arg Asn Thr Gln Ala Ile
    1640                1645                1650 ctc aag gat acc cag ctc cac cta gat gat gct ctc cgg agc caa       5004
Leu Lys Asp Thr Gln Leu His Leu Asp Asp Ala Leu Arg Ser Gln
1655                1660                1665 gag gac ctg aag gaa cag ctg gct atg gtg gag cgc aga gcc aac       5049
Glu Asp Leu Lys Glu Gln Leu Ala Met Val Glu Arg Arg Ala Asn
        1670                1675                1680 ctg ctg cag gct gag atc gag gaa cta cga gcc act ctg gaa cag       5094
Leu Leu Gln Ala Glu Ile Glu Glu Leu Arg Ala Thr Leu Glu Gln
```

```
                Leu  Leu  Gln  Ala  Glu  Ile  Glu  Glu  Leu  Arg  Ala  Thr  Leu  Glu  Gln
                         1685                     1690                     1695 acg  gag  agg  agc  agg  aaa  atc  gca  gaa  cag  gag  ctc  ctg  gat  gcc            5139
Thr  Glu  Arg  Ser  Arg  Lys  Ile  Ala  Glu  Gln  Glu  Leu  Leu  Asp  Ala
1700                     1705                     1710 agt  gaa  cgt  gtt  cag  ctc  ctg  cac  acc  cag  aac  acc  agc  ctg  atc            5184
Ser  Glu  Arg  Val  Gln  Leu  Leu  His  Thr  Gln  Asn  Thr  Ser  Leu  Ile
1715                     1720                     1725 aac  acc  aag  aag  aag  ctg  gag  aca  gac  att  tcc  caa  atc  cag  gga            5229
Asn  Thr  Lys  Lys  Lys  Leu  Glu  Thr  Asp  Ile  Ser  Gln  Ile  Gln  Gly
1730                     1735                     1740 gag  atg  gaa  gac  atc  atc  cag  gaa  gcc  cgc  aat  gca  gaa  gag  aag            5274
Glu  Met  Glu  Asp  Ile  Ile  Gln  Glu  Ala  Arg  Asn  Ala  Glu  Glu  Lys
1745                     1750                     1755 gcc  aag  aag  gcc  atc  act  gat  gct  gcc  atg  atg  gct  gag  gag  ctg            5319
Ala  Lys  Lys  Ala  Ile  Thr  Asp  Ala  Ala  Met  Met  Ala  Glu  Glu  Leu
1760                     1765                     1770 aag  aag  gaa  cag  gac  acc  agc  gcc  cat  ctg  gag  cgg  atg  aag  aag            5364
Lys  Lys  Glu  Gln  Asp  Thr  Ser  Ala  His  Leu  Glu  Arg  Met  Lys  Lys
1775                     1780                     1785 aac  ttg  gaa  cag  acg  gtg  aag  gac  ctg  cag  cat  cgt  ctg  gat  gag            5409
Asn  Leu  Glu  Gln  Thr  Val  Lys  Asp  Leu  Gln  His  Arg  Leu  Asp  Glu
1790                     1795                     1800 gct  gag  cag  ctg  gcc  ctg  aag  ggt  ggg  aag  aag  cag  atc  cag  aaa            5454
Ala  Glu  Gln  Leu  Ala  Leu  Lys  Gly  Gly  Lys  Lys  Gln  Ile  Gln  Lys
1805                     1810                     1815 ctg  gag  gcc  agg  gtt  cgt  gaa  ctt  gaa  ggt  gaa  gtt  gaa  agt  gaa            5499
Leu  Glu  Ala  Arg  Val  Arg  Glu  Leu  Glu  Gly  Glu  Val  Glu  Ser  Glu
1820                     1825                     1830 cag  aag  cgc  aat  gtt  gaa  gct  gtc  aag  ggt  cta  cgc  aaa  cat  gag            5544
Gln  Lys  Arg  Asn  Val  Glu  Ala  Val  Lys  Gly  Leu  Arg  Lys  His  Glu
1835                     1840                     1845 aga  aaa  gtg  aag  gaa  ctc  act  tac  caa  act  gag  gaa  gac  cgc  aag            5589
Arg  Lys  Val  Lys  Glu  Leu  Thr  Tyr  Gln  Thr  Glu  Glu  Asp  Arg  Lys
1850                     1855                     1860 aat  att  ctc  agg  ctg  cag  gac  ctg  gtg  gac  aag  ctg  caa  gca  aag            5634
Asn  Ile  Leu  Arg  Leu  Gln  Asp  Leu  Val  Asp  Lys  Leu  Gln  Ala  Lys
1865                     1870                     1875 gtg  aaa  tcc  tac  aag  aga  caa  gct  gaa  gaa  gcg  gag  gaa  caa  tcc            5679
Val  Lys  Ser  Tyr  Lys  Arg  Gln  Ala  Glu  Glu  Ala  Glu  Glu  Gln  Ser
1880                     1885                     1890 aac  gtc  aac  ctc  tcc  aaa  ttc  cgg  agg  atc  cag  cac  gag  ctg  gag            5724
Asn  Val  Asn  Leu  Ser  Lys  Phe  Arg  Arg  Ile  Gln  His  Glu  Leu  Glu
1895                     1900                     1905 gag  gcc  gag  gaa  agg  gct  gac  att  gct  gag  tcc  cag  gtc  aac  aag            5769
Glu  Ala  Glu  Glu  Arg  Ala  Asp  Ile  Ala  Glu  Ser  Gln  Val  Asn  Lys
1910                     1915                     1920 ctg  agg  gtg  aag  agc  agg  gag  gtt  cac  aca  aaa  atc  ata  agt  gaa            5814
Leu  Arg  Val  Lys  Ser  Arg  Glu  Val  His  Thr  Lys  Ile  Ile  Ser  Glu
1925                     1930                     1935 gag  taa  tttatctaac  tgctgaaagg  tgaccaaaga  aatgcacaaa  atgtgaaaat                 5870
Glu ctttgtcact  ccattttgta  cttatgactt  ttggagataa  aaaatttatc  tgcca               5925
```

<210> SEQ ID NO 6
<211> LENGTH: 1939
<212> TYPE: PRT
<213> ORGANISM: Homo sapiens

<400> SEQUENCE: 6

-continued

```
Met Ser Ser Asp Ser Glu Met Ala Ile Phe Gly Glu Ala Ala Pro Phe
1               5                   10                  15

Leu Arg Lys Ser Glu Arg Glu Arg Ile Glu Ala Gln Asn Lys Pro Phe
            20                  25                  30

Asp Ala Lys Thr Ser Val Phe Val Val Asp Pro Lys Glu Ser Phe Val
            35                  40                  45

Lys Ala Thr Val Gln Ser Arg Glu Gly Gly Lys Val Thr Ala Lys Thr
50                      55                  60

Glu Ala Gly Ala Thr Val Thr Val Lys Asp Asp Gln Val Phe Pro Met
65                      70                  75                  80

Asn Pro Pro Lys Tyr Asp Lys Ile Glu Asp Met Ala Met Met Thr His
                85                  90                  95

Leu His Glu Pro Ala Val Leu Tyr Asn Leu Lys Glu Arg Tyr Ala Ala
                100                 105                 110

Trp Met Ile Tyr Thr Tyr Ser Gly Leu Phe Cys Val Thr Val Asn Pro
                115                 120                 125

Tyr Lys Trp Leu Pro Val Tyr Asn Ala Glu Val Val Thr Ala Tyr Arg
            130                 135                 140

Gly Lys Lys Arg Gln Glu Ala Pro Pro His Ile Phe Ser Ile Ser Asp
145                     150                 155                 160

Asn Ala Tyr Gln Phe Met Leu Thr Asp Arg Glu Asn Gln Ser Ile Leu
                165                 170                 175

Ile Thr Gly Glu Ser Gly Ala Gly Lys Thr Val Asn Thr Lys Arg Val
                180                 185                 190

Ile Gln Tyr Phe Ala Thr Ile Ala Val Thr Gly Glu Lys Lys Lys Glu
                195                 200                 205

Glu Val Thr Ser Gly Lys Met Gln Gly Thr Leu Glu Asp Gln Ile Ile
            210                 215                 220

Ser Ala Asn Pro Leu Leu Glu Ala Phe Gly Asn Ala Lys Thr Val Arg
225                     230                 235                 240

Asn Asp Asn Ser Ser Arg Phe Gly Lys Phe Ile Arg Ile His Phe Gly
                245                 250                 255

Thr Thr Gly Lys Leu Ala Ser Ala Asp Ile Glu Thr Tyr Leu Leu Glu
                260                 265                 270

Lys Ser Arg Val Thr Phe Gln Leu Lys Ala Glu Arg Ser Tyr His Ile
            275                 280                 285

Phe Tyr Gln Ile Met Ser Asn Lys Lys Pro Asp Leu Ile Glu Met Leu
            290                 295                 300

Leu Ile Thr Thr Asn Pro Tyr Asp Tyr Ala Phe Val Ser Gln Gly Glu
305                     310                 315                 320

Ile Thr Val Pro Ser Ile Asp Asp Gln Glu Glu Leu Met Ala Thr Asp
                325                 330                 335

Ser Ala Ile Glu Ile Leu Gly Phe Thr Ser Asp Glu Arg Val Ser Ile
            340                 345                 350

Tyr Lys Leu Thr Gly Ala Val Met His Tyr Gly Asn Met Lys Phe Lys
            355                 360                 365

Gln Lys Gln Arg Glu Glu Gln Ala Glu Pro Asp Gly Thr Glu Val Ala
        370                 375                 380

Asp Lys Ala Ala Tyr Leu Gln Asn Leu Asn Ser Ala Asp Leu Leu Lys
385                     390                 395                 400

Ala Leu Cys Tyr Pro Arg Val Lys Val Gly Asn Glu Tyr Val Thr Lys
                405                 410                 415
```

Gly Gln Thr Val Gln Gln Val Tyr Asn Ala Val Gly Ala Leu Ala Lys
                420                 425                 430

Ala Val Tyr Asp Lys Met Phe Leu Trp Met Val Thr Arg Ile Asn Gln
            435                 440                 445

Gln Leu Asp Thr Lys Gln Pro Arg Gln Tyr Phe Ile Gly Val Leu Asp
        450                 455                 460

Ile Ala Gly Phe Glu Ile Phe Asp Phe Asn Ser Leu Glu Gln Leu Cys
465                 470                 475                 480

Ile Asn Phe Thr Asn Glu Lys Leu Gln Gln Phe Asn His His Met
                485                 490                 495

Phe Val Leu Glu Gln Glu Glu Tyr Lys Lys Glu Gly Ile Glu Trp Thr
            500                 505                 510

Phe Ile Asp Phe Gly Met Asp Leu Ala Ala Cys Ile Glu Leu Ile Glu
        515                 520                 525

Lys Pro Met Gly Ile Phe Ser Ile Leu Glu Glu Glu Cys Met Phe Pro
530                 535                 540

Lys Ala Thr Asp Thr Ser Phe Lys Asn Lys Leu Tyr Glu Gln His Leu
545                 550                 555                 560

Gly Lys Ser Asn Asn Phe Gln Lys Pro Lys Pro Ala Lys Gly Lys Pro
                565                 570                 575

Glu Ala His Phe Ser Leu Ile His Tyr Ala Gly Thr Val Asp Tyr Asn
            580                 585                 590

Ile Ala Gly Trp Leu Asp Lys Asn Lys Asp Pro Leu Asn Glu Thr Val
        595                 600                 605

Val Gly Leu Tyr Gln Lys Ser Ala Met Lys Thr Leu Ala Leu Leu Phe
610                 615                 620

Val Gly Ala Thr Gly Ala Glu Ala Glu Ala Gly Gly Gly Lys Lys Gly
625                 630                 635                 640

Gly Lys Lys Lys Gly Ser Ser Phe Gln Thr Val Ser Ala Leu Phe Arg
                645                 650                 655

Glu Asn Leu Asn Lys Leu Met Thr Asn Leu Arg Ser Thr His Pro His
            660                 665                 670

Phe Val Arg Cys Ile Ile Pro Asn Glu Thr Lys Thr Pro Gly Ala Met
        675                 680                 685

Glu His Glu Leu Val Leu His Gln Leu Arg Cys Asn Gly Val Leu Glu
690                 695                 700

Gly Ile Arg Ile Cys Arg Lys Gly Phe Pro Ser Arg Ile Leu Tyr Ala
705                 710                 715                 720

Asp Phe Lys Gln Arg Tyr Lys Val Leu Asn Ala Ser Ala Ile Pro Glu
                725                 730                 735

Gly Gln Phe Ile Asp Ser Lys Lys Ala Ser Glu Lys Leu Leu Gly Ser
            740                 745                 750

Ile Asp Ile Asp His Thr Gln Tyr Lys Phe Gly His Thr Lys Val Phe
        755                 760                 765

Phe Lys Ala Gly Leu Leu Gly Leu Leu Glu Glu Met Arg Asp Glu Lys
770                 775                 780

Leu Ala Gln Leu Ile Thr Arg Thr Gln Ala Met Cys Arg Gly Phe Leu
785                 790                 795                 800

Ala Arg Val Glu Tyr Gln Lys Met Val Glu Arg Glu Ser Ile Phe
                805                 810                 815

Cys Ile Gln Tyr Asn Val Arg Ala Phe Met Asn Val Lys His Trp Pro
            820                 825                 830

Trp Met Lys Leu Tyr Phe Lys Ile Lys Pro Leu Leu Lys Ser Ala Glu

```
              835                 840                 845
Thr Glu Lys Glu Met Ala Asn Met Lys Glu Glu Phe Glu Lys Thr Lys
        850                 855                 860
Glu Glu Leu Ala Lys Thr Glu Ala Lys Arg Lys Glu Leu Glu Glu Lys
865                 870                 875                 880
Met Val Thr Leu Met Gln Glu Lys Asn Asp Leu Gln Leu Gln Val Gln
                885                 890                 895
Ala Glu Ala Asp Ser Leu Ala Asp Ala Glu Glu Arg Cys Asp Gln Leu
            900                 905                 910
Ile Lys Thr Lys Ile Gln Leu Glu Ala Lys Ile Lys Glu Val Thr Glu
                915                 920                 925
Arg Ala Glu Asp Glu Glu Ile Asn Ala Glu Leu Thr Ala Lys Lys
            930                 935                 940
Arg Lys Leu Glu Asp Glu Cys Ser Glu Leu Lys Lys Asp Ile Asp Asp
945                 950                 955                 960
Leu Glu Leu Thr Leu Ala Lys Val Glu Lys Glu Lys His Ala Thr Glu
                965                 970                 975
Asn Lys Val Lys Asn Leu Thr Glu Glu Met Ala Gly Leu Asp Glu Thr
            980                 985                 990
Ile Ala Lys Leu Thr Lys Glu Lys  Lys Ala Leu Gln Glu  Ala His Gln
                995                 1000                1005
Gln Thr  Leu Asp Asp Leu Gln  Ala Glu Glu Asp Lys  Val Asn Thr
    1010                1015                1020
Leu Thr  Lys Ala Lys Ile Lys  Leu Glu Gln Gln Val  Asp Asp Leu
    1025                1030                1035
Glu Gly  Ser Leu Glu Gln Glu  Lys Lys Ile Arg Met  Asp Leu Glu
    1040                1045                1050
Arg Ala  Lys Arg Lys Leu Glu  Gly Asp Leu Lys Leu  Ala Gln Glu
    1055                1060                1065
Ser Ala  Met Asp Ile Glu Asn  Asp Lys Gln Gln Leu  Asp Glu Lys
    1070                1075                1080
Leu Lys  Lys Lys Glu Phe Glu  Met Ser Gly Leu Gln  Ser Lys Ile
    1085                1090                1095
Glu Asp  Glu Gln Ala Leu Gly  Met Gln Leu Gln Lys  Lys Ile Lys
    1100                1105                1110
Glu Leu  Gln Ala Arg Ile Glu  Glu Leu Glu Glu Glu  Ile Glu Ala
    1115                1120                1125
Glu Arg  Ala Ser Arg Ala Lys  Ala Glu Lys Gln Arg  Ser Asp Leu
    1130                1135                1140
Ser Arg  Glu Leu Glu Glu Ile  Ser Glu Arg Leu Glu  Glu Ala Gly
    1145                1150                1155
Gly Ala  Thr Ser Ala Gln Ile  Glu Met Asn Lys Lys  Arg Glu Ala
    1160                1165                1170
Glu Phe  Gln Lys Met Arg Arg  Asp Leu Glu Glu Ala  Thr Leu Gln
    1175                1180                1185
His Glu  Ala Thr Ala Ala Thr  Leu Arg Lys Lys His  Ala Asp Ser
    1190                1195                1200
Val Ala  Glu Leu Gly Glu Gln  Ile Asp Asn Leu Gln  Arg Val Lys
    1205                1210                1215
Gln Lys  Leu Glu Lys Glu Lys  Ser Glu Met Lys Met  Glu Ile Asp
    1220                1225                1230
Asp Leu  Ala Ser Asn Met Glu  Thr Val Ser Lys Ala  Lys Gly Asn
    1235                1240                1245
```

```
Leu Glu Lys Met Cys Arg Ala Leu Glu Asp Gln Leu Ser Glu Ile
    1250            1255                1260

Lys Thr Lys Glu Glu Glu Gln Arg Leu Ile Asn Asp Leu Thr
    1265            1270                1275

Ala Gln Arg Ala Arg Leu Gln Thr Glu Ser Gly Glu Tyr Ser Arg
    1280            1285                1290

Gln Leu Asp Glu Lys Asp Thr Leu Val Ser Gln Leu Ser Arg Gly
    1295            1300                1305

Lys Gln Ala Phe Thr Gln Gln Ile Glu Glu Leu Lys Arg Gln Leu
    1310            1315                1320

Glu Glu Glu Ile Lys Ala Lys Ser Ala Leu Ala His Ala Leu Gln
    1325            1330                1335

Ser Ser Arg His Asp Cys Asp Leu Leu Arg Glu Gln Tyr Glu Glu
    1340            1345                1350

Glu Gln Glu Ala Lys Ala Glu Leu Gln Arg Ala Met Ser Lys Ala
    1355            1360                1365

Asn Ser Glu Val Ala Gln Trp Arg Thr Lys Tyr Glu Thr Asp Ala
    1370            1375                1380

Ile Gln Arg Thr Glu Glu Leu Glu Glu Ala Lys Lys Lys Leu Ala
    1385            1390                1395

Gln Arg Leu Gln Asp Ala Glu Glu His Val Glu Ala Val Asn Ala
    1400            1405                1410

Lys Cys Ala Ser Leu Glu Lys Thr Lys Gln Arg Leu Gln Asn Glu
    1415            1420                1425

Val Glu Asp Leu Met Ile Asp Val Glu Arg Thr Asn Ala Ala Cys
    1430            1435                1440

Ala Ala Leu Asp Lys Lys Gln Arg Asn Phe Asp Lys Ile Leu Ala
    1445            1450                1455

Glu Trp Lys Gln Lys Cys Glu Glu Thr His Ala Glu Leu Glu Ala
    1460            1465                1470

Ser Gln Lys Glu Ser Arg Ser Leu Ser Thr Glu Leu Phe Lys Ile
    1475            1480                1485

Lys Asn Ala Tyr Glu Glu Ser Leu Asp Gln Leu Glu Thr Leu Lys
    1490            1495                1500

Arg Glu Asn Lys Asn Leu Gln Gln Glu Ile Ser Asp Leu Thr Glu
    1505            1510                1515

Gln Ile Ala Glu Gly Gly Lys Arg Ile His Glu Leu Glu Lys Ile
    1520            1525                1530

Lys Lys Gln Val Glu Gln Glu Lys Ser Glu Leu Gln Ala Ala Leu
    1535            1540                1545

Glu Glu Ala Glu Ala Ser Leu Glu His Glu Glu Gly Lys Ile Leu
    1550            1555                1560

Arg Ile Gln Leu Glu Leu Asn Gln Val Lys Ser Glu Val Asp Arg
    1565            1570                1575

Lys Ile Ala Glu Lys Asp Glu Glu Ile Asp Gln Met Lys Arg Asn
    1580            1585                1590

His Ile Arg Ile Val Glu Ser Met Gln Ser Thr Leu Asp Ala Glu
    1595            1600                1605

Ile Arg Ser Arg Asn Asp Ala Ile Arg Leu Lys Lys Lys Met Glu
    1610            1615                1620

Gly Asp Leu Asn Glu Met Glu Ile Gln Leu Asn His Ala Asn Arg
    1625            1630                1635
```

| | | | | | | | | | |
|---|---|---|---|---|---|---|---|---|---|
| Met | Ala | Ala | Glu | Ala | Leu | Arg | Asn | Tyr | Arg | Asn | Thr | Gln | Ala | Ile |
| 1640 | | | | | 1645 | | | | | 1650 | | | | |

Met Ala Ala Glu Ala Leu Arg Asn Tyr Arg Asn Thr Gln Ala Ile
    1640                1645                1650

Leu Lys Asp Thr Gln Leu His Leu Asp Asp Ala Leu Arg Ser Gln
    1655                1660                1665

Glu Asp Leu Lys Glu Gln Leu Ala Met Val Glu Arg Arg Ala Asn
    1670                1675                1680

Leu Leu Gln Ala Glu Ile Glu Glu Leu Arg Ala Thr Leu Glu Gln
    1685                1690                1695

Thr Glu Arg Ser Arg Lys Ile Ala Glu Gln Glu Leu Leu Asp Ala
    1700                1705                1710

Ser Glu Arg Val Gln Leu Leu His Thr Gln Asn Thr Ser Leu Ile
    1715                1720                1725

Asn Thr Lys Lys Lys Leu Glu Thr Asp Ile Ser Gln Ile Gln Gly
    1730                1735                1740

Glu Met Glu Asp Ile Ile Gln Glu Ala Arg Asn Ala Glu Glu Lys
    1745                1750                1755

Ala Lys Lys Ala Ile Thr Asp Ala Ala Met Met Ala Glu Glu Leu
    1760                1765                1770

Lys Lys Glu Gln Asp Thr Ser Ala His Leu Glu Arg Met Lys Lys
    1775                1780                1785

Asn Leu Glu Gln Thr Val Lys Asp Leu Gln His Arg Leu Asp Glu
    1790                1795                1800

Ala Glu Gln Leu Ala Leu Lys Gly Gly Lys Lys Gln Ile Gln Lys
    1805                1810                1815

Leu Glu Ala Arg Val Arg Glu Leu Glu Gly Glu Val Glu Ser Glu
    1820                1825                1830

Gln Lys Arg Asn Val Glu Ala Val Lys Gly Leu Arg Lys His Glu
    1835                1840                1845

Arg Lys Val Lys Glu Leu Thr Tyr Gln Thr Glu Glu Asp Arg Lys
    1850                1855                1860

Asn Ile Leu Arg Leu Gln Asp Leu Val Asp Lys Leu Gln Ala Lys
    1865                1870                1875

Val Lys Ser Tyr Lys Arg Gln Ala Glu Glu Ala Glu Glu Gln Ser
    1880                1885                1890

Asn Val Asn Leu Ser Lys Phe Arg Arg Ile Gln His Glu Leu Glu
    1895                1900                1905

Glu Ala Glu Glu Arg Ala Asp Ile Ala Glu Ser Gln Val Asn Lys
    1910                1915                1920

Leu Arg Val Lys Ser Arg Glu Val His Thr Lys Ile Ile Ser Glu
    1925                1930                1935

Glu

<210> SEQ ID NO 7
<211> LENGTH: 2633
<212> TYPE: DNA
<213> ORGANISM: Homo sapiens
<220> FEATURE:
<221> NAME/KEY: CDS
<222> LOCATION: (38)..(2584)

<400> SEQUENCE: 7
ccgcggcaag aacatccctc ccagccagca gattaca atg ctg caa act aag gat    55
                                         Met Leu Gln Thr Lys Asp
                                           1               5 ctc atc tgg act ttg ttt ttc ctg gga act gca gtt tct ctg cag gtg    103
Leu Ile Trp Thr Leu Phe Phe Leu Gly Thr Ala Val Ser Leu Gln Val

|   |   |   |   |   |   |   |   |   |   |   |   |   |   |   |   |     |
|---|---|---|---|---|---|---|---|---|---|---|---|---|---|---|---|-----|
|   |   |   | 10 |   |   |   | 15 |   |   |   | 20 |   |   |   |   |     |
| gat | att | gtt | ccc | agc | cag | ggg | gag | atc | agc | gtt | gga | gag | tcc | aaa | ttc | 151 |
| Asp | Ile | Val | Pro | Ser | Gln | Gly | Glu | Ile | Ser | Val | Gly | Glu | Ser | Lys | Phe |     |
|     |     |     | 25  |     |     |     | 30  |     |     |     | 35  |     |     |     |     |     |
| ttc | tta | tgc | caa | gtg | gca | gga | gat | gcc | aaa | gat | aaa | gac | atc | tcc | tgg | 199 |
| Phe | Leu | Cys | Gln | Val | Ala | Gly | Asp | Ala | Lys | Asp | Lys | Asp | Ile | Ser | Trp |     |
|     | 40  |     |     |     | 45  |     |     |     | 50  |     |     |     |     |     |     |     |
| ttc | tcc | ccc | aat | gga | gaa | aag | ctc | acc | cca | aac | cag | cag | cgg | atc | tca | 247 |
| Phe | Ser | Pro | Asn | Gly | Glu | Lys | Leu | Thr | Pro | Asn | Gln | Gln | Arg | Ile | Ser |     |
| 55  |     |     |     | 60  |     |     |     | 65  |     |     |     | 70  |     |     |     |     |
| gtg | gtg | tgg | aat | gat | gat | tcc | tcc | tcc | acc | ctc | acc | atc | tat | aac | gcc | 295 |
| Val | Val | Trp | Asn | Asp | Asp | Ser | Ser | Ser | Thr | Leu | Thr | Ile | Tyr | Asn | Ala |     |
|     |     |     | 75  |     |     |     | 80  |     |     |     | 85  |     |     |     |     |     |
| aac | atc | gac | gac | gcc | ggc | att | tac | aag | tgt | gtg | gtt | aca | ggc | gag | gat | 343 |
| Asn | Ile | Asp | Asp | Ala | Gly | Ile | Tyr | Lys | Cys | Val | Val | Thr | Gly | Glu | Asp |     |
|     | 90  |     |     |     | 95  |     |     |     | 100 |     |     |     |     |     |     |     |
| ggc | agt | gag | tca | gag | gcc | acc | gtc | aac | gtg | aag | atc | ttt | cag | aag | ctc | 391 |
| Gly | Ser | Glu | Ser | Glu | Ala | Thr | Val | Asn | Val | Lys | Ile | Phe | Gln | Lys | Leu |     |
| 105 |     |     |     | 110 |     |     |     | 115 |     |     |     |     |     |     |     |     |
| atg | ttc | aag | aat | gcg | cca | acc | cca | cag | gag | ttc | cgg | gag | ggg | gaa | gat | 439 |
| Met | Phe | Lys | Asn | Ala | Pro | Thr | Pro | Gln | Glu | Phe | Arg | Glu | Gly | Glu | Asp |     |
|     | 120 |     |     |     | 125 |     |     |     | 130 |     |     |     |     |     |     |     |
| gcc | gtg | att | gtg | tgt | gat | gtg | gtc | agc | tcc | ctc | cca | cca | acc | atc | atc | 487 |
| Ala | Val | Ile | Val | Cys | Asp | Val | Val | Ser | Ser | Leu | Pro | Pro | Thr | Ile | Ile |     |
| 135 |     |     |     | 140 |     |     |     | 145 |     |     |     | 150 |     |     |     |     |
| tgg | aaa | cac | aaa | ggc | cga | gat | gtc | atc | ctg | aaa | aaa | gat | gtc | cga | ttc | 535 |
| Trp | Lys | His | Lys | Gly | Arg | Asp | Val | Ile | Leu | Lys | Lys | Asp | Val | Arg | Phe |     |
|     |     |     | 155 |     |     |     | 160 |     |     |     | 165 |     |     |     |     |     |
| ata | gtc | ctg | tcc | aac | aac | tac | ctg | cag | atc | cgg | ggc | atc | aag | aaa | aca | 583 |
| Ile | Val | Leu | Ser | Asn | Asn | Tyr | Leu | Gln | Ile | Arg | Gly | Ile | Lys | Lys | Thr |     |
|     | 170 |     |     |     | 175 |     |     |     | 180 |     |     |     |     |     |     |     |
| gat | gag | ggc | act | tat | cgc | tgt | gag | ggc | aga | atc | ctg | gca | cgg | ggg | gag | 631 |
| Asp | Glu | Gly | Thr | Tyr | Arg | Cys | Glu | Gly | Arg | Ile | Leu | Ala | Arg | Gly | Glu |     |
|     |     | 185 |     |     |     | 190 |     |     |     | 195 |     |     |     |     |     |     |
| atc | aac | ttc | aag | gac | att | cag | gtc | att | gtg | aat | gtg | cca | cct | acc | atc | 679 |
| Ile | Asn | Phe | Lys | Asp | Ile | Gln | Val | Ile | Val | Asn | Val | Pro | Pro | Thr | Ile |     |
|     | 200 |     |     |     | 205 |     |     |     | 210 |     |     |     |     |     |     |     |
| cgg | gcc | agg | cag | aat | att | gtg | aat | gcc | acc | gcc | aac | ctc | ggc | cag | tcc | 727 |
| Arg | Ala | Arg | Gln | Asn | Ile | Val | Asn | Ala | Thr | Ala | Asn | Leu | Gly | Gln | Ser |     |
| 215 |     |     |     | 220 |     |     |     | 225 |     |     |     | 230 |     |     |     |     |
| gtc | acc | ctg | gtg | tgc | gat | gcc | gaa | cgg | ttc | cca | gag | ccc | acc | atg | agc | 775 |
| Val | Thr | Leu | Val | Cys | Asp | Ala | Glu | Arg | Phe | Pro | Glu | Pro | Thr | Met | Ser |     |
|     |     |     | 235 |     |     |     | 240 |     |     |     | 245 |     |     |     |     |     |
| tgg | aca | aag | gat | ggg | gaa | cag | ata | gag | caa | gag | gaa | gac | gat | gag | aag | 823 |
| Trp | Thr | Lys | Asp | Gly | Glu | Gln | Ile | Glu | Gln | Glu | Glu | Asp | Asp | Glu | Lys |     |
|     |     | 250 |     |     |     | 255 |     |     |     | 260 |     |     |     |     |     |     |
| tac | atc | ttc | agc | gac | gat | agt | tcc | cag | ctg | acc | atc | aaa | aag | gtg | gat | 871 |
| Tyr | Ile | Phe | Ser | Asp | Asp | Ser | Ser | Gln | Leu | Thr | Ile | Lys | Lys | Val | Asp |     |
|     | 265 |     |     |     | 270 |     |     |     | 275 |     |     |     |     |     |     |     |
| aag | aac | gac | gag | gct | gag | tac | atc | tgc | att | gct | gag | aac | aag | gct | ggc | 919 |
| Lys | Asn | Asp | Glu | Ala | Glu | Tyr | Ile | Cys | Ile | Ala | Glu | Asn | Lys | Ala | Gly |     |
|     | 280 |     |     |     | 285 |     |     |     | 290 |     |     |     |     |     |     |     |
| gag | cag | gat | gcg | acc | atc | cac | ctc | aaa | gtc | ttt | gca | aaa | ccc | aaa | atc | 967 |
| Glu | Gln | Asp | Ala | Thr | Ile | His | Leu | Lys | Val | Phe | Ala | Lys | Pro | Lys | Ile |     |
| 295 |     |     |     | 300 |     |     |     | 305 |     |     |     | 310 |     |     |     |     |
| aca | tat | gta | gag | aac | cag | act | gcc | atg | gaa | tta | gag | gag | cag | gtc | act | 1015 |
| Thr | Tyr | Val | Glu | Asn | Gln | Thr | Ala | Met | Glu | Leu | Glu | Glu | Gln | Val | Thr |     |
|     |     |     | 315 |     |     |     | 320 |     |     |     | 325 |     |     |     |     |     |
| ctt | acc | tgt | gaa | gcc | tcc | gga | gac | ccc | att | ccc | tcc | atc | acc | tgg | agg | 1063 |

```
                Leu Thr Cys Glu Ala Ser Gly Asp Pro Ile Pro Ser Ile Thr Trp Arg
                                330                 335                 340 act tct acc cgg aac atc agc agc gaa gaa aag act ctg gat ggg cac           1111
Thr Ser Thr Arg Asn Ile Ser Ser Glu Glu Lys Thr Leu Asp Gly His
            345                 350                 355 atg gtg gtg cgt agc cat gcc cgt gtg tcg tcg ctg acc ctg aag agc           1159
Met Val Val Arg Ser His Ala Arg Val Ser Ser Leu Thr Leu Lys Ser
        360                 365                 370 atc cag tac act gat gcc gga gag tac atc tgc acc gcc agc aac acc           1207
Ile Gln Tyr Thr Asp Ala Gly Glu Tyr Ile Cys Thr Ala Ser Asn Thr
375                 380                 385                 390 atc ggc cag gac tcc cag tcc atg tac ctt gaa gtg caa tat gcc cca           1255
Ile Gly Gln Asp Ser Gln Ser Met Tyr Leu Glu Val Gln Tyr Ala Pro
                395                 400                 405 aag cta cag ggc cct gtg gct gtg tac act tgg gag ggg aac cag gtg           1303
Lys Leu Gln Gly Pro Val Ala Val Tyr Thr Trp Glu Gly Asn Gln Val
            410                 415                 420 aac atc acc tgc gag gta ttt gcc tat ccc agt gcc acg atc tca tgg           1351
Asn Ile Thr Cys Glu Val Phe Ala Tyr Pro Ser Ala Thr Ile Ser Trp
        425                 430                 435 ttt cgg gat ggc cag ctg ctg cca agc tcc aat tac agc aat atc aag           1399
Phe Arg Asp Gly Gln Leu Leu Pro Ser Ser Asn Tyr Ser Asn Ile Lys
    440                 445                 450 atc tac aac acc ccc tct gcc agc tat ctg gag gtg acc cca gac tct           1447
Ile Tyr Asn Thr Pro Ser Ala Ser Tyr Leu Glu Val Thr Pro Asp Ser
455                 460                 465                 470 gag aat gat ttt ggg aac tac aac tgt act gca gtg aac cgc att ggg           1495
Glu Asn Asp Phe Gly Asn Tyr Asn Cys Thr Ala Val Asn Arg Ile Gly
                475                 480                 485 cag gag tcc ttc gaa ttc atc ctt gtt caa gca gac acc ccc tct tca           1543
Gln Glu Ser Phe Glu Phe Ile Leu Val Gln Ala Asp Thr Pro Ser Ser
            490                 495                 500 cca tcc atc gac cag gtg gag cca tac tcc agc aca gcc cag gtg cag           1591
Pro Ser Ile Asp Gln Val Glu Pro Tyr Ser Ser Thr Ala Gln Val Gln
        505                 510                 515 ttt gat gaa cca gag gcc aca ggt ggg gtg ccc atc ctc aaa tac aaa           1639
Phe Asp Glu Pro Glu Ala Thr Gly Gly Val Pro Ile Leu Lys Tyr Lys
    520                 525                 530 gct gag tgg aga gca gtg ggt gaa gaa gta tgg cat tcc aag tgg tat           1687
Ala Glu Trp Arg Ala Val Gly Glu Glu Val Trp His Ser Lys Trp Tyr
535                 540                 545                 550 gat gcc aag gaa gcc agc atg gag ggc atc gtc acc atc gtg ggc ctg           1735
Asp Ala Lys Glu Ala Ser Met Glu Gly Ile Val Thr Ile Val Gly Leu
                555                 560                 565 aag ccc gaa aca acg tac gcc gta agg ctg gcg gcg ctc aat ggc aaa           1783
Lys Pro Glu Thr Thr Tyr Ala Val Arg Leu Ala Ala Leu Asn Gly Lys
            570                 575                 580 ggg ctg ggt gag atc agc gcg gcc tcc gag ttc aag acg cag cca gtc           1831
Gly Leu Gly Glu Ile Ser Ala Ala Ser Glu Phe Lys Thr Gln Pro Val
        585                 590                 595 caa ggg gaa ccc agt gca cct aag ctc gaa ggg cag atg gga gag gat           1879
Gln Gly Glu Pro Ser Ala Pro Lys Leu Glu Gly Gln Met Gly Glu Asp
    600                 605                 610 gga aac tct att aaa gtg aac ctg atc aag cag gat gac ggc ggc tcc           1927
Gly Asn Ser Ile Lys Val Asn Leu Ile Lys Gln Asp Asp Gly Gly Ser
615                 620                 625                 630 ccc atc aga cac tat ctg gtc agg tac cga gcg ctc tcc tcc gag tgg           1975
Pro Ile Arg His Tyr Leu Val Arg Tyr Arg Ala Leu Ser Ser Glu Trp
                635                 640                 645
```

-continued

| | | |
|---|---|---|
| aaa cca gag atc agg ctc ccg tct ggc agt gac cac gtc atg ctg aag<br>Lys Pro Glu Ile Arg Leu Pro Ser Gly Ser Asp His Val Met Leu Lys<br>650                        655                    660 | | 2023 |
| tcc ctg gac tgg aat gct gag tat gag gtc tac gtg gtg gct gag aac<br>Ser Leu Asp Trp Asn Ala Glu Tyr Glu Val Tyr Val Val Ala Glu Asn<br>        665                    670                    675 | | 2071 |
| cag caa gga aaa tcc aag gcg gct cat ttt gtg ttc agg acc tcg gcc<br>Gln Gln Gly Lys Ser Lys Ala Ala His Phe Val Phe Arg Thr Ser Ala<br>680                        685                    690 | | 2119 |
| cag ccc aca gcc atc cca gcc aac ggc agc ccc acc tca ggc ctg agc<br>Gln Pro Thr Ala Ile Pro Ala Asn Gly Ser Pro Thr Ser Gly Leu Ser<br>695                700                    705                    710 | | 2167 |
| acc ggg gcc atc gtg ggc atc ctc atc gtc atc ttc gtc ctg ctc ctg<br>Thr Gly Ala Ile Val Gly Ile Leu Ile Val Ile Phe Val Leu Leu Leu<br>        715                    720                    725 | | 2215 |
| gtg gtt gtg gac atc acc tgc tac ttc ctg aac aag tgt ggc ctg ttc<br>Val Val Val Asp Ile Thr Cys Tyr Phe Leu Asn Lys Cys Gly Leu Phe<br>730                        735                    740 | | 2263 |
| atg tgc att gcg gtc aac ctg tgt gga aaa gcc ggg ccc ggg gcc aag<br>Met Cys Ile Ala Val Asn Leu Cys Gly Lys Ala Gly Pro Gly Ala Lys<br>        745                    750                    755 | | 2311 |
| ggc aag gac atg gag gag ggc aag gcc gcc ttc tcg aaa gat gag tcc<br>Gly Lys Asp Met Glu Glu Gly Lys Ala Ala Phe Ser Lys Asp Glu Ser<br>760                        765                    770 | | 2359 |
| aag gag ccc atc gtg gag gtt cga acg gag gag gag agg acc cca aac<br>Lys Glu Pro Ile Val Glu Val Arg Thr Glu Glu Glu Arg Thr Pro Asn<br>775                780                    785                    790 | | 2407 |
| cat gat gga ggg aaa cac aca gag ccc aac gag acc acg cca ctg acg<br>His Asp Gly Gly Lys His Thr Glu Pro Asn Glu Thr Thr Pro Leu Thr<br>        795                    800                    805 | | 2455 |
| gag ccc gag aag ggc ccc gta gaa gca aag cca gag tgc cag gag aca<br>Glu Pro Glu Lys Gly Pro Val Glu Ala Lys Pro Glu Cys Gln Glu Thr<br>810                        815                    820 | | 2503 |
| gaa acg aag cca gcg cca gcc gaa gtc aag acg gtc ccc aat gac gcc<br>Glu Thr Lys Pro Ala Pro Ala Glu Val Lys Thr Val Pro Asn Asp Ala<br>        825                    830                    835 | | 2551 |
| aca cag aca aag gag aac gag agc aaa gca tga tgggtgaaga gaaccgagca<br>Thr Gln Thr Lys Glu Asn Glu Ser Lys Ala<br>840                        845 | | 2604 |
| aagatcaaaa taaaaagtga cacagcagc | | 2633 |

<210> SEQ ID NO 8
<211> LENGTH: 848
<212> TYPE: PRT
<213> ORGANISM: Homo sapiens

<400> SEQUENCE: 8

Met Leu Gln Thr Lys Asp Leu Ile Trp Thr Leu Phe Phe Leu Gly Thr
1                 5                    10                 15

Ala Val Ser Leu Gln Val Asp Ile Val Pro Ser Gln Gly Glu Ile Ser
               20                    25                    30

Val Gly Glu Ser Lys Phe Phe Leu Cys Gln Val Ala Gly Asp Ala Lys
          35                    40                   45

Asp Lys Asp Ile Ser Trp Phe Ser Pro Asn Gly Glu Lys Leu Thr Pro
50                        55                    60

Asn Gln Gln Arg Ile Ser Val Val Trp Asn Asp Asp Ser Ser Ser Thr
65                 70                    75                    80

Leu Thr Ile Tyr Asn Ala Asn Ile Asp Asp Ala Gly Ile Tyr Lys Cys
          85                    90                    95

```
Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
            115                 120                 125

Phe Arg Glu Gly Glu Asp Ala Val Ile Val Cys Asp Val Val Ser Ser
            130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
            195                 200                 205

Asn Val Pro Pro Thr Ile Arg Ala Arg Gln Asn Ile Val Asn Ala Thr
            210                 215                 220

Ala Asn Leu Gly Gln Ser Val Thr Leu Val Cys Asp Ala Glu Arg Phe
225                 230                 235                 240

Pro Glu Pro Thr Met Ser Trp Thr Lys Asp Gly Glu Gln Ile Glu Gln
            245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
            275                 280                 285

Ala Glu Asn Lys Ala Gly Glu Gln Asp Ala Thr Ile His Leu Lys Val
            290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
            325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
            355                 360                 365

Ser Leu Thr Leu Lys Ser Ile Gln Tyr Thr Asp Ala Gly Glu Tyr Ile
            370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
            435                 440                 445

Asn Tyr Ser Asn Ile Lys Ile Tyr Asn Thr Pro Ser Ala Ser Tyr Leu
            450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Phe Glu Phe Ile Leu Val Gln
                485                 490                 495

Ala Asp Thr Pro Ser Ser Pro Ser Ile Asp Gln Val Glu Pro Tyr Ser
            500                 505                 510
```

| | | | | | | | | | | | |
|---|---|---|---|---|---|---|---|---|---|---|---|
|Ser|Thr|Ala|Gln|Val|Gln|Phe|Asp|Glu|Pro|Glu|Ala|Thr|Gly|Gly|Val|
| | |515| | | |520| | | |525| |

Ser Thr Ala Gln Val Gln Phe Asp Glu Pro Glu Ala Thr Gly Gly Val
                515                 520                 525

Pro Ile Leu Lys Tyr Lys Ala Glu Trp Arg Ala Val Gly Glu Val
            530                 535                 540

Trp His Ser Lys Trp Tyr Asp Ala Lys Glu Ala Ser Met Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
            595                 600                 605

Gly Gln Met Gly Glu Asp Gly Asn Ser Ile Lys Val Asn Leu Ile Lys
610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
675                 680                 685

Val Phe Arg Thr Ser Ala Gln Pro Thr Ala Ile Pro Ala Asn Gly Ser
            690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
            755                 760                 765

Phe Ser Lys Asp Glu Ser Lys Glu Pro Ile Val Glu Val Arg Thr Glu
770                 775                 780

Glu Glu Arg Thr Pro Asn His Asp Gly Gly Lys His Thr Glu Pro Asn
785                 790                 795                 800

Glu Thr Thr Pro Leu Thr Glu Pro Gly Lys Gly Pro Val Glu Ala Lys
            805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
            835                 840                 845

<210> SEQ ID NO 9
<211> LENGTH: 1692
<212> TYPE: DNA
<213> ORGANISM: Homo sapiens
<220> FEATURE:
<221> NAME/KEY: CDS
<222> LOCATION: (121)..(1080)

<400> SEQUENCE: 9
attcagactg ccagcacttt gctatctaca gccggggctc ccgagcggca gaaagttccg      60
gccactctct gccgcttggg ttgggcgaaa gccaggaccg tgccgcgcca ccgccaggat     120 atg gag cta ctg tcg cca ccg ctc cgc gac gta gac ctg acg gcc ccc      168

```
Met Glu Leu Leu Ser Pro Pro Leu Arg Asp Val Asp Leu Thr Ala Pro
1               5                   10                  15 gac ggc tct ctc tgc tcc ttt gcc aca acg gac gac ttc tat gac gac    216
Asp Gly Ser Leu Cys Ser Phe Ala Thr Thr Asp Asp Phe Tyr Asp Asp
            20                  25                  30 ccg tgt ttc gac tcc ccg gac ctg cgc ttc ttc gaa gac ctg gac ccg    264
Pro Cys Phe Asp Ser Pro Asp Leu Arg Phe Phe Glu Asp Leu Asp Pro
        35                  40                  45 cgc ctg atg cac gtg ggc gcg ctc ctg aaa ccc gaa gag cac tcg cac    312
Arg Leu Met His Val Gly Ala Leu Leu Lys Pro Glu Glu His Ser His
    50                  55                  60 ttc ccc gcg gcg gtg cac ccg gcc ccg ggc gca cgt gag gac gag cat    360
Phe Pro Ala Ala Val His Pro Ala Pro Gly Ala Arg Glu Asp Glu His
65                  70                  75                  80 gtg cgc gcg ccc agc ggg cac cac cag gcg ggc cgc tgc cta ctg tgg    408
Val Arg Ala Pro Ser Gly His His Gln Ala Gly Arg Cys Leu Leu Trp
                85                  90                  95 gcc tgc aag gcg tgc aag cgc aag acc acc aac gcc gac cgc cgc aag    456
Ala Cys Lys Ala Cys Lys Arg Lys Thr Thr Asn Ala Asp Arg Arg Lys
            100                 105                 110 gcc gcc acc atg cgc gag cgg cgc cgc ctg agc aaa gta aat gag gcc    504
Ala Ala Thr Met Arg Glu Arg Arg Arg Leu Ser Lys Val Asn Glu Ala
        115                 120                 125 ttt gag aca ctc aag cgc tgc acg tcg agc aat cca aac cag cgg ttg    552
Phe Glu Thr Leu Lys Arg Cys Thr Ser Ser Asn Pro Asn Gln Arg Leu
130                 135                 140 ccc aag gtg gag atc ctg cgc aac gcc atc cgc tat atc gag ggc ctg    600
Pro Lys Val Glu Ile Leu Arg Asn Ala Ile Arg Tyr Ile Glu Gly Leu
145                 150                 155                 160 cag gct ctg ctg cgc gac cag gac gcc gcg ccc cct ggc gca gcc gcc    648
Gln Ala Leu Leu Arg Asp Gln Asp Ala Ala Pro Pro Gly Ala Ala Ala
                165                 170                 175 ttc tat gcg ccg ggc ccg ctg ccc ccg ggc cgc ggc ggc gag cac tac    696
Phe Tyr Ala Pro Gly Pro Leu Pro Pro Gly Arg Gly Gly Glu His Tyr
            180                 185                 190 agc ggc gac tcc gac gcg tcc agc ccg cgc tcc aac tgc tcc gac ggc    744
Ser Gly Asp Ser Asp Ala Ser Ser Pro Arg Ser Asn Cys Ser Asp Gly
        195                 200                 205 atg atg gac tac agc ggc ccc ccg agc ggc gcc cgg cgg cgg aac tgc    792
Met Met Asp Tyr Ser Gly Pro Pro Ser Gly Ala Arg Arg Arg Asn Cys
    210                 215                 220 tac gaa ggc gcc tac tac aac gag gcg ccc agc gaa ccc agg ccc ggg    840
Tyr Glu Gly Ala Tyr Tyr Asn Glu Ala Pro Ser Glu Pro Arg Pro Gly
225                 230                 235                 240 aag agt gcg gcg gtg tcg agc cta gac tac ctg tcc agc atc gtg gag    888
Lys Ser Ala Ala Val Ser Ser Leu Asp Tyr Leu Ser Ser Ile Val Glu
                245                 250                 255 cgc atc tcc acc gag agc cct gcg gcg ccc gcc ctg ctg gcg gac        936
Arg Ile Ser Thr Glu Ser Pro Ala Ala Pro Ala Leu Leu Leu Ala Asp
            260                 265                 270 gtg cct tct gag tcg cct ccg cgc agg caa gag gct gcc gcc ccc agc    984
Val Pro Ser Glu Ser Pro Pro Arg Arg Gln Glu Ala Ala Ala Pro Ser
        275                 280                 285 gag gga gag agc agc ggc gac ccc acc cag tca ccg gac gcc gcc ccg    1032
Glu Gly Glu Ser Ser Gly Asp Pro Thr Gln Ser Pro Asp Ala Ala Pro
    290                 295                 300 cag tgc cct gcg ggt gcg aac ccc aac ccg ata tac cag gtg ctc tga    1080
Gln Cys Pro Ala Gly Ala Asn Pro Asn Pro Ile Tyr Gln Val Leu
305                 310                 315
```

-continued

```
ggggatgtg gccgcccaac cccgccaggg atggtgccct agggtccctc gcgcccaaaa      1140
gattgaactt aaatgccccc ctcccaacag cgctttaaaa gcgccatctc ttgaggtagg      1200
agaggcggag aactgaagtt tccgccccc ccgacagggc aaggacacag cgcggttttt       1260
tccacgcagc acccttctcg gagacccatt gcgatggccg ctccgtgttc tcggtgggc       1320 cagagctgaa ccttgagggg ctaggttcac gtttctcgcg ccctccatgg tgagaccctc      1380
gcagacctaa ccctgccccg ggatgcaccg gttatttggg ggggcgtgag acagtgcact      1440
ccggtcccaa atgtagcagg tgtaaccgta acccacccc aacccgtttc ccggttcagg       1500
accacttttt gtaatacttt ttgtaatcta ttcctgtaaa taagagttcg tttgccagag      1560
aggagcccct ggggctgtat ttatctctga ggcagggtgt gtggtgctac agggaatttg      1620
tacgtttata ccgcaggcgg gcgagccgcg ggcgctcgct caggtgatca aaataaaggc      1680
gctaatttat aa                                                         1692
```

<210> SEQ ID NO 10
<211> LENGTH: 319
<212> TYPE: PRT
<213> ORGANISM: Homo sapiens

<400> SEQUENCE: 10

```
Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
                20                  25                  30

Pro Cys Phe Asp Ser Pro Asp Leu Arg Phe Phe Glu Asp Leu Asp Pro
            35                  40                  45

Arg Leu Met His Val Gly Ala Leu Leu Lys Pro Glu Glu His Ser His
        50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Leu Ser Lys Val Asn Glu Ala
        115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Gly Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Ala Arg Arg Arg Asn Cys
    210                 215                 220

Tyr Glu Gly Ala Tyr Tyr Asn Glu Ala Pro Ser Glu Pro Arg Pro Gly
225                 230                 235                 240

Lys Ser Ala Ala Val Ser Ser Leu Asp Tyr Leu Ser Ser Ile Val Glu
                245                 250                 255

Arg Ile Ser Thr Glu Ser Pro Ala Ala Pro Ala Leu Leu Leu Ala Asp
```

```
                260             265             270
Val Pro Ser Glu Ser Pro Pro Arg Arg Gln Glu Ala Ala Pro Ser
        275             280             285
Glu Gly Glu Ser Ser Gly Asp Pro Thr Gln Ser Pro Asp Ala Ala Pro
        290             295             300
Gln Cys Pro Ala Gly Ala Asn Pro Asn Pro Ile Tyr Gln Val Leu
305             310             315

<210> SEQ ID NO 11
<211> LENGTH: 1427
<212> TYPE: DNA
<213> ORGANISM: Homo sapiens
<220> FEATURE:
<221> NAME/KEY: CDS
<222> LOCATION: (43)..(810)

<400> SEQUENCE: 11
cctctcgctg ccgtccaggt gcaccgcctg cctctcagca gg atg gac gtg atg        54
                                              Met Asp Val Met
                                                1 gat ggc tgc cag ttc tca cct tct gag tac ttc tac gac ggc tcc tgc      102
Asp Gly Cys Gln Phe Ser Pro Ser Glu Tyr Phe Tyr Asp Gly Ser Cys
 5              10                  15                  20 ata ccg tcc ccc gag ggt gaa ttt ggg gac gag ttt gtg ccg cga gtg      150
Ile Pro Ser Pro Glu Gly Glu Phe Gly Asp Glu Phe Val Pro Arg Val
             25                  30                  35 gct gcc ttc gga gcg cac aaa gca gag ctg cag ggc tca gat gag gac      198
Ala Ala Phe Gly Ala His Lys Ala Glu Leu Gln Gly Ser Asp Glu Asp
         40                  45                  50 gag cac gtg cga gcg cct acc ggc cac cac cag gct ggt cac tgc ctc      246
Glu His Val Arg Ala Pro Thr Gly His His Gln Ala Gly His Cys Leu
     55                  60                  65 atg tgg gcc tgc aaa gcc tgc aag agg aag tcc acc acc atg gat cgg      294
Met Trp Ala Cys Lys Ala Cys Lys Arg Lys Ser Thr Thr Met Asp Arg
 70                  75                  80 cgg aag gca gcc act atg cgc gag cgg agg cgc ctg aag aag gtc aac      342
Arg Lys Ala Ala Thr Met Arg Glu Arg Arg Arg Leu Lys Lys Val Asn
85                  90                  95                 100 cag gct ttc gaa acc ctc aag agg tgt acc acg acc aac ccc aac cag      390
Gln Ala Phe Glu Thr Leu Lys Arg Cys Thr Thr Thr Asn Pro Asn Gln
                105                 110                 115 agg ctg ccc aag gtg gag atc ctc agg aat gcc atc gcc tac atc gag      438
Arg Leu Pro Lys Val Glu Ile Leu Arg Asn Ala Ile Arg Tyr Ile Glu
            120                 125                 130 agc ctg cag gag ttg ctg aga gag cag gtg gag aac tac tat agc ctg      486
Ser Leu Gln Glu Leu Leu Arg Glu Gln Val Glu Asn Tyr Tyr Ser Leu
        135                 140                 145 ccg gga cag agc tgc tcg gag ccc acc agc ccc acc tcc aac tgc tct      534
Pro Gly Gln Ser Cys Ser Glu Pro Thr Ser Pro Thr Ser Asn Cys Ser
    150                 155                 160 gat ggc atg ccc gaa tgt aac agt cct gtc tgg tcc aga aag agc agt      582
Asp Gly Met Pro Glu Cys Asn Ser Pro Val Trp Ser Arg Lys Ser Ser
165                 170                 175                 180 act ttt gac agc atc tac tgt cct gat gta tca aat gta tat gcc aca      630
Thr Phe Asp Ser Ile Tyr Cys Pro Asp Val Ser Asn Val Tyr Ala Thr
                185                 190                 195 gat aaa aac tcc tta tcc agc ttg gat tgc tta tcc aac ata gtg gac      678
Asp Lys Asn Ser Leu Ser Ser Leu Asp Cys Leu Ser Asn Ile Val Asp
            200                 205                 210 cgg atc acc tcc tca gag caa cct ggg ttg cct ctc cag gat ctg gct      726
```

-continued

```
Arg Ile Thr Ser Ser Glu Gln Pro Gly Leu Pro Leu Gln Asp Leu Ala
            215                 220                 225 tct ctc tct cca gtt gcc agc acc gat tca cag cct cga act cca ggg       774
Ser Leu Ser Pro Val Ala Ser Thr Asp Ser Gln Pro Arg Thr Pro Gly
        230                 235                 240 gct tct agt tcc agg ctt atc tat cat gtg cta tga actaattttc            820
Ala Ser Ser Ser Arg Leu Ile Tyr His Val Leu
245                 250                 255 tggtctatat gacttcttcc aggagggcct aatacacagg acgaagaagg cttcaaaaag     880
tcccaaacca agacaacatg tacataaaga tttcttttca gttgtaaatt tgtaaagatt     940
accttgccac tttataagaa agtgtattta actaaaaagt catcattgca aataatactt    1000
tcttcttctt tattattctt tgcttagata ttaatacata gttccagtaa tactatttct    1060 gataggggc cattgattga gggtagcttg ttcgaatgct taacttatat atacatatat     1120
atatattata aatattgctc atcaaaatgt ctctggtgtt tagagcttta ttttttttctt    1180 taaaacatta aaacagctga gaatcagtta aatggaattt taaatatatt taactatttc    1240
ttttctcttt aatcctttag ttatattgta ttaaataaaa atataatact gcctaatgta    1300 tatatttga tcttttcttg taagaaatgt atcttttaaa tgtaagcaca aaatagtact     1360
ttgtggatca tttcaagata taagaaattt tggaaattcc accataaata aaattttta    1420 ctacaag                                                              1427

<210> SEQ ID NO 12
<211> LENGTH: 255
<212> TYPE: PRT
<213> ORGANISM: Homo sapiens

<400> SEQUENCE: 12

Met Asp Val Met Asp Gly Cys Gln Phe Ser Pro Ser Glu Tyr Phe Tyr
1               5                   10                  15

Asp Gly Ser Cys Ile Pro Ser Pro Glu Gly Glu Phe Gly Asp Glu Phe
            20                  25                  30

Val Pro Arg Val Ala Ala Phe Gly Ala His Lys Ala Glu Leu Gln Gly
        35                  40                  45

Ser Asp Glu Asp Glu His Val Arg Ala Pro Thr Gly His His Gln Ala
    50                  55                  60

Gly His Cys Leu Met Trp Ala Cys Lys Ala Cys Lys Arg Lys Ser Thr
65                  70                  75                  80

Thr Met Asp Arg Arg Lys Ala Ala Thr Met Arg Glu Arg Arg Arg Leu
                85                  90                  95

Lys Lys Val Asn Gln Ala Phe Glu Thr Leu Lys Arg Cys Thr Thr Thr
            100                 105                 110

Asn Pro Asn Gln Arg Leu Pro Lys Val Glu Ile Leu Arg Asn Ala Ile
        115                 120                 125

Arg Tyr Ile Glu Ser Leu Gln Glu Leu Leu Arg Glu Gln Val Glu Asn
    130                 135                 140

Tyr Tyr Ser Leu Pro Gly Gln Ser Cys Ser Glu Pro Thr Ser Pro Thr
145                 150                 155                 160

Ser Asn Cys Ser Asp Gly Met Pro Glu Cys Asn Ser Pro Val Trp Ser
                165                 170                 175

Arg Lys Ser Ser Thr Phe Asp Ser Ile Tyr Cys Pro Asp Val Ser Asn
            180                 185                 190

Val Tyr Ala Thr Asp Lys Asn Ser Leu Ser Ser Leu Asp Cys Leu Ser
        195                 200                 205
```

```
Asn Ile Val Asp Arg Ile Thr Ser Ser Glu Gln Pro Gly Leu Pro Leu
    210                 215                 220
Gln Asp Leu Ala Ser Leu Ser Pro Val Ala Ser Thr Asp Ser Gln Pro
225                 230                 235                 240
Arg Thr Pro Gly Ala Ser Ser Arg Leu Ile Tyr His Val Leu
                245                 250                 255
```

<210> SEQ ID NO 13
<211> LENGTH: 675
<212> TYPE: DNA
<213> ORGANISM: Homo sapiens
<220> FEATURE:
<221> NAME/KEY: CDS
<222> LOCATION: (1)..(675)

<400> SEQUENCE: 13

```
atg gag ctg tat gag aca tcc ccc tac ttc tac cag gaa ccc cgc ttc    48
Met Glu Leu Tyr Glu Thr Ser Pro Tyr Phe Tyr Gln Glu Pro Arg Phe
1               5                   10                  15 tat gat ggg gaa aac tac ctg cct gtc cac ctc cag ggc ttc gaa cca    96
Tyr Asp Gly Glu Asn Tyr Leu Pro Val His Leu Gln Gly Phe Glu Pro
            20                  25                  30 cca ggc tac gag cgg acg gag ctc acc ctg agc ccc gag gcc cca ggg   144
Pro Gly Tyr Glu Arg Thr Glu Leu Thr Leu Ser Pro Glu Ala Pro Gly
        35                  40                  45 ccc ctt gag gac aag ggg ctg ggg acc ccc gag cac tgt cca ggc cag   192
Pro Leu Glu Asp Lys Gly Leu Gly Thr Pro Glu His Cys Pro Gly Gln
    50                  55                  60 tgc ctg ccg tgg gcg tgt aag gtg tgt aag agg aag tcg gtg tcc gtg   240
Cys Leu Pro Trp Ala Cys Lys Val Cys Lys Arg Lys Ser Val Ser Val
65                  70                  75                  80 gac cgg cgg cgg gcg gcc aca ctg agg gag aag cgc agg ctc aag aag   288
Asp Arg Arg Arg Ala Ala Thr Leu Arg Glu Lys Arg Arg Leu Lys Lys
                85                  90                  95 gtg aat gag gcc ttc gag gcc ctg aag aga agc acc ctg ctc aac ccc   336
Val Asn Glu Ala Phe Glu Ala Leu Lys Arg Ser Thr Leu Leu Asn Pro
            100                 105                 110 aac cag cgg ctg ccc aag gtg gag atc ctg cgc agt gcc atc cag tac   384
Asn Gln Arg Leu Pro Lys Val Glu Ile Leu Arg Ser Ala Ile Gln Tyr
        115                 120                 125 atc gag cgc ctc cag gcc ctg ctc agc tcc ctc aac cag gag gag cgt   432
Ile Glu Arg Leu Gln Ala Leu Leu Ser Ser Leu Asn Gln Glu Glu Arg
    130                 135                 140 gac ctc cgc tac cgg ggc ggg ggc ggg ccc cag cca ggg gtg ccc agc   480
Asp Leu Arg Tyr Arg Gly Gly Gly Gly Pro Gln Pro Gly Val Pro Ser
145                 150                 155                 160 gaa tgc agc tct cac agc gcc tcc tgc agt cca gag tgg ggc agt gca   528
Glu Cys Ser Ser His Ser Ala Ser Cys Ser Pro Glu Trp Gly Ser Ala
                165                 170                 175 ctg gag ttc agc gcc aac cca ggg gat cat ctg ctc acg gct gac cct   576
Leu Glu Phe Ser Ala Asn Pro Gly Asp His Leu Leu Thr Ala Asp Pro
            180                 185                 190 aca gat gcc cac aac ctg cac tcc ctc acc tcc atc gtg gac agc atc   624
Thr Asp Ala His Asn Leu His Ser Leu Thr Ser Ile Val Asp Ser Ile
        195                 200                 205 aca gtg gaa gat gtg tct gtg gcc ttc cca gat gaa acc atg ccc aac   672
Thr Val Glu Asp Val Ser Val Ala Phe Pro Asp Glu Thr Met Pro Asn
    210                 215                 220 tag                                                                675
```

<210> SEQ ID NO 14
<211> LENGTH: 224
<212> TYPE: PRT
<213> ORGANISM: Homo sapiens

<400> SEQUENCE: 14

Met Glu Leu Tyr Glu Thr Ser Pro Tyr Phe Tyr Gln Glu Pro Arg Phe
1               5                   10                  15

Tyr Asp Gly Glu Asn Tyr Leu Pro Val His Leu Gln Gly Phe Glu Pro
            20                  25                  30

Pro Gly Tyr Glu Arg Thr Glu Leu Thr Leu Ser Pro Glu Ala Pro Gly
        35                  40                  45

Pro Leu Glu Asp Lys Gly Leu Gly Thr Pro Glu His Cys Pro Gly Gln
    50                  55                  60

Cys Leu Pro Trp Ala Cys Lys Val Cys Lys Arg Lys Ser Val Ser Val
65                  70                  75                  80

Asp Arg Arg Arg Ala Ala Thr Leu Arg Glu Lys Arg Arg Leu Lys Lys
                85                  90                  95

Val Asn Glu Ala Phe Glu Ala Leu Lys Arg Ser Thr Leu Leu Asn Pro
            100                 105                 110

Asn Gln Arg Leu Pro Lys Val Glu Ile Leu Arg Ser Ala Ile Gln Tyr
        115                 120                 125

Ile Glu Arg Leu Gln Ala Leu Leu Ser Ser Leu Asn Gln Glu Glu Arg
    130                 135                 140

Asp Leu Arg Tyr Arg Gly Gly Gly Gly Pro Gln Pro Gly Val Pro Ser
145                 150                 155                 160

Glu Cys Ser Ser His Ser Ala Ser Cys Ser Pro Glu Trp Gly Ser Ala
                165                 170                 175

Leu Glu Phe Ser Ala Asn Pro Gly Asp His Leu Leu Thr Ala Asp Pro
            180                 185                 190

Thr Asp Ala His Asn Leu His Ser Leu Thr Ser Ile Val Asp Ser Ile
        195                 200                 205

Thr Val Glu Asp Val Ser Val Ala Phe Pro Asp Glu Thr Met Pro Asn
    210                 215                 220

<210> SEQ ID NO 15
<211> LENGTH: 3935
<212> TYPE: DNA
<213> ORGANISM: Homo sapiens
<220> FEATURE:
<221> NAME/KEY: CDS
<222> LOCATION: (373)..(1902)

<400> SEQUENCE: 15
ggagagccga aagcggagct cgaaactgac tggaaacttc agtggcgcgg agactcgcca      60
gtttcaaccc cggaaacttt tctttgcagg aggagaagag aaggggtgca agcgccccca     120
cttttgctct ttttcctccc ctcctcctcc tctccaattc gcctccccc acttggagcg      180 ggcagctgtg aactggccac cccgcgcctt cctaagtgct cgccgcggta gccggccgac     240
gcgccagctt ccccgggagc cgcttgctcc gcatccgggc agccgagggg agaggagccc     300
gcgcctcgag tccccgagcc gccgcggctt ctcgcctttc ccggccacca gcccctgcc      360 ccgggcccgc gt atg aat ctc ctg gac ccc ttc atg aag atg acc gac gag     411
              Met Asn Leu Leu Asp Pro Phe Met Lys Met Thr Asp Glu
                1               5                   10 cag gag aag ggc ctg tcc ggc gcc ccc agc ccc acc atg tcc gag gac     459
Gln Glu Lys Gly Leu Ser Gly Ala Pro Ser Pro Thr Met Ser Glu Asp

```
                15                  20                  25
tcc gcg ggc tcg ccc tgc ccg tcg ggc tcc ggc tcg gac acc gag aac      507
Ser Ala Gly Ser Pro Cys Pro Ser Gly Ser Gly Ser Asp Thr Glu Asn
30              35                  40                  45 acg cgg ccc cag gag aac acg ttc ccc aag ggc gag ccc gat ctg aag      555
Thr Arg Pro Gln Glu Asn Thr Phe Pro Lys Gly Glu Pro Asp Leu Lys
                50                  55                  60 aag gag agc gag gag gac aag ttc ccc gtg tgc atc cgc gag gcg gtc      603
Lys Glu Ser Glu Glu Asp Lys Phe Pro Val Cys Ile Arg Glu Ala Val
            65                  70                  75 agc cag gtg ctc aaa ggc tac gac tgg acg ctg gtg ccc atg ccg gtg      651
Ser Gln Val Leu Lys Gly Tyr Asp Trp Thr Leu Val Pro Met Pro Val
        80                  85                  90 cgc gtc aac ggc tcc agc aag aac aag ccg cac gtc aag cgg ccc atg      699
Arg Val Asn Gly Ser Ser Lys Asn Lys Pro His Val Lys Arg Pro Met
    95                  100                 105 aac gcc ttc atg gtg tgg gcg cag gcg gcg cgc agg aag ctc gcg gac      747
Asn Ala Phe Met Val Trp Ala Gln Ala Ala Arg Arg Lys Leu Ala Asp
110                 115                 120                 125 cag tac ccg cac ttg cac aac gcc gag ctc agc aag acg ctg ggc aag      795
Gln Tyr Pro His Leu His Asn Ala Glu Leu Ser Lys Thr Leu Gly Lys
                130                 135                 140 ctc tgg aga ctt ctg aac gag agc gag aag cgg ccc ttc gtg gag gag      843
Leu Trp Arg Leu Leu Asn Glu Ser Glu Lys Arg Pro Phe Val Glu Glu
                145                 150                 155 gcg gag cgg ctg cgc gtg cag cac aag aag gac cac ccg gat tac aag      891
Ala Glu Arg Leu Arg Val Gln His Lys Lys Asp His Pro Asp Tyr Lys
            160                 165                 170 tac cag ccg cgg cgg agg aag tcg gtg aag aac ggg cag gcg gag gca      939
Tyr Gln Pro Arg Arg Arg Lys Ser Val Lys Asn Gly Gln Ala Glu Ala
        175                 180                 185 gag gag gcc acg gag cag acg cac atc tcc ccc aac gcc atc ttc aag      987
Glu Glu Ala Thr Glu Gln Thr His Ile Ser Pro Asn Ala Ile Phe Lys
190                 195                 200                 205 gcg ctg cag gcc gac tcg cca cac tcc tcc tcc ggc atg agc gag gtg      1035
Ala Leu Gln Ala Asp Ser Pro His Ser Ser Ser Gly Met Ser Glu Val
                210                 215                 220 cac tcc ccc ggc gag cac tcg ggg caa tcc cag ggc cca ccg acc cca      1083
His Ser Pro Gly Glu His Ser Gly Gln Ser Gln Gly Pro Pro Thr Pro
                225                 230                 235 ccc acc acc ccc aaa acc gac gtg cag ccg ggc aag gct gac ctg aag      1131
Pro Thr Thr Pro Lys Thr Asp Val Gln Pro Gly Lys Ala Asp Leu Lys
            240                 245                 250 cga gag ggg cgc ccc ttg cca gag ggg ggc aga cag ccc cct atc gac      1179
Arg Glu Gly Arg Pro Leu Pro Glu Gly Gly Arg Gln Pro Pro Ile Asp
        255                 260                 265 ttc cgc gac gtg gac atc ggc gag ctg agc agc gac gtc atc tcc aac      1227
Phe Arg Asp Val Asp Ile Gly Glu Leu Ser Ser Asp Val Ile Ser Asn
270                 275                 280                 285 atc gag acc ttc gat gtc aac gag ttt gac cag tac ctg ccg ccc aac      1275
Ile Glu Thr Phe Asp Val Asn Glu Phe Asp Gln Tyr Leu Pro Pro Asn
                290                 295                 300 ggc cac ccg ggg gtg ccg gcc acg cac ggc cag gtc acc tac acg ggc      1323
Gly His Pro Gly Val Pro Ala Thr His Gly Gln Val Thr Tyr Thr Gly
                305                 310                 315 agc tac ggc atc agc agc acc gcg gcc acc ccg gcg agc gcg ggc cac      1371
Ser Tyr Gly Ile Ser Ser Thr Ala Ala Thr Pro Ala Ser Ala Gly His
            320                 325                 330 gtg tgg atg tcc aag cag cag gcg ccg ccg cca ccc ccg cag cag ccc      1419
```

| | | | | | | | | | | | | | | |
|---|---|---|---|---|---|---|---|---|---|---|---|---|---|---|
| Val | Trp | Met | Ser | Lys | Gln | Gln | Ala | Pro | Pro | Pro | Pro | Gln | Gln | Pro |
| | 335 | | | | 340 | | | | | 345 | | | | |

| cca | cag | gcc | ccg | ccg | gcc | ccg | cag | gcg | ccc | ccg | cag | ccg | cag | gcg | gcg | 1467 |
|---|---|---|---|---|---|---|---|---|---|---|---|---|---|---|---|---|
| Pro | Gln | Ala | Pro | Pro | Ala | Pro | Gln | Ala | Pro | Pro | Gln | Pro | Gln | Ala | Ala | |
| 350 | | | | 355 | | | | | 360 | | | | | | 365 | |

| ccc | cca | cag | cag | ccg | gcg | gca | ccc | ccg | cag | cag | cca | cag | gcg | cac | acg | 1515 |
|---|---|---|---|---|---|---|---|---|---|---|---|---|---|---|---|---|
| Pro | Pro | Gln | Gln | Pro | Ala | Ala | Pro | Pro | Gln | Gln | Pro | Gln | Ala | His | Thr | |
| | | | 370 | | | | | 375 | | | | | 380 | | | |

| ctg | acc | acg | ctg | agc | agc | gag | ccg | ggc | cag | tcc | cag | cga | acg | cac | atc | 1563 |
|---|---|---|---|---|---|---|---|---|---|---|---|---|---|---|---|---|
| Leu | Thr | Thr | Leu | Ser | Ser | Glu | Pro | Gly | Gln | Ser | Gln | Arg | Thr | His | Ile | |
| | | 385 | | | | | 390 | | | | | 395 | | | | |

| aag | acg | gag | cag | ctg | agc | ccc | agc | cac | tac | agc | gag | cag | cag | cag | cac | 1611 |
|---|---|---|---|---|---|---|---|---|---|---|---|---|---|---|---|---|
| Lys | Thr | Glu | Gln | Leu | Ser | Pro | Ser | His | Tyr | Ser | Glu | Gln | Gln | Gln | His | |
| | | 400 | | | | | 405 | | | | | 410 | | | | |

| tcg | ccc | caa | cag | atc | gcc | tac | agc | ccc | ttc | aac | ctc | cca | cac | tac | agc | 1659 |
|---|---|---|---|---|---|---|---|---|---|---|---|---|---|---|---|---|
| Ser | Pro | Gln | Gln | Ile | Ala | Tyr | Ser | Pro | Phe | Asn | Leu | Pro | His | Tyr | Ser | |
| | 415 | | | | | 420 | | | | | 425 | | | | | |

| ccc | tcc | tac | ccg | ccc | atc | acc | cgc | tca | cag | tac | gac | tac | acc | gac | cac | 1707 |
|---|---|---|---|---|---|---|---|---|---|---|---|---|---|---|---|---|
| Pro | Ser | Tyr | Pro | Pro | Ile | Thr | Arg | Ser | Gln | Tyr | Asp | Tyr | Thr | Asp | His | |
| 430 | | | | | 435 | | | | | 440 | | | | | 445 | |

| cag | aac | tcc | agc | tcc | tac | tac | agc | cac | gcg | gca | ggc | cag | ggc | acc | ggc | 1755 |
|---|---|---|---|---|---|---|---|---|---|---|---|---|---|---|---|---|
| Gln | Asn | Ser | Ser | Ser | Tyr | Tyr | Ser | His | Ala | Ala | Gly | Gln | Gly | Thr | Gly | |
| | | | 450 | | | | | 455 | | | | | 460 | | | |

| ctc | tac | tcc | acc | ttc | acc | tac | atg | aac | ccc | gct | cag | cgc | ccc | atg | tac | 1803 |
|---|---|---|---|---|---|---|---|---|---|---|---|---|---|---|---|---|
| Leu | Tyr | Ser | Thr | Phe | Thr | Tyr | Met | Asn | Pro | Ala | Gln | Arg | Pro | Met | Tyr | |
| | | 465 | | | | | 470 | | | | | 475 | | | | |

| acc | ccc | atc | gcc | gac | acc | tct | ggg | gtc | cct | tcc | atc | ccg | cag | acc | cac | 1851 |
|---|---|---|---|---|---|---|---|---|---|---|---|---|---|---|---|---|
| Thr | Pro | Ile | Ala | Asp | Thr | Ser | Gly | Val | Pro | Ser | Ile | Pro | Gln | Thr | His | |
| | 480 | | | | | 485 | | | | | 490 | | | | | |

| agc | ccc | cag | cac | tgg | gaa | caa | ccc | gtc | tac | aca | cag | ctc | act | cga | cct | 1899 |
|---|---|---|---|---|---|---|---|---|---|---|---|---|---|---|---|---|
| Ser | Pro | Gln | His | Trp | Glu | Gln | Pro | Val | Tyr | Thr | Gln | Leu | Thr | Arg | Pro | |
| 495 | | | | | 500 | | | | | 505 | | | | | | |

| tga ggaggcctcc cacgaagggc gaagatggcc gagatgatcc taaaaataac | 1952 |
|---|---|
| cgaagaaaga gaggaccaac cagaattccc tttggacatt tgtgtttttt tgttttttta | 2012 |
| ttttgttttg tttttcttc ttcttcttct tccttaaaga catttaagct aaaggcaact | 2072 |
| cgtacccaaa tttccaagac acaaacatga cctatccaag cgcattaccc acttgtggcc | 2132 |
| aatcagtggc caggccaacc ttggctaaat ggagcagcga aatcaacgag aaactggact | 2192 |
| ttttaaaccc tcttcagagc aagcgtggag gatgatggag aatcgtgtga tcagtgtgct | 2252 |
| aaatctctct gcctgtttgg actttgtaat tattttttta gcagtaatta agaaaaaag | 2312 |
| tcctctgtga ggaatattct ctattttaaa tattttagt atgtactgtg tatgattcat | 2372 |
| taccattttg aggggattta tacatatttt tagataaaat taaatgctct tattttccca | 2432 |
| acagctaaac tactcttagt tgaacagtgt gccctagctt tcttgcaac cagagtattt | 2492 |
| ttgtacagat ttgctttctc ttacaaaaag aaaaaaaaaa tcctgttgta ttaacattta | 2552 |
| aaaacagaat tgtgttatgt gatcagtttt gggggttaac tttgcttaat tcctcaggct | 2612 |
| ttgcgattta aggaggagct gccttaaaaa aaaataagg ccttatttg caattatggg | 2672 |
| agtaaacaat agtctagaga agcatttggt aagctttatc atatatatat tttttaaaga | 2732 |
| agagaaaaac accttgagcc ttaaaacggt gctgctggga acatttgca ctcttttagt | 2792 |
| gcatttcctc ctgccttgc ttgttcactg cagtcttaag aaagaggtaa aaggcaagca | 2852 |
| aaggagatga aatctgttct gggaatgttt cagcagccaa taagtgcccg agcacactgc | 2912 |
| cccggttgc ctgcctgggc cccatgtgga aggcagatgc ctgctcgctc tgtcacctgt | 2972 |

-continued

```
gcctctcaga acaccagcag ttaaccttca agacattcca cttgctaaaa ttatttattt    3032
tgtaaggaga ggttttaatt aaaacaaaaa aaaattcttt tttttttttt tttccaattt    3092
taccttcttt aaaataggtt gttggagctt cctcaaagg gtatggtcat ctgttgttaa    3152
attatgttct taactgtaac cagttttttt ttatttatct ctttaatctt tttttattat    3212
taaaagcaag tttctttgta ttcctcaccc tagatttgta taaatgcctt tttgtccatc    3272
ccttttttct ttgttgtttt tgttgaaaac aaactggaaa cttgtttctt tttttgtata    3332
aatgagagat tgcaaatgta gtgtatcact gagtcatttg cagtgttttc tgccacagac    3392
ctttgggctg ccttatattg tgtgtgtgtg tgggtgtgtg tgtgttttga cacaaaaaca    3452
atgcaagcat gtgtcatcca tatttctcta catcttctct tggagtgagg gaggctacct    3512 ggagggatc agcccactga cagaccttaa tcttaattac tgctgtggct agagagtttg    3572
aggattgctt tttaaaaaag acagcaaact tttttttttta tttaaaaaaa gatatattaa    3632
cagttttaga agtcagtaga ataaaatctt aaagcactca taatatggca tccttcaatt    3692
tctgtataaa agcagatctt tttaaaaaga tacttctgta acttaagaaa cctggcattt    3752
aaatcatatt ttgtctttag gtaaaagctt tggtttgtgt tcgtgttttg tttgtttcac    3812
ttgtttccct cccagcccca aaccttttgt tctctccgtg aaacttacct ttccctttt    3872 ctttctcttt ttttttttg tatattattg tttacaataa atatacattg cattaaaaag    3932
aaa                                                                 3935
```

<210> SEQ ID NO 16
<211> LENGTH: 509
<212> TYPE: PRT
<213> ORGANISM: Homo sapiens

<400> SEQUENCE: 16

```
Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
```

```
            195                 200                 205
Ala Asp Ser Pro His Ser Ser Gly Met Ser Glu Val His Ser Pro
    210                 215                 220

Gly Glu His Ser Gly Gln Ser Gln Gly Pro Thr Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
            340                 345                 350

Pro Pro Ala Pro Gln Ala Pro Pro Gln Pro Gln Ala Ala Pro Pro Gln
        355                 360                 365

Gln Pro Ala Ala Pro Pro Gln Gln Pro Gln Ala His Thr Leu Thr Thr
    370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
                405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
        435                 440                 445

Ser Ser Tyr Tyr Ser His Ala Ala Gly Gln Gly Thr Gly Leu Tyr Ser
    450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
            500                 505

<210> SEQ ID NO 17
<211> LENGTH: 5060
<212> TYPE: DNA
<213> ORGANISM: Homo sapiens
<220> FEATURE:
<221> NAME/KEY: CDS
<222> LOCATION: (158)..(4621)

<400> SEQUENCE: 17
acgcagagcg ctgctgggct gccgggtctc ccgcttcctc ctcctgctcc aagggcctcc       60
tgcatgaggg cgcggtagag acccggaccc gcgccgtgct cctgccgttt cgctgcgctc      120
cgcccgggcc cggctcagcc aggccccgcg gtgagcc atg att cgc ctc ggg gct      175
                                         Met Ile Arg Leu Gly Ala
                                         1               5 ccc cag tcg ctg gtg ctg ctg acg ctg ctc gtc gcc gct gtc ctt cgg       223
```

```
                Pro Gln Ser Leu Val Leu Leu Thr Leu Leu Val Ala Ala Val Leu Arg
                         10                  15                  20 tgt cag ggc cag gat gtc cag gag gct ggc agc tgt gtg cag gat ggg         271
Cys Gln Gly Gln Asp Val Gln Glu Ala Gly Ser Cys Val Gln Asp Gly
         25                  30                  35 cag agg tat aat gat aag gat gtg tgg aag ccg gag ccc tgc cgg atc         319
Gln Arg Tyr Asn Asp Lys Asp Val Trp Lys Pro Glu Pro Cys Arg Ile
     40                  45                  50 tgt gtc tgt gac act ggg act gtc ctc tgc gac gac ata atc tgt gaa         367
Cys Val Cys Asp Thr Gly Thr Val Leu Cys Asp Asp Ile Ile Cys Glu
55                  60                  65                  70 gac gtg aaa gac tgc ctc agc cct gag atc ccc ttc gga gag tgc tgc         415
Asp Val Lys Asp Cys Leu Ser Pro Glu Ile Pro Phe Gly Glu Cys Cys
                 75                  80                  85 ccc atc tgc cca act gac ctc gcc act gcc agt ggg caa cca gga cca         463
Pro Ile Cys Pro Thr Asp Leu Ala Thr Ala Ser Gly Gln Pro Gly Pro
             90                  95                 100 aag gga cag aaa gga gaa cct gga gac atc aag gat att gta gga ccc         511
Lys Gly Gln Lys Gly Glu Pro Gly Asp Ile Lys Asp Ile Val Gly Pro
         105                 110                 115 aaa gga cct cct ggg cct cag gga cct gca ggg gaa caa gga ccc aga         559
Lys Gly Pro Pro Gly Pro Gln Gly Pro Ala Gly Glu Gln Gly Pro Arg
     120                 125                 130 ggg gat cgt ggt gac aaa ggt gaa aaa ggt gcc cct gga cct cgt ggc         607
Gly Asp Arg Gly Asp Lys Gly Glu Lys Gly Ala Pro Gly Pro Arg Gly
135                 140                 145                 150 aga gat gga gaa cct ggg acc cct gga aat cct ggc ccc cct ggt cct         655
Arg Asp Gly Glu Pro Gly Thr Pro Gly Asn Pro Gly Pro Pro Gly Pro
                155                 160                 165 ccc ggc ccc cct ggt ccc cct ggt ctt ggt gga aac ttt gct gcc cag         703
Pro Gly Pro Pro Gly Pro Pro Gly Leu Gly Gly Asn Phe Ala Ala Gln
            170                 175                 180 atg gct gga gga ttt gat gaa aag gct ggt ggc gcc cag ttg gga gta         751
Met Ala Gly Gly Phe Asp Glu Lys Ala Gly Gly Ala Gln Leu Gly Val
        185                 190                 195 atg caa gga cca atg ggc ccc atg gga cct cga gga cct cca ggc cct         799
Met Gln Gly Pro Met Gly Pro Met Gly Pro Arg Gly Pro Pro Gly Pro
    200                 205                 210 gca ggt gct cct ggg cct caa gga ttt caa ggc aat cct ggt gaa cct         847
Ala Gly Ala Pro Gly Pro Gln Gly Phe Gln Gly Asn Pro Gly Glu Pro
215                 220                 225                 230 ggt gaa cct ggt gtc tct ggt ccc atg ggt ccc cgt ggt cct cct ggt         895
Gly Glu Pro Gly Val Ser Gly Pro Met Gly Pro Arg Gly Pro Pro Gly
                235                 240                 245 ccc cct gga aag cct ggt gat gat ggt gaa gct gga aaa cct gga aaa         943
Pro Pro Gly Lys Pro Gly Asp Asp Gly Glu Ala Gly Lys Pro Gly Lys
            250                 255                 260 gct ggt gaa agg ggt ccg cct ggt cct cag ggt gct cgt ggt ttc cca         991
Ala Gly Glu Arg Gly Pro Pro Gly Pro Gln Gly Ala Arg Gly Phe Pro
        265                 270                 275 gga acc cca ggc ctt cct ggt gtc aaa ggt cac aga ggt tat cca ggc         1039
Gly Thr Pro Gly Leu Pro Gly Val Lys Gly His Arg Gly Tyr Pro Gly
    280                 285                 290 ctg gac ggt gct aag gga gag gcg ggt gct cct ggt gtg aag ggt gag         1087
Leu Asp Gly Ala Lys Gly Glu Ala Gly Ala Pro Gly Val Lys Gly Glu
295                 300                 305                 310 agt ggt tcc ccg ggt gag aac gga tct ccg ggc cca atg ggt cct cgt         1135
Ser Gly Ser Pro Gly Glu Asn Gly Ser Pro Gly Pro Met Gly Pro Arg
                315                 320                 325
```

-continued

| | |
|---|---|
| ggc ctg cct ggt gaa aga gga cgg act ggc cct gct ggc gct gcg ggt<br>Gly Leu Pro Gly Glu Arg Gly Arg Thr Gly Pro Ala Gly Ala Ala Gly<br>330                              335                      340 | 1183 |
| gcc cga ggc aac gat ggt cag cca ggc ccc gca ggt cct ccg ggt cct<br>Ala Arg Gly Asn Asp Gly Gln Pro Gly Pro Ala Gly Pro Pro Gly Pro<br>            345                      350                      355 | 1231 |
| gtc ggt cct gct ggt ggt cct ggc ttc cct ggt gct cct gga gcc aag<br>Val Gly Pro Ala Gly Gly Pro Gly Phe Pro Gly Ala Pro Gly Ala Lys<br>360                              365                      370 | 1279 |
| ggt gaa gcc ggc ccc act ggt gcc cgt ggt cct gaa ggt gct caa ggt<br>Gly Glu Ala Gly Pro Thr Gly Ala Arg Gly Pro Glu Gly Ala Gln Gly<br>375                      380                      385                      390 | 1327 |
| cct cgc ggt gaa cct ggt act cct ggg tcc cct ggg cct gct ggt gcc<br>Pro Arg Gly Glu Pro Gly Thr Pro Gly Ser Pro Gly Pro Ala Gly Ala<br>                   395                      400                      405 | 1375 |
| tcc ggt aac cct gga aca gat gga att cct gga gcc aaa gga tct gct<br>Ser Gly Asn Pro Gly Thr Asp Gly Ile Pro Gly Ala Lys Gly Ser Ala<br>            410                      415                      420 | 1423 |
| ggt gct cct ggc att gct ggt gct cct ggc ttc cct ggg cca cgg ggt<br>Gly Ala Pro Gly Ile Ala Gly Ala Pro Gly Phe Pro Gly Pro Arg Gly<br>425                              430                      435 | 1471 |
| cct cct ggc cct caa ggt gca act ggt cct ctg ggc ccg aaa ggt cag<br>Pro Pro Gly Pro Gln Gly Ala Thr Gly Pro Leu Gly Pro Lys Gly Gln<br>440                      445                      450 | 1519 |
| acg ggt gaa cct ggt att gct ggc ttc aaa ggt gaa caa ggc ccc aag<br>Thr Gly Glu Pro Gly Ile Ala Gly Phe Lys Gly Glu Gln Gly Pro Lys<br>455                      460                      465                      470 | 1567 |
| gga gaa cct ggc cct gct ggc ccc cag gga gcc cct gga ccc gct ggt<br>Gly Glu Pro Gly Pro Ala Gly Pro Gln Gly Ala Pro Gly Pro Ala Gly<br>                   475                      480                      485 | 1615 |
| gaa gaa ggc aag aga ggt gcc cgt gga gag cct ggt ggc gtt ggg ccc<br>Glu Glu Gly Lys Arg Gly Ala Arg Gly Glu Pro Gly Gly Val Gly Pro<br>            490                      495                      500 | 1663 |
| atc ggt ccc cct gga gaa aga ggt gct ccc gga aac cgc ggt ttc cca<br>Ile Gly Pro Pro Gly Glu Arg Gly Ala Pro Gly Asn Arg Gly Phe Pro<br>                   505                      510                      515 | 1711 |
| ggt caa gat ggt ctg gca ggt ccc aag gga gcc cct gga gag cga ggg<br>Gly Gln Asp Gly Leu Ala Gly Pro Lys Gly Ala Pro Gly Glu Arg Gly<br>520                              525                      530 | 1759 |
| ccc agt ggt ctt gct ggc ccc aag gga gcc aac ggt gac cct ggc cgt<br>Pro Ser Gly Leu Ala Gly Pro Lys Gly Ala Asn Gly Asp Pro Gly Arg<br>535                      540                      545                      550 | 1807 |
| cct gga gaa cct ggc ctt cct gga gcc cgg ggt ctc act ggc cgc cct<br>Pro Gly Glu Pro Gly Leu Pro Gly Ala Arg Gly Leu Thr Gly Arg Pro<br>                   555                      560                      565 | 1855 |
| ggt gat gct ggt cct caa ggc aaa gtt ggc cct tct gga gcc cct ggt<br>Gly Asp Ala Gly Pro Gln Gly Lys Val Gly Pro Ser Gly Ala Pro Gly<br>            570                      575                      580 | 1903 |
| gaa gat ggt cgt cct gga cct cca ggt cct cag ggg gct cgt ggg cag<br>Glu Asp Gly Arg Pro Gly Pro Pro Gly Pro Gln Gly Ala Arg Gly Gln<br>585                              590                      595 | 1951 |
| cct ggt gtc atg ggt ttc cct ggc ccc aaa ggt gcc aac ggt gag cct<br>Pro Gly Val Met Gly Phe Pro Gly Pro Lys Gly Ala Asn Gly Glu Pro<br>600                              605                      610 | 1999 |
| ggc aaa gct ggt gag aag gga ctg cct ggt gct cct ggt ctg agg ggt<br>Gly Lys Ala Gly Glu Lys Gly Leu Pro Gly Ala Pro Gly Leu Arg Gly<br>615                      620                      625                      630 | 2047 |
| ctt cct ggc aaa gat ggt gag aca ggt gct gca gga ccc cct ggc cct<br>Leu Pro Gly Lys Asp Gly Glu Thr Gly Ala Ala Gly Pro Pro Gly Pro<br>                   635                      640                      645 | 2095 |

| | |
|---|---|
| gct gga cct gct ggt gaa cga ggc gag cag ggt gct cct ggg cca tct<br>Ala Gly Pro Ala Gly Glu Arg Gly Glu Gln Gly Ala Pro Gly Pro Ser<br>650                     655                   660 | 2143 |
| ggg ttc cag gga ctt cct ggc cct cct ggt ccc cca ggt gaa ggt gga<br>Gly Phe Gln Gly Leu Pro Gly Pro Pro Gly Pro Pro Gly Glu Gly Gly<br>     665                   670                   675 | 2191 |
| aaa cca ggt gac cag ggt gtt ccc ggt gaa gct gga gcc cct ggc ctc<br>Lys Pro Gly Asp Gln Gly Val Pro Gly Glu Ala Gly Ala Pro Gly Leu<br>680                     685                   690 | 2239 |
| gtg ggt ccc agg ggt gaa cga ggt ttc cca ggt gaa cgt ggc tct ccc<br>Val Gly Pro Arg Gly Glu Arg Gly Phe Pro Gly Glu Arg Gly Ser Pro<br>695                     700                   705                 710 | 2287 |
| ggt gcc cag ggc ctc cag ggt ccc cgt ggc ctc ccc ggc act cct ggc<br>Gly Ala Gln Gly Leu Gln Gly Pro Arg Gly Leu Pro Gly Thr Pro Gly<br>               715                   720                   725 | 2335 |
| act gat ggt ccc aaa ggt gca tct ggc cca gca ggc ccc cct ggc gca<br>Thr Asp Gly Pro Lys Gly Ala Ser Gly Pro Ala Gly Pro Pro Gly Ala<br>730                     735                   740 | 2383 |
| cag ggc cct cca ggt ctt cag gga atg cct ggc gag agg gga gca gct<br>Gln Gly Pro Pro Gly Leu Gln Gly Met Pro Gly Glu Arg Gly Ala Ala<br>               745                   750                   755 | 2431 |
| ggt atc gct ggg ccc aaa ggc gac agg ggt gac gtt ggt gag aaa ggc<br>Gly Ile Ala Gly Pro Lys Gly Asp Arg Gly Asp Val Gly Glu Lys Gly<br>760                     765                   770 | 2479 |
| cct gag gga gcc cct gga aag gat ggt gga cga ggc ctg aca ggt ccc<br>Pro Glu Gly Ala Pro Gly Lys Asp Gly Gly Arg Gly Leu Thr Gly Pro<br>775                     780                   785                 790 | 2527 |
| att ggc ccc cct ggc cca gct ggt gct aac ggc gag aag gga gaa gtt<br>Ile Gly Pro Pro Gly Pro Ala Gly Ala Asn Gly Glu Lys Gly Glu Val<br>               795                   800                   805 | 2575 |
| gga cct cct ggt cct gca gga agt gct ggt gct cgt ggc gct ccg ggt<br>Gly Pro Pro Gly Pro Ala Gly Ser Ala Gly Ala Arg Gly Ala Pro Gly<br>810                     815                   820 | 2623 |
| gaa cgt gga gag act ggc ccc ccc gga cca gcg gga ttt gct ggg cct<br>Glu Arg Gly Glu Thr Gly Pro Pro Gly Pro Ala Gly Phe Ala Gly Pro<br>               825                   830                   835 | 2671 |
| cct ggt gct gat ggc cag cct ggg gcc aag ggt gag caa gga gag gcc<br>Pro Gly Ala Asp Gly Gln Pro Gly Ala Lys Gly Glu Gln Gly Glu Ala<br>840                     845                   850 | 2719 |
| ggc cag aaa ggc gat gct ggt gcc cct ggt cct cag ggc ccc tct gga<br>Gly Gln Lys Gly Asp Ala Gly Ala Pro Gly Pro Gln Gly Pro Ser Gly<br>855                     860                   865                 870 | 2767 |
| gca cct ggg cct cag ggt cct act gga gtg act ggt cct aaa gga gcc<br>Ala Pro Gly Pro Gln Gly Pro Thr Gly Val Thr Gly Pro Lys Gly Ala<br>               875                   880                   885 | 2815 |
| cga ggt gcc caa ggc ccc ccg gga gcc act gga ttc cct gga gct gct<br>Arg Gly Ala Gln Gly Pro Pro Gly Ala Thr Gly Phe Pro Gly Ala Ala<br>890                     895                   900 | 2863 |
| ggc cgc gtt gga ccc cca ggc tcc aat ggc aac cct gga ccc cct ggt<br>Gly Arg Val Gly Pro Pro Gly Ser Asn Gly Asn Pro Gly Pro Pro Gly<br>               905                   910                   915 | 2911 |
| ccc cct ggt cct tct gga aaa gat ggt ccc aaa ggt gct cga gga gac<br>Pro Pro Gly Pro Ser Gly Lys Asp Gly Pro Lys Gly Ala Arg Gly Asp<br>920                     925                   930 | 2959 |
| agc ggc ccc cct ggc cga gct ggt gaa ccc ggc ctc caa ggt cct gct<br>Ser Gly Pro Pro Gly Arg Ala Gly Glu Pro Gly Leu Gln Gly Pro Ala<br>935                     940                   945                 950 | 3007 |
| gga ccc cct ggc gag aag gga gag cct gga gat gac ggt ccc tct ggt<br>Gly Pro Pro Gly Glu Lys Gly Glu Pro Gly Asp Asp Gly Pro Ser Gly | 3055 |

-continued

```
                    955                 960                 965
gcc gaa ggt cca cca ggt ccc cag ggt ctg gct ggt cag aga ggc atc    3103
Ala Glu Gly Pro Pro Gly Pro Gln Gly Leu Ala Gly Gln Arg Gly Ile
        970                 975                 980 gtc ggt ctg cct ggg caa cgt ggt gag aga gga ttc cct ggc ttg cct    3151
Val Gly Leu Pro Gly Gln Arg Gly Glu Arg Gly Phe Pro Gly Leu Pro
            985                 990                 995 ggc cca tcg ggt gag ccc ggc  aag cag ggt gct cct  gga gca tct      3196
Gly Pro Ser Gly Glu Pro Gly  Lys Gln Gly Ala Pro  Gly Ala Ser
        1000                1005                1010 gga gac aga ggt cct cct ggc  ccc gtg ggt cct cct  ggc ctg acg      3241
Gly Asp Arg Gly Pro Pro Gly  Pro Val Gly Pro Pro  Gly Leu Thr
    1015                1020                1025 ggt cct gca ggt gaa ccc gga  cga gag gga agc ccc  ggt gct gat      3286
Gly Pro Ala Gly Glu Pro Gly  Arg Glu Gly Ser Pro  Gly Ala Asp
    1030                1035                1040 ggc ccc cct ggc aga gat ggc  gct gct gga gtc aag  ggt gat cgt      3331
Gly Pro Pro Gly Arg Asp Gly  Ala Ala Gly Val Lys  Gly Asp Arg
    1045                1050                1055 ggt gag act ggt gct gtg gga  gct cct gga gcc cct  ggg ccc cct      3376
Gly Glu Thr Gly Ala Val Gly  Ala Pro Gly Ala Pro  Gly Pro Pro
    1060                1065                1070 ggc tcc cct ggc ccc gct ggt  cca act ggc aag caa  gga gac aga      3421
Gly Ser Pro Gly Pro Ala Gly  Pro Thr Gly Lys Gln  Gly Asp Arg
    1075                1080                1085 gga gaa gct ggt gca caa ggc  ccc atg gga ccc tca  gga cca gct      3466
Gly Glu Ala Gly Ala Gln Gly  Pro Met Gly Pro Ser  Gly Pro Ala
    1090                1095                1100 gga gcc cgg gga atc cag ggt  cct caa ggc ccc aga  ggt gac aaa      3511
Gly Ala Arg Gly Ile Gln Gly  Pro Gln Gly Pro Arg  Gly Asp Lys
    1105                1110                1115 gga gag gct gga gag cct ggc  gag aga ggc ctg aag  gga cac cgt      3556
Gly Glu Ala Gly Glu Pro Gly  Glu Arg Gly Leu Lys  Gly His Arg
    1120                1125                1130 ggc ttc act ggt ctg cag ggt  ctg ccc ggc cct cct  ggt cct tct      3601
Gly Phe Thr Gly Leu Gln Gly  Leu Pro Gly Pro Pro  Gly Pro Ser
    1135                1140                1145 gga gac caa ggt gct tct ggt  cct gct ggt cct tct  ggc cct aga      3646
Gly Asp Gln Gly Ala Ser Gly  Pro Ala Gly Pro Ser  Gly Pro Arg
    1150                1155                1160 ggt cct cct ggc ccc gtc ggt  ccc tct ggc aaa gat  ggt gct aat      3691
Gly Pro Pro Gly Pro Val Gly  Pro Ser Gly Lys Asp  Gly Ala Asn
    1165                1170                1175 gga atc cct ggc ccc att ggg  cct cct ggt ccc cgt  gga cga tca      3736
Gly Ile Pro Gly Pro Ile Gly  Pro Pro Gly Pro Arg  Gly Arg Ser
    1180                1185                1190 ggc gaa acc ggt cct gct ggt  cct cct gga aat cct  ggg ccc cct      3781
Gly Glu Thr Gly Pro Ala Gly  Pro Pro Gly Asn Pro  Gly Pro Pro
    1195                1200                1205 ggt cct cca ggt ccc cct ggc  cct ggc atc gac atg  tcc gcc ttt      3826
Gly Pro Pro Gly Pro Pro Gly  Pro Gly Ile Asp Met  Ser Ala Phe
    1210                1215                1220 gct ggc tta ggc ccg aga gag  aag ggc ccc gac ccc  ctg cag tac      3871
Ala Gly Leu Gly Pro Arg Glu  Lys Gly Pro Asp Pro  Leu Gln Tyr
    1225                1230                1235 atg cgg gcc gac cag gca gcc  ggt ggc ctg aga cag  cat gac gcc      3916
Met Arg Ala Asp Gln Ala Ala  Gly Gly Leu Arg Gln  His Asp Ala
    1240                1245                1250 gag gtg gat gcc aca ctc aag  tcc ctc aac aac cag  att gag agc      3961
```

-continued

```
Glu Val Asp Ala Thr Leu Lys Ser Leu Asn Asn Gln Ile Glu Ser
    1255                1260                1265 atc cgc agc ccc gag ggc tcc cgc aag aac cct gct cgc acc tgc      4006
Ile Arg Ser Pro Glu Gly Ser Arg Lys Asn Pro Ala Arg Thr Cys
1270                1275                1280 aga gac ctg aaa ctc tgc cac cct gag tgg aag agt gga gac tac      4051
Arg Asp Leu Lys Leu Cys His Pro Glu Trp Lys Ser Gly Asp Tyr
    1285                1290                1295 tgg att gac ccc aac caa ggc tgc acc ttg gac gcc atg aag gtt      4096
Trp Ile Asp Pro Asn Gln Gly Cys Thr Leu Asp Ala Met Lys Val
1300                1305                1310 ttc tgc aac atg gag act ggc gag act tgc gtc tac ccc aat cca      4141
Phe Cys Asn Met Glu Thr Gly Glu Thr Cys Val Tyr Pro Asn Pro
    1315                1320                1325 gca aac gtt ccc aag aag aac tgg tgg agc agc aag agc aag gag      4186
Ala Asn Val Pro Lys Lys Asn Trp Trp Ser Ser Lys Ser Lys Glu
1330                1335                1340 aag aaa cac atc tgg ttt gga gaa acc atc aat ggt ggc ttc cat      4231
Lys Lys His Ile Trp Phe Gly Glu Thr Ile Asn Gly Gly Phe His
    1345                1350                1355 ttc agc tat gga gat gac aat ctg gct ccc aac act gcc aac gtc      4276
Phe Ser Tyr Gly Asp Asp Asn Leu Ala Pro Asn Thr Ala Asn Val
1360                1365                1370 cag atg acc ttc cta cgc ctg ctg tcc acg gaa ggc tcc cag aac      4321
Gln Met Thr Phe Leu Arg Leu Leu Ser Thr Glu Gly Ser Gln Asn
    1375                1380                1385 atc acc tac cac tgc aag aac agc att gcc tat ctg gac gaa gca      4366
Ile Thr Tyr His Cys Lys Asn Ser Ile Ala Tyr Leu Asp Glu Ala
1390                1395                1400 gct ggc aac ctc aag aag gcc ctg ctc atc cag ggc tcc aat gac      4411
Ala Gly Asn Leu Lys Lys Ala Leu Leu Ile Gln Gly Ser Asn Asp
    1405                1410                1415 gtg gag atc cgg gca gag ggc aat agc agg ttc acg tac act gcc      4456
Val Glu Ile Arg Ala Glu Gly Asn Ser Arg Phe Thr Tyr Thr Ala
1420                1425                1430 ctg aag gat ggc tgc acg aaa cat acc ggt aag tgg ggc aag act      4501
Leu Lys Asp Gly Cys Thr Lys His Thr Gly Lys Trp Gly Lys Thr
    1435                1440                1445 gtt atc gag tac cgg tca cag aag acc tca cgc ctc ccc atc att      4546
Val Ile Glu Tyr Arg Ser Gln Lys Thr Ser Arg Leu Pro Ile Ile
1450                1455                1460 gac att gca ccc atg gac ata gga ggg ccc gag cag gaa ttc ggt      4591
Asp Ile Ala Pro Met Asp Ile Gly Gly Pro Glu Gln Glu Phe Gly
    1465                1470                1475 gtg gac ata ggg ccg gtc tgc ttc ttg taa aaacctgaac ccagaaacaa    4641
Val Asp Ile Gly Pro Val Cys Phe Leu
1480                1485 cacaatccgt tgcaaaccca aggacccaa gtactttcca atctcagtca ctctaggact  4701
ctgcactgaa tggctgacct gacctgatgt ccattcatcc caccctctca cagttcggac  4761
ttttctcccc tctctttcta agagacctga actgggcaga ctgcaaaata aaatctcggt  4821
gttctattta tttattgtct tcctgtaaga ccttcgggtc aaggcagagg caggaaacta  4881
actggtgtga gtcaaatgcc ccctgagtga ctgcccccag cccaggccag aagacctccc  4941
ttcaggtgcc gggcgcagga actgtgtgtg tcctacacaa tggtgctatt ctgtgtcaaa  5001
cacctctgta tttttttaaaa catcaattga tattaaaaat gaaagagatta ttggaaagt   5060

<210> SEQ ID NO 18
```

<211> LENGTH: 1487
<212> TYPE: PRT
<213> ORGANISM: Homo sapiens

<400> SEQUENCE: 18

```
Met Ile Arg Leu Gly Ala Pro Gln Ser Leu Val Leu Leu Thr Leu Leu
1               5                   10                  15

Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
    210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
        275                 280                 285

His Arg Gly Tyr Pro Gly Leu Asp Gly Ala Lys Gly Glu Ala Gly Ala
    290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
        355                 360                 365

Gly Ala Pro Gly Ala Lys Gly Glu Ala Gly Pro Thr Gly Ala Arg Gly
    370                 375                 380

Pro Glu Gly Ala Gln Gly Pro Arg Gly Glu Pro Gly Thr Pro Gly Ser
```

```
                385                 390                 395                 400
        Pro Gly Pro Ala Gly Ala Ser Gly Asn Pro Gly Thr Asp Gly Ile Pro
                        405                 410                 415
        Gly Ala Lys Gly Ser Ala Gly Ala Pro Gly Ile Ala Gly Ala Pro Gly
                        420                 425                 430
        Phe Pro Gly Pro Arg Gly Pro Pro Gly Pro Gln Gly Ala Thr Gly Pro
                        435                 440                 445
        Leu Gly Pro Lys Gly Gln Thr Gly Glu Pro Gly Ile Ala Gly Phe Lys
                        450                 455                 460
        Gly Glu Gln Gly Pro Lys Gly Glu Pro Gly Pro Ala Gly Pro Gln Gly
        465                 470                 475                 480
        Ala Pro Gly Pro Ala Gly Glu Glu Gly Lys Arg Gly Ala Arg Gly Glu
                        485                 490                 495
        Pro Gly Gly Val Gly Pro Ile Gly Pro Pro Gly Glu Arg Gly Ala Pro
                        500                 505                 510
        Gly Asn Arg Gly Phe Pro Gly Gln Asp Gly Leu Ala Gly Pro Lys Gly
                        515                 520                 525
        Ala Pro Gly Glu Arg Gly Pro Ser Gly Leu Ala Gly Pro Lys Gly Ala
                        530                 535                 540
        Asn Gly Asp Pro Gly Arg Pro Gly Glu Pro Gly Leu Pro Gly Ala Arg
        545                 550                 555                 560
        Gly Leu Thr Gly Arg Pro Gly Asp Ala Gly Pro Gln Gly Lys Val Gly
                        565                 570                 575
        Pro Ser Gly Ala Pro Gly Glu Asp Gly Arg Pro Gly Pro Pro Gly Pro
                        580                 585                 590
        Gln Gly Ala Arg Gly Gln Pro Gly Val Met Gly Phe Pro Gly Pro Lys
                        595                 600                 605
        Gly Ala Asn Gly Glu Pro Gly Lys Ala Gly Glu Lys Gly Leu Pro Gly
                        610                 615                 620
        Ala Pro Gly Leu Arg Gly Leu Pro Gly Lys Asp Gly Glu Thr Gly Ala
        625                 630                 635                 640
        Ala Gly Pro Pro Gly Pro Ala Gly Pro Ala Gly Glu Arg Gly Glu Gln
                        645                 650                 655
        Gly Ala Pro Gly Pro Ser Gly Phe Gln Gly Leu Pro Gly Pro Pro Gly
                        660                 665                 670
        Pro Pro Gly Glu Gly Gly Lys Pro Gly Asp Gln Gly Val Pro Gly Glu
                        675                 680                 685
        Ala Gly Ala Pro Gly Leu Val Gly Pro Arg Gly Glu Arg Gly Phe Pro
                        690                 695                 700
        Gly Glu Arg Gly Ser Pro Gly Ala Gln Gly Leu Gln Gly Pro Arg Gly
        705                 710                 715                 720
        Leu Pro Gly Thr Pro Gly Thr Asp Gly Pro Lys Gly Ala Ser Gly Pro
                        725                 730                 735
        Ala Gly Pro Pro Gly Ala Gln Gly Pro Pro Gly Leu Gln Gly Met Pro
                        740                 745                 750
        Gly Glu Arg Gly Ala Ala Gly Ile Ala Gly Pro Lys Gly Asp Arg Gly
                        755                 760                 765
        Asp Val Gly Glu Lys Gly Pro Glu Gly Ala Pro Gly Lys Asp Gly Gly
                        770                 775                 780
        Arg Gly Leu Thr Gly Pro Ile Gly Pro Pro Gly Pro Ala Gly Ala Asn
        785                 790                 795                 800
        Gly Glu Lys Gly Glu Val Gly Pro Pro Gly Pro Ala Gly Ser Ala Gly
                        805                 810                 815
```

Ala Arg Gly Ala Pro Gly Glu Arg Gly Glu Thr Gly Pro Gly Pro
                820                 825                 830

Ala Gly Phe Ala Gly Pro Pro Gly Ala Asp Gly Gln Pro Gly Ala Lys
            835                 840                 845

Gly Glu Gln Gly Glu Ala Gly Gln Lys Gly Asp Ala Gly Ala Pro Gly
        850                 855                 860

Pro Gln Gly Pro Ser Gly Ala Pro Gly Pro Gln Gly Pro Thr Gly Val
865                 870                 875                 880

Thr Gly Pro Lys Gly Ala Arg Gly Ala Gln Gly Pro Pro Gly Ala Thr
                885                 890                 895

Gly Phe Pro Gly Ala Ala Gly Arg Val Gly Pro Pro Gly Ser Asn Gly
            900                 905                 910

Asn Pro Gly Pro Pro Gly Pro Pro Gly Pro Ser Gly Lys Asp Gly Pro
            915                 920                 925

Lys Gly Ala Arg Gly Asp Ser Gly Pro Pro Gly Arg Ala Gly Glu Pro
930                 935                 940

Gly Leu Gln Gly Pro Ala Gly Pro Pro Gly Glu Lys Gly Glu Pro Gly
945                 950                 955                 960

Asp Asp Gly Pro Ser Gly Ala Glu Gly Pro Pro Gly Pro Gln Gly Leu
                965                 970                 975

Ala Gly Gln Arg Gly Ile Val Gly Leu Pro Gly Gln Arg Gly Glu Arg
            980                 985                 990

Gly Phe Pro Gly Leu Pro Gly Pro Ser Gly Glu Pro Gly Lys Gln Gly
            995                 1000                1005

Ala Pro Gly Ala Ser Gly Asp Arg Gly Pro Pro Gly Pro Val Gly
    1010                1015                1020

Pro Pro Gly Leu Thr Gly Pro Ala Gly Glu Pro Gly Arg Glu Gly
    1025                1030                1035

Ser Pro Gly Ala Asp Gly Pro Pro Gly Arg Asp Gly Ala Ala Gly
    1040                1045                1050

Val Lys Gly Asp Arg Gly Glu Thr Gly Ala Val Gly Ala Pro Gly
    1055                1060                1065

Ala Pro Gly Pro Pro Gly Ser Pro Gly Pro Ala Gly Pro Thr Gly
    1070                1075                1080

Lys Gln Gly Asp Arg Gly Glu Ala Gly Ala Gln Gly Pro Met Gly
    1085                1090                1095

Pro Ser Gly Pro Ala Gly Ala Arg Gly Ile Gln Gly Pro Gln Gly
    1100                1105                1110

Pro Arg Gly Asp Lys Gly Glu Ala Gly Glu Pro Gly Glu Arg Gly
    1115                1120                1125

Leu Lys Gly His Arg Gly Phe Thr Gly Leu Gln Gly Leu Pro Gly
    1130                1135                1140

Pro Pro Gly Pro Ser Gly Asp Gln Gly Ala Ser Gly Pro Ala Gly
    1145                1150                1155

Pro Ser Gly Pro Arg Gly Pro Pro Gly Pro Val Gly Pro Ser Gly
    1160                1165                1170

Lys Asp Gly Ala Asn Gly Ile Pro Gly Pro Ile Gly Pro Pro Gly
    1175                1180                1185

Pro Arg Gly Arg Ser Gly Glu Thr Gly Pro Ala Gly Pro Pro Gly
    1190                1195                1200

Asn Pro Gly Pro Pro Gly Pro Pro Gly Pro Pro Gly Pro Gly Ile
    1205                1210                1215

```
Asp Met Ser Ala Phe Ala Gly Leu Gly Pro Arg Glu Lys Gly Pro
    1220                1225                1230

Asp Pro Leu Gln Tyr Met Arg Ala Asp Gln Ala Ala Gly Gly Leu
    1235                1240                1245

Arg Gln His Asp Ala Glu Val Asp Ala Thr Leu Lys Ser Leu Asn
    1250                1255                1260

Asn Gln Ile Glu Ser Ile Arg Ser Pro Glu Gly Ser Arg Lys Asn
    1265                1270                1275

Pro Ala Arg Thr Cys Arg Asp Leu Lys Leu Cys His Pro Glu Trp
    1280                1285                1290

Lys Ser Gly Asp Tyr Trp Ile Asp Pro Asn Gln Gly Cys Thr Leu
    1295                1300                1305

Asp Ala Met Lys Val Phe Cys Asn Met Glu Thr Gly Glu Thr Cys
    1310                1315                1320

Val Tyr Pro Asn Pro Ala Asn Val Pro Lys Lys Asn Trp Trp Ser
    1325                1330                1335

Ser Lys Ser Lys Glu Lys Lys His Ile Trp Phe Gly Glu Thr Ile
    1340                1345                1350

Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
    1415                1420                1425

Phe Thr Tyr Thr Ala Leu Lys Asp Gly Cys Thr Lys His Thr Gly
    1430                1435                1440

Lys Trp Gly Lys Thr Val Ile Glu Tyr Arg Ser Gln Lys Thr Ser
    1445                1450                1455

Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485

<210> SEQ ID NO 19
<211> LENGTH: 7137
<212> TYPE: DNA
<213> ORGANISM: Homo sapiens
<220> FEATURE:
<221> NAME/KEY: CDS
<222> LOCATION: (61)..(7011)

<400> SEQUENCE: 19
cggccaggtg tgtgggactg aagttcttgg agaagggagt ccaactcttc aaggtgaact      60 atg acc act tta ctc tgg gtt ttc gtg act ctg agg gtc atc act gca     108
Met Thr Thr Leu Leu Trp Val Phe Val Thr Leu Arg Val Ile Thr Ala
  1               5                  10                  15 gct gtc act gta gaa act tca gac cat gac aac tcg ctg agt gtc agc     156
Ala Val Thr Val Glu Thr Ser Asp His Asp Asn Ser Leu Ser Val Ser
             20                  25                  30 atc ccc caa ccg tcc ccg ctg agg gtc ctc ctg ggg acc tcc ctc acc     204
Ile Pro Gln Pro Ser Pro Leu Arg Val Leu Leu Gly Thr Ser Leu Thr
         35                  40                  45
```

| | |
|---|---|
| atc ccc tgc tat ttc atc gac ccc atg cac cct gtg acc acc gcc cct<br>Ile Pro Cys Tyr Phe Ile Asp Pro Met His Pro Val Thr Thr Ala Pro<br>50                         55                    60 | 252 |
| tct acc gcc cca ctg gcc cca aga atc aag tgg agc cgt gtg tcc aag<br>Ser Thr Ala Pro Leu Ala Pro Arg Ile Lys Trp Ser Arg Val Ser Lys<br>65                      70                   75                  80 | 300 |
| gag aag gag gta gtg ctg ctg gtg gcc act gaa ggg cgc gtg cgg gtc<br>Glu Lys Glu Val Val Leu Leu Val Ala Thr Glu Gly Arg Val Arg Val<br>                    85                   90                      95 | 348 |
| aac agt gcc tat cag gac aag gtc tca ctg ccc aac tac ccg gcc atc<br>Asn Ser Ala Tyr Gln Asp Lys Val Ser Leu Pro Asn Tyr Pro Ala Ile<br>            100                 105               110 | 396 |
| ccc agt gac gcc acc ttg gaa gtc cag agc ctg cgc tcc aat gac tct<br>Pro Ser Asp Ala Thr Leu Glu Val Gln Ser Leu Arg Ser Asn Asp Ser<br>            115                 120               125 | 444 |
| ggg gtc tac cgc tgc gag gtg atg cat ggc atc gag gac agc gag gcc<br>Gly Val Tyr Arg Cys Glu Val Met His Gly Ile Glu Asp Ser Glu Ala<br>130                      135                 140 | 492 |
| acc ctg gaa gtc gtg gtg aaa ggc atc gtg ttc cat tac aga gcc atc<br>Thr Leu Glu Val Val Val Lys Gly Ile Val Phe His Tyr Arg Ala Ile<br>145                      150                 155               160 | 540 |
| tct aca cgc tac acc ctc gac ttt gac agg gcg cag cgg gcc tgc ctg<br>Ser Thr Arg Tyr Thr Leu Asp Phe Asp Arg Ala Gln Arg Ala Cys Leu<br>                    165                 170               175 | 588 |
| cag aac agt gcc atc att gcc acg cct gag cag ctg cag gcc gcc tac<br>Gln Asn Ser Ala Ile Ile Ala Thr Pro Glu Gln Leu Gln Ala Ala Tyr<br>            180                 185               190 | 636 |
| gaa gac ggc ttc cac cag tgt gac gcc ggc tgg ctg gct gac cag act<br>Glu Asp Gly Phe His Gln Cys Asp Ala Gly Trp Leu Ala Asp Gln Thr<br>195                      200                 205 | 684 |
| gtc aga tac ccc atc cac act ccc cgg gaa ggc tgc tat gga gac aag<br>Val Arg Tyr Pro Ile His Thr Pro Arg Glu Gly Cys Tyr Gly Asp Lys<br>210                      215                 220 | 732 |
| gat gag ttt cct ggt gtg agg acg tat ggc atc cga gac acc aac gag<br>Asp Glu Phe Pro Gly Val Arg Thr Tyr Gly Ile Arg Asp Thr Asn Glu<br>225                      230                 235               240 | 780 |
| acc tat gat gtg tac tgc ttc gcc gag gag atg gag ggt gag gtc ttt<br>Thr Tyr Asp Val Tyr Cys Phe Ala Glu Glu Met Glu Gly Glu Val Phe<br>                    245                 250               255 | 828 |
| tat gca aca tct cca gag aag ttc acc ttc cag gaa gca gcc aat gag<br>Tyr Ala Thr Ser Pro Glu Lys Phe Thr Phe Gln Glu Ala Ala Asn Glu<br>            260                 265               270 | 876 |
| tgc cgg cgg ctg ggt gcc cgg ctg gcc acc acg ggc cac gtc tac ctg<br>Cys Arg Arg Leu Gly Ala Arg Leu Ala Thr Thr Gly His Val Tyr Leu<br>275                      280                 285 | 924 |
| gcc tgg cag gct ggc atg gac atg tgc agc gcc ggc tgg ctg gcc gac<br>Ala Trp Gln Ala Gly Met Asp Met Cys Ser Ala Gly Trp Leu Ala Asp<br>290                      295                 300 | 972 |
| cgc agc gtg cgc tac ccc atc tcc aag gcc cgg ccc aac tgc ggt ggc<br>Arg Ser Val Arg Tyr Pro Ile Ser Lys Ala Arg Pro Asn Cys Gly Gly<br>305                      310                 315               320 | 1020 |
| aac ctc ctg ggc gtg agg acc gtc tac gtg cat gcc aac cag acg ggc<br>Asn Leu Leu Gly Val Arg Thr Val Tyr Val His Ala Asn Gln Thr Gly<br>                    325                 330               335 | 1068 |
| tac ccc gac ccc tca tcc cgc tac gac gcc atc tgc tac aca ggt gaa<br>Tyr Pro Asp Pro Ser Ser Arg Tyr Asp Ala Ile Cys Tyr Thr Gly Glu<br>            340                 345               350 | 1116 |
| gac ttt gtg gac atc cca gaa aac ttc ttt gga gtg ggg ggt gag gag<br>Asp Phe Val Asp Ile Pro Glu Asn Phe Phe Gly Val Gly Gly Glu Glu<br>355                      360                 365 | 1164 |

```
gac atc acc gtc cag aca gtg acc tgg cct gac atg gag ctg cca ctg      1212
Asp Ile Thr Val Gln Thr Val Thr Trp Pro Asp Met Glu Leu Pro Leu
    370             375                 380 cct cga aac atc act gag ggt gaa gcc cga ggc agc gtg atc ctt acc      1260
Pro Arg Asn Ile Thr Glu Gly Glu Ala Arg Gly Ser Val Ile Leu Thr
385                 390                 395                 400 gta aag ccc atc ttc gag gtc tcc ccc agt ccc ctg gaa ccc gag gag      1308
Val Lys Pro Ile Phe Glu Val Ser Pro Ser Pro Leu Glu Pro Glu Glu
                405                 410                 415 ccc ttc acg ttt gcc cct gaa ata ggg gcc act gcc ttc gct gag gtt      1356
Pro Phe Thr Phe Ala Pro Glu Ile Gly Ala Thr Ala Phe Ala Glu Val
                420                 425                 430 gag aat gag act gga gag gcc acc agg ccc tgg ggc ttt ccc aca cct      1404
Glu Asn Glu Thr Gly Glu Ala Thr Arg Pro Trp Gly Phe Pro Thr Pro
            435                 440                 445 ggc ctg ggc cct gcc acg gca ttc acc agt gag gac ctc gtc gtg cag      1452
Gly Leu Gly Pro Ala Thr Ala Phe Thr Ser Glu Asp Leu Val Val Gln
        450                 455                 460 gtg acc gct gtc cct ggg cag ccg cat ttg cca ggg ggg gtc gtc ttc      1500
Val Thr Ala Val Pro Gly Gln Pro His Leu Pro Gly Gly Val Val Phe
465                 470                 475                 480 cac tac cgc ccg gga ccc acc cgc tac tcg ctg acc ttt gag gag gca      1548
His Tyr Arg Pro Gly Pro Thr Arg Tyr Ser Leu Thr Phe Glu Glu Ala
                485                 490                 495 cag cag gcc tgc cct ggc acg ggg gcg gtc att gcc tcg ccg gag cag      1596
Gln Gln Ala Cys Pro Gly Thr Gly Ala Val Ile Ala Ser Pro Glu Gln
                500                 505                 510 ctc cag gcc gcc tac gaa gca ggc tat gag cag tgt gac gcc ggc tgg      1644
Leu Gln Ala Ala Tyr Glu Ala Gly Tyr Glu Gln Cys Asp Ala Gly Trp
            515                 520                 525 ctg cgg gac cag acc gtc aga tac ccc att gtg agc cca cgg acc cca      1692
Leu Arg Asp Gln Thr Val Arg Tyr Pro Ile Val Ser Pro Arg Thr Pro
        530                 535                 540 tgc gtg ggt gac aag gac agc agc cca ggg gtc agg acc tat ggc gtg      1740
Cys Val Gly Asp Lys Asp Ser Ser Pro Gly Val Arg Thr Tyr Gly Val
545                 550                 555                 560 cgc cca tca aca gag acc tac gat gtc tac tgc ttt gta gac aga ctt      1788
Arg Pro Ser Thr Glu Thr Tyr Asp Val Tyr Cys Phe Val Asp Arg Leu
                565                 570                 575 gag ggg gag gtg ttc ttc gcc aca cgc ctt gag cag ttc acc ttc cag      1836
Glu Gly Glu Val Phe Phe Ala Thr Arg Leu Glu Gln Phe Thr Phe Gln
                580                 585                 590 gaa gca ctg gag ttc tgt gaa tct cac aat gcc act gcc acc acg ggc      1884
Glu Ala Leu Glu Phe Cys Glu Ser His Asn Ala Thr Ala Thr Thr Gly
            595                 600                 605 cag ctc tac gcc gcc tgg agc cgc ggc ctg gac aag tgc tat gcc ggc      1932
Gln Leu Tyr Ala Ala Trp Ser Arg Gly Leu Asp Lys Cys Tyr Ala Gly
        610                 615                 620 tgg ctg gcc gac ggc agc ctc cgc tac ccc atc gtc acc cca agg cct      1980
Trp Leu Ala Asp Gly Ser Leu Arg Tyr Pro Ile Val Thr Pro Arg Pro
625                 630                 635                 640 gcc tgc ggt ggg gac aag cca ggc gtg aga acg gtc tac ctc tac cct      2028
Ala Cys Gly Gly Asp Lys Pro Gly Val Arg Thr Val Tyr Leu Tyr Pro
                645                 650                 655 aac cag acg ggc ctc cca gac cca ctg tcc cgg cac cat gcc ttc tgc      2076
Asn Gln Thr Gly Leu Pro Asp Pro Leu Ser Arg His His Ala Phe Cys
                660                 665                 670 ttc cga ggc att tca gcg gtt cct tct cca gga gaa gaa gag ggt ggc      2124
Phe Arg Gly Ile Ser Ala Val Pro Ser Pro Gly Glu Glu Glu Gly Gly
```

```
                675                 680                 685
aca ccc aca tca ccc tct ggt gtg gag gag tgg atc gtg acc caa gtg      2172
Thr Pro Thr Ser Pro Ser Gly Val Glu Glu Trp Ile Val Thr Gln Val
690                 695                 700 gtt cct ggt gtg gct gct gtc ccc gta gaa gag gag aca act gct gta      2220
Val Pro Gly Val Ala Ala Val Pro Val Glu Glu Glu Thr Thr Ala Val
705                 710                 715                 720 ccc tca ggg gag act act gcc atc cta gag ttc acc acc gag cca gaa      2268
Pro Ser Gly Glu Thr Thr Ala Ile Leu Glu Phe Thr Thr Glu Pro Glu
                725                 730                 735 aac cag aca gaa tgg gaa cca gcc tat acc cca gtg ggc aca tcc ccg      2316
Asn Gln Thr Glu Trp Glu Pro Ala Tyr Thr Pro Val Gly Thr Ser Pro
            740                 745                 750 ctg cca ggg atc ctt cct act tgg cct cct act ggc gcc gaa aca gag      2364
Leu Pro Gly Ile Leu Pro Thr Trp Pro Pro Thr Gly Ala Glu Thr Glu
        755                 760                 765 gaa agt aca gaa ggc cct tct gca act gaa gtg ccc tct gcc tca gag      2412
Glu Ser Thr Glu Gly Pro Ser Ala Thr Glu Val Pro Ser Ala Ser Glu
770                 775                 780 gaa cca tcc ccc tca gag gtg cca ttc ccc tca gag gag cca tcc ccc      2460
Glu Pro Ser Pro Ser Glu Val Pro Phe Pro Ser Glu Glu Pro Ser Pro
785                 790                 795                 800 tca gag gaa cca ttc ccc tca gtg agg cca ttc ccc tca gtg gag ctg      2508
Ser Glu Glu Pro Phe Pro Ser Val Arg Pro Phe Pro Ser Val Glu Leu
                805                 810                 815 ttc ccc tca gag gag cca ttc ccc tcc aag gag cca tcc ccc tca gag      2556
Phe Pro Ser Glu Glu Pro Phe Pro Ser Lys Glu Pro Ser Pro Ser Glu
            820                 825                 830 gaa cca tca gcc tca gaa gag ccg tat aca cct tca ccc ccc gag ccc      2604
Glu Pro Ser Ala Ser Glu Glu Pro Tyr Thr Pro Ser Pro Pro Glu Pro
        835                 840                 845 agc tgg act gag ctg ccc agc tct ggg gag gaa tct ggg gcc cct gat      2652
Ser Trp Thr Glu Leu Pro Ser Ser Gly Glu Glu Ser Gly Ala Pro Asp
850                 855                 860 gtc agt ggt gac ttc aca ggc agt gga gat gtt tca gga cac ctt gac      2700
Val Ser Gly Asp Phe Thr Gly Ser Gly Asp Val Ser Gly His Leu Asp
865                 870                 875                 880 ttc agt ggg cag ctg tca ggg gac agg gca agt gga ctg ccc tct gga      2748
Phe Ser Gly Gln Leu Ser Gly Asp Arg Ala Ser Gly Leu Pro Ser Gly
                885                 890                 895 gac ctg gac tcc agt ggt ctt act tcc aca gtg ggc tca ggc ctg act      2796
Asp Leu Asp Ser Ser Gly Leu Thr Ser Thr Val Gly Ser Gly Leu Thr
            900                 905                 910 gtg gaa agt gga cta ccc tca ggg gat gaa gag aga att gag tgg ccc      2844
Val Glu Ser Gly Leu Pro Ser Gly Asp Glu Glu Arg Ile Glu Trp Pro
        915                 920                 925 agc act cct acg gtt ggt gaa ctg ccc tct gga gct gag atc cta gag      2892
Ser Thr Pro Thr Val Gly Glu Leu Pro Ser Gly Ala Glu Ile Leu Glu
930                 935                 940 ggc tct gcc tct gga gtt ggg gat ctc agt gga ctt cct tct gga gaa      2940
Gly Ser Ala Ser Gly Val Gly Asp Leu Ser Gly Leu Pro Ser Gly Glu
945                 950                 955                 960 gtt cta gag acc tct gcc tct gga gta gga gac ctc agt ggg ctt cct      2988
Val Leu Glu Thr Ser Ala Ser Gly Val Gly Asp Leu Ser Gly Leu Pro
                965                 970                 975 tct gga gaa gtt cta gag acc act gcc cct gga gta gag gac atc agc      3036
Ser Gly Glu Val Leu Glu Thr Thr Ala Pro Gly Val Glu Asp Ile Ser
            980                 985                 990 ggg ctt cct tct gga gaa gtt cta  gag acc act gcc cct   gga gta gag   3084
```

```
                 Gly Leu Pro Ser Gly Glu Val Leu Glu Thr Thr Ala Pro Gly Val Glu
                             995                 1000                1005 gac atc agc ggg ctt cct tct gga gaa gtt cta gag acc act gcc       3129
Asp Ile Ser Gly Leu Pro Ser Gly Glu Val Leu Glu Thr Thr Ala
1010                1015                1020 cct gga gta gag gac atc agc ggg ctt cct tct gga gaa gtt cta       3174
Pro Gly Val Glu Asp Ile Ser Gly Leu Pro Ser Gly Glu Val Leu
1025                1030                1035 gag acc act gcc cct gga gta gag gac atc agc ggg ctt cct tct       3219
Glu Thr Thr Ala Pro Gly Val Glu Asp Ile Ser Gly Leu Pro Ser
1040                1045                1050 gga gaa gtt cta gag acc act gcc cct gga gta gag gac atc agc       3264
Gly Glu Val Leu Glu Thr Thr Ala Pro Gly Val Glu Asp Ile Ser
1055                1060                1065 ggg ctt cct tct gga gaa gtt cta gag acc gct gcc cct gga gta       3309
Gly Leu Pro Ser Gly Glu Val Leu Glu Thr Ala Ala Pro Gly Val
1070                1075                1080 gag gac atc agc ggg ctt cct tct gga gaa gtt cta gag acc gct       3354
Glu Asp Ile Ser Gly Leu Pro Ser Gly Glu Val Leu Glu Thr Ala
1085                1090                1095 gcc cct gga gta gag gac atc agc ggg ctt cct tct gga gaa gtt       3399
Ala Pro Gly Val Glu Asp Ile Ser Gly Leu Pro Ser Gly Glu Val
1100                1105                1110 cta gag acc gct gcc cct gga gta gag gac atc agc ggg ctt cct       3444
Leu Glu Thr Ala Ala Pro Gly Val Glu Asp Ile Ser Gly Leu Pro
1115                1120                1125 tct gga gaa gtt cta gag acc gct gcc cct gga gta gag gac atc       3489
Ser Gly Glu Val Leu Glu Thr Ala Ala Pro Gly Val Glu Asp Ile
1130                1135                1140 agc ggg ctt cct tct gga gaa gtt cta gag acc gct gcc cct gga       3534
Ser Gly Leu Pro Ser Gly Glu Val Leu Glu Thr Ala Ala Pro Gly
1145                1150                1155 gta gag gac atc agc ggg ctt cct tct gga gaa gtt cta gag acc       3579
Val Glu Asp Ile Ser Gly Leu Pro Ser Gly Glu Val Leu Glu Thr
1160                1165                1170 gct gcc cct gga gta gag gac atc agc ggg ctt cct tct gga gaa       3624
Ala Ala Pro Gly Val Glu Asp Ile Ser Gly Leu Pro Ser Gly Glu
1175                1180                1185 gtt cta gag acc gct gcc cct gga gta gag gac atc agc ggg ctt       3669
Val Leu Glu Thr Ala Ala Pro Gly Val Glu Asp Ile Ser Gly Leu
1190                1195                1200 cct tct gga gaa gtt cta gag act gct gcc cct gga gta gag gac       3714
Pro Ser Gly Glu Val Leu Glu Thr Ala Ala Pro Gly Val Glu Asp
1205                1210                1215 atc agc ggg ctt cct tct gga gaa gtt cta gag act gct gcc cct       3759
Ile Ser Gly Leu Pro Ser Gly Glu Val Leu Glu Thr Ala Ala Pro
1220                1225                1230 gga gta gag gac atc agc ggg ctt cct tct gga gaa gtt cta gag       3804
Gly Val Glu Asp Ile Ser Gly Leu Pro Ser Gly Glu Val Leu Glu
1235                1240                1245 act gct gcc cct gga gta gag gac atc agc ggg ctt cct tct gga       3849
Thr Ala Ala Pro Gly Val Glu Asp Ile Ser Gly Leu Pro Ser Gly
1250                1255                1260 gaa gtt cta gag act gct gcc cct gga gta gag gac atc agc ggg       3894
Glu Val Leu Glu Thr Ala Ala Pro Gly Val Glu Asp Ile Ser Gly
1265                1270                1275 ctt cct tct gga gaa gtt cta gag act act gcc cct gga gta gag       3939
Leu Pro Ser Gly Glu Val Leu Glu Thr Thr Ala Pro Gly Val Glu
1280                1285                1290
```

| | | | | | | | | | | | | |
|---|---|---|---|---|---|---|---|---|---|---|---|---|
| gag | atc | agc | ggg | ctt | cct | tct | gga | gaa | gtt | cta | gag | act | act | gcc | 3984 |
| Glu | Ile | Ser | Gly | Leu | Pro | Ser | Gly | Glu | Val | Leu | Glu | Thr | Thr | Ala | |
| | 1295 | | | | 1300 | | | | | 1305 | | | | | |

| cct | gga | gta | gat | gag | atc | agt | ggg | ctt | cct | tct | gga | gaa | gtt | cta | 4029 |
| Pro | Gly | Val | Asp | Glu | Ile | Ser | Gly | Leu | Pro | Ser | Gly | Glu | Val | Leu | |
| 1310 | | | | | 1315 | | | | | 1320 | | | | | |

| gag | act | act | gcc | cct | gga | gta | gag | gag | atc | agc | ggg | ctt | cct | tct | 4074 |
| Glu | Thr | Thr | Ala | Pro | Gly | Val | Glu | Glu | Ile | Ser | Gly | Leu | Pro | Ser | |
| 1325 | | | | | 1330 | | | | | 1335 | | | | | |

| gga | gaa | gtt | cta | gag | act | tct | acc | tct | gcg | gta | ggg | gac | ctc | agt | 4119 |
| Gly | Glu | Val | Leu | Glu | Thr | Ser | Thr | Ser | Ala | Val | Gly | Asp | Leu | Ser | |
| 1340 | | | | | 1345 | | | | | 1350 | | | | | |

| gga | ctt | cct | tct | gga | gga | gaa | gtt | cta | gag | att | tct | gtc | tct | gga | 4164 |
| Gly | Leu | Pro | Ser | Gly | Gly | Glu | Val | Leu | Glu | Ile | Ser | Val | Ser | Gly | |
| 1355 | | | | | 1360 | | | | | 1365 | | | | | |

| gta | gag | gac | atc | agt | ggg | ctt | cct | tct | gga | gag | gtt | gta | gag | act | 4209 |
| Val | Glu | Asp | Ile | Ser | Gly | Leu | Pro | Ser | Gly | Glu | Val | Val | Glu | Thr | |
| 1370 | | | | | 1375 | | | | | 1380 | | | | | |

| tct | gcc | tct | gga | ata | gag | gat | gtc | agt | gaa | ctt | cct | tca | gga | gaa | 4254 |
| Ser | Ala | Ser | Gly | Ile | Glu | Asp | Val | Ser | Glu | Leu | Pro | Ser | Gly | Glu | |
| 1385 | | | | | 1390 | | | | | 1395 | | | | | |

| ggt | cta | gag | acc | tct | gct | tct | gga | gta | gag | gac | ctc | agc | agg | ctc | 4299 |
| Gly | Leu | Glu | Thr | Ser | Ala | Ser | Gly | Val | Glu | Asp | Leu | Ser | Arg | Leu | |
| 1400 | | | | | 1405 | | | | | 1410 | | | | | |

| cct | tct | gga | gaa | gaa | gtt | cta | gag | att | tct | gcc | tct | gga | ttt | ggg | 4344 |
| Pro | Ser | Gly | Glu | Glu | Val | Leu | Glu | Ile | Ser | Ala | Ser | Gly | Phe | Gly | |
| 1415 | | | | | 1420 | | | | | 1425 | | | | | |

| gac | ctc | agt | gga | gtt | cct | tct | gga | gga | gaa | ggt | cta | gag | acc | tct | 4389 |
| Asp | Leu | Ser | Gly | Val | Pro | Ser | Gly | Gly | Glu | Gly | Leu | Glu | Thr | Ser | |
| 1430 | | | | | 1435 | | | | | 1440 | | | | | |

| gct | tct | gaa | gta | ggg | act | gac | ctc | agt | ggg | ctt | cct | tct | gga | agg | 4434 |
| Ala | Ser | Glu | Val | Gly | Thr | Asp | Leu | Ser | Gly | Leu | Pro | Ser | Gly | Arg | |
| 1445 | | | | | 1450 | | | | | 1455 | | | | | |

| gag | ggt | cta | gag | act | tca | gct | tct | gga | gct | gag | gac | ctc | agt | ggg | 4479 |
| Glu | Gly | Leu | Glu | Thr | Ser | Ala | Ser | Gly | Ala | Glu | Asp | Leu | Ser | Gly | |
| 1460 | | | | | 1465 | | | | | 1470 | | | | | |

| ttg | cct | tct | gga | aaa | gaa | gac | ttg | gtg | ggg | tca | gct | tct | gga | gac | 4524 |
| Leu | Pro | Ser | Gly | Lys | Glu | Asp | Leu | Val | Gly | Ser | Ala | Ser | Gly | Asp | |
| 1475 | | | | | 1480 | | | | | 1485 | | | | | |

| ttg | gac | ttg | ggc | aaa | ctg | cct | tct | gga | act | cta | gga | agt | ggg | caa | 4569 |
| Leu | Asp | Leu | Gly | Lys | Leu | Pro | Ser | Gly | Thr | Leu | Gly | Ser | Gly | Gln | |
| 1490 | | | | | 1495 | | | | | 1500 | | | | | |

| gct | cca | gaa | aca | agt | ggt | ctt | ccc | tct | gga | ttt | agt | ggt | gag | tat | 4614 |
| Ala | Pro | Glu | Thr | Ser | Gly | Leu | Pro | Ser | Gly | Phe | Ser | Gly | Glu | Tyr | |
| 1505 | | | | | 1510 | | | | | 1515 | | | | | |

| tct | ggg | gtg | gac | ctt | gga | agt | ggc | cca | ccc | tct | ggc | ctg | cct | gac | 4659 |
| Ser | Gly | Val | Asp | Leu | Gly | Ser | Gly | Pro | Pro | Ser | Gly | Leu | Pro | Asp | |
| 1520 | | | | | 1525 | | | | | 1530 | | | | | |

| ttt | agt | gga | ctt | cca | tct | gga | ttc | cca | act | gtt | tcc | cta | gtg | gat | 4704 |
| Phe | Ser | Gly | Leu | Pro | Ser | Gly | Phe | Pro | Thr | Val | Ser | Leu | Val | Asp | |
| 1535 | | | | | 1540 | | | | | 1545 | | | | | |

| tct | aca | ttg | gtg | gaa | gtg | gtc | aca | gcc | tcc | act | gca | agt | gaa | ctg | 4749 |
| Ser | Thr | Leu | Val | Glu | Val | Val | Thr | Ala | Ser | Thr | Ala | Ser | Glu | Leu | |
| 1550 | | | | | 1555 | | | | | 1560 | | | | | |

| gaa | ggg | agg | gga | acc | att | ggc | atc | agt | ggt | gca | gga | gaa | ata | tct | 4794 |
| Glu | Gly | Arg | Gly | Thr | Ile | Gly | Ile | Ser | Gly | Ala | Gly | Glu | Ile | Ser | |
| 1565 | | | | | 1570 | | | | | 1575 | | | | | |

| gga | ctg | ccc | tcc | agt | gag | ctg | gac | att | agt | ggg | aga | gct | agt | gga | 4839 |
| Gly | Leu | Pro | Ser | Ser | Glu | Leu | Asp | Ile | Ser | Gly | Arg | Ala | Ser | Gly | |
| 1580 | | | | | 1585 | | | | | 1590 | | | | | |

```
ctc cct tca gga act gaa ctc agt ggc caa gca tct ggg tct cct         4884
Leu Pro Ser Gly Thr Glu Leu Ser Gly Gln Ala Ser Gly Ser Pro
    1595                1600                1605 gat gtc agt ggg gaa ata cct gga ctc ttt ggt gtc agt gga cag         4929
Asp Val Ser Gly Glu Ile Pro Gly Leu Phe Gly Val Ser Gly Gln
1610                1615                1620 cca tca ggg ttt cct gac act agt ggg gaa aca tct gga gtg act         4974
Pro Ser Gly Phe Pro Asp Thr Ser Gly Glu Thr Ser Gly Val Thr
    1625                1630                1635 gag ctt agc ggg ctg tcc tct gga caa cca ggt gtt agt gga gaa         5019
Glu Leu Ser Gly Leu Ser Ser Gly Gln Pro Gly Val Ser Gly Glu
1640                1645                1650 gca tct gga gtt ctt tat ggc act agt caa ccc ttt ggc ata act         5064
Ala Ser Gly Val Leu Tyr Gly Thr Ser Gln Pro Phe Gly Ile Thr
    1655                1660                1665 gat ctg agt gga gaa aca tct ggg gtc cct gat ctc agt ggg cag         5109
Asp Leu Ser Gly Glu Thr Ser Gly Val Pro Asp Leu Ser Gly Gln
1670                1675                1680 cct tca ggg tta cca ggg ttc agt ggg gca aca tca gga gtc cct         5154
Pro Ser Gly Leu Pro Gly Phe Ser Gly Ala Thr Ser Gly Val Pro
    1685                1690                1695 gac ctg gtt tct ggt acc acg agt ggc agc ggt gaa tct tct ggg         5199
Asp Leu Val Ser Gly Thr Thr Ser Gly Ser Gly Glu Ser Ser Gly
1700                1705                1710 att aca ttt gtg gac acc agt ttg gtt gaa gtg gcc cct act aca         5244
Ile Thr Phe Val Asp Thr Ser Leu Val Glu Val Ala Pro Thr Thr
    1715                1720                1725 ttt aaa gaa gaa gaa ggc tta ggg tct gtg aac ctc agt ggc ctc         5289
Phe Lys Glu Glu Glu Gly Leu Gly Ser Val Glu Leu Ser Gly Leu
1730                1735                1740 cct tcc gga gag gca gat ctg tca ggc aaa tct ggg atg gtg gat         5334
Pro Ser Gly Glu Ala Asp Leu Ser Gly Lys Ser Gly Met Val Asp
    1745                1750                1755 gtc agt gga cag ttt tct gga aca gtc gat tcc agt ggg ttt aca         5379
Val Ser Gly Gln Phe Ser Gly Thr Val Asp Ser Ser Gly Phe Thr
1760                1765                1770 tcc cag act ccg gaa ttc agt ggc cta cca agt ggc ata gct gag         5424
Ser Gln Thr Pro Glu Phe Ser Gly Leu Pro Ser Gly Ile Ala Glu
    1775                1780                1785 gtc agt gga gaa tcc tcc aga gct gag att ggg agc agc ctg ccc         5469
Val Ser Gly Glu Ser Ser Arg Ala Glu Ile Gly Ser Ser Leu Pro
1790                1795                1800 tcg gga gca tat tat ggc agt gga act cca tct agt ttc ccc acg         5514
Ser Gly Ala Tyr Tyr Gly Ser Gly Thr Pro Ser Ser Phe Pro Thr
    1805                1810                1815 gtc tct ctt gta gac aga act ttg gtg gaa tct gta acc cag gct         5559
Val Ser Leu Val Asp Arg Thr Leu Val Glu Ser Val Thr Gln Ala
1820                1825                1830 cca aca gcc caa gag gca gga gaa ggg cct tct ggc att tta gaa         5604
Pro Thr Ala Gln Glu Ala Gly Glu Gly Pro Ser Gly Ile Leu Glu
    1835                1840                1845 ctc agt ggt gct cat tct gga gca cca gac atg tct ggg gag cat         5649
Leu Ser Gly Ala His Ser Gly Ala Pro Asp Met Ser Gly Glu His
1850                1855                1860 tct gga ttt ctg gac cta agt ggg ctg cag tcc ggg ctg ata gag         5694
Ser Gly Phe Leu Asp Leu Ser Gly Leu Gln Ser Gly Leu Ile Glu
    1865                1870                1875 ccc agc gga gag cca cca ggt act cca tat ttt agt ggg gat ttt         5739
Pro Ser Gly Glu Pro Pro Gly Thr Pro Tyr Phe Ser Gly Asp Phe
```

```
                1880                1885                1890
gcc agc acc acc aat gta agt gga gaa tcc tct gta gcc atg ggc    5784
Ala Ser Thr Thr Asn Val Ser Gly Glu Ser Ser Val Ala Met Gly
    1895                1900                1905 acc agt gga gag gcc tca gga ctt cca gaa gtt act tta atc act    5829
Thr Ser Gly Glu Ala Ser Gly Leu Pro Glu Val Thr Leu Ile Thr
    1910                1915                1920 tct gag ttc gtg gag ggt gtt act gaa cca act att tct cag gaa    5874
Ser Glu Phe Val Glu Gly Val Thr Glu Pro Thr Ile Ser Gln Glu
    1925                1930                1935 cta ggc caa agg ccc cct gtg aca cac aca ccc cag ctt ttt gag    5919
Leu Gly Gln Arg Pro Pro Val Thr His Thr Pro Gln Leu Phe Glu
    1940                1945                1950 tcc agt gga aaa gtc tcc aca gct ggg gac att agt gga gct acc    5964
Ser Ser Gly Lys Val Ser Thr Ala Gly Asp Ile Ser Gly Ala Thr
    1955                1960                1965 cca gtg ctc cct ggg tct gga gta gaa gta tca tca gtc cca gaa    6009
Pro Val Leu Pro Gly Ser Gly Val Glu Val Ser Ser Val Pro Glu
    1970                1975                1980 tct agc agt gag acg tcc gcc tat cct gaa gct ggg ttc ggg gca    6054
Ser Ser Ser Glu Thr Ser Ala Tyr Pro Glu Ala Gly Phe Gly Ala
    1985                1990                1995 tct gcc gcc cct gag gcc agc aga gaa gat tct ggg tcc cct gat    6099
Ser Ala Ala Pro Glu Ala Ser Arg Glu Asp Ser Gly Ser Pro Asp
    2000                2005                2010 ctg agt gaa acc acc tct gca ttc cac gaa gct aac ctt gag aga    6144
Leu Ser Glu Thr Thr Ser Ala Phe His Glu Ala Asn Leu Glu Arg
    2015                2020                2025 tcc tct ggc cta gga gtg agc ggc agc act ttg aca ttt caa gaa    6189
Ser Ser Gly Leu Gly Val Ser Gly Ser Thr Leu Thr Phe Gln Glu
    2030                2035                2040 ggc gag gcg tcc gct gcc cca gaa gtg agt gga gaa tcc acc acc    6234
Gly Glu Ala Ser Ala Ala Pro Glu Val Ser Gly Glu Ser Thr Thr
    2045                2050                2055 acc agt gat gtg ggg aca gag gca cca ggc ttg cct tca gcc act    6279
Thr Ser Asp Val Gly Thr Glu Ala Pro Gly Leu Pro Ser Ala Thr
    2060                2065                2070 ccc acg gct tct gga gac agg act gaa atc agc gga gac ctg tct    6324
Pro Thr Ala Ser Gly Asp Arg Thr Glu Ile Ser Gly Asp Leu Ser
    2075                2080                2085 ggt cac acc tcg cag ctg ggc gtt gtc atc agc acc agc atc cca    6369
Gly His Thr Ser Gln Leu Gly Val Val Ile Ser Thr Ser Ile Pro
    2090                2095                2100 gag tct gag tgg acc cag cag acc cag cgc cct gca gag acg cat    6414
Glu Ser Glu Trp Thr Gln Gln Thr Gln Arg Pro Ala Glu Thr His
    2105                2110                2115 cta gaa att gag tcc tca agc ctc ctg tac tca gga gaa gag act    6459
Leu Glu Ile Glu Ser Ser Ser Leu Leu Tyr Ser Gly Glu Glu Thr
    2120                2125                2130 cac aca gtc gaa aca gcc acc tcc cca aca gat gct tcc atc cca    6504
His Thr Val Glu Thr Ala Thr Ser Pro Thr Asp Ala Ser Ile Pro
    2135                2140                2145 gct tct ccg gaa tgg aaa cgt gaa tca gaa tca act gct gca gac    6549
Ala Ser Pro Glu Trp Lys Arg Glu Ser Glu Ser Thr Ala Ala Asp
    2150                2155                2160 cag gag gta tgt gag gag ggc tgg aac aag tac cag ggc cac tgt    6594
Gln Glu Val Cys Glu Glu Gly Trp Asn Lys Tyr Gln Gly His Cys
    2165                2170                2175 tac cgc cac ttc ccg gac cgc gag acc tgg gtg gat gct gag cgc    6639
```

```
Tyr Arg His Phe Pro Asp Arg Glu Thr Trp Val Asp Ala Glu Arg
    2180                2185                2190 cgg tgt cgg gag cag cag tca cac ctg agc agc atc gtc acc ccc    6684
Arg Cys Arg Glu Gln Gln Ser His Leu Ser Ser Ile Val Thr Pro
2195                2200                2205 gag gag cag gag ttt gtc aac aac aat gcc caa gac tac cag tgg    6729
Glu Glu Gln Glu Phe Val Asn Asn Asn Ala Gln Asp Tyr Gln Trp
    2210                2215                2220 atc ggc ctg aac gac agg acc atc gaa ggg gac ttc cgc tgg tca    6774
Ile Gly Leu Asn Asp Arg Thr Ile Glu Gly Asp Phe Arg Trp Ser
    2225                2230                2235 gat gga cac ccc atg caa ttt gag aac tgg cgc ccc aac cag cct    6819
Asp Gly His Pro Met Gln Phe Glu Asn Trp Arg Pro Asn Gln Pro
    2240                2245                2250 gac aac ttt ttt gcc gct gga gag gac tgt gtg gtg atg atc tgg    6864
Asp Asn Phe Phe Ala Ala Gly Glu Asp Cys Val Val Met Ile Trp
    2255                2260                2265 cac gag aag ggc gag tgg aat gat gtt ccc tgc aat tac cac ctc    6909
His Glu Lys Gly Glu Trp Asn Asp Val Pro Cys Asn Tyr His Leu
    2270                2275                2280 ccc ttc acg tgt aaa aag ggc aca gcc acc acc tac aaa cgc aga    6954
Pro Phe Thr Cys Lys Lys Gly Thr Ala Thr Thr Tyr Lys Arg Arg
    2285                2290                2295 cta cag aag cgg agc tca cgg cac cct cgg agg agc cgc ccc agc    6999
Leu Gln Lys Arg Ser Ser Arg His Pro Arg Arg Ser Arg Pro Ser
    2300                2305                2310 aca gcc cac tga gaagagcttc caggacgcac ccaggacgct gagcccagga    7051
Thr Ala His
    2315 gcctgccagg ctgacgtgca tcccacccag acggtgtcct cttcttgtcg ctttttgtca    7111 tataaggaat cccattaaaa aaaaaa                                    7137

<210> SEQ ID NO 20
<211> LENGTH: 2316
<212> TYPE: PRT
<213> ORGANISM: Homo sapiens

<400> SEQUENCE: 20

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Gly Thr Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
        115                 120                 125

Gly Val Tyr Arg Cys Glu Val Met His Gly Ile Glu Asp Ser Glu Ala
    130                 135                 140

Thr Leu Glu Val Val Val Lys Gly Ile Val Phe His Tyr Arg Ala Ile
```

-continued

```
            145                 150                 155                 160
Ser Thr Arg Tyr Thr Leu Asp Phe Asp Arg Ala Gln Arg Ala Cys Leu
                        165                 170                 175

Gln Asn Ser Ala Ile Ile Ala Thr Pro Glu Gln Leu Gln Ala Ala Tyr
                        180                 185                 190

Glu Asp Gly Phe His Gln Cys Asp Ala Gly Trp Leu Ala Asp Gln Thr
                        195                 200                 205

Val Arg Tyr Pro Ile His Thr Pro Arg Glu Gly Cys Tyr Gly Asp Lys
            210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Gly Glu Val Phe
                        245                 250                 255

Tyr Ala Thr Ser Pro Glu Lys Phe Thr Phe Gln Glu Ala Ala Asn Glu
                        260                 265                 270

Cys Arg Arg Leu Gly Ala Arg Leu Ala Thr Thr Gly His Val Tyr Leu
                        275                 280                 285

Ala Trp Gln Ala Gly Met Asp Met Cys Ser Ala Gly Trp Leu Ala Asp
                        290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                        325                 330                 335

Tyr Pro Asp Pro Ser Ser Arg Tyr Asp Ala Ile Cys Tyr Thr Gly Glu
                        340                 345                 350

Asp Phe Val Asp Ile Pro Glu Asn Phe Phe Gly Val Gly Gly Glu Glu
                        355                 360                 365

Asp Ile Thr Val Gln Thr Val Thr Trp Pro Asp Met Glu Leu Pro Leu
            370                 375                 380

Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
                        405                 410                 415

Pro Phe Thr Phe Ala Pro Glu Ile Gly Ala Thr Ala Phe Ala Glu Val
                        420                 425                 430

Glu Asn Glu Thr Gly Glu Ala Thr Arg Pro Trp Gly Phe Pro Thr Pro
                        435                 440                 445

Gly Leu Gly Pro Ala Thr Ala Phe Thr Ser Glu Asp Leu Val Val Gln
            450                 455                 460

Val Thr Ala Val Pro Gly Gln Pro His Leu Pro Gly Val Val Phe
465                 470                 475                 480

His Tyr Arg Pro Gly Pro Thr Arg Tyr Ser Leu Thr Phe Glu Glu Ala
                        485                 490                 495

Gln Gln Ala Cys Pro Gly Thr Gly Ala Val Ile Ala Ser Pro Glu Gln
                        500                 505                 510

Leu Gln Ala Ala Tyr Glu Ala Gly Tyr Glu Gln Cys Asp Ala Gly Trp
            515                 520                 525

Leu Arg Asp Gln Thr Val Arg Tyr Pro Ile Val Ser Pro Arg Thr Pro
            530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
                        565                 570                 575
```

```
Glu Gly Glu Val Phe Ala Thr Arg Leu Glu Gln Phe Thr Phe Gln
            580                 585                 590

Glu Ala Leu Glu Phe Cys Ser His Asn Ala Thr Ala Thr Thr Gly
        595                 600                 605

Gln Leu Tyr Ala Ala Trp Ser Arg Gly Leu Asp Lys Cys Tyr Ala Gly
    610                 615                 620

Trp Leu Ala Asp Gly Ser Leu Arg Tyr Pro Ile Val Thr Pro Arg Pro
625                 630                 635                 640

Ala Cys Gly Gly Asp Lys Pro Gly Val Arg Thr Val Tyr Leu Tyr Pro
                645                 650                 655

Asn Gln Thr Gly Leu Pro Asp Pro Leu Ser Arg His His Ala Phe Cys
            660                 665                 670

Phe Arg Gly Ile Ser Ala Val Pro Ser Pro Gly Glu Glu Glu Gly Gly
        675                 680                 685

Thr Pro Thr Ser Pro Ser Gly Val Glu Glu Trp Ile Val Thr Gln Val
        690                 695                 700

Val Pro Gly Val Ala Ala Val Pro Val Glu Glu Thr Thr Ala Val
705                 710                 715                 720

Pro Ser Gly Glu Thr Thr Ala Ile Leu Glu Phe Thr Thr Glu Pro Glu
                725                 730                 735

Asn Gln Thr Glu Trp Glu Pro Ala Tyr Thr Pro Val Gly Thr Ser Pro
            740                 745                 750

Leu Pro Gly Ile Leu Pro Thr Trp Pro Pro Thr Gly Ala Glu Thr Glu
        755                 760                 765

Glu Ser Thr Glu Gly Pro Ser Ala Thr Glu Val Pro Ser Ala Ser Glu
    770                 775                 780

Glu Pro Ser Pro Ser Glu Val Pro Phe Pro Ser Glu Glu Pro Ser Pro
785                 790                 795                 800

Ser Glu Glu Pro Phe Pro Ser Val Arg Pro Phe Pro Ser Val Glu Leu
                805                 810                 815

Phe Pro Ser Glu Glu Pro Phe Pro Ser Lys Glu Pro Ser Pro Ser Glu
            820                 825                 830

Glu Pro Ser Ala Ser Glu Pro Tyr Thr Pro Ser Pro Pro Glu Pro
        835                 840                 845

Ser Trp Thr Glu Leu Pro Ser Ser Gly Glu Glu Ser Gly Ala Pro Asp
    850                 855                 860

Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
                885                 890                 895

Asp Leu Asp Ser Ser Gly Leu Thr Ser Thr Val Gly Ser Gly Leu Thr
            900                 905                 910

Val Glu Ser Gly Leu Pro Ser Gly Asp Glu Arg Ile Glu Trp Pro
        915                 920                 925

Ser Thr Pro Thr Val Gly Glu Leu Pro Ser Gly Ala Glu Ile Leu Glu
    930                 935                 940

Gly Ser Ala Ser Gly Val Gly Asp Leu Ser Gly Leu Pro Ser Gly Glu
945                 950                 955                 960

Val Leu Glu Thr Ser Ala Ser Gly Val Gly Asp Leu Ser Gly Leu Pro
                965                 970                 975

Ser Gly Glu Val Leu Glu Thr Thr Ala Pro Gly Val Glu Asp Ile Ser
            980                 985                 990
```

Gly Leu Pro Ser Gly Glu Val Leu Glu Thr Thr Ala Pro Gly Val Glu
            995                 1000                1005

Asp Ile Ser Gly Leu Pro Ser Gly Glu Val Leu Glu Thr Thr Ala
    1010                1015                1020

Pro Gly Val Glu Asp Ile Ser Gly Leu Pro Ser Gly Glu Val Leu
    1025                1030                1035

Glu Thr Thr Ala Pro Gly Val Glu Asp Ile Ser Gly Leu Pro Ser
    1040                1045                1050

Gly Glu Val Leu Glu Thr Thr Ala Pro Gly Val Glu Asp Ile Ser
    1055                1060                1065

Gly Leu Pro Ser Gly Glu Val Leu Glu Thr Ala Ala Pro Gly Val
    1070                1075                1080

Glu Asp Ile Ser Gly Leu Pro Ser Gly Glu Val Leu Glu Thr Ala
    1085                1090                1095

Ala Pro Gly Val Glu Asp Ile Ser Gly Leu Pro Ser Gly Glu Val
    1100                1105                1110

Leu Glu Thr Ala Ala Pro Gly Val Glu Asp Ile Ser Gly Leu Pro
    1115                1120                1125

Ser Gly Glu Val Leu Glu Thr Ala Ala Pro Gly Val Glu Asp Ile
    1130                1135                1140

Ser Gly Leu Pro Ser Gly Glu Val Leu Glu Thr Ala Ala Pro Gly
    1145                1150                1155

Val Glu Asp Ile Ser Gly Leu Pro Ser Gly Val Leu Glu Thr
    1160                1165                1170

Ala Ala Pro Gly Val Glu Asp Ile Ser Gly Leu Pro Ser Gly Glu
    1175                1180                1185

Val Leu Glu Thr Ala Ala Pro Gly Val Glu Asp Ile Ser Gly Leu
    1190                1195                1200

Pro Ser Gly Glu Val Leu Glu Thr Ala Ala Pro Gly Val Glu Asp
    1205                1210                1215

Ile Ser Gly Leu Pro Ser Gly Glu Val Leu Glu Thr Ala Ala Pro
    1220                1225                1230

Gly Val Glu Asp Ile Ser Gly Leu Pro Ser Gly Glu Val Leu Glu
    1235                1240                1245

Thr Ala Ala Pro Gly Val Glu Asp Ile Ser Gly Leu Pro Ser Gly
    1250                1255                1260

Glu Val Leu Glu Thr Ala Ala Pro Gly Val Glu Asp Ile Ser Gly
    1265                1270                1275

Leu Pro Ser Gly Glu Val Leu Glu Thr Thr Ala Pro Gly Val Glu
    1280                1285                1290

Glu Ile Ser Gly Leu Pro Ser Gly Glu Val Leu Glu Thr Thr Ala
    1295                1300                1305

Pro Gly Val Asp Glu Ile Ser Gly Leu Pro Ser Gly Glu Val Leu
    1310                1315                1320

Glu Thr Thr Ala Pro Gly Val Glu Glu Ile Ser Gly Leu Pro Ser
    1325                1330                1335

Gly Glu Val Leu Glu Thr Ser Thr Ser Ala Val Gly Asp Leu Ser
    1340                1345                1350

Gly Leu Pro Ser Gly Gly Glu Val Leu Glu Ile Ser Val Ser Gly
    1355                1360                1365

Val Glu Asp Ile Ser Gly Leu Pro Ser Gly Glu Val Val Glu Thr
    1370                1375                1380

Ser Ala Ser Gly Ile Glu Asp Val Ser Glu Leu Pro Ser Gly Glu

```
                1385                1390                1395

Gly Leu Glu Thr Ser Ala Ser Gly Val Glu Asp Leu Ser Arg Leu
        1400                1405                1410

Pro Ser Gly Glu Glu Val Leu Glu Ile Ser Ala Ser Gly Phe Gly
        1415                1420                1425

Asp Leu Ser Gly Val Pro Ser Gly Gly Glu Gly Leu Glu Thr Ser
        1430                1435                1440

Ala Ser Glu Val Gly Thr Asp Leu Ser Gly Leu Pro Ser Gly Arg
        1445                1450                1455

Glu Gly Leu Glu Thr Ser Ala Ser Gly Ala Glu Asp Leu Ser Gly
        1460                1465                1470

Leu Pro Ser Gly Lys Glu Asp Leu Val Gly Ser Ala Ser Gly Asp
        1475                1480                1485

Leu Asp Leu Gly Lys Leu Pro Ser Gly Thr Leu Gly Ser Gly Gln
        1490                1495                1500

Ala Pro Glu Thr Ser Gly Leu Pro Ser Gly Phe Ser Gly Glu Tyr
        1505                1510                1515

Ser Gly Val Asp Leu Gly Ser Gly Pro Pro Ser Gly Leu Pro Asp
        1520                1525                1530

Phe Ser Gly Leu Pro Ser Gly Phe Pro Thr Val Ser Leu Val Asp
        1535                1540                1545

Ser Thr Leu Val Glu Val Val Thr Ala Ser Thr Ala Ser Glu Leu
        1550                1555                1560

Glu Gly Arg Gly Thr Ile Gly Ile Ser Gly Ala Gly Glu Ile Ser
        1565                1570                1575

Gly Leu Pro Ser Ser Glu Leu Asp Ile Ser Gly Arg Ala Ser Gly
        1580                1585                1590

Leu Pro Ser Gly Thr Glu Leu Ser Gly Gln Ala Ser Gly Ser Pro
        1595                1600                1605

Asp Val Ser Gly Glu Ile Pro Gly Leu Phe Gly Val Ser Gly Gln
        1610                1615                1620

Pro Ser Gly Phe Pro Asp Thr Ser Gly Glu Thr Ser Gly Val Thr
        1625                1630                1635

Glu Leu Ser Gly Leu Ser Ser Gly Gln Pro Gly Val Ser Gly Glu
        1640                1645                1650

Ala Ser Gly Val Leu Tyr Gly Thr Ser Gln Pro Phe Gly Ile Thr
        1655                1660                1665

Asp Leu Ser Gly Glu Thr Ser Gly Val Pro Asp Leu Ser Gly Gln
        1670                1675                1680

Pro Ser Gly Leu Pro Gly Phe Ser Gly Ala Thr Ser Gly Val Pro
        1685                1690                1695

Asp Leu Val Ser Gly Thr Thr Ser Gly Ser Gly Glu Ser Ser Gly
        1700                1705                1710

Ile Thr Phe Val Asp Thr Ser Leu Val Glu Val Ala Pro Thr Thr
        1715                1720                1725

Phe Lys Glu Glu Glu Gly Leu Gly Ser Val Glu Leu Ser Gly Leu
        1730                1735                1740

Pro Ser Gly Glu Ala Asp Leu Ser Gly Lys Ser Gly Met Val Asp
        1745                1750                1755

Val Ser Gly Gln Phe Ser Gly Thr Val Asp Ser Ser Gly Phe Thr
        1760                1765                1770

Ser Gln Thr Pro Glu Phe Ser Gly Leu Pro Ser Gly Ile Ala Glu
        1775                1780                1785
```

```
Val Ser Gly Glu Ser Ser Arg Ala Glu Ile Gly Ser Ser Leu Pro
    1790            1795                1800

Ser Gly Ala Tyr Tyr Gly Ser Gly Thr Pro Ser Ser Phe Pro Thr
    1805            1810                1815

Val Ser Leu Val Asp Arg Thr Leu Val Glu Ser Val Thr Gln Ala
    1820            1825                1830

Pro Thr Ala Gln Glu Ala Gly Glu Gly Pro Ser Gly Ile Leu Glu
    1835            1840                1845

Leu Ser Gly Ala His Ser Gly Ala Pro Asp Met Ser Gly Glu His
    1850            1855                1860

Ser Gly Phe Leu Asp Leu Ser Gly Leu Gln Ser Gly Leu Ile Glu
    1865            1870                1875

Pro Ser Gly Glu Pro Pro Gly Thr Pro Tyr Phe Ser Gly Asp Phe
    1880            1885                1890

Ala Ser Thr Thr Asn Val Ser Gly Glu Ser Val Ala Met Gly
    1895            1900                1905

Thr Ser Gly Glu Ala Ser Gly Leu Pro Glu Val Thr Leu Ile Thr
    1910            1915                1920

Ser Glu Phe Val Glu Gly Val Thr Glu Pro Thr Ile Ser Gln Glu
    1925            1930                1935

Leu Gly Gln Arg Pro Pro Val Thr His Thr Pro Gln Leu Phe Glu
    1940            1945                1950

Ser Ser Gly Lys Val Ser Thr Ala Gly Asp Ile Ser Gly Ala Thr
    1955            1960                1965

Pro Val Leu Pro Gly Ser Gly Val Glu Val Ser Ser Val Pro Glu
    1970            1975                1980

Ser Ser Ser Glu Thr Ser Ala Tyr Pro Glu Ala Gly Phe Gly Ala
    1985            1990                1995

Ser Ala Ala Pro Glu Ala Ser Arg Glu Asp Ser Gly Ser Pro Asp
    2000            2005                2010

Leu Ser Glu Thr Thr Ser Ala Phe His Glu Ala Asn Leu Glu Arg
    2015            2020                2025

Ser Ser Gly Leu Gly Val Ser Gly Ser Thr Leu Thr Phe Gln Glu
    2030            2035                2040

Gly Glu Ala Ser Ala Ala Pro Glu Val Ser Gly Glu Ser Thr Thr
    2045            2050                2055

Thr Ser Asp Val Gly Thr Glu Ala Pro Gly Leu Pro Ser Ala Thr
    2060            2065                2070

Pro Thr Ala Ser Gly Asp Arg Thr Glu Ile Ser Gly Asp Leu Ser
    2075            2080                2085

Gly His Thr Ser Gln Leu Gly Val Val Ile Ser Thr Ser Ile Pro
    2090            2095                2100

Glu Ser Glu Trp Thr Gln Gln Thr Gln Arg Pro Ala Glu Thr His
    2105            2110                2115

Leu Glu Ile Glu Ser Ser Ser Leu Leu Tyr Ser Gly Glu Glu Thr
    2120            2125                2130

His Thr Val Glu Thr Ala Thr Ser Pro Thr Asp Ala Ser Ile Pro
    2135            2140                2145

Ala Ser Pro Glu Trp Lys Arg Glu Ser Glu Ser Thr Ala Ala Asp
    2150            2155                2160

Gln Glu Val Cys Glu Glu Gly Trp Asn Lys Tyr Gln Gly His Cys
    2165            2170                2175
```

```
Tyr Arg His Phe Pro Asp Arg Glu Thr Trp Val Asp Ala Glu Arg
    2180                2185                2190

Arg Cys Arg Glu Gln Gln Ser His Leu Ser Ser Ile Val Thr Pro
    2195                2200                2205

Glu Glu Gln Glu Phe Val Asn Asn Asn Ala Gln Asp Tyr Gln Trp
    2210                2215                2220

Ile Gly Leu Asn Asp Arg Thr Ile Glu Gly Asp Phe Arg Trp Ser
    2225                2230                2235

Asp Gly His Pro Met Gln Phe Glu Asn Trp Arg Pro Asn Gln Pro
    2240                2245                2250

Asp Asn Phe Phe Ala Ala Gly Glu Asp Cys Val Val Met Ile Trp
    2255                2260                2265

His Glu Lys Gly Glu Trp Asn Asp Val Pro Cys Asn Tyr His Leu
    2270                2275                2280

Pro Phe Thr Cys Lys Lys Gly Thr Ala Thr Thr Tyr Lys Arg Arg
    2285                2290                2295

Leu Gln Lys Arg Ser Ser Arg His Pro Arg Arg Ser Arg Pro Ser
    2300                2305                2310

Thr Ala His
    2315

<210> SEQ ID NO 21
<211> LENGTH: 1108
<212> TYPE: DNA
<213> ORGANISM: Homo sapiens
<220> FEATURE:
<221> NAME/KEY: CDS
<222> LOCATION: (143)..(1096)

<400> SEQUENCE: 21
gagtgagtga gagggcagag gaaatactca atctgtgcca ctcactgcct tgagcctgct      60
tcctcactcc aggactgcca gaggctcact cccttgagcc tgcttcctca ctccaggact     120
gccagaggaa gcaatcacca aa atg aag act gct tta att ttg ctc agc att     172
                         Met Lys Thr Ala Leu Ile Leu Leu Ser Ile
                          1               5                  10 ttg gga atg gcc tgt gct ttc tca atg aaa aat ttg cat cga aga gtc     220
Leu Gly Met Ala Cys Ala Phe Ser Met Lys Asn Leu His Arg Arg Val
            15                  20                  25 aaa ata gag gat tct gaa gaa aat ggg gtc ttt aag tac agg cca cga     268
Lys Ile Glu Asp Ser Glu Glu Asn Gly Val Phe Lys Tyr Arg Pro Arg
        30                  35                  40 tat tat ctt tac aag cat gcc tac ttt tat cct cat tta aaa cga ttt     316
Tyr Tyr Leu Tyr Lys His Ala Tyr Phe Tyr Pro His Leu Lys Arg Phe
    45                  50                  55 cca gtt cag ggc agt agt gac tca tcc gaa gaa aat gga gat gac agt     364
Pro Val Gln Gly Ser Ser Asp Ser Ser Glu Glu Asn Gly Asp Asp Ser
60                  65                  70 tca gaa gag gag gag gaa gaa gag gag act tca aat gaa gga gaa aac     412
Ser Glu Glu Glu Glu Glu Glu Glu Thr Ser Asn Glu Gly Glu Asn
75                  80                  85                  90 aat gaa gaa tcg aat gaa gat gaa gac tct gag gct gag aat acc aca     460
Asn Glu Glu Ser Asn Glu Asp Glu Asp Ser Glu Ala Glu Asn Thr Thr
                95                 100                 105 ctt tct gct aca aca ctg ggc tat gga gag gac gcc acg cct ggc aca     508
Leu Ser Ala Thr Thr Leu Gly Tyr Gly Glu Asp Ala Thr Pro Gly Thr
            110                 115                 120 ggg tat aca ggg tta gct gca atc cag ctt ccc aag aag gct ggg gat     556
Gly Tyr Thr Gly Leu Ala Ala Ile Gln Leu Pro Lys Lys Ala Gly Asp
```

```
                125                 130                 135
ata aca aac aaa gct aca aaa gag aag gaa agt gat gaa gaa gag       604
Ile Thr Asn Lys Ala Thr Lys Glu Lys Glu Ser Asp Glu Glu Glu
    140                 145                 150 gag gaa gag gaa gga aat gaa aac gaa gaa agc gaa gca gaa gtg gat   652
Glu Glu Glu Glu Gly Asn Glu Asn Glu Glu Ser Glu Ala Glu Val Asp
155                 160                 165                 170 gaa aac gaa caa ggc ata aac ggc acc agt acc aac agc aca gag gca   700
Glu Asn Glu Gln Gly Ile Asn Gly Thr Ser Thr Asn Ser Thr Glu Ala
                175                 180                 185 gaa aac ggc aac ggc agc agc gga gga gac aat gga gaa gaa ggg gaa   748
Glu Asn Gly Asn Gly Ser Ser Gly Gly Asp Asn Gly Glu Glu Gly Glu
            190                 195                 200 gaa gaa agt gtc act gga gcc aat gca gaa ggc acc aca gag acc gga   796
Glu Glu Ser Val Thr Gly Ala Asn Ala Glu Gly Thr Thr Glu Thr Gly
        205                 210                 215 ggg cag ggc aag ggc acc tcg aag aca aca acc tct cca aat ggt ggg   844
Gly Gln Gly Lys Gly Thr Ser Lys Thr Thr Thr Ser Pro Asn Gly Gly
    220                 225                 230 ttt gaa cct aca acc cca cca caa gtc tat aga acc act tcc cca cct   892
Phe Glu Pro Thr Thr Pro Pro Gln Val Tyr Arg Thr Thr Ser Pro Pro
235                 240                 245                 250 ttt ggg aaa acc acc acc gtt gaa tac gag ggg gag tac gaa tac acg   940
Phe Gly Lys Thr Thr Thr Val Glu Tyr Glu Gly Glu Tyr Glu Tyr Thr
                255                 260                 265 ggc gtc aat gaa tac gac aat gga tat gaa atc tat gaa agt gag aac   988
Gly Val Asn Glu Tyr Asp Asn Gly Tyr Glu Ile Tyr Glu Ser Glu Asn
            270                 275                 280 ggg gaa cct cgt ggg gac aat tac cga gcc tat gaa gat gag tac agc   1036
Gly Glu Pro Arg Gly Asp Asn Tyr Arg Ala Tyr Glu Asp Glu Tyr Ser
        285                 290                 295 tac ttt aaa gga caa ggc tac gat ggc tat gat ggt cag aat tac tac   1084
Tyr Phe Lys Gly Gln Gly Tyr Asp Gly Tyr Asp Gly Gln Asn Tyr Tyr
    300                 305                 310 cac cac cag tga agctccagcc tg                                     1108
His His Gln
315

<210> SEQ ID NO 22
<211> LENGTH: 317
<212> TYPE: PRT
<213> ORGANISM: Homo sapiens

<400> SEQUENCE: 22

Met Lys Thr Ala Leu Ile Leu Leu Ser Ile Leu Gly Met Ala Cys Ala
1               5                   10                  15

Phe Ser Met Lys Asn Leu His Arg Arg Val Lys Ile Glu Asp Ser Glu
                20                  25                  30

Glu Asn Gly Val Phe Lys Tyr Arg Pro Arg Tyr Tyr Leu Tyr Lys His
            35                  40                  45

Ala Tyr Phe Tyr Pro His Leu Lys Arg Phe Pro Val Gln Gly Ser Ser
        50                  55                  60

Asp Ser Ser Glu Glu Asn Gly Asp Asp Ser Glu Glu Glu Glu Glu Glu
65                  70                  75                  80

Glu Glu Glu Thr Ser Asn Glu Gly Glu Asn Asn Glu Ser Asn Glu
                85                  90                  95

Asp Glu Asp Ser Glu Ala Glu Asn Thr Thr Leu Ser Ala Thr Thr Leu
            100                 105                 110
```

```
Gly Tyr Gly Glu Asp Ala Thr Pro Gly Thr Gly Tyr Thr Gly Leu Ala
            115                 120                 125
Ala Ile Gln Leu Pro Lys Lys Ala Gly Asp Ile Thr Asn Lys Ala Thr
        130                 135                 140
Lys Glu Lys Glu Ser Asp Glu Glu Glu Glu Glu Glu Glu Glu Gly Asn
145                 150                 155                 160
Glu Asn Glu Glu Ser Glu Ala Glu Val Asp Glu Asn Glu Gln Gly Ile
                165                 170                 175
Asn Gly Thr Ser Thr Asn Ser Thr Glu Ala Glu Asn Gly Asn Gly Ser
            180                 185                 190
Ser Gly Gly Asp Asn Gly Glu Glu Gly Glu Glu Ser Val Thr Gly
        195                 200                 205
Ala Asn Ala Glu Gly Thr Thr Glu Thr Gly Gly Gln Gly Lys Gly Thr
    210                 215                 220
Ser Lys Thr Thr Thr Ser Pro Asn Gly Gly Phe Glu Pro Thr Thr Pro
225                 230                 235                 240
Pro Gln Val Tyr Arg Thr Thr Ser Pro Pro Phe Gly Lys Thr Thr Thr
                245                 250                 255
Val Glu Tyr Glu Gly Glu Tyr Glu Tyr Thr Gly Val Asn Glu Tyr Asp
            260                 265                 270
Asn Gly Tyr Glu Ile Tyr Glu Ser Glu Asn Gly Glu Pro Arg Gly Asp
        275                 280                 285
Asn Tyr Arg Ala Tyr Glu Asp Glu Tyr Ser Tyr Phe Lys Gly Gln Gly
    290                 295                 300
Tyr Asp Gly Tyr Asp Gly Gln Asn Tyr Tyr His His Gln
305                 310                 315

<210> SEQ ID NO 23
<211> LENGTH: 498
<212> TYPE: DNA
<213> ORGANISM: Homo sapiens
<220> FEATURE:
<221> NAME/KEY: CDS
<222> LOCATION: (19)..(321)

<400> SEQUENCE: 23
cgcagccacc gagacacc atg aga gcc ctc aca ctc ctc gcc cta ttg gcc        51
                   Met Arg Ala Leu Thr Leu Leu Ala Leu Leu Ala
                    1               5                   10 ctg gcc gca ctt tgc atc gct ggc cag gca ggt gcg aag ccc agc ggt        99
Leu Ala Ala Leu Cys Ile Ala Gly Gln Ala Gly Ala Lys Pro Ser Gly
            15                  20                  25 gca gag tcc agc aaa ggt gca gcc ttt gtg tcc aag cag gag ggc agc       147
Ala Glu Ser Ser Lys Gly Ala Ala Phe Val Ser Lys Gln Glu Gly Ser
        30                  35                  40 gag gta gtg aag aga ccc agg cgc tac ctg tat caa tgg ctg gga gcc       195
Glu Val Val Lys Arg Pro Arg Arg Tyr Leu Tyr Gln Trp Leu Gly Ala
    45                  50                  55 cca gtc ccc tac ccg gat ccc ctg gag ccc agg agg gag gtg tgt gag       243
Pro Val Pro Tyr Pro Asp Pro Leu Glu Pro Arg Arg Glu Val Cys Glu
60                  65                  70                  75 ctc aat ccg gac tgt gac gag ttg gct gac cac atc ggc ttt cag gag       291
Leu Asn Pro Asp Cys Asp Glu Leu Ala Asp His Ile Gly Phe Gln Glu
                80                  85                  90 gcc tat cgg cgc ttc tac ggc ccg gtc tag ggtgtcgctc tgctggcctg         341
Ala Tyr Arg Arg Phe Tyr Gly Pro Val
            95                  100 gccggcaacc ccagttctgc tcctctccag gcaccttct ttcctcttcc ccttgccctt      401
```

```
gccctgacct cccagcccta tgatgtggg gtccccatca tcccagctgc tcccaaataa    461
actccagaag aggaatctga aaaaaaaaaa aaaaaaa                             498
```

<210> SEQ ID NO 24
<211> LENGTH: 100
<212> TYPE: PRT
<213> ORGANISM: Homo sapiens

<400> SEQUENCE: 24

```
Met Arg Ala Leu Thr Leu Leu Ala Leu Leu Ala Ala Leu Cys
1               5                   10                  15

Ile Ala Gly Gln Ala Gly Ala Lys Pro Ser Gly Ala Glu Ser Ser Lys
                20                  25                  30

Gly Ala Ala Phe Val Ser Lys Gln Glu Gly Ser Glu Val Val Lys Arg
            35                  40                  45

Pro Arg Arg Tyr Leu Tyr Gln Trp Leu Gly Ala Pro Val Pro Tyr Pro
    50                  55                  60

Asp Pro Leu Glu Pro Arg Arg Glu Val Cys Glu Leu Asn Pro Asp Cys
65                  70                  75                  80

Asp Glu Leu Ala Asp His Ile Gly Phe Gln Glu Ala Tyr Arg Arg Phe
                85                  90                  95

Tyr Gly Pro Val
            100
```

<210> SEQ ID NO 25
<211> LENGTH: 2383
<212> TYPE: DNA
<213> ORGANISM: Homo sapiens
<220> FEATURE:
<221> NAME/KEY: CDS
<222> LOCATION: (320)..(1825)

<400> SEQUENCE: 25

```
ctccttcaag ccctcagtca gttgtgcagg agaaaggggg cggttggctt tctcctttca    60
agaacgagtt attttcagct gctgactgga gacggtgcac gtctggatac gagagcattt   120
ccactatggg actggataca aacacacacc cggcagactt caagagtctc agactgagga   180
gaaagccttt ccttctgctg ctactgctgc tgccgctgct tttgaaagtc cactcctttc   240 atggttttc ctgccaaacc agaggcacct ttgctgctgc cgctgttctc tttggtgtca   300
ttcagcggct ggccagagg atg aga ctc ccc aaa ctc ctc act ttc ttg ctt   352
                     Met Arg Leu Pro Lys Leu Leu Thr Phe Leu Leu
                     1               5                   10 tgg tac ctg gct tgg ctg gac ctg gaa ttc atc tgc act gtg ttg ggt   400
Trp Tyr Leu Ala Trp Leu Asp Leu Glu Phe Ile Cys Thr Val Leu Gly
            15                  20                  25 gcc cct gac ttg ggc cag aga ccc cag ggg acc agg cca gga ttg gcc   448
Ala Pro Asp Leu Gly Gln Arg Pro Gln Gly Thr Arg Pro Gly Leu Ala
        30                  35                  40 aaa gca gag gcc aag gag agg ccc ccc ctg gcc cgg aac gtc ttc agg   496
Lys Ala Glu Ala Lys Glu Arg Pro Pro Leu Ala Arg Asn Val Phe Arg
    45                  50                  55 cca ggg ggt cac agc tat ggt ggg ggg gcc acc aat gcc aat gcc agg   544
Pro Gly Gly His Ser Tyr Gly Gly Gly Ala Thr Asn Ala Asn Ala Arg
60                  65                  70                  75 gca aag gga ggc acc ggg cag aca gga ggc ctg aca cag ccc aag aag   592
Ala Lys Gly Gly Thr Gly Gln Thr Gly Gly Leu Thr Gln Pro Lys Lys
                80                  85                  90
```

-continued

```
gat gaa ccc aaa aag ctg ccc ccc aga ccg ggc ggc cct gaa ccc aag    640
Asp Glu Pro Lys Lys Leu Pro Pro Arg Pro Gly Gly Pro Glu Pro Lys
         95                 100                 105 cca gga cac cct ccc caa aca agg cag gct aca gcc cgg act gtg acc    688
Pro Gly His Pro Pro Gln Thr Arg Gln Ala Thr Ala Arg Thr Val Thr
            110                 115                 120 cca aaa gga cag ctt ccc gga ggc aag gca ccc cca aaa gca gga tct    736
Pro Lys Gly Gln Leu Pro Gly Gly Lys Ala Pro Pro Lys Ala Gly Ser
        125                 130                 135 gtc ccc agc tcc ttc ctg ctg aag aag gcc agg gag ccc ggg ccc cca    784
Val Pro Ser Ser Phe Leu Leu Lys Lys Ala Arg Glu Pro Gly Pro Pro
140                 145                 150                 155 cga gag ccc aag gag ccg ttt cgc cca ccc ccc atc aca ccc cac gag    832
Arg Glu Pro Lys Glu Pro Phe Arg Pro Pro Pro Ile Thr Pro His Glu
                160                 165                 170 tac atg ctc tcg ctg tac agg acg ctg tcc gat gct gac aga aag gga    880
Tyr Met Leu Ser Leu Tyr Arg Thr Leu Ser Asp Ala Asp Arg Lys Gly
            175                 180                 185 ggc aac agc agc gtg aag ttg gag gct ggc ctg gcc aac acc atc acc    928
Gly Asn Ser Ser Val Lys Leu Glu Ala Gly Leu Ala Asn Thr Ile Thr
        190                 195                 200 agc ttt att gac aaa ggg caa gat gac cga ggt ccc gtg gtc agg aag    976
Ser Phe Ile Asp Lys Gly Gln Asp Asp Arg Gly Pro Val Val Arg Lys
205                 210                 215 cag agg tac gtg ttt gac att agt gcc ctg gag aag gat ggg ctg ctg   1024
Gln Arg Tyr Val Phe Asp Ile Ser Ala Leu Glu Lys Asp Gly Leu Leu
220                 225                 230                 235 ggg gcc gag ctg cgg atc ttg cgg aag aag ccc tcg gac acg gcc aag   1072
Gly Ala Glu Leu Arg Ile Leu Arg Lys Lys Pro Ser Asp Thr Ala Lys
                240                 245                 250 cca gcg gcc ccc gga ggc ggg cgg gct gcc cag ctg aag ctg tcc agc   1120
Pro Ala Ala Pro Gly Gly Gly Arg Ala Ala Gln Leu Lys Leu Ser Ser
            255                 260                 265 tgc ccc agc ggc cgg cag ccg gcc tcc ttg ctg gat gtg cgc tcc gtg   1168
Cys Pro Ser Gly Arg Gln Pro Ala Ser Leu Leu Asp Val Arg Ser Val
        270                 275                 280 cca ggc ctg gac gga tct ggc tgg gag gtg ttc gac atc tgg aag ctc   1216
Pro Gly Leu Asp Gly Ser Gly Trp Glu Val Phe Asp Ile Trp Lys Leu
285                 290                 295 ttc cga aac ttt aag aac tcg gcc cag ctg tgc ctg gag ctg gag gcc   1264
Phe Arg Asn Phe Lys Asn Ser Ala Gln Leu Cys Leu Glu Leu Glu Ala
300                 305                 310                 315 tgg gaa cgg ggc agg gcc gtg gac ctc cgt ggc ctg ggc ttc gac cgc   1312
Trp Glu Arg Gly Arg Ala Val Asp Leu Arg Gly Leu Gly Phe Asp Arg
                320                 325                 330 gcc gcc cgg cag gtc cac gag aag gcc ctg ttc ctg gtg ttt ggc cgc   1360
Ala Ala Arg Gln Val His Glu Lys Ala Leu Phe Leu Val Phe Gly Arg
            335                 340                 345 acc aag aaa cgg gac ctg ttc ttt aat gag att aag gcc cgc tct ggc   1408
Thr Lys Lys Arg Asp Leu Phe Phe Asn Glu Ile Lys Ala Arg Ser Gly
        350                 355                 360 cag gac gat aag acc gtg tat gag tac ctg ttc agc cag cgg cga aaa   1456
Gln Asp Asp Lys Thr Val Tyr Glu Tyr Leu Phe Ser Gln Arg Arg Lys
365                 370                 375 cgg cgg gcc cca ctg gcc act cgc cag ggc aag cga ccc agc aag aac   1504
Arg Arg Ala Pro Leu Ala Thr Arg Gln Gly Lys Arg Pro Ser Lys Asn
380                 385                 390                 395 ctt aag gct cgc tgc agt cgg aag gca ctg cat gtc aac ttc aag gac   1552
Leu Lys Ala Arg Cys Ser Arg Lys Ala Leu His Val Asn Phe Lys Asp
                400                 405                 410
```

| | | | | | | | | | | | | | | | |
|---|---|---|---|---|---|---|---|---|---|---|---|---|---|---|---|
| atg | ggc | tgg | gac | gac | tgg | atc | atc | gca | ccc | ctt | gag | tac | gag | gct | ttc | 1600 |
| Met | Gly | Trp | Asp | Asp | Trp | Ile | Ile | Ala | Pro | Leu | Glu | Tyr | Glu | Ala | Phe | |
| | | | 415 | | | | 420 | | | | | 425 | | | | |
| cac | tgc | gag | ggg | ctg | tgc | gag | ttc | cca | ttg | cgc | tcc | cac | ctg | gag | ccc | 1648 |
| His | Cys | Glu | Gly | Leu | Cys | Glu | Phe | Pro | Leu | Arg | Ser | His | Leu | Glu | Pro | |
| | | | 430 | | | | 435 | | | | | 440 | | | | |
| acg | aat | cat | gca | gtc | atc | cag | acc | ctg | atg | aac | tcc | atg | gac | ccc | gag | 1696 |
| Thr | Asn | His | Ala | Val | Ile | Gln | Thr | Leu | Met | Asn | Ser | Met | Asp | Pro | Glu | |
| | | 445 | | | | | 450 | | | | | 455 | | | | |
| tcc | aca | cca | ccc | acc | tgc | tgt | gtg | ccc | acg | cgg | ctg | agt | ccc | atc | agc | 1744 |
| Ser | Thr | Pro | Pro | Thr | Cys | Cys | Val | Pro | Thr | Arg | Leu | Ser | Pro | Ile | Ser | |
| 460 | | | | | 465 | | | | | 470 | | | | | 475 | |
| atc | ctc | ttc | att | gac | tct | gcc | aac | aac | gtg | gtg | tat | aag | cag | tat | gag | 1792 |
| Ile | Leu | Phe | Ile | Asp | Ser | Ala | Asn | Asn | Val | Val | Tyr | Lys | Gln | Tyr | Glu | |
| | | | | 480 | | | | | 485 | | | | | 490 | | |
| gac | atg | gtc | gtg | gag | tcg | tgt | ggc | tgc | agg | tag | cagcactggc | | cctctgtctt | | | 1845 |
| Asp | Met | Val | Val | Glu | Ser | Cys | Gly | Cys | Arg | | | | | | | |
| | | | | 495 | | | | 500 | | | | | | | | | cctgggtggc acatcccaag agccccttcc tgcactcctg gaatcacaga ggggtcagga 1905 agctgtggca ggagcatcta cacagcttgg gtgaaagggg attccaataa gcttgctcgc 1965 tctctgagtg tgacttgggc taaaggcccc cttttatcca caagttcccc tggctgagga 2025 ttgctgcccg tctgctgatg tgaccagtgg caggcacagg tccagggaga cagactctga 2085 atgggactga gtcccaggaa acagtgcttt ccgatgagac tcagcccacc atttctcctc 2145 acctgggcct tctcagcctc tggactctcc taagcacctc tcaggagagc cacaggtgcc 2205 actgcctcct caaatcacat ttgtgcctgg tgacttcctg tccctgggac agttgagaag 2265 ctgactgggc aagagtggga gagaagagga gagggcttgg atagagttga ggagtgtgag 2325 gctgttagac tgttagattt aaatgtatat tgatgagata aaaagcaaaa ctgtgcct 2383

<210> SEQ ID NO 26
<211> LENGTH: 501
<212> TYPE: PRT
<213> ORGANISM: Homo sapiens

<400> SEQUENCE: 26

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
        50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu

```
             145                 150                 155                 160
         Pro Phe Arg Pro Pro Ile Thr Pro His Glu Tyr Met Leu Ser Leu
                         165                 170                 175

Tyr Arg Thr Leu Ser Asp Ala Asp Arg Lys Gly Gly Asn Ser Ser Val
                             180                 185                 190

Lys Leu Glu Ala Gly Leu Ala Asn Thr Ile Thr Ser Phe Ile Asp Lys
                         195                 200                 205

Gly Gln Asp Asp Arg Gly Pro Val Val Arg Lys Gln Arg Tyr Val Phe
                     210                 215                 220

Asp Ile Ser Ala Leu Glu Lys Asp Gly Leu Leu Gly Ala Glu Leu Arg
         225                 230                 235                 240

Ile Leu Arg Lys Lys Pro Ser Asp Thr Ala Lys Pro Ala Ala Pro Gly
                         245                 250                 255

Gly Gly Arg Ala Ala Gln Leu Lys Leu Ser Ser Cys Pro Ser Gly Arg
                     260                 265                 270

Gln Pro Ala Ser Leu Leu Asp Val Arg Ser Val Pro Gly Leu Asp Gly
                     275                 280                 285

Ser Gly Trp Glu Val Phe Asp Ile Trp Lys Leu Phe Arg Asn Phe Lys
                 290                 295                 300

Asn Ser Ala Gln Leu Cys Leu Glu Leu Glu Ala Trp Glu Arg Gly Arg
         305                 310                 315                 320

Ala Val Asp Leu Arg Gly Leu Gly Phe Asp Arg Ala Ala Arg Gln Val
                         325                 330                 335

His Glu Lys Ala Leu Phe Leu Val Phe Gly Arg Thr Lys Lys Arg Asp
                     340                 345                 350

Leu Phe Phe Asn Glu Ile Lys Ala Arg Ser Gly Gln Asp Asp Lys Thr
                 355                 360                 365

Val Tyr Glu Tyr Leu Phe Ser Gln Arg Arg Lys Arg Ala Pro Leu
                     370                 375                 380

Ala Thr Arg Gln Gly Lys Arg Pro Ser Lys Asn Leu Lys Ala Arg Cys
         385                 390                 395                 400

Ser Arg Lys Ala Leu His Val Asn Phe Lys Asp Met Gly Trp Asp Asp
                         405                 410                 415

Trp Ile Ile Ala Pro Leu Glu Tyr Glu Ala Phe His Cys Glu Gly Leu
                     420                 425                 430

Cys Glu Phe Pro Leu Arg Ser His Leu Glu Pro Thr Asn His Ala Val
                     435                 440                 445

Ile Gln Thr Leu Met Asn Ser Met Asp Pro Glu Ser Thr Pro Pro Thr
         450                 455                 460

Cys Cys Val Pro Thr Arg Leu Ser Pro Ile Ser Ile Leu Phe Ile Asp
         465                 470                 475                 480

Ser Ala Asn Asn Val Val Tyr Lys Gln Tyr Glu Asp Met Val Val Glu
                         485                 490                 495

Ser Cys Gly Cys Arg
                     500

<210> SEQ ID NO 27
<211> LENGTH: 1378
<212> TYPE: DNA
<213> ORGANISM: Homo sapiens
<220> FEATURE:
<221> NAME/KEY: CDS
<222> LOCATION: (276)..(1130)

<400> SEQUENCE: 27
```

-continued

```
ggtagcagca tccaccgggc gggaggtcgg aggcagcaag gccttaaagg ctactgagtg      60
cgccggccgt tccgtgtcca gaacctcccc tactcctccg ccttctcttc cttggccgcc     120
caccgccaag ttccgactcc ggttttcgcc tttgcaaagc ctaaggagga ggttaggaac     180
agccgcgccc ccctccctgc ggccgccgcc cctgcctct cggctctgct ccctgccgcg      240
tgcgcctggg ccgtgcgccc cggcaggcgc cagcc atg tcg atg ctg ccg tcg       293
                                       Met Ser Met Leu Pro Ser
                                         1               5
```

| | | | | | | | | | | | | | | | | |
|---|---|---|---|---|---|---|---|---|---|---|---|---|---|---|---|---|
| ttt | ggc | ttt | acg | cag | gag | caa | gtg | gcg | tgc | gtg | tgc | gag | gtt | ctg | cag | 341 |
| Phe | Gly | Phe | Thr | Gln | Glu | Gln | Val | Ala | Cys | Val | Cys | Glu | Val | Leu | Gln | |
| | | | 10 | | | | 15 | | | | 20 | | | | | |

| caa | ggc | gga | aac | ctg | gag | cgc | ctg | ggc | agg | ttc | ctg | tgg | tca | ctg | ccc | 389 |
|---|---|---|---|---|---|---|---|---|---|---|---|---|---|---|---|---|
| Gln | Gly | Gly | Asn | Leu | Glu | Arg | Leu | Gly | Arg | Phe | Leu | Trp | Ser | Leu | Pro | |
| | | 25 | | | | 30 | | | | 35 | | | | | | |

| gcc | tgc | gac | cac | ctg | cac | aag | aac | gag | agc | gta | ctc | aag | gcc | aag | gcg | 437 |
|---|---|---|---|---|---|---|---|---|---|---|---|---|---|---|---|---|
| Ala | Cys | Asp | His | Leu | His | Lys | Asn | Glu | Ser | Val | Leu | Lys | Ala | Lys | Ala | |
| | 40 | | | | 45 | | | | 50 | | | | | | | |

| gtg | gtc | gcc | ttc | cac | cgc | ggc | aac | ttc | cgt | gag | ctc | tac | aag | atc | ctg | 485 |
|---|---|---|---|---|---|---|---|---|---|---|---|---|---|---|---|---|
| Val | Val | Ala | Phe | His | Arg | Gly | Asn | Phe | Arg | Glu | Leu | Tyr | Lys | Ile | Leu | |
| 55 | | | | 60 | | | | 65 | | | | | 70 | | | |

| gag | agc | cac | cag | ttc | tcg | cct | cac | aac | cac | ccc | aaa | ctg | cag | caa | ctg | 533 |
|---|---|---|---|---|---|---|---|---|---|---|---|---|---|---|---|---|
| Glu | Ser | His | Gln | Phe | Ser | Pro | His | Asn | His | Pro | Lys | Leu | Gln | Gln | Leu | |
| | | | | 75 | | | | | 80 | | | | 85 | | | |

| tgg | ctg | aag | gcg | cat | tac | gtg | gag | gcc | gag | aag | ctg | cgc | ggc | cga | ccc | 581 |
|---|---|---|---|---|---|---|---|---|---|---|---|---|---|---|---|---|
| Trp | Leu | Lys | Ala | His | Tyr | Val | Glu | Ala | Glu | Lys | Leu | Arg | Gly | Arg | Pro | |
| | | | 90 | | | | | 95 | | | | | 100 | | | |

| ctg | ggc | gcc | gtg | ggc | aaa | tat | cgg | gtg | cgc | cga | aaa | ttt | cca | ctg | ccg | 629 |
|---|---|---|---|---|---|---|---|---|---|---|---|---|---|---|---|---|
| Leu | Gly | Ala | Val | Gly | Lys | Tyr | Arg | Val | Arg | Arg | Lys | Phe | Pro | Leu | Pro | |
| | | | 105 | | | | | 110 | | | | | 115 | | | |

| cgc | acc | atc | tgg | gac | ggc | gag | gag | acc | agc | tac | tgc | ttc | aag | gag | aag | 677 |
|---|---|---|---|---|---|---|---|---|---|---|---|---|---|---|---|---|
| Arg | Thr | Ile | Trp | Asp | Gly | Glu | Glu | Thr | Ser | Tyr | Cys | Phe | Lys | Glu | Lys | |
| | | 120 | | | | | 125 | | | | | 130 | | | | |

| tcg | agg | ggt | gtc | ctg | cgg | gag | tgg | tac | gcg | cac | aat | ccc | tac | cca | tcg | 725 |
|---|---|---|---|---|---|---|---|---|---|---|---|---|---|---|---|---|
| Ser | Arg | Gly | Val | Leu | Arg | Glu | Trp | Tyr | Ala | His | Asn | Pro | Tyr | Pro | Ser | |
| 135 | | | | 140 | | | | | 145 | | | | | 150 | | |

| ccg | cgt | gag | aag | cgg | gag | ctg | gcc | gag | gcc | acc | ggc | ctc | acc | acc | acc | 773 |
|---|---|---|---|---|---|---|---|---|---|---|---|---|---|---|---|---|
| Pro | Arg | Glu | Lys | Arg | Glu | Leu | Ala | Glu | Ala | Thr | Gly | Leu | Thr | Thr | Thr | |
| | | | | 155 | | | | | 160 | | | | | 165 | | |

| cag | gtc | agc | aac | tgg | ttt | aag | aac | cgg | agg | caa | aga | gac | cgg | gcc | gcg | 821 |
|---|---|---|---|---|---|---|---|---|---|---|---|---|---|---|---|---|
| Gln | Val | Ser | Asn | Trp | Phe | Lys | Asn | Arg | Arg | Gln | Arg | Asp | Arg | Ala | Ala | |
| | | | 170 | | | | | 175 | | | | | 180 | | | |

| gag | gcc | aag | gaa | agg | gag | aac | acc | gaa | aac | aat | aac | tcc | tcc | tcc | aac | 869 |
|---|---|---|---|---|---|---|---|---|---|---|---|---|---|---|---|---|
| Glu | Ala | Lys | Glu | Arg | Glu | Asn | Thr | Glu | Asn | Asn | Asn | Ser | Ser | Ser | Asn | |
| | | | 185 | | | | | 190 | | | | | 195 | | | |

| aag | cag | aac | caa | ctc | tct | cct | ctg | gaa | ggg | ggc | aag | ccg | ctc | atg | tcc | 917 |
|---|---|---|---|---|---|---|---|---|---|---|---|---|---|---|---|---|
| Lys | Gln | Asn | Gln | Leu | Ser | Pro | Leu | Glu | Gly | Gly | Lys | Pro | Leu | Met | Ser | |
| | | 200 | | | | | 205 | | | | | 210 | | | | |

| agc | tca | gaa | gag | gaa | ttc | tca | cct | ccc | caa | agt | cca | gac | cag | aac | tcg | 965 |
|---|---|---|---|---|---|---|---|---|---|---|---|---|---|---|---|---|
| Ser | Ser | Glu | Glu | Glu | Phe | Ser | Pro | Pro | Gln | Ser | Pro | Asp | Gln | Asn | Ser | |
| 215 | | | | 220 | | | | | 225 | | | | | 230 | | |

| gtc | ctt | ctg | ctg | cag | ggc | aat | atg | ggc | cac | gcc | agg | agc | tca | aac | tat | 1013 |
|---|---|---|---|---|---|---|---|---|---|---|---|---|---|---|---|---|
| Val | Leu | Leu | Leu | Gln | Gly | Asn | Met | Gly | His | Ala | Arg | Ser | Ser | Asn | Tyr | |
| | | | 235 | | | | | 240 | | | | | 245 | | | |

| tct | ctc | ccg | ggc | tta | aca | gcc | tcg | cag | ccc | agt | cac | ggc | ctg | cag | acc | 1061 |
|---|---|---|---|---|---|---|---|---|---|---|---|---|---|---|---|---|
| Ser | Leu | Pro | Gly | Leu | Thr | Ala | Ser | Gln | Pro | Ser | His | Gly | Leu | Gln | Thr | |
| | | 250 | | | | | 255 | | | | | 260 | | | | |

| cac | cag | cat | cag | ctc | caa | gac | tct | ctg | ctc | ggc | ccc | ctc | acc | tcc | agt | 1109 |
|---|---|---|---|---|---|---|---|---|---|---|---|---|---|---|---|---|
| His | Gln | His | Gln | Leu | Gln | Asp | Ser | Leu | Leu | Gly | Pro | Leu | Thr | Ser | Ser | |
| | | 265 | | | | | 270 | | | | | 275 | | | | |

```
ctg gtg gac ttg ggg tcc taa gtggggaggg actggggcct cgaagggatt    1160
Leu Val Asp Leu Gly Ser
    280 cctggagcag caaccactgc agcgactagg gacacttgta aatagaaatc aggaacattt    1220 ttgcagcttg tttctggagt tgtttgcgca taaaggaatg gtggactttc acaaatatct    1280 ttttaaaaat caaaaccaac agcgatctca agcttaatct cctcttctct ccaactcttt    1340 ccacttttgc attttccttc ccaatgcaga gatcaggg                           1378
```

<210> SEQ ID NO 28
<211> LENGTH: 284
<212> TYPE: PRT
<213> ORGANISM: Homo sapiens

<400> SEQUENCE: 28

```
Met Ser Met Leu Pro Ser Phe Gly Phe Thr Gln Glu Gln Val Ala Cys
1               5                   10                  15

Val Cys Glu Val Leu Gln Gln Gly Gly Asn Leu Glu Arg Leu Gly Arg
            20                  25                  30

Phe Leu Trp Ser Leu Pro Ala Cys Asp His Leu His Lys Asn Glu Ser
        35                  40                  45

Val Leu Lys Ala Lys Ala Val Val Ala Phe His Arg Gly Asn Phe Arg
    50                  55                  60

Glu Leu Tyr Lys Ile Leu Glu Ser His Gln Phe Ser Pro His Asn His
65                  70                  75                  80

Pro Lys Leu Gln Gln Leu Trp Leu Lys Ala His Tyr Val Glu Ala Glu
                85                  90                  95

Lys Leu Arg Gly Arg Pro Leu Gly Ala Val Gly Lys Tyr Arg Val Arg
            100                 105                 110

Arg Lys Phe Pro Leu Pro Arg Thr Ile Trp Asp Gly Glu Glu Thr Ser
        115                 120                 125

Tyr Cys Phe Lys Glu Lys Ser Arg Gly Val Leu Arg Glu Trp Tyr Ala
    130                 135                 140

His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Thr Glu Asn
            180                 185                 190

Asn Asn Ser Ser Ser Asn Lys Gln Asn Gln Leu Ser Pro Leu Glu Gly
        195                 200                 205

Gly Lys Pro Leu Met Ser Ser Ser Glu Glu Glu Phe Ser Pro Pro Gln
    210                 215                 220

Ser Pro Asp Gln Asn Ser Val Leu Leu Leu Gln Gly Asn Met Gly His
225                 230                 235                 240

Ala Arg Ser Ser Asn Tyr Ser Leu Pro Gly Leu Thr Ala Ser Gln Pro
                245                 250                 255

Ser His Gly Leu Gln Thr His Gln His Gln Leu Gln Asp Ser Leu Leu
            260                 265                 270

Gly Pro Leu Thr Ser Ser Leu Val Asp Leu Gly Ser
        275                 280
```

<210> SEQ ID NO 29
<211> LENGTH: 2590
<212> TYPE: DNA

```
<213> ORGANISM: Homo sapiens
<220> FEATURE:
<221> NAME/KEY: CDS
<222> LOCATION: (546)..(1112)
<220> FEATURE:
<221> NAME/KEY: CDS
<222> LOCATION: (2036)..(2071)

<400> SEQUENCE: 29
caggcgctgg cgcacatggg aggcaaagac agacagggtg cggtcaggca gcagggccag      60
ggcggctggg ttaactcagt tgtgccacgg gagaaaacgg ggtggtgggt tcctcccctc     120
tcccggggac gggggggcact gcagttttgg ggccctgagt aactacagcc cagaagcgac     180
ctcccagttc ctccgcatcc ccagagacgg aacgatgccc ccaaagacca gccccgcccc     240
ccccaccccc gccaaagcgt ggccacagaa ggccgaggga cgcggcgggc gctgctcgag     300
gagcctccgg gctgagaggg gcggggcgtg cgcggggag gggccgggac gccgctataa     360
aggcgcagct cggggccccg ctccggcccg ggacgcacat gtgcgcgcga cgcccggcag     420
ctgccaccgc ggggcgcagc cgagaccccg cgcctcgccc cggccggccc gcgaggcccg     480
cggcggccgc aggaggcggc atgagcagcc cgcgacagag ctgacgccgc gccccgcccg     540 gcccc atg tcc ttc gcc acg ctg cgc ccg gcg ccg ccg ggc cgc tac ctg       590
      Met Ser Phe Ala Thr Leu Arg Pro Ala Pro Pro Gly Arg Tyr Leu
      1               5                  10                  15 tac ccc gag gtg agc ccg ctg tcg gag gac gag gac cgc ggc agc gac         638
Tyr Pro Glu Val Ser Pro Leu Ser Glu Asp Glu Asp Arg Gly Ser Asp
                20                  25                  30 agc tcg ggc tcc gac gag aaa ccc tgt cgc gtg cac gcg gcg cgc tgc         686
Ser Ser Gly Ser Asp Glu Lys Pro Cys Arg Val His Ala Ala Arg Cys
        35                  40                  45 ggc ctc cag ggc gcc cgg cgg agg gcg ggg ggc cgg cgg gcc ggg ggc         734
Gly Leu Gln Gly Ala Arg Arg Arg Ala Gly Gly Arg Arg Ala Gly Gly
    50                  55                  60 ggg ggg cca ggg ggc cgg cca ggc cgt gag ccc cgg cag cgg cac acg         782
Gly Gly Pro Gly Gly Arg Pro Gly Arg Glu Pro Arg Gln Arg His Thr
65                  70                  75 gcg aac gcg cgc gag cga gac cgc acc aac agc gtg aac acg gcc ttc         830
Ala Asn Ala Arg Glu Arg Asp Arg Thr Asn Ser Val Asn Thr Ala Phe
80                  85                  90                  95 acg gcg ctg cgc acg ctg atc ccc acc gag ccc gcc gac cgc aag ctc         878
Thr Ala Leu Arg Thr Leu Ile Pro Thr Glu Pro Ala Asp Arg Lys Leu
                100                 105                 110 tcc aag att gag acg ctg cgc ctg gcc tcc agc tac atc tcg cac ctg         926
Ser Lys Ile Glu Thr Leu Arg Leu Ala Ser Ser Tyr Ile Ser His Leu
            115                 120                 125 ggc aac gtg ctg ctg gcg ggc gag gcc tgc ggc gac gga cag ccc tgc         974
Gly Asn Val Leu Leu Ala Gly Glu Ala Cys Gly Asp Gly Gln Pro Cys
        130                 135                 140 cac tcc ggg ccc gcc ttc ttc cac gcg gcg cgc gcc ggc agc ccc ccg        1022
His Ser Gly Pro Ala Phe Phe His Ala Ala Arg Ala Gly Ser Pro Pro
    145                 150                 155 ccg ccg ccc ccg ccg cct ccc gcc cgc gac ggc gag aac acc cag ccc        1070
Pro Pro Pro Pro Pro Pro Ala Arg Asp Gly Glu Asn Thr Gln Pro
160                 165                 170                 175 aaa cag atc tgc acc ttc tgc ctc agc aac cag aga aag ttg                1112
Lys Gln Ile Cys Thr Phe Cys Leu Ser Asn Gln Arg Lys Leu
                180                 185 gtgagcacgg gccgtggggc gccgaggggg gcctccaacg cgcccctcag cccacacctg     1172
ccaggcagag gaggcgaggc cacacgggca gggctcccca acagggcaca ggcaggcaca     1232
```

```
cctgtaacac aggcctgccg ggggctgggg ccttctcctg gggctcctct cgagggcgtc    1292
cctaggacac tcggctccca gtggagtgtg gagtcccctg cagggagctg catgaggggt    1352
aagagctagg gatggccaaa ggggcccacc cagggcgggg aggctgggga gctggaccag    1412
gccgctgcaa gcttcccttt tcagtaagtt gaaaggcgga gtgaaaacag ctgagttcag    1472
aaagtaagag gctgcaaggc aagagaggaa ggaccccggg ttcttagccc ctgcggccca    1532
gcactggctt aagccatctt gggcacctgc tgtccgtccc ccacctaggc cgcacaccaa    1592
gacaccaggt cctgtagggc tgcccgagac gtgggccatg gacacgaag gcagaggctg     1652 gcaggagatg tgggggctgg gggtgagggc ccctgcagga gacgctggcc agctgtgatt    1712
tacagctcct gctgtgcttg gtggcaccgg aaaagcaggg tgagcaggga gaaaatacgg    1772
cacggctttt cccaatcccc atttcctctc cagacagcac gcgcgagctc ctggggcctg    1832
aacatctggg aaatttaatt ttacaatttc ggctgtgcag cagtatgctc ccctccccaa    1892
aacgcttgag ggaagctggg gagagccggg aaggaggtgc cttggcgctg ccacctgag    1952 atggcaccca gcaggaggc cagagaggcg cagactggcg ctgggctctg ccggggcctg     2012
acactcctcc ctcccctctg cag agc aag gac cgc gac aga aag aca gcg att    2065
                         Ser Lys Asp Arg Asp Arg Lys Thr Ala Ile
                             190                 195 cgc agt taggaggtgg ccggcagcag ccaggaggca gacgctgctg ggggaggtgg        2121
Arg Ser
200 acgcccgggg tgactgcaga cagcccccac cttggacctg agctgggcaa ggcccaccgc    2181 aagcatgccc ccaggccagc cctggctgcg agcggggccg agggacagac ggacgtacag    2241 acaggcgccg gcagcgggac tctgcgctgg ccccagcacc tgcccgggcc cactggaact    2301 ttctgcgctg gcttttcttc cggccactgt gtgatggcat cttgtgtttt tgatatgata    2361 atataaagtc tgaaaatttt gtataattaa aaacaaaaca gtatcttcca aatatggagg    2421 ccaactgtcc tcatgaaagg ttcagaatcc accccagcc cccagcctga gcctccattc     2481 ccacccttgg tggtcccatc ctccttgggc caagtacccc ggctccctgg aagcccccca    2541 ctttccaggc tcagggccac ccctcccctgg gctgaggcgg tgaggatgg               2590

<210> SEQ ID NO 30
<211> LENGTH: 201
<212> TYPE: PRT
<213> ORGANISM: Homo sapiens

<400> SEQUENCE: 30

Met Ser Phe Ala Thr Leu Arg Pro Ala Pro Gly Arg Tyr Leu Tyr
1               5                   10                  15

Pro Glu Val Ser Pro Leu Ser Glu Asp Glu Asp Arg Gly Ser Asp Ser
                20                  25                  30

Ser Gly Ser Asp Glu Lys Pro Cys Arg Val His Ala Ala Arg Cys Gly
            35                  40                  45

Leu Gln Gly Ala Arg Arg Ala Gly Gly Arg Ala Gly Gly Gly
        50                  55                  60

Gly Pro Gly Gly Arg Pro Gly Arg Glu Pro Arg Gln Arg His Thr Ala
65                  70                  75                  80

Asn Ala Arg Glu Arg Asp Arg Thr Asn Ser Val Asn Thr Ala Phe Thr
                85                  90                  95

Ala Leu Arg Thr Leu Ile Pro Thr Glu Pro Ala Asp Arg Lys Leu Ser
            100                 105                 110
```

-continued

```
Lys Ile Glu Thr Leu Arg Leu Ala Ser Ser Tyr Ile Ser His Leu Gly
        115                 120                 125

Asn Val Leu Leu Ala Gly Glu Ala Cys Gly Asp Gly Gln Pro Cys His
    130                 135                 140

Ser Gly Pro Ala Phe Phe His Ala Ala Arg Ala Gly Ser Pro Pro Pro
145                 150                 155                 160

Pro Pro Pro Pro Pro Ala Arg Asp Gly Glu Asn Thr Gln Pro Lys
            165                 170                 175

Gln Ile Cys Thr Phe Cys Leu Ser Asn Gln Arg Lys Leu Ser Lys Asp
            180                 185                 190

Arg Asp Arg Lys Thr Ala Ile Arg Ser
        195                 200
```

SCAFFOLD-FREE SELF-ORGANIZED 3D SYNTHETIC TISSUE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690128_401 D1_SEQUENCE_LISTING.txt. The text file is 312 KB, was created on May 22, 2016, and is being submitted electronically via EFS-Web.

TECHNICAL FIELD

The present invention relates to the field of regenerative medicine. More particularly, the present invention relates to a synthetic tissue capable of functioning after implantation, a method for producing the same, and use of the same. The synthetic tissue of the present invention has biological integration capability.

BACKGROUND ART

Recently, regenerative therapy has attracted attention as a novel approach to severe organ failure or intractable diseases. Regenerative therapy is a combination of genetic engineering, cell tissue engineering, regenerative medicine, and the like. Many researchers over the world are vigorously working on this important and challenging subject of research in the 21-century advanced medical practice.

The scale of the market associated with regenerative medicine (tissue engineering) is estimated as about 500 billion US dollars in the world and about 50 billion US dollars in Japan according to the material prepared by the New Energy and industrial Technology Development Organization. Only tissue engineering products account for about 100 billion US dollars in the world. The regenerative medicine is greatly expected to create the next-generation industry.

The present inventors have made efforts to develop regenerative therapy in the field of musculoskeletal and cardiovascular tissues, and have reported a combination therapy of cell implantation and a growth factor administration, or a tissue implantation regeneration therapy based on tissue engineering. However, regenerative therapy based on cell or tissue implantation requires a source of autologous cells. A stable and abundant source of such cells is urgently required and important. A number of cells in musculoskeletal tissue have a high level of self-repairing ability. It has been reported that there is a stem cell among the cells of the musculoskeletal tissue.

It has been demonstrated that a cell derived from skeletal muscle (Jankowiski R. J., Huand J. et al, Gene Ther., 9:642-647, 2002), fat (Wickham M. Q. et al., Clin. Orthop., 2003, 412, 196-212), umbilical cord blood (Lee O. K. et al., Blood, 2004, 103:1669-75), tendon (Salingcarnboriboon R., Exp. Cell. Res., 287:289-300, 2002), bone marrow (Pitterger M. F. et al., Science, 284:143-147, 1999), and synovium (Arthritis Rheum. 2001 44:1928-42) is undifferentiated and has the potential to differentiate into various cells.

Conventionally, when cell therapy is performed for repair or regeneration of tissue, most research employs a biological scaffold to maintain the accumulation of cells, allow cells to grow, maintain pluripotency, protect cells from mechanical stress on a treated site, or the like. However, most scaffolds contain a biological (animal) material, a biomacromolecule material, or the like, of which influence on the safety of organism cannot be fully predicted.

A cell implanting method without a scaffold has been reported by Kushida A., Yamato M., Konno C., Kikuchi A., Sakurai Y., Okano T., J. Biomed. Mater. Res., 45:355-362, 1999, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be assembled, for example.

When a nano-biointerface technology is used to fix a temperature responsive polymer (PIPAAm) onto a plastic mold, such as a Petri dish, for cell culture, the polymer surface is reversibly changed at 31° C. between hydrophilicity and hydrophobicity. Specifically, when the temperature is 31° C. or more, the surface of the Petri dish is hydrophobic so that cells or the like can adhere thereto. In this situation, the cells secrete extracellular matrix (ECM; for example, adhesion molecules which are proteins having a function like a "glue") and adhere to the surface of the Petri dish, so that the cells can grow. See, Okano T., Yamada N., Sakai H., Sakurai Y., J. Biomed. Mater. Res., 1993, 27:1243-1251; Kushida A., Yamato M., Konno C., Kikuchi A., Sakurai Y., Okano T., J. Biomed. Mater. Res. 45:355-362, 1999; and Shimizu T., Yamato M., Akutsu T. et al., Circ. Res., 2002, Feb. 22; 90 (3):e40.

When the temperature is 31° C. or less, the surface of the Petri dish is hydrophilic. The cells which have adhered to the Petri dish are readily detached, though the cells still maintain adhesion molecules. This is because the surface of the Petri dish to which the cells have adhered no longer exists at 31° C. or less.

Even when such a Petri dish having a fixed temperature responsive polyer (e.g., tradename: UpCell and RepCell) is used to culture cells and detach the cells, an extracellular matrix is not appropriately provided. Thus, there has been no actually practical synthetic tissue developed. See, Okano T., Yamada N., Sakai H., Sakurai Y., J. Biomed. Mater. Res., 1993, 27:1243-1251; Kushida, A., Yamato M., Konno C., Kikuchi A., Sakurai Y., Okano T., J. Biomed. Mater. Res. 45:355-362, 1999; and Shimizu T., Yamato M., Akutsu T. et al., Circ. Res., 2002, Feb. 22; 90(3):e40.

WO00/51527 and WO03/024463 reported that cells are cultured on a semipermeable membrane using alginate gel. However, the resultant tissue is poorly integrated with an extracellular matrix and is not free of a scaffold. In addition, the cells in the tissue are not self organized. The tissue has no self-supporting ability. The cells no longer have a differentiation potential. The tissue loses morphological plasticity in terms of three-dimensional structure. Therefore, the tissue is not suitable for cell implantation.

Use of a scaffold is considered to be problematic in implantation therapy because of adverse side effects. Therefore, there is a demand for the advent of a scaffold-free technique.

Conventional methods for producing tissue sheets have the following drawbacks: it is not possible to produce a very large sized sheet; it is not possible to produce a sheet having biological integration in three dimensions; when a sheet is detached after sheet production, the sheet is broken into pieces; and the like.

Therefore, there is a keen demand for a synthetic tissue, which is developed by culture processes, capable of withstanding an implantation operation, capable of being used in an actual operation.

By conventional techniques, it is difficult to isolate a synthetic tissue from a culture base material after tissue culture, and it is substantially impossible to produce a large sized tissue piece. Therefore, conventional synthetic tissues, such as tissue sheets, cannot be used in medical application in view of size, structure, mechanical strength, and the like. It is difficult to develop a synthetic tissue using conventional techniques. Therefore, unfortunately their supplies are limited.

An object of the present invention is to provide a synthetic tissue produced by cell culture, which is feasible to implantation surgery.

Specifically, an object of the present invention is to provide a synthetic tissue having a three-dimensional structure and self-supporting ability, being free of a scaffold, and maintaining a differentiation potential if the tissue possesses it.

Still another object of the present invention is to provide a method and a pharmaceutical agent for treating an injury of a tissue or the like when a replacement or resurfacing therapy is required.

DISCLOSURE OF THE INVENTION

The above-described objects were achieved in part based on the invention of the following synthetic tissue. When a cell was cultured in medium containing an extracellular matrix (ECM) synthesis promoting agent, cells and ECM produced by the cells are integrated to formed a tissue, which was readily detached from the culture dish.

The above-described objects were achieved by providing a synthetic tissue of the present invention which is free of a scaffold, has self-supporting ability, is easily formed into a three-dimensional structure, has morphological plasticity, has excellent ability to biologically adhere to surroundings, has a differentiation potential, and the like, and finding that the synthetic tissue is effective for a replacement or resurfacing therapy at an injured site.

The present invention also provides a method for producing an implantable synthetic tissue, which has biological integration and does not require assembling layers.

The above-described objects were achieved by finding that the thickness of the synthetic tissue of the present invention can be adjusted to a desired value by regulating a physical or chemical stimulus on the synthetic tissue.

The present inventors realized the formation of a three-dimensional synthetic tissue (cellular therapeutic system) comprising cultured cells (e.g., fat-derived cells, etc.) and material produced by the cells without a scaffold.

The synthetic tissue of the present invention can be constructed into various shapes and has a sufficient strength. Therefore, it is easy to surgically manipulate (e.g., implant, etc.) the synthetic tissue of the present invention. According to the present invention, a large quantity (e.g., $10^6$ to $10^8$) of cells can be securely supplied to a local site by means of tissue implantation.

In the matrix, cell adhesion molecules, such as collagen (e.g., type I, type III), fibronectin, vitronectin, and the like, are present in large amounts. Particularly, the cell adhesion molecules are integrated throughout the matrix.

Therefore, the tissue has excellent ability of biologically adhesion to surroundings of the implanted site. Thus, the synthetic tissue complex biologically adheres to an implanted site tissue very quickly. In addition, by changing culture conditions, the synthetic tissue can be differentiated into a bone or cartilage tissue. The maintenance of a differentiation potential is a feature of the synthetic tissue of the present invention which was first found by the present inventors. The synthetic tissue is effective as a safe and efficient cell therapy system.

An object of the present invention is to provide a clinical application of the synthetic tissue regeneration of a joint tissue. The present invention provides the above-described synthetic tissue or a complex of a cell and a component derived from the cell, thereby making it possible to develop therapies for bone regeneration at a conventionally intractable site, in which both periosteum and bone cortex are inflamed; partial thickness cartilage injury which does not bleach the subchondral bone, and injury of a meniscus, a tendon, a ligament, an intervertebral disk, cardiac muscle in an avascular area or a poor circulation site.

Thus, the present invention provides the following.
1. An implantable synthetic tissue.
2. A synthetic tissue according to item 1, which is biologically organized in the third dimensional direction.
3. A synthetic tissue according to item 1, which has biological integration capability with surroundings.
4. A synthetic tissue according to item 3, wherein the biological integration capability includes capability to adhere to surrounding cells and/or extracellular matrices.
5. A synthetic tissue according to item 1, which comprises cells.
6. A synthetic tissue according to item 1, which is substantially made of cells and a material derived from the cells.
7. A synthetic tissue according to item 1, which is substantially made of cells and an extracellular matrix (ECM) derived from the cells.
8. A synthetic tissue according to item 7, wherein the extracellular matrix contains at least one selected from the group consisting of collagen I, collagen III, vitronectin and fibronectin.
9. A synthetic tissue according to item 7, wherein the extracellular matrix contains collagen I, collagen III, vitronectin and fibronectin.
10. A synthetic tissue according to item 7, wherein the extracellular matrix contains vitronectin.
11. A synthetic tissue according to item 7, wherein the extracellular matrix contains fibronectin.
12. A synthetic tissue according to item 7, wherein the extracellular matrix contains collagen I and collagen III, the collagen constitutes 5% to 25% of the tissue, and the ratio of the collagen I to the collagen III is between 1:10 and 10:1.
13. A synthetic tissue according to item 7, wherein the extracellular matrix and the cells are integrated together into a three-dimensional structure.
14. A synthetic tissue according to item 7, wherein the extracellular matrix is diffusedly distributed in the tissue.
15. A synthetic tissue according to item 1, wherein an extracellular matrix is diffusedly distributed, and the distribution densities of the extracellular matrix in two arbitrary sections of 1 $cm^2$ in the tissue have a ratio within a range of about 1:3 to about 3:1.
16. A synthetic tissue according to item 1, which is heterologous, allogenic, isologous, or autogenous.
17. A synthetic tissue according to item 1, which is free of scaffolds.
18. A synthetic tissue according to item 1, which is used to implant cells.

19. A synthetic tissue according to item 1, which is large sized.
20. A synthetic tissue according to item 1, which has a volume of at least about 20 mm$^3$.
21. A synthetic tissue according to item 1, which is flexible.
22. A synthetic tissue according to item 1, which is expandable and contractile.
23. A synthetic tissue according to item 1, which can withstand heart pulsation.
24. A synthetic tissue according to item 1, which is biologically organized in all three dimensional directions.
25. A synthetic tissue according to item 24, wherein the biological integration is selected from the group consisting of internal binding of extracellular matrix, electrical integration, and intercellular signal transduction.
26. A synthetic tissue according to item 1, which has a tissue strength which allows the synthetic tissue to be clinically applicable.
27. A synthetic tissue according to item 26, wherein the strength is a break strength of about 0.02 N to about 2 N.
28. A synthetic tissue according to item 26, wherein the tissue strength is sufficient to provide self-supporting ability.
29. A synthetic tissue according to item 28, wherein the self-supporting ability is characterized in that the synthetic tissue is not substantially broken when the synthetic tissue is picked up using forceps having a tip area of 0.05 to 3.0 mm$^2$.
30. A synthetic tissue according to item 28, wherein the self-supporting ability is characterized in the at the synthetic tissue is not broken when the synthetic tissue is picked up with a hand.
31. A synthetic tissue according to item 26, wherein the site to which the synthetic tissue is intended to be applied, includes a heart.
32. A synthetic tissue according to item 26, wherein the site to which the synthetic tissue is intended to be applied, includes an intervertebral disk, a meniscus, a cartilage, a bone, a ligament, or a tendon.
33. A synthetic tissue according to item 26, wherein:
    the synthetic tissue is a cartilage, an intervertebral disk, a meniscus, a ligament, or a tendon; and
    the synthetic tissue remains attached without an additional fixation procedure, after the synthetic tissue is implanted into an injured portion of the intra-articular tissue.
34. A method for producing a synthetic tissue, comprising the steps of:
    A) providing cells;
    B) placing the cells in a container, the container having cell culture medium containing an ECM synthesis promoting agent and having a sufficient base area which can accommodate a synthetic tissue having a desired size;
    C) culturing the cells in the container along with the cell culture medium containing the ECM synthesis promoting agent for a period of time sufficient for formation of the synthetic tissue having the desired size; and
    D) detaching the cells from the container.
35. A method according to item 34, wherein a stimulus for inducing tissue contraction is applied in the detaching step.
36. A method according to item 35, wherein the stimulus includes a physical or chemical stimulus.
37. A method according to item 36, wherein the physical stimulus includes shaking of the container, pipetting, or deformation of the container.
38. A method according to item 34, wherein the detaching step includes adding an actin regulatory agent.
39. A method according to item 38, wherein the actin regulatory agent includes a chemical substance selected from the group consisting of actin depolymerizing agents and actin polymerizing agents.
40. A method according to item 39, wherein the actin depolymerizing agent is selected from the group consisting of Slingshot, cofilin, cyclase associated protein (CAP), actin interacting protein 1 (AIP1), actin depolymerizing factor (ADF), destrin, depactin, actophorin, cytochalasin, and NGF (nerve growth factor).
41. A method according to item 39, wherein the actin polymerizing agent is selected from the group consisting of RhoA, mDi, profilin, Rac1, IRSp53, WAVE2, ROCK, LIM kinase, cofilin, cdc42, N-WASP, Arp2/3, Drf3, Mena, lysophosphatidic acid (LPA), insulin, platelet derived growth factor (PDGF) a, PDGFb, chemokine, and transforming growth factor (TGF) β.
42. A method according to item 34, wherein the container is free of scaffolds.
43. A method according to item 34, wherein the cells are first cultured in monolayer culture.
44. A method according to item 34, wherein the ECM synthesis promoting agent includes TGFβ1, TFGβ3, ascorbic acid, ascorbic acid 2-phosphate, or a derivative or salt thereof.
45. A method according to item 44, wherein the ascorbic acid, ascorbic acid 2-phosphate, or the derivative or salt thereof is present at a concentration of at least 0.1 mM.
46. A method according to item 44, wherein the TGFβ1 or TFGβ3 is present at a concentration of at least 1 ng/ml.
47. A method according to item 34, wherein the cells are placed at a concentration of $5 \times 10^4$ to $5 \times 10^6$ cells per 1 cm$^2$, and the ECM synthesis promoting agent is ascorbic acid, ascorbic acid 2-phosphate, or a derivative or salt thereof, and the ascorbic acid, ascorbic acid 2-phosphate, or the derivative or salt thereof is provided at a concentration of at least 0.1 mM.
48. A method according to item 34, further comprising causing the synthetic tissue to detach from the container and self-contract.
49. A method according to item 48, wherein the detaching and self-contraction are achieved by providing a physical stimulus to the container.
50. A method according to item 48, wherein the detachment and self-contraction are achieved by providing a chemical stimulus to the container.
51. A method according to item 34, wherein the sufficient period of time is at least 3 days.
52. A method according to item 34, wherein the sufficient period of time is at least 3 days and a period of time required for the synthetic tissue to be spontaneously detached from the container at a maximum.
53. A method according to item 52, wherein the period of time required for the synthetic tissue to be spontaneously detached from the container is at least 40 days.
54. A method according to item 34, further comprising: causing the synthetic tissue to differentiate.
55. A method according to item 54, wherein the differentiation includes osteogenesis, chondrogenesis, adipogenesis, tendon differentiation, and ligament differentiation.
56. A method according to item 55, wherein the osteogenesis is performed in medium containing dexamethasone, β-glycerophosphate, and ascorbic acid 2-phosphate.
57. A method according to item 56, wherein the medium contains at least one selected from the group consisting of BMP (bone morphogenetic protein)-2, BMP-4, and BMP-7.

58. A method according to item 55, wherein the chondrogenesis is performed in medium containing pyrubic acid, dexamethasone, ascorbic acid 2-phosphate, insulin, transferrin, and selenious acid.
59. A method according to item 58, wherein the medium contains at least one selected from the group consisting of BMP-2, BMP-4, BMP-7, TGF (transforming frowth factor)-β1 and TGF-β3.
60. A method according to item 54, wherein the differentiation step is performed before or after the detaching step.
61. A method according to item 54, wherein the differentiation step is performed after the detaching step.
62. A method according to item 34, wherein the cell includes cells of 3 or more passages.
63. A method according to item 34, wherein the cells include cells of 3 to 8 passages.
64. A method according to item 34, wherein the cells are provided at a cell density of $5.0 \times 10^4$ to $5.0 \times 10^6$ cells/cm$^2$.
65. A method according to item 34, wherein the cells include myoblasts.
66. A method according to item 34, wherein the cells include fat-derived cells.
67. A method according to item 34, wherein the cells include synovium-derived cells.
68. A method according to item 34, wherein the cells include mesenchymal stem cells.
69. A method according to item 68, wherein the mesenchymal stem cells are derived from an adipose tissue, a synovial membrane, a tendon, a bone, or a bone marrow.
70. A method according to item 34, further comprising: producing a plurality of the synthetic tissues and attaching the plurality of the synthetic tissues together to be integrated.
71. A cell culture composition for producing a synthetic tissue from cells, comprising:
    A) an element for maintaining the cells; and
    B) an extracellular matrix synthesis promoting agent.
72. A method according to item 68, wherein the ECM synthesis promoting agent includes TGFβ1, TFGβ, ascorbic acid, ascorbic acid 2-phosphate, or a derivative or salt thereof.
73. A method according to item 72, wherein TGFβ1 or TFGβ is present at a concentration of at least 1 ng/ml, or ascorbic acid, ascorbic acid 2-phosphate, or the derivative or salt thereof is present at a concentration of at least 0.1 mM.
74. A complex for reinforcing a portion of an organism, comprising cells and a component derived from the cells.
75. A complex according to item 74, which haa biological integration capability with surroundings.
76. A complex according to item 75, wherein the biological integration capability include capability to adhere to surrounding cells and/or extracellular matrices.
77. A complex according to item 74, which is substantially made of cells and a material derived from the cells.
78. A complex according to item 74, which is substantially made of cells and an extracellular matrix derived from the cells.
79. A synthetic tissue according to item 78, wherein the extracellular matrix is selected from the group consisting of collagen I, collagen III, vitronectin and fibronectin.
80. A complex according to item 78, wherein the extracellular matrix and the cells are integrated together into a three-dimensional structure.
81. A complex according to item 78, wherein the extracellular matrix is provided on a surface of the complex.
82. A complex according to item 78, wherein the extracellular matrix is diffusedly distributed on a surface of the complex.
83. A complex according to item 74, wherein an extracellular matrix is diffusedly distributed on a surface of the complex, and the distribution densities of the extracellular matrix in two arbitrary sections of 1 cm$^2$ in the complex have a ratio within a range of about 1:3 to about 3:1.
84. A complex according to item 78, wherein the extracellular matrix includes fibronectin or vitronectin.
85. A complex according to item 74, which is heterologous, allogenic, isologous, or autogenous.
86. A complex according to item 74, wherein the portion includes a bag-shaped organ.
87. A complex according to item 86, wherein the bag-shaped organ includes a heart.
88. A complex according to item 74, wherein the portion includes a bone or cartilage tissue.
89. A complex according to item 74, wherein the portion includes avascular tissue.
90. A complex according to item 74, wherein the portion includes an intervertebral disk, a meniscus, a ligament, or a tendon.
91. A complex according to item 74, wherein the reinforcement is achieved by replacing the portion with the complex or providing the complex to cover the portion, or both.
92. A complex according to item 74, which resists the expansion and contraction of the portion.
93. A complex according to item 74, which has biological integration.
94. A complex according to item 74, wherein the biological integration selected from the group consisting of internal binding of extracellular matrix, electrical integration, and intercellular signal transduction.
95. A complex according to item 74, which is formed by culturing cells in the presence of an ECM synthesis promoting agent.
96. A complex according to item 74, which has self-supporting ability.
97. A method for reinforcing a portion of an organism, comprising the steps of:
    A) replacing the portion with a complex comprising cells and a component derived from the cells or providing the complex to cover the portion, or both; and
    B) holding the complex for a sufficient period of time for biologically adhering the complex to the portion.
98. A method according to item 97, wherein the adhesion is achieved by adhesion between extracellular matrix and extracellular matrix.
99. A method according to item 97, which has biological integration capability with surroundings.
100. A method according to item 99, wherein the biological integration capability include capability to, adhere to surrounding cells and/or extracellular matrices.
101. A method according to item 97, which is substantially made of cells and a material derived from the cells.
102. A method according to item 97, which is substantially made of cells and an extracellular matrix derived from the cells.
103. A method according to item 102, wherein the extracellular matrix contains one selected from the group consisting of collagen I, collagen III, vitronectin and fibronectin.
104. A method according to item 102, wherein the extracellular matrix contains all of collagen I, collagen III, vitronectin and fibronectin.
105. A method according to item 102, wherein the extracellular matrix contains vitronectin.

106. A method according to item 102, wherein the extracellular matrix contains fibronectin.
107. A method according to item 97, wherein an extracellular matrix is provided on a surface of the complex.
108. A method according to item 97, wherein an extracellular matrix is diffusedly distributed on a surface of the complex.
109. A method according to item 97, wherein an extracellular matrix is diffusedly distributed on a surface of the complex, and the distribution densities of the extracellular matrix in two arbitrary sections of 1 cm² have a ratio within a range of about 1:3 to about 3:1.
110. A complex according to item 97, wherein an extracellular matrix is diffusedly distributed on a surface of the complex, and the distribution densities of the extracellular matrix in two arbitrary sections of 1 cm² have a ratio within a range of about 1:2 to about 2:1.
111. A method according to item 97, which is heterologous, allogenic, isologous, or autogenous.
112. A method according to item 97, wherein the portion includes a bag-shaped organ.
113. A method according to item 112, wherein the bag-shaped organ includes a heart.
114. A method according to item 97, wherein the complex resists the expansion and contraction of the portion.
115. A method according to item 97, wherein the complex has biological integration.
116. A method according to item 115, wherein the biological integration selected from the group consisting of internal binding of extracellular matrix, electrical integration, and intercellular signal transduction.
117. A method according to item 97, further comprising: forming the complex by culturing the cells in the presence of an ECM synthesis promoting agent.
118. A method according to item 97, wherein the portion is a heart and the heart has a disease or disorder selected from the group consisting of heart failure, ischemic heart disease, myocardial infarct, cardiomyopathy, myocarditis, hypertrophic cardiomyopathy, dilated phase hypertrophic cardiomyopathy, and dilated cardiomyopathy.
119. A method according to item 97, wherein the portion includes an avascular lesion.
120. A method according to item 97, wherein the portion includes a vascular lesion.
121. A method according to item 97, wherein the portion includes a bone or a cartilage.
122. A method according to item 97, wherein the portion includes an intervertebral disk, a meniscus, a ligament, or a tendon.
123. A method according to item 97, wherein the portion includes a bone or a cartilage, and the bone or the cartilage is damaged or degenerated.
124. A method according to item 97, wherein the portion includes intractable fracture, osteonecrosis, cartilage injury, meniscus injury, ligament injury, tendon injury, cartilage degeneration, meniscus degeneration, intervertebral disk denaturation, ligament degeneration, or tendon degeneration.
125. A method according to item 97, wherein the sufficient period of time is at least 10 days.
126. A method according to item 97, wherein the complex has self-supporting ability.
127. A method according to item 97, which has biological integration capability with surroundings.
128. A method according to item 97, which is substantially made of cells and an extracellular matrix derived from the cells.
129. A method according to item 97, further comprising implanting another synthetic tissue.
130. A method according to item 129, wherein the other synthetic tissue is an artificial bone or a microfibrous collagen medical device.
131. A method according to item 97, which is substantially made of cells and an extracellular matrix derived from the cells, wherein the other synthetic tissue is an artificial bone or a microfibrous collagen medical device.
132. A method according to item 130, the artificial bone includes hydroxyapatite.
133. A method for treating a portion of an organism, comprising the steps of:
A) replacing the portion with a complex comprising cells and a component derived from the cells or providing the complex to cover the portion, or both; and
B) holding the complex for a sufficient period of time for restoring a condition of the portion.
134. A method according to item 133, wherein the treatment is for the treatment, prevention, or reinforcement of a disease, disorder, or condition of a heart, a bone, a cartilage, a ligament, a tendon, a meniscus, of an intervertebral disk.
135. A method according to item 133, wherein the complex has self-supporting ability.
136. A method according to item 133, wherein the complex has biological integration capability with surroundings.
137. A method according to item 133, wherein the complex is substantially made of cells and an extracellular matrix derived from the cells.
138. A method according to item 133, further comprising implanting another synthetic tissue in addition to the replacement or coverage of the portion.
139. A method according to item 138, wherein the other synthetic tissue includes an artificial bone or a microfibrous collagen medical device.
140. A method according to item 133, which is substantially made of cells and an extracellular matrix derived from the cells, wherein the other synthetic tissue includes an artificial bone or a microfibrous collagen medical device.
141. A method according to item 139, the artificial bone includes hydroxyapatite.
142. A method for producing a synthetic tissue, comprising the steps of:
A) providing cells;
B) placing the cells in a container, the container having cell culture medium containing an ECM synthesis promoting agent and having a sufficient base area which can accommodate a synthetic tissue having a desired size;
C) culturing the cells in the container along with the cell culture medium containing the ECM synthesis promoting agent for a period of time sufficient for to/mat ion of the synthetic tissue having the desired size; and
D) regulating a thickness of the synthetic tissue by a physical or chemical stimulus to a desired thickness.
143. A method according to item 142, wherein the physical stimulus includes shear stress between the synthetic tissue and the container, deformation of the base of the container, shaking of the container, or pipetting.
144. A method according to item 142, wherein the chemical stimulus is obtained by using a chemical substance selected from the group consisting of actin depolymerizing agents and actin polymerizing agents.
145. A method according to item 144, wherein the actin depolymerizing agent is selected from the group consisting of Slingshot, cofilin, CAP (cyclase associated protein), AIP1 (actin interacting protein 1), ADF (actin depolymerizing factor), destrin, depactin, actophorin, cytochalasin, and NGF (nerve growth factor).
146. A method according to item 144, wherein the actin polymerizing agent is selected from the group consisting of RhoA, mDi, profilin, Rac1, IRSp53, WAVE2, ROCK, LIM kinase, cofilin, cdc42, N-WASP, Arp2/3, Drf3, Mena, LPA (lysophosphatidic acid), insulin, PDGF (platelet derived growth factor), PDGFb, chemokine, and TGF (transforming growth factor) β.
147. A method according to item 144, wherein the desired thickness is regulated by adjusting a ratio of the actin depolymerizing agent to the actin polymerizing agent.
148. A method according to item 142, further comprising: producing a plurality of the synthetic tissues and attaching the plurality of the synthetic tissues together to be integrated.
149. A tissue complex, comprising an implantable synthetic tissue and another synthetic tissue.
150. A tissue complex according to item 149, wherein the implantable synthetic tissue is substantially made of cells and a material derived from the cells.
151. A tissue complex according to item 149, wherein the implantable synthetic tissue is substantially made of cells and an extracellular matrix derived from the cells.
152. A tissue complex according to item 151, wherein the extracellular matrix is selected from the group consisting of collagen I, collagen III, vitronectin, and fibronectin.
153. A tissue complex according to item 151, wherein the extracellular matrix contains all of collagen I, collagen III, vitronectin, and fibronectin.
154. A tissue complex according to item 149, wherein the other synthetic tissue includes an artificial bone or a microfibrous collagen medical device.
155. A tissue complex according to item 154, the artificial bone includes hydroxyapatite.
156. A tissue complex according to item 149, the implantable synthetic tissue is biologically integrated with the other synthetic tissue.
157. A tissue complex according to item 156, wherein the biological integration is achieved via an extracellular matrix.
158. A composition for use in producing a synthetic tissue having a desired thickness, comprising a chemical substance selected from the group consisting of actin depolymerizing agents and actin polymerizing agents.
159. A composition according to item 158, wherein the actin depolymerizing agent is selected from the group consisting of Slingshot, cofilin, CAP (cyclase associated protein), AIP1 (actin interacting protein 1), ADF (actin depolymerizing factor), destrin, depactin, actophorin, cytochalasin, and NGF (nerve growth factor).
160. A composition according to item 158, wherein the actin polymerizing agent is selected from the group consisting of RhoA, mDi, profilin, Rac1, IRSp53, WAVE2, ROCK, LIMkinase, cofilin, cdc42, N-WASP, Arp2/3, Drf3, Mena, LPA (lysophosphatidic acid), insulin, PDGF (platelet derived growth factor) a, PDGFb, chemokine, and TGF (transforming growth factor) β.

Hereinafter, the present invention will be described by way of preferable examples. It will be understood by those skilled in the art that the examples of the present invention can be appropriately made or carried out based on the description of the present specification and commonly used techniques well known in the art. The function and effect of the present invention can be easily recognized by those skilled in the art.

The present invention provides a scaffold-free synthetic tissue or complex. By providing such a scaffold-free synthetic tissue, a therapeutic method and a therapeutic agent for providing an excellent therapeutic result after implantation can be obtained.

The scaffold-free synthetic tissue of the present invention solves a long outstanding problem with biological formulations, which is attributed to contamination of the scaffold itself. Despite the absence of a scaffold, the therapeutic effect is comparable with, or more satisfactory than conventional techniques.

In addition, when a scaffold is used, the alignment of implanted cells in the scaffold, the cell-to-cell adhesion, the in vivo alteration of the scaffold itself (eliciting inflammation), the integration of the scaffold to recipient tissue, and the like become problematic. These problems can be solved by the present invention.

The synthetic tissue and the complex of the present invention are also self-organized, and have biological integration inside thereof. Also on this point, the present invention is distinguished from conventional cell therapies.

It is easy to form a three-dimensional structure with the synthetic tissue or complex of the present invention, and thus it is easy to design it into a desired form. The versatility of the synthetic tissue and the complex of the present invention should be noted.

The synthetic tissue and the complex of the present invention have biological integration with recipient tissues, such as adjacent tissues, cells, and the like. Therefore, the post-operational stability is satisfactory, and cells are securely supplied to a local site, for example. An effect of the present invention is that the satisfactory biological integration capability allows the formation of a tissue complex with another synthetic tissue or the like, resulting in a complicated therapy.

Another effect of the present invention is that differentiation can be induced after the synthetic tissue or the complex is provided. Alternatively, differentiation is induced before providing a synthetic tissue and/or a complex, and thereafter, the synthetic tissue and/or the complex are developed.

Another effect of the present invention is that the implantation of the synthetic tissue of the present invention provides a satisfactory tissue replacement ability and a comprehensive supply of cells for filling or covering an implanted site, compared to conventional cell-only implantation and sheet implantation.

The present invention provides an implantable synthetic tissue with biological integration capability. The above-described features and effects of the present invention make it possible to treat a site which cannot be considered as an implantation site for conventional synthetic products. The synthetic tissue of the present invention has biological integration and actually works in implantation therpies. The synthetic tissue is for the first time provided by the present invention, but is not provided by conventional techniques. The synthetic tissue or composite of the present invention has the sufficient ability to integrating with adjacent tissues, cells or the like during implantation (preferably, due to extracellular matrix). Therefore, post-operational restoration is excellent. Such a synthetic tissue, which has biological integration capability in all of the three dimensions, cannot be achieved by conventional techniques. Therefore, the present invention provides a therapeutic effect which cannot be achieved by conventional synthetic tissue.

In addition, the present invention provides medical treatment which provides a therapeutic effect by filling, replacing, and/or covering a lesion.

In addition, when the synthetic tissue of the present invention is used in combination with, another synthetic tissue (e.g., an artificial bone made of hydroxyapatite, a microfibrous collagen medical device, etc.), the synthetic tissue of the present invention is biologically integrated with the other synthetic tissue, so that the acceptance of the synthetic tissue makes it possible to organize more complicated tissue complex which is not conventionally expected.

An extracellular matrix or a cell adhesion molecule, such as fibronectin, vitronectin, or the like, is distributed throughout the synthetic tissue of the present invention. In the cell sheet engineering, a cell adhesion molecule is localized on a bottom surface of culture cells which is attached to a Petri dish. In the sheet provided by the cell sheet engineering, cells are major components of the sheet. The sheet is intended to provide a mass of cells with an adhesion molecule attached on the bottom surface. The synthetic tissue of the present invention is a real "tissue" such that an extracellular matrix three-dimensionally integrates with cells. Thus, the present invention is significantly distinguished from conventional techniques including the cell sheet engineering.

A cell implanting method without a scaffold has been reported by a Tokyo Women's Medical University group, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be piled up, for example. Such a problem is solved by the present invention.

A cell/matrix complex developed by the present invention does not require a temperature sensitive culture dish unlike the cell sheet technique. It is easy for the cell/matrix complex to form into a contractile three-dimensional tissue. There is no technique in the world other than the present invention, which can produce a contractile three-dimensional complex having 10 or more layers of cells without using so-called feeder cells, such as rodent stroma cells, in about three weeks. By adjusting conditions for matrix synthesis of the cell, it is possible to produce a complex having a strength which allows surgical manipulation, such as holding or transferring the complex, without a special instrument. Therefore, the present invention is an original, epoch-making technique in the world for reliably and safely perform cell implantation.

BRIEF DESCRIPTION OF THE DRAWINGS

FIG. 3 shows a high magnification view of a synthetic tissue on day 3, 7, 14, and 21 of culture. As can be seen, the synthetic tissue is already developed at day 3 but the matrix is scarce. The matrix is getting dense with time.

FIG. 5 shows exemplary histology of normal tissue (normal skin tissue, synovial membrane tissue, tendon tissue, cartilage tissue, and meniscus tissue):

FIG. 23 shows an in vitro cartilage implantation experiment using a synthetic tissue of the present invention and the results. The upper portion shows a diagram of explant culture. It is shown that a synthetic tissue is adhered to a partial thickness cartilage injury (in vitro). A superficial zone was removed, followed by digestion with chondroitinase ABC (Hinziker E B, JBJS, 1996). The lower left portion is lower magnification histology (×40). The lower right portion is higher magnification histology (×200). As can be seen, the synthetic tissue is tightly attached to the injured surface.

FIG. 29 shows the result of a meniscus repair experiment using a synthetic tissue of the present invention. The left portion of the figure shows that a medial femoral condyle bone and an anterior horn of medial meniscus are exposed. The right figure shows a 6.5-mm defect in a medial knee joint in the anterior horn of medial meniscus.

FIG. 30 shows a meniscus repair procedure. The left portion shows a defect before the implantation of a synovial membrane-derived synthetic tissue (lower left). The right portion shows the defect after the implantation of the synovial membrane-derived synthetic tissue.

DESCRIPTION OF SEQUENCING LIST

Figure 1:
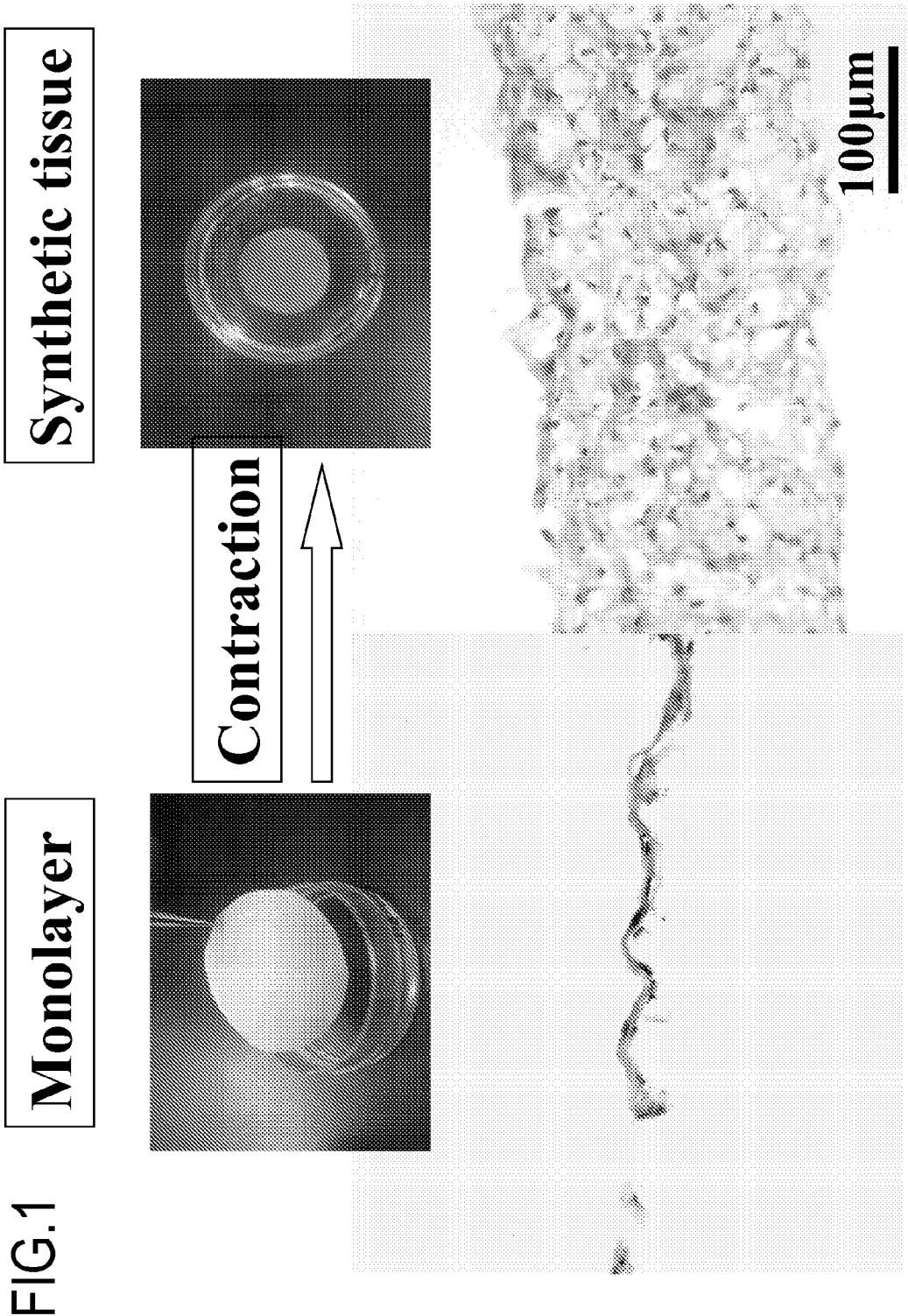
FIG. 1 shows macroscopy and histology of exemplary synthetic tissues using synovial cells.

SEQ ID NO.: 1 indicates the nucleic acid sequence of myosin heavy chain IIa (human: Accession No. NM_017534).

SEQ ID NO.: 2 indicates the amino acid sequence of myosin heavy chain IIa (human: Accession No. NM_017534).

SEQ ID NO.: 3 indicates the nucleic acid sequence of myosin heavy chain IIb (human: Accession No. NM_017533).

SEQ ID NO.: 4 indicates the amino acid sequence of myosin heavy chain IIb (human: Accession No. NM_017533).

SEQ ID NO.: 5 indicates the nucleic acid sequence of myosin heavy chain IId (IIx) (human: Accession No. NM_005963).

SEQ ID NO.: 6 indicates the amino acid sequence of myosin heavy chain IId (IIx) (human: Accession No. NM_005963).

SEQ ID NO.: 7 indicates the nucleic acid sequence of CD56 (human: Accession No. U63041).

SEQ ID NO.: 8 indicates the amino acid sequence of CD56 (human: Accession No. U63041).

SEQ ID NO.: 9 indicates the nucleic acid sequence of human MyoD (GENBANK Accession No. X56677).

SEQ ID NO.: 10 indicates a polypeptide sequence encoded by the nucleic acid sequence of SEQ ID NO.: 2.

SEQ ID NO.: 11 indicates the nucleic acid sequence of human myogenic factor 5 (MYF5) (GENBANK Accession No. NM_005593).

SEQ ID NO.: 12 indicates a polypeptide sequence encoded by the nucleic acid sequence of SEQ ID NO.: 3.

SEQ ID NO.: 13 indicates the nucleic acid sequence of human myogenin (myogenic factor 4) (GENBANK Accession No. BT007233).

SEQ ID NO.: 14 indicates a polypeptide sequence encoded by the nucleic acid sequence of SEQ ID NO.: 13.

SEQ ID NO.: 15 indicates the nucleic acid sequence of Sox9 (human: Accession No. NM_000346=a marker specific to a chondrocyte).

SEQ ID NO.: 16 indicates a polypeptide sequence encoded by the nucleic acid sequence of SEQ ID NO.: 15.

SEQ ID NO.: 17 indicates the nucleic acid sequence of Col 2A1 (human: Accession No. NM_001844=a marker specific to a chondrocyte).

SEQ ID NO.: 18 indicates a polypeptide sequence encoded by the nucleic acid sequence of SEQ ID NO.: 17.

SEQ ID NO.: 19 indicates the nucleic acid sequence of Aggrecan (human:Accession No. NM_001135=a marker specific to a chondrocyte).

SEQ ID NO.: 20 indicates a polypeptide sequence encoded by the nucleic acid sequence of SEQ ID NO.: 19.

SEQ ID NO.: 21 indicates the nucei acid sequence of Bone sialoprotein (human: Accession No. NM_004967=a marker specific to an osteoblast).

SEQ ID NO.: 22 indicates a polypeptide sequence encoded by the nucleic acid sequence of SEQ ID NO.: 21.

SEQ ID NO.: 23 indicates the nucleic acid sequence of Osteocalcin (human: Accession No. NM_199173=a marker specific to an osteoblast).

SEQ ID NO.: 24 indicates a polypeptide sequence encoded by the nucleic acid sequence of SEQ ID NO.: 23.

SEQ ID NO.: 25 indicates the nucleic acid sequence of GDF5 (human: Accession No. NM_000557=a marker specific to a ligament cell).

SEQ ID NO.: 26 indicates a polypeptide sequence encoded by the nucleic acid sequence of SEQ ID NO.: 25.

SEQ ID NO.: 27 indicates the nucleic acid sequence of Six1 (human: Accession No. NM_005982=a marker specific to a ligament cell).

SEQ ID NO.: 28 indicates a polypeptide sequence encoded by the nucleic acid sequence of SEQ ID NO.: 27.

SEQ ID NO.: 29 indicates the nucleic acid sequence of Scleraxis (human: Accession No. BK000280=a marker specific to a ligament cell).

SEQ ID NO.: 30 indicates a polypeptide sequence encoded by the nucleic acid sequence of SEQ ID NO.: 29.

BEST MODE FOR CARRYING OUT THE INVENTION

The present invention will be described below. It should be understood throughout the present specification that articles for singular forms include the concept of their plurality unless otherwise mentioned. Therefore, articles or adjectives for singular forms (e.g., "a", "an", "the", and the like in English) include the concept of their plurality unless otherwise specified. Also, it should be also understood that terms as used herein have definitions ordinarily used in the art unless otherwise mentioned. Therefore, all technical and scientific terms used herein have the samemeanings as commonly understood by those skilled in the relevant art. Otherwise, the present application (including definitions) takes precedence.

(Definition of Terms)

The definitions of specific terms used herein are described below.

(Regenerative Medicine)

As used herein, the term "regeneration" refers to a phenomenon in which when an individual organism loses a portion of tissue, the remaining tissue grows and recovers. The extent or manner of regeneration varies depending among animal species or among tissues in the same individual. Most human tissues have limited regeneration capability, and therefore, complete regeneration is not expected if a large portion of tissue is lost. In the case of severe damage, a tissue may grow which has strong proliferation capability different from that of lost tissue, resulting in incomplete regeneration where the damaged tissue is incompletely regenerated and the function of the tissue cannot be recovered. In this case, a structure made of a bioabsorbable material is used to prevent a tissue having strong proliferation capability from infiltrating the injured portion of the tissue so as to secure space for proliferation of the damaged tissue. Further, by supplementing with a cell growth factor, the regeneration capability of the damaged tissue is enhanced. Such a regeneration technique is applied to cartilages, bones, hearts, and peripheral nerves, for example. It has been so far believed that cartilages, nerve cells, and cardiac muscles have no or poor regeneration capability. Recently, it was reported that there are tissue (somatic stem cells), which have both the capability of differentiating into these tissues and self-proliferation capability. Expectations are running high for regenerative medicine using stem cells. Embryonic stem cells (ES cells) also have the capability of differentiating into all tissues. Efforts have been made to use ES cells for regeneration of complicated organs, such as kidney, liver, and the like, but have not yet been realized.

The term "cell" is herein used in its broadest sense in the art, referring to a structural unit of tissue of a multicellular organism, which is capable of self replicating, has genetic information and a mechanism for expressing it, and is surrounded by a membrane structure which isolates the living body from the outside. In the method of the present invention, any cell can be used as a subject. The number of cells used in the present invention can be counted through an optical microscope. When counting using an optical microscope, the number of nuclei is counted. Tissues are sliced into tissue sections, which are then stained with hematoxylin-eosin (HE) to variegate nuclei derived from extracellular matrices (e.g., elastin or collagen) and cells. These tissue sections are observed under an optical microscope and the number of nuclei in a particular area (e.g., 200 μm×200 μm) can be estimated to be the number of cells. Cells used herein may be either naturally-occurring cells or artificially modified cells (e.g., fusion cells, genetically modified cells, etc.). Examples of cell sources include, but are not limited to, a single-cell culture; the embryo, blood of a normally-grown transgenic animal; a cell mixture of cells derived from normally-grown cell lines; and the like. Primary culture cells may be used. Alternatively, subcultrue cells may also be used. Preferably, when subculture cells are used, the cells are preferably of 3 to 8 passages. As used herein, cell density may be represented by the number of cells per unit area (e.g., $cm^2$).

As used herein, the term "stem cell" refers to a cell capable of self replication and pluripotency. Typically, stem cells can regenerate an injured tissue. Stem cells used herein may be, but are not limited to, embryonic stem (ES) cells or tissue stem cells (also called tissular stem cell, tissue-specific stem cell, or somatic stem cell). A stem cell may be an artificially produced cell (e.g., fusion cells, reprogrammed cells, or the like used herein) as long as it can have the above-described abilities. Embryonic stem cells are pluripotent stem cells derived from early embryos. An embryonic stem cell was first established in 1981, and has been applied to production of knockout mice since 1989. In 1998, a human embryonic stem cell was established, which is currently becoming available for regenerative medicine. Tissue stem cells have a relatively limited level of differentiation unlike embryonic stem cells. Tissue stem cells are present in tissues and have an undifferentiated intracellular structure. Tissue stem cells have a higher nucleus/cytoplasm ratio and have few intracellular organelles. Most tissue stem cells have pluripotency, a long cell cycle, and proliferative ability beyond the life of the individual. As used herein, stem cells may be preferably embryonic stem cells, though tissue stem cells may also be employed depending on the circumstance.

Tissue stem cells are separated into categories of sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, hepatic stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified as, long as they can achieve the intended treatment.

The origin of a stem cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells, hematopoietic stem cells, mesenchymal stem cells, and the like. Stem cells of mesoderm origin are mostly present in organs, including hepatic stem cells, pancreatic stem cells, and the like. As used herein, somatic cells may be derived from any mesenchyme. Preferably, somatic cells derived from mesenchyme may be employed.

As cells for use in construction of a synthetic tissue or three-dimensional structure of the present invention, differentiated cells or stem cells derived from the above-described ectoderm, endoderm, or mesoderm may be employed, for example. Examples of such cells include mesenchymal cells. In a certain embodiment, as such cells, myoblasts (e.g., skeletal myoblast, etc.), fibroblasts, synovial cells, and the like may be employed. As such cells, differentiated cells or stem cells can be used as they are. Cells differentiated from stem cells into a desired direction can be used.

As used herein, the term "mesenchymal stem cell" refers to a stem cell found in mesenchyme. The term "mesenchymal stem cell" may be herein abbreviated as "MSC". Mesenchyme refers to a population of free cells which are in the asterodal shape or have irregular projections and bridge gaps between epithelial tissues, and which are recognized in each stage of development of multicellular animals. Mesenchyme also refers to tissue formed with intracellular cement associated with the cells. Mesenchymal stem cells have proliferation ability and the ability to differentiate into osteocytes, chondrocytes, muscle cells, stroma cells, tendon cells, and adipocytes. Mesenchymal stem cells are employed in order to culture or grow bone marrow cells or the like collected from patients, or differentiate them into chondrocytes or osteoblasts. Mesenchymal stem cells are also employed as reconstruction material, such as alveolar bones; bones, cartilages or joints for arthropathy or the like; and the like. There is a large demand for mesenchymal stem cells. A synthetic tissue or three-dimensional structure of the present invention comprising mesenchymal stem cells or differentiated mesenchymal stem cells is particularly useful when a structure is required in these applications.

As used herein, the term "isolated" means that naturally accompanying material is at least reduced, or preferably substantially completely eliminated, in normal circumstances. Therefore, the term "isolated cell" refers to a cell substantially free of other accompanying substances (e.g., other cells, proteins, nucleic acids, etc.) in natural circumstances. The term "isolated tissue" refers to a tissue substantially free of substances other than that tissue (e.g., in the case of synthetic tissues or complexes, substances, scaffolds, sheets, coats, etc. used when the synthetic tissue is produced). As used herein, the term "isolated" refers to a scaffold-free state. Therefore, it will be understood that the synthetic tissue or complex of the present invention in the isolated state may contain components (e.g., medium, etc.) used in the production of it. The term "isolated" in relation to nucleic acids or polypeptides means that, for example, the nucleic acids or the polypeptides are substantially free of cellular substances or culture media when they are produced by recombinant DNA techniques; or precursory chemical substances or other chemical substances when they are chemically synthesized. Isolated nucleic acids are preferably free of sequences naturally flanking the nucleic acid within an organism from which the nucleic acid is derived (i.e., sequences positioned at the 5' terminus and the 3' terminus of the nucleic acid).

As used herein, the term "scaffold-free" indicates that a synthetic tissue does not substantially contain a material (scaffold) which is conventionally used for production of a synthetic tissue. Examples of such a scaffold include, but are not limited to, chemical polymeric compounds, ceramics, or biological formulations such as polysaccharides, collagens, gelatins, hyaluronic acids, and the like. A scaffold is a material which is substantially solid and has a strength which allows it to support cells or tissue.

As used herein, the term "established" in relation to cells refers to a state of a cell in which a particular property (pluripotency) of the cell is maintained and the cell undergoes stable proliferation under culture conditions. Therefore, established stem cells maintain pluripotency.

As used herein, the term "non-embryonic" refers to not being directly derived from early embryos. Therefore, the term "non-embryonic" refers to cells derived from parts of the body other than early embryos. Also, modified embryonic stem cells (e.g., genetically modified or fusion embryonic stem cells, etc.) are encompassed by non-embryonic cells.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, adipocytes, osteocytes, chondrocytes, and the like.

As used herein, the term "tissue" refers to a group of cells having the same function and form in cellular organisms. In multicellular organisms, constituent cells are usually differentiated so that the cells have specialized functions, resulting in division of labor. Therefore, multicellular organisms are not simple cell aggregations, but constitute organic or social cell groups having a certain function and structure. Examples of tissues include, but are not limited to, integument tissue, connective tissue, muscular tissue, nervous tissue, and the like. Tissue targeted by the present invention may be derived from any organ or part of an organism. In a preferable embodiment of the present invention, tissue targeted by the present invention includes, but is not limited to, a bones, a cartilage, a tendon, a ligament, a meniscus, an intervertebral disk, a periosteum, a blood vessel, a blood vessel-like tissue, a heart, a cardiac valve, a pericardium, a dura mater, and the like.

As used herein, the term "cell sheet" refers to a structure comprising a monolayer of cells. Such a cell sheet has at least a two-dimensional biological integration. The sheet having biological integration is characterized in that after the sheet is produced, the connection between cells is not substantially destroyed even when the sheet is handled singly. Such biological integration includes intracellular connection via an extracellular matrix. It will be understood that the cell sheet may partially include a two or three-layer structure.

As used herein, the term "synthetic tissue" refers to tissue having a state different from natural states. Typically, a synthetic tissue is herein prepared by cell culture. Tissue which is removed from an organism and is not subjected to any treatment is not referred to as a synthetic tissue. Therefore, a synthetic tissue may include materials derived from organisms and materials not derived from organisms. The synthetic tissue of the present invention typically comprises a cell and/or a biological material, and may comprise other materials. More preferably, a synthetic tissue of the present invention is composed substantially only of a cell and/or a biological material. Such a biological material is preferably derived from cells constituting the tissue (e.g., extracellular matrix, etc.).

As used herein, the term "implantable synthetic tissue" refers to a synthetic tissue, which can be used for actual clinical implantation and can function as a tissue at the implantation site for a certain period of time after implantation. Implantable synthetic tissue typically has sufficient biocompatibility, sufficient affinity, and the like.

The sufficient strength of an implantable synthetic tissue varies depending on a part targeted by implantation, but can be determined as appropriate by those skilled in the art. The strength is sufficient to provide self-supporting ability, and can be determined depending on the environment of implantation. The strength can be measured by measuring stress or distortion characteristics or conducting s creep characteristics indentation test as described below. The strength may also be evaluated by observing the maximum load.

The sufficient size of an implantable synthetic tissue varies depending on a part targeted by implantation, but can be determined as appropriate by those skilled in the art. The size can be determined depending on the environment of implantation.

However, an implantable synthetic tissue preferably has at least a certain size. Such a size (e.g., area) is at least 1 $cm^2$, preferably at least 2 $cm^2$, more preferably at least 3 $cm^2$, even more preferably at least 4 $cm^2$, at least 5 $cm^2$, at least 6 $cm^2$, at least 7 $cm^2$, at least 8 $cm^2$, at least 9 $cm^2$, at least 10 $cm^2$, at least 15 $cm^2$, or at least 20 $cm^2$. An essence of the present invention is that a synthetic tissue of any size (area, volume) can be produced, i.e., the size is not particularly limited.

When the size is represented by the volume, the size may be, but is not limited to, at least 2 $mm^3$, or at least 40 $mm^3$. The size may be 2 $mm^3$ or less or 40 $mm^3$ or more.

The sufficient thickness of an implantable synthetic tissue varies depending on a part targeted by implantation, but can be determined as appropriate by those skilled in the art. The thickness can be determined depending on the environment of implantation. The thickness may exceed 5 mm. When an implantable synthetic tissue is implanted into the heart, the tissue may only have these minimum thicknesses. When implantable synthetic tissue is used in other applications, the tissue may preferably have a greater thickness. In such a case, for example, an implantable synthetic tissue has preferably a thickness of at least 2 mm, more preferably at least 3 mm, and even more preferably 5 mm. For example, when an implantable synthetic tissue is applied to a bone, a cartilage, a ligament, a tendon, or the like, similar to the case of a heart, the tissue has a thickness of at least about 1 mm (e.g., at least 2 mm, more preferably at least 3 mm, and even more preferably 5 mm), or 5 mm or more or less than 1 mm. An essence of the present invention is that a synthetic tissue or complex of any thickness can be produced, i.e., the size is not particularly limited.

The sufficient biocompatibility of implantable synthetic tissue varies depending on a part targeted by implantation, but can be determined as appropriate by those skilled in the art. However, an implantable synthetic tissue preferably has at least a certain level of biocompatibility. Typically, a desired level of biocompatibility is, for example, such that biological integration to surrounding tissues is achieved without any inflammation, any immune reaction or the like. The present invention is not limited to this. In some cases (e.g., corneas, etc.), an immune reaction is less likely to occur. Therefore, an implantable synthetic tissue has biocompatibility to an extent, which achieves the object of the present invention even when an immune reaction is likely to occur in other organs. Examples of parameters indicating biocompatibility include, but are not limited to, the presence or absence of an extracellular matrix, the presence or absence of an immune reaction, the degree of inflammation, and the like. Such biocompatibility can be determined by examining the compatibility of a synthetic tissue at an implantation site after implantation (e.g., confirming that an implanted synthetic tissue is not destroyed). See "Hito Ishoku Zoki Kyozetsu Hanno no Byori Soshiki Shindan Kijyun Kanbetsu Shindan to Seiken Hyohon no Toriatsukai (Zufu) Jinzo Ishoku, Kanzo Ishoku Oyobi Shinzo Ishoku [Pathological Tissue Diagnosis Criterion for Human Transplanted Organ Rejection Reaction Handling of Differential Diagnosis and Biopsy Specimen (Illustrated Book) Kidney Transplantation, Liver Transplantation and Heart Transplantation]" The Japan Society for Transplantation and The Japanese Society for Pathology editors, Kanehara Shuppan Kabushiki Kaisha (1998). According to this document, biocompatibility is divided into Grade 0, 1A, 1B, 2, 3A, 3B, and 4. At Grade 0 (no acute rejection), no acute rejection reaction, cardiomyocyte failure, or the like is found in biopsy specimens. At Grade 1A (focal, mild acute rejection), there is focal infiltration of large lymphocytes around blood vessels or into interstitial tissue, while there is no damage to cardiomyocytes. This observation is obtained in one or a plurality of biopsy specimens. At Grade 1B (diffuse, mild acute rejection), there is diffuse infiltration of large lymphocytes around blood vessels or into interstitial tissue or both, while there is no damage to cardiomyocytes. At Grade 2 (focal, moderate acute rejection), there is a single observed infiltration focus of inflammatory cells clearly bordered from the surrounding portions. Inflammation cells are large activated lymphocytes and may include eosinophils. Damage to cardiomyocytes associated with modification of cardiac muscle is observed in lesions. At Grade 3A (multifocal, moderate acute rejection), there are multiple infiltration foci of inflammatory cells which are large activated lymphocytes and may include eosinophils. Two or more of the multiple inflammatory infiltration foci of inflammatory cells have damages to cardiomyocytes. In some cases, there is also rough infiltration of inflammatory cells into the endocardium. The infiltration foci are observed in one or a plurality of biopsy specimens. At Grade 3B (multifocal, borderline severe acute rejection), there are more confluent and diffuse infiltration foci of inflammatory cells found in more biopsy specimens than those observed at Grade 3A. There is infiltration of inflammatory cells including large lymphocytes and eosinophils, in some cases neutrophils, as well as damage to cardiomyocytes. There is no hemorrhage. At Grade 4 (severe acute rejection), there is infiltration of various inflammatory cells including activated lymphocytes, eosinophils, and neutrophils. There is always damage to cardiomyocytes and necrosis of cardiomyocytes. Edema, hemorrhage, and/or angitis are also typically observed. Infiltration of inflammatory cells into the endocardium, which is different from the "Quilty" effect, is typically observed. When a therapy is strongly conducted using an immunosuppressant for a considerably long period of time, edema and hemorrhage may be more significant than infiltration.

The sufficient affinity of an implantable synthetic tissue varies depending on a part targeted by implantation, but can be determined as appropriate by those skilled in the art. Examples of parameters for affinity include, but are not limited to, biological integration capability between an implanted synthetic tissue and its implantation site, and the like. Such affinity can be determined based on the presence of biological integration at an implantation site after implantation. Preferable affinity is herein such that an implanted synthetic tissue has the same function as that of a site in which the tissue is implanted, for example.

As used herein, the term "self-supporting ability" in relation to a tissue (e.g., a synthetic tissue, etc.) refers to a property of the synthetic tissue such that when it is restrained on at least one point thereof, it is not substantially destroyed. Self-supporting ability is herein observed if a tissue (e.g., a synthetic tissue) is picked up by using forceps with a tip having a thickness of 0.5 to 3.0 mm (preferably, forceps with a tip having a thickness of 1 to 2 mm or 1 mm; the forceps preferably have a bent tip) and the tissue is not substantially destroyed. Such forceps are commercially available (e.g., from Natsume Seisakusho, etc.) A force exerted for picking up a tissue is comparable with a force typically exerted by a medical practioner handing a tissue. Therefore, the self-supporting ability of a tissue can also be represented by a property such that the tissue is not destroyed when it is picked up by a hand. Such forceps are, for example, but are not limited to, a pair of curved fine forceps (e.g., No. A-11 (tip: 1.0 mm in thickness) and No. A-12-2 (tip: 0.5 mm in thickness) commercially available from Natsume Seisakusho). A bent tip is suitable for picking up a synthetic tissue. The forceps are not limited to a bent tip type.

When a joint is treated, replacement is majorly performed. The strength of a synthetic tissue of the present invention required in such a case is such that a minimum self-supporting ability is obtained. Cells contained in the synthetic tissue are subsequently replaced with cells in an affected portion. The replacing cells produce a matrix which enhances the mechanical strength, so that the joint is healed. It will also be understood that the present invention may be used in conjunction with an artificial joint.

In the present invention, self-supporting ability plays an important role in evaluating the supporting ability of a synthetic tissue which is actually produced. When a synthetic tissue of the present invention is produced, the synthetic tissue is formed in the shape of a cell sheet in a container. Thereafter, the sheet is detached. With conventional techniques, the sheet is usually destroyed due to lack of self-supporting ability. Therefore, in conventional technology, an implantable synthetic tissue cannot be substantially produced. Especially, when a large-sized synthetic tissue is required, conventional techniques are not adequate. According to the technique of the present invention, a synthetic tissue can be produced, which has a sufficient strength which allows the tissue to be detached from a container without being destroying, i.e., the tissue already has self-supporting ability when being detached. This is true even when the synthetic tissue is in the form of a monolayer sheet before being detached. It will be understood that the monolayer may partially include a two or three-layer structure. Thus, it will be understood that the synthetic tissue of the present invention is applicable in substantially any chosen therapy. In addition, typically, after a synthetic tissue is produced and detached, the strength and self-supporting ability of the synthetic tissue are increased as observed in the present invention. Therefore, in the present invention, it will be understood that the self-supporting ability evaluated upon production may be an important aspect. In the present invention, the strength upon implantation is also important. It may also be important to evaluate the self-supporting ability of a synthetic tissue when a predetermined time has passed after the production of the tissue. Therefore, it will be understood that the self supporting ability at the time of implantation after transport, can be determined by calculating the time that has elapsed since production of the tissue, based on the above-described relationship.

As used herein, the term "membranous tissue" refers to a tissue in the form of membrane and is also referred to as "planar tissue". Examples of membranous tissue include tissues of organs (e.g., periosteum, pericardium, duramater, cornea, etc.).

As used herein, the term "organ" refers to a structure which is a specific part of an individual organism where a certain function of the individual organism is locally performed and which is morphologically independent. Generally, in multicellular organisms (e.g., animals and plants), organs are made of several tissues in specific spatial arrangement and tissue is made of a number of cells. Examples of such organs include, but are not limited to, skin, blood vessel, cornea, kidney, heart, liver, umbilical cord, intestine, nerve, lung, placenta, pancreas, brain, joint, bone, cartilage, peripheral limbs, retina, and the like. Examples of such organs include, but are not limited to, organs of the skin system, the parenchyma pancreas system, the pancreatic duct system, the hepatic system, the blood system, the myocardial system, the skeletal muscle system, the osteoblast system, the skeletal myoblast system, the nervous system, the blood vessel endothelial system, the pigment system, the smooth muscle system, the fat system, the bone system, the cartilage system, and the like.

As used herein, the term "bag-shaped organ" refers to an organ which has a three-dimensional expanse and the inside of which may be connected via a tubular tissue to the outside. Examples of bag-shaped organs include, but are not limited to, heart, liver, kidney, stomach, spleen, and the like.

In one embodiment, the present invention targets an intervertebral disk, a cartilage, a joint, a bone, a meniscus, a synovial membrane, a ligament, a tendon, and the like.

In a preferable embodiment, the present invention targets blood vessels, blood vessel-like tissue, heart, heart valves, pericardia, dura mater, cornea, and bones. In another preferable embodiment, examples of organs targeted by the present invention include, but are not limited to, skeletal muscle, fat, and the like in addition to what is described above.

As used herein, the term "cover" or "wrap" in relation to a synthetic tissue, a three-dimensional structure, or the like, which is wrapped around a certain part (e.g., an injured site, etc.), means that the synthetic tissue or the like is arranged so as to cover the part (i.e., conceal an injury or the like). The terms "wrap" and "arrange (or locate) so as to cover" are used interchangeably. By observing the spatial relationship between the part and the synthetic tissue or the like, it can be determined whether or not the part is covered by the synthetic tissue or the like. In a preferable embodiment, in a covering step, a synthetic tissue or the like can be wrapped one turn around a certain site.

As used herein, the term "replace" means that a lesion (a site of an organism) is replaced, and cells which have originally been in a lesion are replaced with cells supplied by a synthetic tissue or a complex according to the present invention. Examples of a disease for which replacement is suitable' include, but not limited to, a ruptured site, and the like. The term "fill" may be used in place of the term "replace" in the present specification.

A "sufficient time required for a synthetic tissue to biologically integrate with a part" herein varies depending on a combination of the part and the synthetic tissue, but can be determined as appropriate by those skilled in the art based on the combination. Examples of such a time include, but are not limited to, 1 week, 2 weeks, 1 month, 2 months, 3 months, 6 months, 1 year, and the like, after operation. In the present invention, a synthetic tissue preferably comprises substantially only cells and materials derived from the cells, and therefore, there is no particular material which needs to be extracted after operation. Therefore, the lower limit of the sufficient time is not particularly important. Thus, in this case, a longer time is more preferable. If the time is substantially extremely long, reinforcement is substantially completed.

As used herein, the term "immune reaction" refers to a reaction due to the dysfunction of immunological tolerance between a graft and a host. Examples of immune reactions include, but are not limited to, a hyperacute rejection reaction (within several minutes after implantation) (immune reaction caused by antibodies, such as β-Gal or the like), an acute rejection reaction (reaction caused by cellular immunity about 7 to 21 days after implantation), a chronic rejection reaction (rejection reaction caused by cellular immunity 3 or more months after operation), and the like.

As used herein, the elicitation of an immune reaction can be confirmed by pathological and histological examination of the type, number, or the like of infiltration of (immunological) cells into implanted tissue using staining (e.g., HE staining, etc.), immunological staining, or microscopic inspection of tissue sections.

As used herein, the term "calcification" refers to precipitation of calcareous substances in organisms.

"Calcification" in vivo can be determined herein by staining (e.g., Alizarin Red staining) and measuring calcium concentration. Specifically, implanted tissue is taken out; the tissue section is dissolved by acid treatment or the like; and the atomic absorption of the solution is measured by a trace element quantifying device.

As used herein, the term "within organism (s) (or in organism(s))" or "in vivo" refers to the inner part of organism(s). In a specific context, "within organism (s)" refers to a position at which a subject tissue or organ is placed.

As used herein, "in vitro" indicates that a part of an organism is extracted or released outside the organism for various purposes of research (e.g., in a test tube). The term in vitro is in contrast to the term in vivo.

As used herein, the term "ex vivo" refers to a series of operations where target cells into which a gene will be introduced are extracted from a subject; a therapeutic gene is introduced in vitro into the cells; and the cells are returned into the same subject.

As used herein, the term "material derived from cell (s)" refers to any material originating from the cell (s), including, but not being limited to, materials constituting the cell(s), materials secreted by the cell(s), materials metabolized by the cell(s), and the like. Representative examples of materials derived from cells include, but are not limited to, extracellular matrices, hormones, cytokines, and the like. Materials derived from cells typically have substantially no adverse effect on the cells and their hosts. Therefore, when the material is contained in a synthetic tissue, a three-dimensional structure, or the like, the material typically has substantially no adverse effect on the synthetic tissue, three-dimensional structure, or the like.

As used herein, the term "extracellular matrix" (ECM) refers to a substance existing between somatic cells no matter whether the cells are epithelial cells or non-epithelial cells. Extracellular matrices are typically produced by cells, and therefore, are biological materials. Extracellular matrices are involved in supporting tissue as well as in internal environmental structure essential for survival of all somatic cells. Extracellular matrices are generally produced from connective tissue Cells. Some extracellular matrices are secreted from cells possessing basal membrane, such as epithelial cells or endothelial cells. Extracellular matrices are roughly divided into fibrous components and matrices filling there between: Fibrous components include collagen fibers and elastic fibers. A basic component of matrices is a glycosaminoglycan (acidic mucopolysaccharide), most of which is bound to non-collagenous protein to forma polymer of a proteoglycan (acidic mucopolysaccharide-protein complex). In addition, matrices include glycoproteins, such as laminin of basal membrane, microfibrils around elastic fibers, fibers, fibronectins on cell surfaces, and the like. Particularly differentiated tissue has the same basic structure. For example, in hyaline cartilage, chondroblasts characteristically produce a large amount of cartilage matrices including proteoglycans. In bones, osteoblasts produce bone matrices which cause calcification. Herein, examples of typical extracellular matrix include, but not limited to, collagen I, collagen III, collagen V, elastin, vitronectin, fibronectin, proteoglycans (for example, decolin, byglican, fibromodulin, lumican, hyaluronic acid, etc.). Various types of extracellular matrix may be utilized in the present invention as long as cell adhesion is achieved.

In one embodiment of the present invention, the synthetic tissue, three-dimensional structure, or the like of the present invention may be advantageously similar to the composition of an extracellular matrix (e.g., elastin, collagen (e.g., Type I, Type III, Type IV, etc.), laminin, etc.) of a site of an organ for which implantation is intended. In the present invention, extracellular matrices include cell adhesion molecules. As used herein, the terms "cell adhesion molecule" and "adhesion molecule" are used interchangeably, referring to a molecule capable of mediating the joining of two or more cells (cell adhesion) or adhesion between a substrate and a cell. In general, cell adhesion molecules are divided into two groups: molecules involved in cell-cell adhesion (intercellular adhesion) (cell-cell adhesion molecules) and molecules involved in cell-extracellular matrix adhesion (cell-substrate adhesion) (cell-substrate adhesion molecules). A synthetic tissue or three-dimensional structure of the present invention typically comprises such a cell adhesion molecule. Therefore, cell adhesion molecules herein include a protein of a substrate and a protein of a cell (e.g., integrin, etc.) in cell-substrate adhesion. A molecule other than proteins falls within the concept of cell adhesion molecule as long as it can mediate cell adhesion.

It should be noted that the synthetic tissue or complex of the present invention comprises cells and a ■ material (natively) derived from the cell. ■ Therefore, such materials including ECMs form a complicated composition containing collagen I, collagen III, collagen V, elastin, fibronectin, vitronectin, proteoglycans (for example, decolin, byglican, fibromodulin, lumican, hyaluronic acid, etc.). Conventionally a synthetic tissue containg such cell-derived ingredients has not been provided. To obtain a synthetic tissue having such a composition is substantially impossible when an artificial material is used. Thus, a composition containing such ingredients (particularly, collagen I, collagen III and the like) is recognized to be a native composition.

More preferably, an extracellular matrix includes all the collagen (for example, Types I, Type III, etc.), vitronectin, and fibronectin. Especially, a synthetic tissue containing vitronectin and/or fibronectin has not been provided before. Therefore, the synthetic tissue and the complex according to the present invention are recognized to be new in this regard.

As used herein, the term "provided" or "distributed" in relation to an extracellular matrix and the synthetic tissue of the present invention indicates that the extracellular matrix is present in the synthetic tissue. It should be understood that such superficial provision can be visualized and observed by immunologically staining an extracellular matrix of interest.

As used herein, the term "in a diffused manner" or "diffusedly" in relation to the distribution of an extracellular matrix indicates that the extracellular matrix is not localized. Such distribution of an extracellular matrix has a ratio of the distribution densities of two arbitrary sections of 1 cm$^2$ within a range of typically about 1:10 to about 10:1, and representatively about 1:3 to about 3:1, and preferably about 1:2 to about 2:1, and more preferably about 1:1 (i.e., substantially evenly distributed over the synthetic tissue. When an extracellular matrix is distributed on a surface of the synthetic tissue of the present invention, but not local- ized, the synthetic tissue of the present invention has biological integration capability evenly with respect to the surrounding. Therefore, the synthetic tissue of the present invention has an excellent effect of recovery after implantation.

For cell-dell adhesion, cadherin, a number of molecules belonging in an immunoglobulin superfamily (NCAML1, ICAM, fasciclin II, III, etc.), selectin, and the like are known, each of which is known to join cell membranes via a specific molecular reaction. Therefore, in one embodiment, the synthetic tissue, three-dimensional structure, or the like of the present invention preferably has substantially the same composition of cadherin, immunoglobulin superfamily molecules, or the like as that of a site for which implantation is intended.

Thus, various molecules are involved in cell adhesion and have different functions. Those skilled in the art can appropriately select a molecule to be contained in a synthetic tissue or three-dimensional structure of the present invention depending on the purpose. Techniques for cell adhesion are well known as described above and as described in, for example, "Saibogaimatorikkusu—Rinsho heno Oyo—[Extracellular matrix—Clinical Applications—], Medical Review.

It can be determined whether or not a certain molecule is a cell adhesion molecule, by an assay, such as biochemical quantification (an SDS-PAG method, a labeled-collagen method, etc.), immunological quantification (au enzyme antibody method, a fluorescent antibody method, an immunohistological study, etc.), a PCR method, a hybridization method, or the like, in which a positive reaction is detected. Examples of such a cell adhesion molecule include, but are not limited to, collagen, integrin, fibronectin, laminin, vitronectin, fibrinogen, an immunoglobulin superfamily member (e.g., CD2, CD4, CD8, ICM1, ICAM2, VCAM1) selectin, cadherin, and the like. Most of these cell adhesion molecules transmit into a cell an auxiliary signal for cell activation due to intercellular interaction as well as cell adhesion. Therefore, an adhesion molecule for use in an implant of the present invention preferably transmits an auxiliary signal for cell activation into a cell. This is because cell activation can promote growth of cells originally present or aggregating in a tissue or organ at an injured site after application of an implant thereto. It can be determined whether or not such an auxiliary signal can be transmitted into a cell, by an assay, such as biochemical quantification (an SDS-PAG method, a labeled-collagen method, etc.), immunological quantification (an enzyme antibody method, a fluorescent antibody method, an immunohistological study, etc.) a PDR method, a hybridization method, or the like, in which a positive reaction is detected.

An example of a cell adhesion molecule is cadherin which is present in many cells capable of being fixed to tissue. Cadherin can be used in a preferable embodiment of the present invention. Examples of a cell adhesion molecule in cells of blood and the immune system which are not fixed to tissue, include, but are not limited to, immunoglobulin superfamily molecules (LFA-3, CD2, CD4, CD8, ICAM-1, ICAM2, VCAM1, etc.); integrin family molecules (LFA-1, Mac-1, gpIIbIIIa, p150, p95, VLA1, VLA2, VLA3, VLA4, VLA5, VLA6, etc.); selectin family molecules (L-selectin, E-selectin, P-selectin, etc.), and the like. Therefore, such a molecule may be useful for treatment of a tissue or organ of blood and the immune system.

Nonfixed cells need to be adhered to a specific tissue in order to act on the tissue. In this case, it is believed that cell-cell adhesion is gradually enhanced via a first adhesion by a selectin molecule or the like which is constantly expressed and a second adhesion by a subsequently activated integrin molecule. Therefore, in the present invention, a cell adhesion molecule for mediating the first adhesion and another cell adhesion molecule for mediating the second adhesion may be used together.

As used herein, the term "actin regulatory agent" refers to a substance which interacts directly or indirectly with actin in cells to change the form or state of the actin. It should be understood that actin regulatory agents are categorized into two classes, actin depolymerizing agents and actin polymerizing agents, depending on the action on actin. Examples of actin depolymerizing agents include, but are not limited to, Slingshot, cofilin, CAP (cyclase associated protein), ADF (actin depolymerizing factor), destrin, depactin, actophorin, cytochalasin, NGF (nerve growth factor), and the like. Examples of actin polymerizing agents include, but are not limited to, RhoA, mDi, profilin, Rac1, IRSp 53, Wave2, profilin, ROCK, Lim kinase, cofilin, cdc42, N-WASP, Arp2/3, Drf3, IRSp53, Mena, LPA (lysophosphatidic acid), insulin, PDGF (platelet-derived growth factor) a, PDGFb, chemokine, TGF (transforming growth factor) b, and the like. The above-described actin regulatory agents include some substances which can be identified by the following assay. Interaction of an actin regulatory agent with respect to actin is assayed as follows. Actin is visualized using an actin staining reagent (Molecular Probes, Texas Red-X phalloidin) or the like. By observing actin aggregation or cell outgrowth under a microscope, the presence of the interaction is determined by confirming the aggregation and reconstruction of actin and/or an increase in the cell outgrowth rate. The determination may be performed quantitatively or qualitatively. The above-described actin regulatory agents are used in the present invention so as to promote the detachment or a multilayer structure of the synthetic tissue. When an actin regulatory agent used in the present invention is derived from an organism, the organism may be a mammalian species, such as human, mouse, bovine, or the like.

The above-described agents involved in actin polymerization control actin polymerization in relation to Rho and the examples of the agents include the following (see, for example, "Saibokokkaku/Undo ga wakaru (Understanding of cytoskeleton/movement)", (Ed./Hiroaki Miki), Yodosha).

Actin polymerization (see Takenaka T et al. J.Cell Sci., 114: 1801-1809, 2001)

RhoA→mDi→profilin⇒ actin polymerization

RhoA→ROCK/Rho→LIM kinase→phosphorylation of (suppression)⇒ actin polymerization

Rac1→IRSp53→WAVE2→profilin, Arp2/3⇒ actin polymerization cdc42→N-WASP—profilin, Arp2/3⇒ actin polymerization cdc42→Drf3—IRSp53→Mena⇒ actin polymerization (In the above descriptions, → indicates a signal transduction pathway such as phosphorylation. In the present invention any agent involved in such a pathway can be utilized.

Actin Depolymerization

Slingshot→dephosphorization of cofilin (activation)⇒ actin depolymerization

Actin depolymerization is controlled by a balance between phosphorylation by LIM kinase activity of cofilin and dephosphorization by Slingshot. As another agent for activating cofilin, CAP (cyclase-associated protein) and AIPI (actin-interacting-protein 1) are identified. It is recognized that any suitable agent can be used.

LPA (lysophosphatidic acid) of any chain length can be used.

Any chemokine can be used. However, examples of preferable chemokine include interleukin 8, MIP-1, SDF-1 and the like.

Any TGFβ can be used. However, examples of preferable TGFβ include TGF-β1 and TGF-β3. TGF-β1 and TGF-β3 has an extracellular matrix generation promoting activity. Thus, in the present invention, TGF-β1 and TGF-β3 are used with an attention.

As used herein, the term "tissue strength" refers to a parameter which indicates a function of a tissue or organ and a physical strength of the tissue or organ. Tissue strength can be generally determined by measuring tensile strength (e.g., break strength, modulus of rigidity, Young's modulus, etc.). Such a general tensile test is well known. By analyzing data obtained by a general tensile test, various data, such as break strength, modulus of rigidity, Young's modulus, and the like, can be obtained. These values can be herein used as indicators of tissue strength. Typically, tissue strength which allows clinical applications is herein required.

Figure 46:
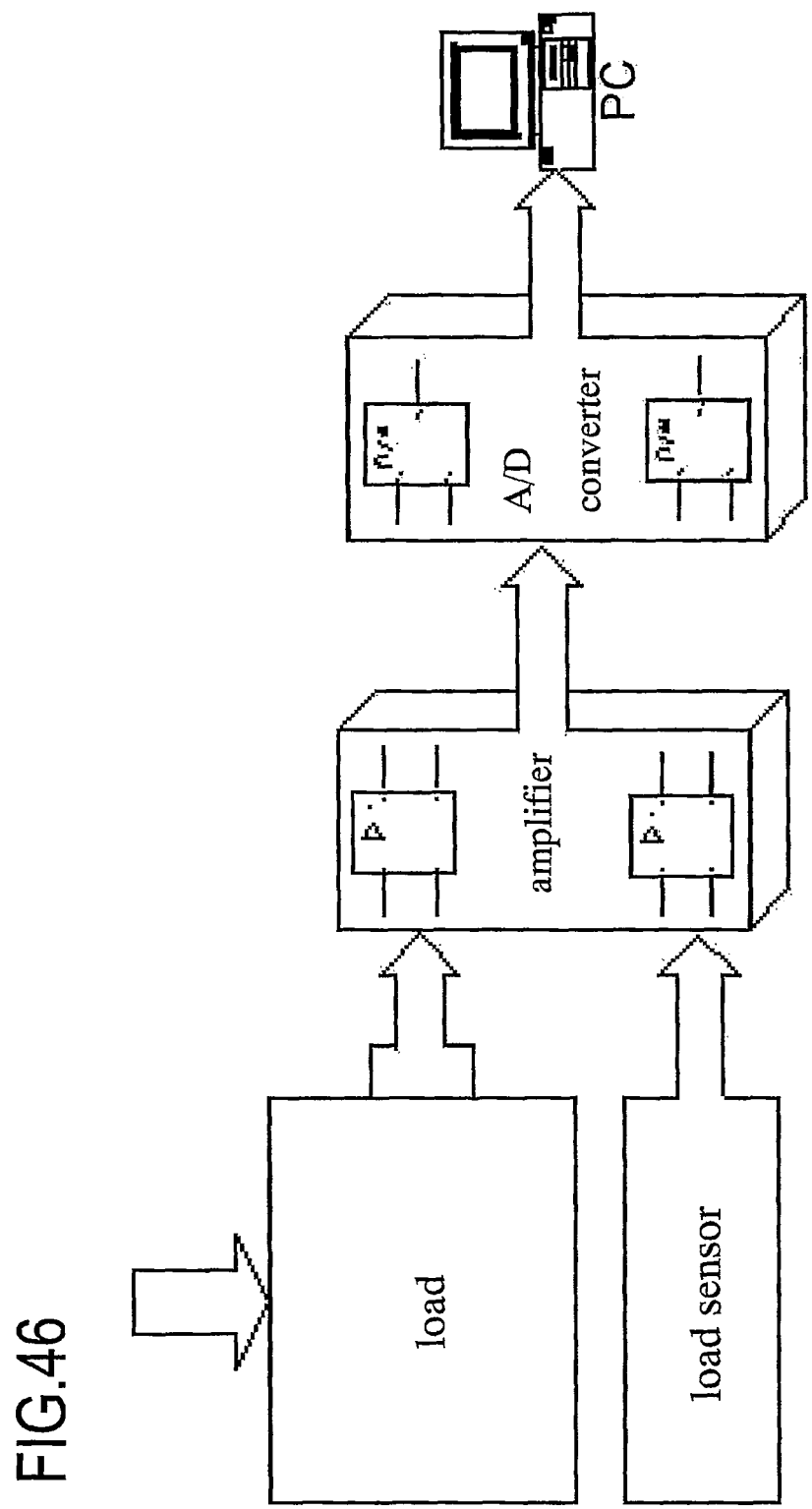
FIG. 46 shows a diagram for explaining a technique for measuring stress and distortion characteristics to determine tensile strength.
Figure 47:
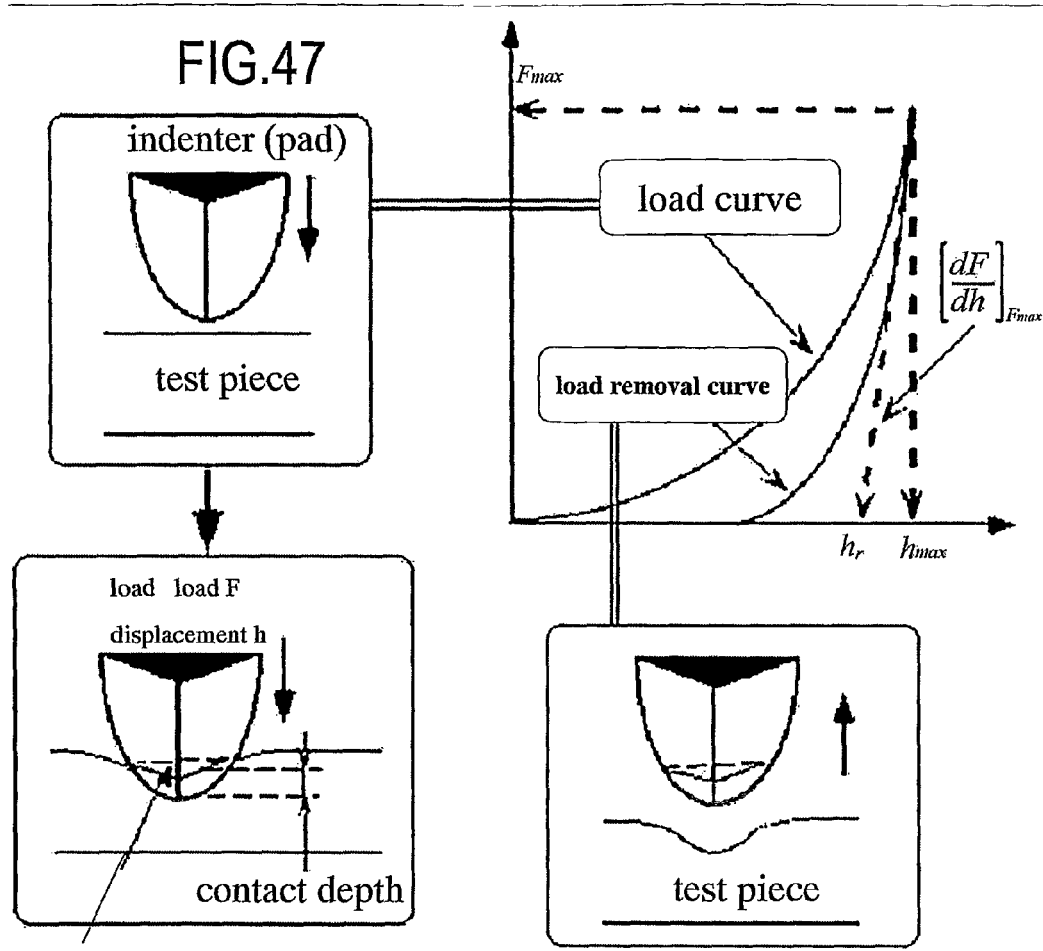
FIG. 47 shows a principle for obtaining a load/removal of a load curve.

The tensile strength of a synthetic tissue, three-dimensional structure, or the like of the present invention can be determined by measuring the stress and distortion characteristics thereof. Briefly, a load is applied to a sample; the resultant distortion and the load are input to respective A/D converters (e.g., ELK-5000) (1 ch: distortion, 2 ch: load); the stress and distortion characteristics are measured to determine the tensile strength of the sample (FIG. 46). Tensile strength can also be determined by testing creep characteristics. A creep characteristics indentation test is conducted to investigate how a sample is extended over time while a constant load is applied to the sample. For small materials, thin materials, and the like, an indentation test is conducted using, for example, a triangular pyramid-shaped indenter with a tip having a radius of about 0.1 μm to about 1 μm. Initially, the indenter is pushed into a test piece so that a load is given to the test piece. When the indenter reaches from several tens of nanometers to several micrometers deep in the test piece, the indenter is drawn off to remove the load. FIG. 47 shows a load/removal of load curve obtained by the above-described test method. Rigidity, Young's modulus, or the like can be obtained based on the behavior of the load and the push depth derived from the curve.

The tensile strength of the synthetic tissue of the present invention may be low. The tensile strength becomes higher when the matrix concentration is increased, and becomes lower when the cell to matrix ratio is increased. The present invention is characterized in that the strength can be adjusted as necessary. The present invention is also characterized in that the strength can be high or low relative to that of a tissue to be implanted. Therefore, it is recognized that the strength can be set to comply with any desired site.

As used herein, the term "physiologically active substance" refers to a substance capable of acting on a cell or tissue. Physiologically active substances include cytokines and growth factors. A cellular physiologically active substance may be naturally-occurring or synthesized. Preferably, a cellular physiologically active substance is one that is produced by a cell or one that has a function similar thereto. As used herein, a cellular physiologically active substance may be in the form of a protein or a nucleic acid or in other forms. In actual practice, cellular physiologically active substances are typically proteins. In the present invention, a physiologically active substance may be used to promote the affinity of an implanted synthetic tissue of the present invention, for example.

The term "cytokine" is used herein in the broadest sense in the art and refers to a physiologically active substance which is produced from a cell and acts on the same or different cell. Cytokines are generally proteins or polypeptides having a function of controlling an immune response, regulating the endocrine system, regulating the nervous system, acting against a tumor, acting against a virus, regulating cell growth, regulating cell differentiation, or the like. Cytokines are herein in the form of a protein or a nucleic acid or in other forms. In actual practice, cytokines are typically proteins.

The terms "growth factor" or "cell growth factor" are used herein interchangeably and each refers to a substance which promotes or controls cell growth. Growth factors are also called "proliferation factors" or "development factors". Growth factors may be added to cell or tissue culture medium, substituting for serum macromolecules. It has been revealed that a number of growth factors have a function of controlling differentiation in addition to a function of promoting cell growth.

Examples of cytokines representatively include, but are not limited to, interleukins, chemokines, hematopoietic factors such as colony stimulating factors, a tumor necrosis factor, interferons, a platelet-derived growth factor (PDGF), an epidermal growth factor (EGF), a fibroblast growth factor (FGF), a hepatocyte growth factor (HGF), a vascular endothelial cell growth factor (VEGF), cardiotrophin, and the like, which have proliferative activity.

Cellular physiologically active substances, such as cytokines, growth factors, and the like, typically have redundancy in function. Accordingly, reference herein to a particular cytokine or growth factor by one name or function also includes any other names or functions by which the factor is known to those of skill in the art, as long as the factor has the activity of a cellular physiologically active substance for use in the present invention. Cytokines or growth factors can be used in a therapeutic or pharmaceutical agent according to a preferable embodiment of the present invention as long as they have preferable activity as described herein.

Therefore, in one embodiment of the present invention, it was revealed that when such a cytokine or growth factor (e.g., BMP-2, etc.) is provided to an implantation site (e.g., an injured site of a cartilage, etc.) concomitantly with a synthetic tissue or three-dimensional structure of the present invention, the affinity of the synthetic tissue or three-dimensional structure and an improvement in the function of the implantation site are observed. Thus, the present invention also provides such a combined therapy.

As used herein, the term "differentiation" refers to a developmental process of the state of the complex parts of organisms, such as cells, tissues, or organs and a process in which a characteristic tissue or organ is formed. The term "differentiation" is mainly used in embryology, developmental biology, and the like. In organisms, various tissues and organs are formed from divisions of a fertilized ovum (a single cell) to an adult. At early developmental stages (i.e., before cell division or after insufficient cell division), each cell or cell group has no morphological or functional feature and is not much distinguishable. Such a state is referred to as "undifferentiated". "Differentiation" may occur at the level of organs. A cell constituting an organ may develop into various cells or cell groups having different features. This phenomenon is also referred to as differentiation within an organ in the formation of the organ. Therefore, a synthetic tissue or three-dimensional structure of the present invention may comprise a tissue including differentiated cells.

When differentiation is required to produce a synthetic tissue of the present invention, the differentiation may be performed either before or after the organization of the cells.

As used herein, the terms "differentiation agent" and "differentiation promoting agent" are used interchangeably and refer to any agent which is known to promote differentiation of cells (e.g., chemical substances, temperature, etc.). Examples of such an agent include, but are not limited to, various environmental factors, such as temperature, humidity, pH, salt concentration, nutrients, metals, gas, organic solvent, pressure, chemical substances (e.g., steroids, antibiotics, etc.), and the like, or arbitrary combinations thereof. Representative examples of differentiation agents include, but are not limited to, cellular physiologically active substances. Representative examples of cellular physiologically active substances include, but are not limited to, DNA demethylating agents (e.g., 5-azacytidine, etc.), histone deacetylating agents (e.g., trichosanthin, etc.), intranuclear receptor ligands (e.g., retinoic acid (ATRA) vitamin $D_3$, T3, etc.) cell growth factors (e.g., activin, IGF-1, FGF, PDGF, TGF-β, BMP2/4, etc.), cytokines (e.g., LIF, IL-2, IL-6, etc.), hexamethylenebisacetoamides, dimethylacetoamides, dibutyl cAMPs, dimethylsulfoxides, iododeoxyuridines, hydroxyl ureas, cytosine arabinosides, mitomycin C, sodium lactate, aphydicolin, fluorodeoxyuridine, polybren hexadimetrine bromide, selenium, and the like.

Specific examples of differentiation agents are described below. These differentiation agents may be used singly or in combination.

A) Cornea: epidermal growth factor (EGF);
B) Skin (keratinocyte): TGF-β, FGF-7 (KGF: keratinocyte growth factor), EGF;
C) Vascular endothelium: VEGF, FGF, angiopoietin;
D) Kidney: LIF, BMP, FGF, GDNF;
E) Heart: HGF, LIF, VEGF;
F) Liver: HGF, TGF-β, IL-6, EGF, VEGF;
G) Umbilical endothelium: VEGF;
H) Intestinal epithelium: EGF, IGF-I, HGF, KGF, TGF-β, IL-11;
I) Nerve: nerve growth factor (NGF), BDNF (brain-derived neurotrophic factor), GDNF (glial-derived neurotrophic factor), neurotrophin, IL-6, TGF-β, TNF;
J) Glia cell: TGF-β, TNF-α, EGF, LIF, IL-6;
K) Peripheral nerve cell: bFGF, LIF, TGF-β, IL-6, VEGF;
L) Lung (alveolarepithelium): TGF-β, IL-13, IL-1β, KGF, HGF;
M) Placenta: growth hormone (GH), IGF, prolactin, LIF, IL-1, activin A, EGF;
N) Pancreatic epithelium: growth hormone, prolactin;
O) Pancreatic Langerhans' cells: TGF-β, IGF, PDGF, EGF, TGF-β, TRH (thyroropin);
P) Synovial cell: FGF, TGF-β (particularly, TGF-β1, TGF-β3);
Q) Osteoblast: BMP (particularly, BMP-2, BMP-4, BMP-7), FGF;
R) Chondroblast: FGF, TGF-β (particularly, TGF-β1, TGF-β3), BMP (particularly, BMP-2, BMP-4, BMP-7), TNF-α, IGF;
S) Retinal cell: FGF, CNTF (cilliary neurotrophic factor);
T) Fat cell: insulin, IGF, LIF; and
U) Muscle cell: LIF, TNF-α, FGF.

As used herein, the term "osteogenesis" indicates that any cell is caused to differentiate into a osteocyte. It is known that osteogenesis is promoted in the presence of dexamethasone, β-glycerophosphate, and ascorbic acid 2-phosphate. An osteogenic agent (BMP, (particularly, BMP-2, BMP-4, BMP-7)) may be added to promote osteogenesis.

As used herein, the term "chondrogenesis" refers to differentiation of any cell into a chondrocyte. It is known that chondrogenesis is promoted in the presence of pyrubic acid, dexamethasone, ascorbic acid 2-phosphate, insulin, transferrine, and selenious acid. An bone morphogenetic protein (BMP, (particularly, BMP-2, BMP-4, BMP-7)), TGF-β (particularly, TGF-β1 and TGF-β), FGF, TNF-α and the like may be added to promote chondrogenesis.

As used herein, the term "adipogenesis" refers to differentiation of any cell into an adipocyte. It is known that adipogenesis is promoted in the presence of insulin, IGF, LIF, and ascorbic acid 2-phosphate.

As used herein, the terms "implant", "graft", and "tissue graft" are used interchangeably, referring to homologous or heterologous tissue or a cell group, or an artificial material, which is inserted into a particular site of a body and thereafter forms a part of the body. Therefore, a synthetic tissue or three-dimensional structure of the present invention can be used as an implant. Examples of conventional grafts include, but are not limited to, organs or portions of organs, blood vessels, blood vessel-like tissue, heart, cardiac valves, pericardia, dura matter, joint capsule, bone, cartilage, cornea, tooth, and the like. Therefore, grafts encompass any one of these which is inserted into an injured part so as to compensate for the lost portion. Grafts include, but are not limited to, autografts, allografts, and xenografts, which depend on the type of their donor.

As used herein, the term "autograft" (a tissue, a cell, an organ, etc.) refers to a graft (a tissue, a cell, an organ, etc.) which is implanted into the same individual from which the graft is derived. As used herein, the term "autograft" (a tissue, a cell, an organ, etc.) may encompass a graft from a genetically identical individual (e.g. an identical twin) in a broad sense. As used herein, the teams "autologous" and "derived from a subject" are used interchangeably. Therefore, the term "not derived from a subject" in relation to a graft indicates that the graft is not autologous (i.e., heterologous).

As used herein, the term "allograft (a tissue, a cell, an organ, etc.)" refers to a graft (a tissue, a cell, an organ, etc.) which is transplanted from a donor genetically different from, though of the same species, as the recipient. Since an allograft is genetically different from the recipient, the allograft (a tissue, a cell, an organ, etc.) may elicit an immune reaction in the recipient. Examples of such grafts (a tissue, a cell, an organ, etc.) include, but are not limited to, grafts derived from parents (a tissue, a cell, an organ, etc.). The synthetic tissue of the present invention can be an allograft, which has been demonstrated to have satisfactory therapeutic results. Attention should be paid to the synthetic tissue of the present invention.

As used herein, the term "xenograft" (a tissue, a cell, an organ, etc.) refers to a graft (a tissue, a cell, an organ, etc.) which is implanted from a different species. Therefore, for example, when a human is a recipient, a porcine-derived graft (a tissue, a cell, an organ, etc.) is called a xenograft (a tissue, a cell, an organ, etc.).

As used herein, "recipient" (acceptor) refers to an individual which receives a graft (a tissue, a cell, an organ, etc.) or implanted matter (a tissue, a cell, an organ, etc.) and is also called "host". In contrast, an individual providing a graft (a tissue, a cell, an organ, etc.) or implanted matter (a tissue, a cell, an organ, etc.) is called. "donor" (provider).

With a synthetic tissue forming technique of the present invention, a synthetic tissue derived from any cell can be used. This is because a synthetic tissue (e.g., membranous tissues, organs, etc.) formed by the method of the present invention can exhibit a desired function while the tissue injury rate is maintained at a level which does not interfere with the therapy (i.e., a low level). Conventionally, tissues or organs are used as grafts without modification. In contrast to this, the present invention provides a tissue comprising three-dimensionally connected cells. Such a synthetic three-dimensional tissue cannot be achieved by conventional techniques, and therefore, constitutes one significant effect of the present invention.

As used herein, the term "subject" refers to an organism to which treatment of the present invention is applied and is also referred to as "patient". A patient or subject may be preferably a human.

Cells optionally used in a synthetic tissue, three-dimensional structure, or tissue graft of the present invention may be derived from a syngeneic origin (self origin), an allogenic origin (non-self origin), or a heterologous origin. In view of rejection reactions, syngeneic cells are preferable. If rejection reactions do not raise problems, allogenic cells may be employed. Cells which elicit rejection reactions can be employed by optionally treating the cells in a manner that overcomes rejection reactions. Procedures for avoiding rejection reactions are known in the art (see, for example, "Shin Gekagaku Taikei, Dai 12 Kan, Zoki Ishoku (Shinzo Ishoku-Hai Ishoku Gijutsuteki, Rinriteki Seibi kara Jisshi ni Mukete [New Whole Surgery, Vol. 12, Organ Transplantation (Heart Transplantation Lung Transplantation From Technical and Ethical Improvements to Practice)" (Revised 3rd ed.), Nakayama Shoten]. Examples of such methods include, but are not limited to, a method using immunosuppressants or steroidal drugs, and the like. For example, there are currently the following immunosuppressants for preventing rejection reactions: "cyclosporine" (SANDIMMUNE/NEORAL); "tacrolimus" (PROGRAF); "azathioprine" (IMURAN); "steroid hormone" (prednine, methylprednine); and "T-cell antibodies" (OKT3, ATG, etc.). A method which is used worldwide as a preventive immunosuppression therapy in many facilities, is the concurrent use of three drugs: cyclosporine, azathioprine, and steroid hormone. An immunosuppressant is desirably administered concurrently with a pharmaceutical agent of the present invention. The present invention is not limited to this. An immunosuppressant may be administered before or after a regeneration/therapeutic method of the present invention as long as an immunosuppression effect can be achieved.

Cells used in the present invention may be derived from any organism (e.g., vertebrates and invertebrates). Preferably, cells derived from vertebrates are used. More preferably, cells derived from mammals (e.g., primates, rodents, etc.) are used. Even more preferably, cells derived from primates are used. Most preferably, cells derived from a human are used. Typically, cells from the same species as the host are preferably used.

Examples of an affected portion of a subject treated by a synthetic tissue of the present invention include, but are not limited to, the heart suffering from a heart disease (e.g., heart failure, ischemic heart diseases, myocardial infarct, cardiomyopathy, myocarditis, hypertrophic cardiomyopathy, dilated hypertrophic cardiomyopathy, and dilated cardiomyopathy); blood vessels in a pericardium patch, infarcted myocardium lower and upper limbs; a joint injury or denaturation; a cartilage injury or denaturation; osteonecrosis; meniscus injury or denaturation; intervertebral disk denaturation; ligament injury or denaturation; a fracture; implantation to a patient having a joint, cartilage, or bone having bone loss; an injured cornea; and the like.

Tissues targeted by the present invention may be any organ of an organism and may be derived from any organism. Examples of organisms targeted by the present invention include vertebrates and invertebrates. Preferably, organisms targeted by the present invention are mammals (e.g., primates, rodents, etc.). More preferably, organisms targeted by the present invention are primates. Most preferably, organisms targeted by the present invention are humans.

As used herein, the term "flexibility" in relation to a synthetic tissue refers to an ability to resist physical stimuli from external environments (e.g., pressure). A synthetic tissue having flexibility is preferable when the implantation site moves or deforms autonomously or by external effects.

As used herein, the term "extendibility and contractibility" in relation to a synthetic tissue refers to an ability to resist extending or contracting stimuli from external environments (e.g., pulsation). A synthetic tissue having extendibility and contractibility is preferable when the implantation site is subjected to extending or contracting stimuli. Examples of implantation sites, which are subjected to extending or contracting stimuli, include, but are not limited to, heart, muscle, joint, cartilage, tendon, and the like. In one embodiment, extendibility and contractibility capable of withstanding the pulsation motion of the heart may be required.

As used herein, the term "part" or "portion" refers to any part or portion, tissue, cell, or organ in the body. Examples of such parts, tissues, cells, and organs include, but are not limited to, a portion which can be treated with skeletalmyoblasts, fibroblasts, synovial cells, stem cells, and the like. A marker specific to a portion may be any parameter, such as a nucleic acid molecule (expression of mRNA), a protein, an extracellular matrix, a specific phenotype, a specific shape of a cell, or the like. Therefore, markers which are not specified herein may be used to identify a synthetic tissue of the present invention as long as these markers can indicate cells derived from a portion. Representative examples of portions, but are not limited to, portions of the heart other than the adult myocardium, portions containing mesenchymal stem cells or cells derived therefrom, other tissues, other organs, myoblasts (e.g., skeletal myoblasts), fibroblasts, synovial cells, and the like.

For observing a cartilage tissue, following markers can be used as index.

Sox9 (human: Accession No. NM_000346) is a marker specific to a chondrocyte. The marker can be confirmed mainly by observing the presence of mRNA (Kulyk W M, Franklin Hoffman L M. Sox9 expression during chondrogenesis in micromass cultures of embryonic limb mesenchyme. Exp Cell Res. 2000 Mar. 15, 255(2):327-32.).

Col 2A1 (human: Accession No. NM_001844) is a marker specific to a chondrocyte. The marker can be confirmed mainly by observing the presence of mRNA (Kulyk W M, Franklin J L, Hoffman LM. Sox9 expression during chondrogenesis in micromass cultures of embryonic limb mesenchyme. Exp Cell Res. 2000 Mar. 15; 255(2):327-32.).

Aggrecan (human: Accession No. NM_001135) is a marker specific to a chondrocyte. The marker can be confirmed mainly by observing the presence of mRNA (Kulyk W M, Franklin J L, Hoffman L M. Sox9 expression during chondrogenesis in micromass cultures of embryonic limb mesenchyme. Exp Cell Res. 2000 Mar. 15; 255(2):327-32.).

Bone sialoprotein (human: Accession No. NM_004967) is a marker specific to an osteoblast. The marker can be confirmed mainly by observing the presence of mRNA (Haase H R, Ivanovski S, Waters M J, Bartold P M. Growth hormone regulates osteogenic marker mRNA expression in human periodontal fibroblasts and alveolar bone-derived cells. J Periodontal Res. 2003 August; 38(4):366-74.).

Osteocalcin (human: Accession No. NM_199173) is a marker specific to an osteoblast. The marker can be confirmed mainly by observing the presence of mRNA (Haase H R, Ivanovski S, Waters M J, Bartold P M. Growth hormone regulates osteogenic marker mRNA expression in human periodontal fibroblasts and alveolar bone-derived cells. J Periodontal Res. 2003 August; 38(4):366-74.).

GDF5 (human: Accession No. NM_000557) is a marker specific to a ligament cell. The marker can be confirmed mainly by observing the presence of mRNA (Wolfman N M, Hattersley G, Cox K, Celeste A J, Nelson R, Yamaji N, Dube J L, DiBlasio-Smith E, Nove J, Song J J, Wozney J M, Rosen V. Ectopic induction of tendon and ligament in rats by growth and differentiation factors 5, 6, and 7, members of the TGF-beta gene family. J Clin Invest. 1997 Jul. 15; 100(2):321-30.).

Six1 (human: Accession No. NM_005982) is a marker specific to a ligament cell (Dreyer S D, Naruse T, Morello R, Zabel B, Winterpacht A, Johnson R L, Lee B, Oberg K C. Lmx1b expression during joint and tendon formation: localization and evaluation of potential downstream targets. Gene Expr Patterns. 2004 July; 4(4):397-405.). The marker can be confirmed mainly by observing the presence of mRNA.

Scleraxis (human: Accession No. BK000280) is a marker specific to a ligament cell (Brent A E, Schweitzer R, Tabin C J. A somitic compartment of tendon progenitors. Cell. 2003 Apr. 18; 113(2):235-48.). The marker can be confirmed mainly by observing the presence of mRNA.

A "part other than the myocardium of an adult" and a "part other than the heart of an adult" can be identified using markers characteristic to cells derived from the myocardium of an adult or the heart of an adult including skeletalmyoblasts, fibroblasts, synovial cells, stem cells, or the like (hereinafter referred to as a "non-adult myocardial marker" or a "non-adult heart marker", respectively). If the marker is expressed by less than about 100%, preferably less than about 80%, more preferably less than about 50%, even more preferably less than about 25%, in some cases less than about 1%, the above-described parts can be identified. Examples of such markers include, but are not limited to, myosin heavy chain IIa, myosin heavy chain IIb, myosin heavy chain IId (IIx), CD56, MyoD, Myf5, myogenin, and the like. Therefore, non-adult myocardial markers which are not specified herein may be used to identify a synthetic tissue of the present invention as long as these markers can indicate cells derived from parts other than the myocardium of an adult. Also, non-adult heart markers which are not specified herein may be used to identify a synthetic tissue of the present invention as long as these markers can indicate cells derived from parts other than the heart of an adult.

Myosin heavy chain IIa (human: Accession No. NM_017534; SEQ ID NOs. 1 and 2), myosin heavy chain IIb (human: Accession No. NM_017533; SEQ ID NOs. 3 and 4), and myosin heavy chain IId (IIx) (human: Accession No. NM_005963; SEQ ID NOs. 5 and 6) are markers specific to myoblasts (Havenith M. G., Visser R., Schrijvers-van Schendel J. M., Bosman F. T., "Muscle Fiber Typing in Routinely Processed Skeletal Muscle With Monoclonal Antibodies", Histochemistry, 1990; 93 (5):497-499). These markers can be confirmed mainly by observing the presence of proteins. An antibody against myosin heavy chain IIa, myosin heavy chain IIb, and myosin heavy chain IId (IIx) is, for example, MY-32 available from Sigma. This antibody is specific to skeletal muscles and does not bind to myocardium (Webster C., Pavlath G. K., Parks D. R., Walsh F. S., Blau H. M., Exp. Cell. Res., 1988 January; 174 (1):252-65; and Havenith M. G., Visser R., Schrijvers-van Schendel J. M., Bosman F. T., Muscle Fiber Typing in Routinely Processed Skeletal Muscle with Monoclonal Antibodies, Histochemistry, 1990, 93(5):497-499).

CD56 (human: Accession No. U63041; SEQ ID NOs. 7 and 8) is a marker specific to myoblasts. This marker can be confirmed mainly by observing the presence of mRNA.

MyoD (human: Accession No. X56677; SEQ ID NOs. 9 and 10) is a marker specific to myoblasts. This marker can be confirmed mainly by observing the presence of mRNA.

Myf5 (human: Accession No. NM_005593; SEQ ID NOs. 11 and 12) is a marker specific to myoblasts. This marker can be confirmed mainly by observing the presence of mRNA.

Myogenin (human: Accession No. BT007233; SEQ ID NOs. 13 and 14) is a marker specific to myoblasts. This marker can be confirmed mainly by observing the presence of mRNA.

In other embodiments, other markers specific to other tissues can be utilized. Examples of such markers include, but are not limited to, Oct-3/4, SSEA-1, Rex-1, Otx2, and the like for embryonic stem cells; VE-cadherin, Flk-1, Tie-1, PECAM1, vWF, c-kit, CD34, Thy1, Sca-1, and the like for endothelial cells; skeletal muscle α actin in addition to the above-described markers for skeletal muscles; Nestin, Glu receptor, NMDA receptor, GFAP, neuregulin-1, and the like for nerve cells; c-kit, CD34, Thy1, Sca-1, GATA-1, GATA-2, FOG, and the like for hematopoietic cells.

As used herein, the term "derived" in relation to cells means that the cells are separated, isolated, or extracted from a cell mass, tissue, or organ in which the cells have been originally present, or that the cells are induced from stem cells.

As used herein, the term "applicable to heart" means that the heart applied has an ability to pulsate. A tissue applicable to heart has strength such that the tissue can withstand dilation and contraction of the pulsating heart. Here, applicability to the heart includes applicability to the myocardium. Applicability to heart may be determined by confirming that a recipient having an implanted graft survives.

As used herein, the term "three-dimensional structure" refers to an object which comprises cells having intracellular intergration or alignment and extends three-dimensionally, particularly matrices are oriented three-dimensionally and cells are arranged three-dimensionally.

As used herein, the term "biological integration" in relation to the relationship between biological entities such as cells means that there is certain interaction between the biological entities. Examples of such interaction includes, but are not limited to, interaction via biological molecules (e.g., extracellular matrix), interaction via signal transduction, electrical interaction (electrical integration, such as synchronization of electrical signal's or the like), and the like. Biological integration includes biological integration in a synthetic tissue and biological integration of a synthetic tissue with its surroundings (e.g., surrounding tissues and cells after implantation, etc.). In order to confirm interactions, an assay appropriate to a characteristic of the interaction is employed. In order to confirm physical interactions via biological molecules, the strength of a synthetic tissue, a three-dimensional structure, or the like is measured (e.g., a tensile test). In order to confirm interaction via signal transduction, gene expression or the like is investigated. In order to confirm electrical interactions, the electric potential of a synthetic tissue, a three-dimensional structure, or the like is measured to determine whether or not the electric potential is propagated with constant waves. In the present invention, biological integration is provided in all three dimensions. Preferably, there is biological integration substantially uniformly in all directions in a three-dimensional space. In another embodiment, the synthetic tissue, a three-dimensional structure, and the like, which has substantially uniform two-dimensional biological integration and slightly weaker biological integration in the third dimension, may be employed. Biological integration via an extracellular matrix can be confirmed based on the degree of staining by staining the extracellular matrix. As a method for observing biological integration in vivo, there is an integration experiment using cartilage. In this experiment, a surface of the cartilage is removed and digested with chondroitinase ABC (Hunziker E. B. et al., J. Bone Joint Surg. Am., 1996 May; 78 (5): 721-33). Thereafter, a tissue of interest is implanted onto a cut surface, followed by culturing for about 7. The subsequent integration is observed (FIG. 23). It will be understood that a capability to adhere to surrounding cells can be determined with the above-described cartilage experiment.

A synthetic tissue, three-dimensional structure, or the like of the present invention may be provided using known preparation methods, as a pharmaceutical product, or alternatively, as an animal drug, a quasi-drug, a marine drug, a cosmetic product, and the like.

Animals targeted by the present invention include any organism as long as it has organs (e.g., animals (e.g., vertebrates, invertebrate)). Preferably, the animal is a vertebrate (e.g., Myxiniformes, Petronyzoniformes, Chondrichthyes, Osteichthyes, amphibian, reptilian, avian, mammalian, etc.), more preferably mammalian (e.g., monotremata, marsupialia, edentate, dermoptera, chiroptera, carnivore, insectivore, proboscides, perissodactyla, artiodactyla, tubulidentata, pholidota, sirenia, cetacean, primates, rodentia, lagomorpha, etc.). Illustrative examples of a subject include, but are not limited to, animals, such as cattle, pigs, horses, chickens, cats, dogs, and the like. More preferably, primates (e.g., chimpanzee, Japanese monkey, human, etc.) are used. Most preferably, a human is used. This is because there is limitation to implantation therapies.

When the present invention is used as a pharmaceutical agent, it may further comprise a pharmaceutically acceptable carrier or the like. A pharmaceutically acceptable carrier contained in a medicament of the present invention includes any material known in the art.

Examples of such a pharmaceutically acceptable carrier include, but are not limited to, antioxidants, preservatives, colorants, flavoring agents, diluents, emulsifiers, suspending agents, solvents, filler's, bulking agents, buffers, delivery vehicles, agricultural or pharmaceutical adjuvants, and the like.

The amount of a pharmaceutical agent (e.g., a synthetic tissue, a pharmaceutical compound used in conjunction therewith, etc.) used in the treatment method of the present invention can be easily determined by those skilled in the art with reference to the purpose of use, a target disease (type, severity, and the like), the patient's age, weight, sex, and case history, the form or type of the cell, and the like. The frequency of the treatment method of the present invention applied to a subject (or patient) is also determined by those skilled in the art with respect to the purpose of use, target disease (type, severity, and the like), the patient's age, weight, sex, and case history, the progression of the therapy, and the like. Examples of the frequency include once per day to several months (e.g., once per week to once per month). Preferably, administration is performed once per week to month with reference to the progression.

As used herein, the term "administer" in relation to a synthetic tissue, three-dimensional structure, or the like of the present invention or a pharmaceutical agent comprising it, means that they are administered singly or in combination with other therapeutic agents. A synthetic tissue of the present invention may be introduced into therapy sites (e.g., impaired heart, etc.) by the following methods, in the following forms, and in the following amounts. Examples of the introduction methods include, but are not limited to, direct attachment, suture after attachment, insertion, and the like. For example, a synthetic tissue and a three-dimensional structure of the present invention may be applied by the above-described methods to an impaired site of ischemic myocardial tissue caused by myocardial infarct, angina pectoris, or the like. Combinations may be administered either concomitantly (e.g., as an admixture), separately but simultaneously or concurrently; or sequentially. This includes presentations in which the combined agents are administered together as a therapeutic mixture, and also procedures in which the combined agents are administered separately but simultaneously (e.g., a synthetic tissue or the like is directly provided by operation, while other pharmaceutical agents are provided by intravenous injection). "Combination" administration further includes the separate administration of one of the compounds or agents given first, followed by the second.

As used herein, the term "reinforcement" means that the function of a targeted part of an organism is improved.

As used herein, the term "instructions" describe how to handle reagents, usage, a preparation method, a method of producing a synthetic tissue, a method of administering a medicament of the present invention, a method for diagnosis, or the like for persons who administer, or are administered, the medicament or the like or persons who diagnose or are diagnosed (e.g, physicians, patients, and the like). The instructions describe a statement indicating an appropriate method for administering a diagnostic, a medicament, or the like of the present invention. The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the Internet).

As used herein, the term "extracellular matrix synthesis promoting agent" or "ECM synthesis promoting agent" refers to an agent which promotes the production of an extracellular matrix of a cell. In the present invention, when an ECM synthesis promoting agent is added to a cell sheet, an environment which promotes self-contraction of cells after a cell sheet is detached from a culture container. The sheet is biologically organized in three-dimensional directions. Examples of such an agent representatively include agents capable of promoting the secretion of an extracellular matrix (e.g., TGF-β1, TGF-β3, etc.). Examples of an ECM synthesis promoting agent representatively include, but are not limited to, TGF-β1, TGF-β3, ascorbic acid, ascorbic acid 2-phosphate, or a derivative or salt thereof: Preferably, an ECM synthesis promoting agent may be preferably a component of an extracellular matrix of a part targeted by application and/or a component(s) capable of promoting the secretion of an extracellular matrix in an amount similar thereto. When an ECM synthesis promoting agent comprises a plurality of components, the components may be components of an extracellular matrix of a part targeted by application and/or components capable of promoting the secretion of an extracellular matrix in an amount similar thereto.

As used herein, the term "ascorbic acid or a derivative thereof" includes ascorbic acid and an analog thereto (e.g., ascorbic acid 2-phosphate, ascorbic acid 1-phosphate, etc.), and a salt thereof (e.g., sodium salt, magnesium salt, etc.). Ascorbic acid is preferably, but is not limited to, an L-isomer.

(Description of the Preferred Embodiments)

Hereinafter, preferable embodiments of the present invention will be described. The following embodiments are provided for a better understanding of the present invention and the scope of the present invention should not be limited to the following description. It will be clearly appreciated by those skilled in the art that variations and modifications can be made without departing from the scope of the present invention with reference to the specification.

In an aspect of the present invention, the synthetic tissue and complex of the present invention is free of injury caused by a protein degrading enzyme, such as, representatively, dispase, trypsin, or the like, during culture. Therefore, the synthetic tissue and complex; which is detached from the base material, can be recovered as a cell mass holding proteins between cells (e.g., an extracellular matrix) and having a certain level of strength. The synthetic tissue and complex also retain intact functions, such as an intracellular linking manner, alignment, and the like. When typical protein degrading enzymes (e.g., trypsin, etc.) are used to detach the three-dimensional structure or synthetic tissue, substantially no cell-to-cell link or cell-to-extracellular matrix link are retained, so that cells are individually separated. Among these protein degrading enzymes, dispase destroys basement membrane-like proteins between cells and base materials substantially completely. In this case, however, the resultant three-dimensional structure or synthetic tissue has weak strength. In contrast, the three-dimensional structure or synthetic tissue of the present invention can both substantially completely retain each of the desmosome structure and the basement membrane-like protein, resulting in the above-described various effects.

In the method of the present invention, the period of time required for culture may be determined depending on the application of the synthetic tissue or three-dimensional structure. In order to detach and recover the cultured synthetic tissue or three-dimensional structure from the support material, the cultured synthetic tissue or three-dimensional structure is detached directly, or with macromolecular membrane being attached thereto. Note that the synthetic tissue or three-dimensional structure may be detached in culture medium in which cells have been cultured, or alternatively, in other isotonic solutions. Such solutions may be selected depending on the purpose. When a monolayer cell sheet is prepared, examples of the macromolecular membrane, which is optionally attached to the cell sheet or three-dimensional structure, include, but are not limited to, hydrophilized polyvinylidene difluoride (PVDF), polypropylene, polyethylene, cellulose and derivatives thereof, chitin, chitosan, collagen, paper (e.g., Japan paper, etc.), urethane, net-like or stockinette-like macromolecular materials (e.g., spandex, etc.), and the like. When a net-like or stockinette-like macromolecular material is employed, the synthetic tissue or complex has a higher degree of freedom, so that the contraction/relaxation function thereof can be increased. A method for producing the synthetic tissue or three-dimensional structure comprising cells of the present invention is not particularly limited. For example, the synthetic tissue or three-dimensional structure of the present invention can be produced by utilizing the above-described cultured cell sheet attached to a macromolecular membrane.

In order to detach and recover the synthetic tissue or complex with a high yield from the cell culture support, the cell culture support is tapped or shaken, or the medium is stirred with a pipette. These procedures may be performed singly or in combination. In addition, the synthetic tissue or complex may be detached and recovered by deforming the base of the culture container or rinsing the container with isotonic solution or the like. By stretching the synthetic tissue or complex in a specific direction after being detached from the base material, the complex is provided with alignment. Stretching may be performed by using a tensile device (e.g., Tensilon, etc.), or simply forceps, or the like. A stretching method is not particularly limited. By providing alignment, it is possible to confer directionality to the motion of the cell sheet or complex itself. Therefore, for example, it is possible to allow the synthetic tissue or complex to move in accordance with the motion of a specific organ. The synthetic tissue or complex can be efficiently applied to organs.

The thus-obtained synthetic tissue or complex cannot be obtained by conventional techniques.

The synthetic tissue and the complex according to the present invention includes an abundance of adhesion molecules such as extracellular matrix which may include collagen (types I, III, etc.), vironectin, and fibronectin, and can be accepted by the surrounding tissue. Thus, implanted cells can be stably accepted by the implantation site. In conventional cell implantation, it was difficult for cells to be stably accepted by the implantation site not only in cells implantation without a scaffold, but also in cell implantation using an additional stabilizing treatment (e.g., sewing of a patch, scaffold, etc.). However, use of the present invention facilitates stabilization. When only cells are used, reinforcement by another tissue, fixing scaffold, or the like is necessary. According to the present invention, without requiring such means, cells which may have pluripotency included in the synthetic tissue or complex can be stably accepted by the implantation portion without an additional fixing means.

(Preparation of Synthetic Tissue Using an ECM Synthesis Promoting Agent)

In another aspect, the present invention provides a method for producing a synthetic tissue. The method for producing a synthetic tissue comprises the steps of: A) providing a cell; B) placing the cell in a container containing a cell culture medium including an ECM synthesis promoting agent, wherein the container has a base with an area sufficient to accommodate a desired size of the synthetic tissue; and C) culturing the cell in the container for a period of time sufficient to form the synthetic tissue having the desired size.

The above-described cell may be any cell. A method for providing a cell is well known in the art. For example, a tissue is extracted and cells are isolated from the tissue. Alternatively, cells are isolated from body fluid containing blood cells or the like. Alternatively, a cell line is prepared in an artificial culture. The present invention is not limited to this. Cells used herein may be any stem cells or differentiated cells, particularly including myoblasts, mesenchymal stem cells, adipocytes, synovial cells, bone marrow cells, and the like. Examples of mesenchymal stem cells used herein include adipose tissue-derived stem cells, bone marrow-derived stem cells, and the like.

The method for producing a synthetic tissue of the present invention employs a cell culture medium containing an ECM synthesis promoting agent. Examples of such an ECM synthesis promoting agent include, but are not limited to, ascorbic acid or a derivative thereof, ascorbic acid 1-phosphate, ascorbic acid 2-phosphate, L-ascorbic acid, and the like.

The cell culture medium used in the present invention may be any medium which allows a cell of interest to grow. Examples of such a medium include, but are not limited to, DMEM, MEM, F12, DME, RPMI1640, MCDB104, 199, MCDB153, L15, SkBM, Basal medium, and the like which are supplemented with glucose, FCS (fetal calf serum), antibiotics (penicillin, streptomycin, etc.) as appropriate.

The container used in the present invention may be any container typically used in the art which has a base with an area sufficient to accommodate a desired size of the synthetic tissue. Examples of such a container include, but are not limited to petri dishes, flasks, mold containers, and the like, and preferably containers having a large area of the base (e.g., at least 1 $cm^2$). The material of the container may be any material and include, but are not limited to, glass, plastic (e.g., polystyrene, polycarbonate, etc.) silicone, and the like.

In a preferable embodiment, the method for producing a synthetic tissue according to the present invention further comprises detaching a produced synthetic tissue. As used herein, the term "detach" indicates that after a synthetic tissue of the present invention is formed in a container, the synthetic tissue is removed from the container. The detachment can be achieved by, for example, physical means (e.g., pipetting of medium, etc.), chemical means (addition of a substance), or the like. In the present invention, a synthetic tissue can be detached by providing a stimulus around the synthetic tissue by physical means or chemical means, but not by aggressive means (e.g., treatment with a protein degrading enzyme, etc.) to the synthetic tissue. Thus, the present invention provides ease of handling, which cannot be conventionally achieved, and the resulting synthetic tissue is substantially intact, resulting in a high-performance implant.

In a preferable embodiment, the present invention further comprises detaching cells which construct a synthetic tissue. In a more preferable embodiment, the detaching step includes applying a stimulus for contracting a synthetic tissue, including a physical stimulus (e.g., pipetting, etc.). Such a physical stimulus is not directly applied to the produced synthetic tissue. This is a preferable feature of the present invention. Since a physical stimulus is not directly applied to a synthetic tissue, it is possible to suppress damage to the synthetic tissue. Alternatively, the detaching step includes chemical means, such as adding an actin regulatory agent. Such an actin regulatory agent includes a chemical substance selected from the group consisting of actin depolymerizing agents and actin polymerizing agents. Examples of actin depolymerizing agents include, but are not limited to, ADF (actin depolymerizing factor), destrin, depactin, actophorin, cytochalasin, NGF (nerve growth factor), and the like. Examples of actin polymerizing agents include, but are not limited to, LPA (lysophosphatidic acid), insulin, PDGFm, chemokine, TGF b, and the like.

Though not wishing to be bound by any theory, these actin regulatory agents may cause actomyocin-based cytoskeleton to contract or extend, thereby regulating contraction and extension of a cell itself. As a result, a synthetic tissue itself may be promoted to or inhibited from being detached from the base of a container.

In another embodiment, the synthetic tissue and complex of the present invention are characterized in that they are produced from cells which are cultured in monolayer culture. Despite monolayer culture, synthetic tissues having various thicknesses can be constructed. This is an unexpected effect. Conventionally, for example, a thick tissue cannot be constructed without using a multilayer structure when a temperature responsive sheet or the like is used. The present invention is the first to achieve a method for constructing a three-dimensional structure, which does not require a scaffold and can construct the contractile organization including ten or more layers. A typical cell implantation method which does not employ a scaffold is a cell sheet engineering technique utilizing a temperature sensitive culture dish disclosed by Kushida A., Yamato M., Konno C., Kikuchi A., Sakurai Y., Okano T., J. Biomed. Mater. Res., 45:355-362, 1999. The technique has won international recognition as an original technique. However, this cell sheet technique has a problem in that a single sheet is weak in many cases, and requires modification such as layering sheets for obtaining the strength resistant to an surgical operation such as implantation.

A cell/matrix complex developed by the present invention does not require a temperature sensitive culture dish unlike the cell sheet technique. The cell/matrix complex is easy to form into a contractile three-dimensional tissue. There is no technique in the world other than the present invention, which can produce a contractile three-dimensional complex having 10 or more layers without using so-called feeder cells, such as rodent stroma cells, after approximately three weeks. By adjusting conditions for matrix production of the synovial cell, it is possible to produce a complex having a strength which allows surgical manipulation, such as holding or transferring the complex, without a special instrument. Therefore, the present invention is an original, epoch-making technique in the world for reliably and safely perform cell implantation.

In a preferable embodiment, the ECM synthesis promoting agent used in the method for producing a synthetic tissue of the present invention includes ascorbic acid 2-phosphate (Hata R., Senoo H., J. Cell Physiol., 1989, 138(1):8-16). In the present invention, by adding a certain amount or more of ascorbic acid 2-phosphate, it, is possible to promote production of an extracellular matrix, so that the resultant synthetic tissue or complex is made strong to become easy to be detached. Thereafter, self contraction is elicited by applying a stimulus for detachment. Hata et al. do not report that, after adding such an ascorbic acid and culturing, a tissue becomes strong and obtains a property to be easy to be detached. Though not wishing to be bound by any theory, a significant difference is that Hata et al. used a significantly different cell density. Hata et al. does not suggest an effect of making a tissue rigid. Such an effect that the tissue is made rigid, an effect of contraction, and an effect that the tissue becomes easy to be detached are first found in the present invention. The synthetic tissue according to the present invention is recognized to be totally different from the synthetic tissue which has been fabricated conventionally at least on the point that it is produced through the process of making rigid, contraction, and detachment.

Contraction when the culture is detached and promotion in constructing a three-dimensional structure, a contractile three-dimensional tissue, or the like are surprising effects. Such effects have not been reported conventionally.

In a preferable embodiment, ascorbic acid 2-phosphate used in the present invention typically has a concentration of at least 0.01 mM, preferably at least 0.05 mM, more preferably at least 0.1 mM, even more preferably at least 0.2 mM, still more preferably at least 0.5 mM, and still even more preferably 1.0 mM. Herein, any concentration of 0.1 mM or higher may be employed. However, there may be an aspect in which a concentration of 10 mM or lower is desired.

In a certain preferable embodiment the ECM synthesis promoting agent of the present invention includes ascorbic acid 2-phosphate or a salt thereof, and L-ascorbic acid or a salt thereof.

In a preferable embodiment, after the culturing step, the synthetic tissue production method of the present invention further comprises, detaching the synthetic tissue and allowing the synthetic tissue to perform self contraction. The detachment can be accelerated by applying a physical stimulus (e.g., application of shear stress, pipetting, deformation of the container, etc.). Self-contraction naturally takes place when a stimulus is applied after the detachment. When a chemical stimulus is applied, self-contraction and detachment occurs simultaneously. By self-contraction, biological integration is accelerated particularly in the third dimension (the direction perpendicular to the two-dimensional directions in the case of tissue on a sheet). Therefore, a synthetic tissue of the present invention may have a three-dimensional structure.

In a synthetic tissue production method of the present invention, the sufficient time preferably means at least 3 days, though it varies depending on the application of a synthetic tissue of interest. An exemplary period of time is 3 to 7 days.

In another embodiment, the synthetic tissue production method of the present invention may further comprise causing a synthetic tissue to differentiate. By differentiation, the synthetic tissue can have a form closer to that of a desired tissue. An example of such differentiation is, but is not limited to, chondrogenesis and osteogenesis. In a preferable embodiment, osteogenesis may be performed in medium containing dexamethasone, β-glycerophosphate, and ascorbic acid 2-phosphate. More preferably, bone morphogenetic proteins (BMPs) Are added. This is because such BMP-2, BMP-4, and BMP-7 proteins promote osteogenesis.

In another embodiment, a method of producing the synthetic tissue of the present invention is a process of differentiating a synthetic tissue. A form of differentiation includes performing a differentiation of cartilage. In the preferable embodiment, chondrogenesis is performed in a medium including pyruvic acid, dexamethasone, ascorbic acid 2-phosphate, insulin, transferrin, and selenious acid. More preferably, bone morphogenetic proteins (such as BMP-2, BMP-4, BMP-7), transforming growth factors (such as TGF-β1, TGF-β3) are added. This is because such BMPs promote chondrogenesis.

An important point in the present invention is that it is possible to fabricate a tissue having a pluripotency into various differentiated cells such as bone, cartilage, and the like. Conventionally, differentiation into a cartilage tissue is difficult in other synthetic tissues which are scaffold-free. If a certain size is required, conventionally, it was necessary to coculture with a scaffold, construct a three-dimensional structure, and add a chondrogenesis medium. Conventionally, scaffold-free differentiation into cartilage was difficult. The present invention is the first to enable differentiation into cartilage in a synthetic tissue. This is not an effect which has not been obtained conventionally, and is a characteristic effect of the present invention. In a treatment which aims to regenerate a tissue, a method for performing a treatment efficiently and safely by using a tissue of sufficient size without a scaffold was difficult. The present invention achieves a significant effect on this point. Particularly, the present invention is significant on the point that it becomes possible to easily manipulate differentiated cells such as cartilage, which has been impossible conventionally. Conventionally, for example, cells can be collected to a pellete shape and the aggregation of cells can be differentiated to obtain a tissue of about 2 mm³. For obtaining a tissue larger than this size, it was necessary to use a scaffold.

The differentiation step in synthetic tissue production of the present invention may be performed before or after providing cells.

In the present invention, primary culture cells can be used. The present invention is not limited to this. Subcultured cells (e.g., three or more passages) can also be used. Preferably, when subculture cells are used, the cells are preferably of four passages or more, more preferably of 5 passages or more, and even more preferably of 6 passages or more. The upper limit of cell density is increased with an increase in the number of passages within a certain range. This is because a denser synthetic tissue can be produced. The present invention is not limited to this. It seems that a certain range of passages (e.g., 3 to 8 passages) are preferable.

In the present invention, the cells are preferably provided at a cell density of $5.0 \times 10^4/cm^2$ or more. The present invention is not limited to this. This is because a higher cell density can provide a synthetic tissue having a greater strength. It will be understood that the lower limit of the cell density may be lower than the above-described density. It will also be understood that those skilled. In the art can define the lower limit based on the present specification.

In one embodiment of the present invention, for example, a myoblast, a synovial cell, an adipocyte, and a mesenchymal stem sell (e.g., derived from adipose tissue or bone marrow) can be used. The present invention is not limited to this. These cells can be applied to, for example, a heart, a bone, a cartilage, a tendon, a ligament, a joint, a meniscus, and the like.

(Synthetic Tissue and Complex)

In another aspect, the present invention provides a functional synthetic tissue or complex. The functional synthetic tissue of the present invention is herein an implantable synthetic tissue. Attempts have been heretofore made to produce synthetic tissues by cell culture. However, there were no synthetic tissues suitable for implantation in terms of size, strength, physical injuries when it is detached from a culture container, or the like. The present invention provides a tissue culture method in which cells are cultured in the presence of an ECM synthesis promoting agent as described above, so that there is no problem in terms of size, strength, and the like and there is no difficulty in detaching tissues. An implantable synthetic tissue is provided only after such a tissue culture method is achieved.

Another aspect of the present invention provides cells, and a complex including factors derived from the cells. Herein, it is recognized that, preferably, the complex substantially comprises cells, and the factors derived from the cells. Herein, the complex of the present invention is provided for reinforcing, repairing, or regenerating a part of an organism.

As used herein, the term "complex" means that cells and other components are integrated into a complex by some kind of interactivity. Therefore, the complex of the present invention often has an appearance like a synthetic tissue, and it is recognized that the meaning of the term "complex" overlaps with what is referred to by a synthetic tissue.

The present invention provides a scaffold-free synthetic tissue or complex. A therapeutic method and a therapeutic agent for providing an excellent condition after implantation can be obtained by providing such a scaffold-free synthetic tissue.

The scaffold-free synthetic tissue of the present invention solves a long outstanding problem with biological formulations, which is attributed to contamination of the scaffold itself. Despite the absence of a scaffold, the therapeutic effect is comparable with, or more satisfactory than, conventional techniques.

In addition, when a scaffold is used, the alignment of implanted cells in the scaffold, the cell-to-cell adhesion, the in vivo alteration of the scaffold itself (eliciting inflammation), the acceptance of the scaffold by the recipient tissue, and the like become problematic. These problems can be solved by the present invention.

The synthetic tissue and the complex of the present invention are also self-organized, and have biological integration inside thereof. Also in this point, the present invention is distinguished from conventional cell therapies.

The synthetic tissue and the complex of the present invention are easily used to form a three-dimensional structure, and is thus easy to be designed into a desired form. The versatility of the synthetic tissue and the complex of the present invention should be noted.

The synthetic tissue and the complex of the present invention have biological integration with recipient tissues, such as surrounding tissues, cells, and the like. Therefore, the post-operational acceptance is satisfactory, and cells are reliably supplied to a local site, for example. An effect of the present invention is that the satisfactory biological integration capability allows the formation of a tissue complex with another synthetic tissue or the like, resulting in a complicated therapy.

Another effect of the present invention is that differentiation can be induced after the synthetic tissue or the complex is provided. Alternatively, differentiation is induced before providing a synthetic tissue and/or a complex, and thereafter, the synthetic tissue and/or the complex are formed.

Another effect of the present invention is that the cell implantation of the present invention provides a satisfactory replacement ability and a comprehensive supply of cells for covering an implanted site, compared to conventional cell-only implantation and sheet implantation.

The present invention provides an implantable synthetic tissue. The above-described features and effects of the present invention become it possible to treat a site which cannot be considered as an implantation site for conventional synthetic products. The present invention makes it possible to provide a synthetic tissue or a three-dimensional structure using not only a heart muscle but also cells derived from other parts. The synthetic tissue of the present invention has biological integration and actually works in implantation therapies. The synthetic tissue is first provided by the present invention, but is not provided by conventional techniques.

In addition, the present invention provides medical treatment which provides a therapeutic effect by filling, replacing, and/or covering an affected portion.

In addition, when the synthetic tissue of the present invention is used in combination with another synthetic tissue (e.g., an artificial bone made of hydroxyapatite, a microfibrous collagen medical device, etc.), the synthetic tissue of the present invention is biologically integrated with the other synthetic tissue, so that the acceptance of the synthetic tissue can be improved to an extent which is not conventionally expected.

An extracellular matrix or a cell adhesion molecule, such as fibronectin, vitronectin, or the like, is distributed throughout the synthetic tissue of the present invention. In the cell sheet engineering, a cell adhesion molecule is localized on a surface of culture cells which is attached to a culture dish. In the sheet of the cell sheet engineering, cells are major components of the sheet. The sheet is nearly amass of cells, on the bottom surface of which an adhesion molecule (glue) is added. The synthetic tissue of the present invention is a real "tissue" such that an extracellular matrix wraps cells. Thus, the present invention is significantly distinguished from conventional techniques.

A cell implanting method without a scaffold has been reported by Kushida A., Yamato M., Konno C., Kikuchi A., Sakurai Y., Okano T., J. Biomed. Mater. Res., 45:355-362, 1999, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be assembled, for example. Such a problem is solved by the present invention.

A cell/matrix complex developed by the present invention does not require a temperature sensitive culture dish unlike the cell sheet technique. The cell/matrix complex is easily formed into a contractile three-dimensional tissue. There is no technique in the world other than the present invention, which can produce a contractile three-dimensional complex having 10 or more layers without using so-called feeder cells, such as rodent stroma cells, after approximately three weeks. By adjusting conditions for matrix production of the synovial cell, it is possible to produce a complex having a strength which allows surgical manipulation, such as holding or transferring the complex, without a special instrument. Therefore, the present invention is an original, epoch-making technique in the world for reliably and safely performing cell implantation.

In a preferable embodiment, the synthetic tissue of the present invention has a biological integration capability to the surroundings. As used herein the term "surroundings" typically means surroundings to be implanted, and examples thereof include tissues, cells and the like. The biological integration capability with surrounding tissues, cells, and the like can be confirmed by, for example, photomicrograph, physical test, staining of a biological marker, or the like. Conventional synthetic tissues have a low affinity for adjacent tissues in which they are implanted. It was not even assumed that conventional synthetic tissues have the biological integration capability. Conventional synthetic tissues depend on a regeneration capability of an organism, and serves as a temporary solution until autologous cells gather and regenerate. These conventional synthetic tissues are not intended to for a permanent use. Therefore, the synthetic tissue of the present invention should be contemplated as an implantation treatment in the true sense. The biological integration capability referred to by in the present invention preferably includes an adhesion capability to surrounding cells. Such an adhesion capability can be measured by an in vitro culturing assay (see FIG. 23) with a tissue section (e.g., a cartilage section).

As used herein, the term "disease" to be treated by the present invention refers to any disease accompanying degeneration, necrosis, injury or the like, and examples thereof including, osteoarthritis, osteochondral injury, intractable fracture, osteonecrosis, cartilage injury, meniscus injury, ligament injury, tendon injury, cartilage degeneration, meniscus degeneration, intervertebral disk denaturation, ligament degeneration, or tendon degeneration, or any heart diseases having an injured-tissue. Examples of such heart diseases include heart failure, intractable heart failure, myocardial infarct, cardiomyopathy, dilated cardiomyopathy, hypertrophic cardiomyopathy, dilated phase hypertrophic cardiomyopathy, and the like. The combined therapy of the present invention may be applied to a regeneration of an injury in an organ other than a heart, as long as regeneration of a tissue injury is the goal. In a specific embodiment, a disease to be treated by the method of the present invention is intractable heart failure.

As used herein, the term "prophylaxis" or "prevention" in relation to a certain disease or disorder refers to a treatment which keeps such a condition from happening before the condition is caused, or causes the condition to occur at a reduced level or to be delayed.

As used herein, the term "therapy" in relation to a certain disease or disorder means that when such a condition occurs, such a disease or disorder is prevented from deteriorating, preferably is retained as it is, more preferably is diminished, and even more preferably extinguished. As used herein, the term "radical therapy" refers to a therapy which eradicates the root or cause of a pathological process. Therefore, when a radical therapy is made for a disease, there in principle is no recurrence of the disease.

As used herein, the term "prognosis" is also referred to as "prognostic treatment". The term "prognosis" in relation to a certain disease or disorder refers to a diagnosis or treatment of such a condition after a therapy.

In a preferable embodiment, the synthetic tissue or complex of the present invention has a three-dimensional, biological integration. As described in other portions of the specification, examples of biological integration include, but are not limited to, physical integration or connection via extracellular matrices, electrical integration, and the like. Particularly, in a preferable embodiment including the cells, it is important that extracellular matrix in a tissue is biologically organized. Such a synthetic tissue which is biologically organized has not been provided. Thus, the synthetic tissue of this embodiment according to the present invention is new also in view of the structure. Further, the preferable embodiment having a biological integration capability with the surroundings provides a synthetic tissue which has not exist conventionally on the point that the synthetic tissue can form a part of an organism after implantation. The present invention can provide an synthetic tissue which does not include any cell, even a cell which has been frozen once and died. The tissue is still unique on the point that it has an affinity with the surrounding even in such a case.

In one embodiment, the synthetic tissue of the present invention is different from conventional synthetic tissues in that the former comprises a cell. Particularly, a high density that the density of $5 \times 10^6/cm^2$ at maximum can be included is important. The present invention is important on tha point that it is suitable for implanting cells rather than implanting the tissue.

Preferably, a synthetic tissue of the present invention substantially comprise cells or a material derived from the cells. Since the synthetic tissue is composed substantially of only cells and a cell-derived material (e.g., extracellular matrix, etc.), the synthetic tissue can have an increased level of biocompatibility and affinity. As used herein, the terms "substantially comprise . . . ", "substantially made of . . . ", and "substantially contain . . . " mean that cells and substanced derived from the cells are included, and also any other substance may be included as long as it does not cause any harmful effect (herein, mainly, bad effect on implantation), and should understood as such herein. Such substances which do not cause any harmful effect are known to those skilled in the art or can be confirmed by conducting an easy test. Typically, such substances are, but not limited to, any additives permitted by the Health, Labor and Welfare Ministry, Food and Drug Administration (FDA) or the like, ingredients involved in cell culture, and the like. The cell-derived material representatively includes extracellular matrices. Particularly, the synthetic tissue or complex of the present invention preferably comprises a cell and an extracellular matrix at an appropriate ratio thereof. Such an appropriate ratio of a cell and an extracellular matrix is from about 1:3 to about 20:1. The strength of the tissue is adjusted by the ratio between a cell and an extracellular matrix. The ratio between a cell and an extracellular matrix is adjusted for use in accordance with application of cell implantation and physical environment at the implantation site. Preferable ratio varies depending on the treatment to be aimed. Such a variation is apparent to those skilled in the art and can be estimated by investigating the ratio of a cell in an organ which is a target and an extracellular matrix.

Preferably, a synthetic tissue substantially comprising cells and an extracellular matrix derived from the cells has not been known. Therefore, the present invention provides a totally new synthetic tissue.

Preferably, an extracellular matrix which forms the present invention includes, collagen I, collagen III, vitronectin, fibronectin, and the like. It is preferable that a variety of extracellular matrix includes all the listed ingredients, and that they are integrated and mixed. Alternatively, it is preferable that extracellular matrix is dispersed across the entire body. Such a distribution has a significant effect on the point that compatibility and affinity with the environment can be improved when implanted. The present invention is known to be characterized in that adhesion to intercellular matrix which promotes cell adhesion to a matrix, cell extension, and cell chemotaxis is also promoted by including collagen (Types I, III), vitronectin, fibronectin, and the like. However, a synthetic tissue which includes collagen (Types I, III), vitronectin, fibronectin, and the like has not been provided. It is not intended to be constrained by the theory, but, collagen (Types I, III), vitronectin, fibronectin, and the like are contemplated to have a function in exercising the biological integration capability with the surrounding. Therefore, in the preferable embodiment, it is advantageous that vitronectin are positioned to be dispersed on a surface of the synthetic tissue or complex of the present invention. It is considered that adhesion, affinity, and stability after implantation are significantly different.

It is preferable that the fibronectin is also positioned in the synthetic tissue or complex of the present invention. It is known that fibronectin has a function in cell adhesion, control of a shape of a cell, and adjustment in cell migration. A synthetic tissue in which fibronectin is expresse has not been provided. It is not intended to be contrained by the theory, fibronection is also contemplated to have a function in exercising the biological integration capability with the surrounding. Therefore, in the preferable embodiment, it is advantageous that fibronectin are also positioned to be dispersed on a surface of the synthetic tissue or complex of the present invention. It is considered that adhesion, affinity, and stability after implantation are significantly different.

In the preferred embodiment, it is understood that to position extracellular matrix used in the present invention on the synthetic tissue or complex can be readily achieved by the synthetic tissue production method of the present invention. It is also understood that the production method is not limited to this.

In more preferable embodiment, it is advantageous to position the extracellular matrix used in the present invention to be dispersed. Positioning extracellular matrix into such a dispersed state was impossible in conventional synthetic tissues. It is understood the present invention is the first to provide such a tissue.

In the preferred embodiment, regarding extracellular matrix positioned to be dispersed on the synthetic tissue or complex, when distribution densities in any two section of 1 cm$^2$ are compared, the ratio is preferably within the range of about 1:3 to 3:1. Measurement of distribution densities can be performed by any method known in the field of the art, for example, immune staining or the like.

In the preferred embodiment, regarding extracellular matrix used in the present invention, when distribution densities in any two section of 1 cm$^2$ are compared, the ratio is preferably within the range of about 1:2 to 2:1, and further preferably, about 1.5:1 to 1.5:1. It is advantageous that extracellular matrix is uniformly dispersed. Preferably, extracellular matrix is dispersed substantially uniform, but it is not limited to this.

In one embodiment, extracellular matrix positioned in the present invention may include collagen I, collagen III, vitronectin, fibronectin or the like.

In an alternative embodiment, the synthetic tissue or complex of the present invention may employ heterologous cells, allogenic cells, isogenic cells or autologous cells. In the present invention, it is found that even allogenic cells, particularly, mesenchymal cells are used, no adverse reactions, such as immune rejection reactions, is generated. Thus, the present invention ends to the development of the treatment of ex vivo, and also a therapy which produces a synthetic tissue using cells of others and utilize the tissue without using an immuno rejection suppressor or the like.

In one preferred embodiment, the cells included in the synthetic tissue or complex of the present invention may be stem cells, differentiation cells, or they may include both. In the preferred embodiment, the cells included the three directional structure are mesenchymal cells. It is not intended to restrained to the theory, the mesenchymal cells are preferably used because the mesenchymal cells are highly compatible with various organs such as heart, and may have capability to differentiate into various organs such as a heart.

Such mesenchymal cells may be mesenchymal stem cells, or may be mesenchymal differentiation cells.

Examples of the mesenchymal cells used in the present invention include, but not limited to, bone marrow cells, adipocyte, synovial cell, myoblast, skeletal muscle cells, and the like. Examples of mesenchymal cells as used herein include stem cells derived from an adipose tissue, stem cells derived from a bone marrow, and the like.

In the preferred embodiment, it is advantageous that the cells used in the present invention are cells derived from the subject to which the synthetic tissue or complex is applied. In such a case, cells as used herein also referred to as autologous cells. By using autologous cells, immune rejection reactions can be prevented or reduced.

Alternatively, in another embodiment, the cells as used herein may not be cells derived from a subject to which the synthetic tissue or complex is applied. In such a case, it is preferable that measures are taken to prevent immune rejection reactions.

The synthetic tissue or complex of the present invention may be provided as a drug. Alternatively, the synthetic tissue or complex may be prepared by a physician for therapy, or, a physician may first prepare the cells, and then the third party may culture the cells prepare as a third-dimension structure for use in a surgery. In such a case, culturing cells is not necessarily performed by a physician, but can be performed by those skilled in the art of cell culture. Those skilled in the art can determine culturing conditions in accordance with a variety of the cells and an implantation site to be targeted after reading the disclosure herein.

In another embodiment, the synthetic tissue or complex of the present invention is preferably isolated. In this case, the term "isolate" means that the synthetic tissue is detached from a scaffold, a support, and a culture medium used in culture. If a synthetic tissue of the present invention is substantially free of materials, such as a scaffold and the like, it is possible to suppress adverse reactions after implantation, such as immune rejection reactions, inflammation reactions, and the like.

The base area of the synthetic tissue according to the present invention may be, for example, 1 $cm^2$ to 20 $cm^2$. However, the area is not limited to this range and may be smaller than 1 $cm^2$, or greater than 20 $cm^2$. It is understood that the essential feature of the present invention is that a tissue of any size (area, volume) can be produced, and it is not limited in the size.

In a preferable embodiment, the synthetic tissue of the present invention is thick. The term "thick" in relation to a synthetic tissue typically means that the synthetic tissue has a thickness which provides a strength sufficient to cover a site to which the synthetic tissue is implanted. Such a thickness is, for example, at least about 50 μm, more preferably at least about 100 μm, at least about 200 μm, at least about 300 μm, even more preferably at least about 400 μm, still more preferably at least about 500 μm, and still even more preferably about 1 mm. It is recognized that, in some cases, a tissue having a thickness of 3 mm or greater and a tissue having a thickness of 5 mm or greater can be produced. Alternatively, such a thickness may be, 1 mm or less. It is understood that an essential feature of the present invention is that a tissue or a complex having any thickness can produced, and the tissue or complex is not limited in the size.

The present invention provides a scaffold-free synthetic tissue or complex. By providing such a scaffold-free synthetic tissue, a therapeutic method and a therapeutic agent for providing an excellent condition after implantation can be obtained.

The scaffold-free synthetic tissue of the present invention solves a long outstanding problem with biological formulations, which is attributed to contamination of the scaffold itself. Despite the absence of a scaffold, the therapeutic effect is comparable with or more satisfactory than conventional techniques.

In addition, when a scaffold is used, the alignment of implanted cells in the scaffold, the cell-to-cell adhesion, the in vivo alteration of the scaffold itself (eliciting inflammation), the acceptance of the scaffold to recipient tissue, and the like become problematic. These problems can be solved by the present invention.

The synthetic tissue and the complex of the present invention are also self-organized, and have biological integration inside thereof. Also in this point, the present invention is distinguished from conventional cell therapies.

The synthetic tissue and the complex of the present invention are easy to form a three-dimensional structure, and is thus easy to be designed into a desired form. The versatility of the synthetic tissue and the complex of the present invention should be noted.

The synthetic tissue and the complex of the present invention have biological integration with recipient tissues, such as surrounding tissues, cells, and the like. Therefore, the post-operational acceptance is satisfactory, and cells are reliably supplied to a local site, for example. An effect of the present invention is that the satisfactory biological integration capability allows the formation of a tissue complex with another synthetic tissue or the like, resulting in a more complex therapy.

Another effect of the present invention is that differentiation can be induced after the synthetic tissue or the complex is provided. Alternatively, differentiation is induced before providing a synthetic tissue and/or a complex, and thereafter, the synthetic tissue and/or the complex are formed.

Another effect of the present invention is that the cell implantation of the present invention provides a satisfactory replacement and a comprehensive supply of cells for covering an implanted site, compared to conventional cell-only implantation and sheet implantation.

The present invention provides an implantable synthetic tissue having biological integration capability. The above-described features and effects of the present invention become it possible to treat a site which cannot be considered as an implantation site for conventional synthetic products. The present invention makes it possible to provide a synthetic tissue or a three-dimensional structure. The synthetic tissue of the present invention has biological integration and actually works in implantation therapies. The synthetic tissue is first provided by the present invention, but is not provided by conventional techniques.

In addition, the present invention provides medical treatment which provides a therapeutic effect by filling, replacing, and/or covering an affected portion.

In addition, when the synthetic tissue of the present invention is used in combination with another synthetic tissue (e.g., an artificial bone made of hydroxyapatite, a microfibrous collagen medical device, etc.), the synthetic tissue of the present invention is biologically integrated with the other synthetic tissue, so that the acceptance of the synthetic tissue can be improved to an extent which is not conventionally expected.

An extracellular matrix or a cell adhesion molecule, such as fibronectin, vitronectin, or the like, is distributed throughout the synthetic tissue of the present invention. In cell sheet engineering, a cell adhesion molecule is localized on a surface of culture cells which is attached to a culture dish. In the sheet of the cell sheet engineering, the cells are major components of the sheet. The sheet is nearly a mass of cells, on the bottom surface of which an adhesion molecule (glue) is added. On the other hand, the synthetic tissue of the present invention is a real "tissue" such that an extracellular matrix covers cells. Thus, the present invention is significantly distinguished from conventional techniques.

A cell implanting method without a scaffold has been reported by Kushida A., Yamato M., Konno C., Kikuchi A., Sakurai Y., Okano T., J. Biomed. Mater. Res., 45:355-362, 1999, in which a cell sheet is produced using a temperature sensitive culture dish. Such a cell sheet engineering technique is internationally appraised due to its originality. However, a single sheet obtained by this technique is fragile. In order to obtain the strength that can withstand surgical manipulation, such as implantation, a plurality of sheets need to be assembled, for example. Such a problem is solved by the present invention.

A cell/matrix complex developed by the present invention does not require a temperature sensitive culture dish unlike the cell sheet technique. The cell/matrix complex is easy to form into a contractile three-dimensional tissue. There is no technique in the world other than the present invention, which can produce a contractile three-dimensional complex having 10 or more layers without using so-called feeder cells, such as rodent stroma cells, at about three weeks. By adjusting conditions for matrix production of the cell, it is possible to produce a complex having a strength which allows surgical manipulation, such as holding or transferring the complex, without a special instrument. Therefore, the present invention is an original, epoch-making technique in the world for reliably and safely performing cell implantation.

In another embodiment, the synthetic tissue or complex of the present invention is flexible. Due to the flexibility, the synthetic tissue is particularly suitable for reinforcement of motile organs. Examples of motile organs include, but are not limited to, hearts, blood vessels, muscles, and the like.

In another embodiment, the synthetic tissue or complex of the present invention has dilation/contraction ability. Due to the dilation/contraction ability, the synthetic tissue is suitable for organs which expand and contract, including, for example, hearts, muscles, and the like. The dilation/contraction ability cannot be achieved by cell sheet or the like prepared by conventional methods. Preferably, a synthetic tissue of the present invention has a sufficient strength to withstand the pulsation motion of a heart. The strength sufficient to withstand pulsation motion is, but is not limited to, at least about 50% of the strength of naturally-occurring myocardium, preferably at least about 75%, and more preferably at least about 100%.

In a preferable embodiment, the synthetic tissue or complex of the present invention has biological integration in all three dimensions. There are some synthetic tissues prepared by conventional methods, which have biological integration in two dimensions to some degree. However, no tissue having biological integration in all three dimensions can be prepared by conventional methods. Therefore, since the synthetic tissue of the present invention has biological integration in all three dimensions, the synthetic tissue is substantially implantable in any application.

Examples of biological integration which is an indicator of a synthetic tissue or complex of the present invention, include, but are not limited to, interconnection of extracellular matrices, electrical integration, the presence of intracellular signal transduction, and the like. The interaction of extracellular matrices can be observed with a microscope by staining intracellular adhesion as appropriate. Electrical integration can be observed by measuring electric potential.

In a preferable embodiment, the synthetic tissue of the present invention has a sufficient tissue strength for clinical applications. The sufficient tissue strength for clinical applications varies depending on a site to which the synthetic tissue is applied. Such a strength can be determined by those skilled in the art with reference to the disclosure of the specification and techniques well known in the art. The tensile strength of the synthetic tissue of the present invention may be low. The tensile strength becomes higher when the matrix concentration is increased, and becomes lower when the cell ratio is increased. The present invention is characterized in that the strength can be adjusted as necessary. The present invention is also characterized in that the strength can approximate to be high or low relative to that of a tissue to be implanted. Therefore, it is recognized that the goal can be set to comply with any site.

In another embodiment, it is preferable that a strength of the synthetic tissue or complex is sufficient for having a self-supporting ability. Conventional synthetic tissues do not have a self-supporting ability after production. Therefore, when conventional synthetic tissues are transferred, at least a part of them are injured. However, when the technique of the present invention is used, the synthetic tissue having the self-supporting ability is provided. This means that the present invention provides the synthetic tissue which cannot be provided by conventional techniques. Preferable self-supporting ability is such that, when a tissue is picked up with a tweezers having tips of 0.5 to 3 mm (preferably, tips of 1 to 2 mm, and more preferably, tips of 1 mm), the tissue is not substantially destroyed. Herein, whether the tissue is not substantially destroyed can be confirmed with eyes, but can be confirmed by performing, for example, a water leakage test after the tissue is picked up in the above-described conditions and confirming that water does not leak. Alternatively, the self-supporting ability as described above can also be confirmed by not being destroyed when picked up by fingers, instead of tweezers.

In a particular embodiment of the present invention, the above-described clinical application is intended to a bone, a joint, a cartilage, a meniscus, a tendon, a ligament, a kidney, a liver, a synovial membrane, a heart, and the like. The origin of cells contained in the synthetic tissue of the present invention is not affected by clinical applications.

Also, when a synthetic tissue of the present invention is applied to a cartilage, the attachment ability of the synthetic tissue can be tested by determining whether or not the synthetic tissue remains attached without an additional fixation procedure when the synthetic tissue is implanted into an injured portion of the intra-articular tissue (e.g., 2, 3 minutes after).

In another aspect, the present invention provides a cell culture composition for producing synthetic tissue from a cell. The cell culture composition contains an ingredient (e.g., commercially available medium, etc.) for maintaining or growing the cell, and an ECM synthesis promoting agent. The ECM synthesis promoting agent has been described in detail in the above description of the synthetic tissue production method. Therefore, the ECM synthesis promoting agent includes ascorbic acid or a derivative thereof (e.g., TGF-$\beta$1, TGF-$\beta$3, ascorbic acid 1-phosphate or a salt thereof, ascorbic acid 2-phosphate or a salt thereof, L-ascorbic acid or a salt thereof, etc.). The culture composition of the present invention contains ascorbic acid 2-phosphate or a salt thereof at a concentration of at least 0.1 mM. Alternatively, in the case of a condensed culture composition, the condensed culture composition contains ascorbic acid 2-phosphate or a salt thereof at a concentration which becomes at least 0.1 mM after preparation. Ascorbic acid 2-phosphate or a salt thereof contained in the culture composition of the present invention is present at a concentration of at least 0.1 mM. When the culture composition of the present invention is condensed, ascorbic acid 2-phosphate or a salt thereof contained therein is present at a concentration of at least 0.1 mM after formulation. It seems that 0.1 mM or more ascorbic acids have substantially a constant effect. Thus, 0.1 mM can be said to be sufficient. For TGF-$\beta$1 and TGF-$\beta$3, 1 ng/ml or more, representatively 10 ng/ml, may be sufficient.

Alternatively, the present invention may provide a composition for producing a synthetic tissue, comprising such an ECM synthesis promoting agent.

In another embodiment of the present invention, an ECM synthesis promoting agent used in the synthetic tissue production method of the present invention includes ascorbic acid 2-phosphate (Hata R., Senoo H., J. Cell Physiol., 1989, 138(1):8-16). In the present invention, by adding an at least predetermined amount of ascorbic acid 2-phosphate, the production of an extracellular matrix is promoted. As a result, the resultant synthetic tissue or complex is made rigid, and therefore, becomes easy to be detached. Thereafter, the tissue undergoes self-contraction in response to a stimulus of detachment. Hata et al. does not disclose that the culture in medium supplemented with ascorbic acid causes the tissue to be rigid and thus confers to the tissue a property of being easily detached. Though not wishing to be bound by any theory, a significant difference between the present invention and Hata et al. is present in cell density. Also, Hata et al. does not suggest the effect of facilitating detachment of cells from a container for culture. The present invention is the first to find the effect of tissue contraction on development of three-dimensional synthetic tissue from monolayer cultured cells. The synthetic tissue of the present invention can be absolutely distinguished from conventional synthetic tissues, since the synthetic tissue of the present invention is produced via the procedures of tissue detachment and subsequent tissue contraction.

In a preferable embodiment, ascorbic acid 2-phosphate used in the present invention is typically present at a concentration of at least 0.01 mM, preferably at least 0.05 mM, more preferably at least 0.1 mM, even more preferably at least 0.2 mM, and still more preferably at least 0.5 mM, and still even more preferably 1.0 mM.

In one embodiment of the present invention, the cell density is, but is not particularly limited to, $5 \times 10^4$ to $5 \times 10^6$ cells per 1 $cm^2$. These conditions may be, for example, applied to myoblast. In this case, preferably, the ECM synthesis promoting agent may be ascorbic acids and may be provided at a concentration of at least 0.1 mM. This is because a thick synthetic tissue can be produced. In this case, if the concentration is increased, a synthetic tissue having a dense extracellular matrix is produced. If the concentration is low, the amount of an extracellular matrix is decreased but the self-supporting ability is maintained.

(Synthetic Tissue for Replacement and Coverage)

In another aspect, the present invention provides a synthetic tissue or complex for reinforcement of a portion of an animal organism. The synthetic tissue or complex capable of such reinforcement is a technique achieved only after the synthetic tissue production method of the present invention is provided. Since the synthetic tissue or complex of the present invention has self-supporting ability, it can be used in applications which are not conventionally provided (e.g., filling (replacement) reinforcement, whole reinforcement, no-leakage reinforcement, coverage, etc.). The present invention has a significant effect such that the filling and replacement reinforcement (i.e., cell supply) was significantly improved. The present invention also allows differentiation induction, which enlarges the range of application of the present invention.

In a specific embodiment of the present invention, the above-described reinforcement may be achieved by disposing a synthetic tissue of the present invention to cover the above-described portion. It is not possible to use a synthetic tissue provided by conventional methods to perform treatment by covering the above-described portion (i.e., replacement and/or coverage application). Thus, the synthetic tissue of the present invention can provide applications which cannot be achieved by conventional techniques.

Therefore, in the above-described specific embodiment, the synthetic tissue or complex of the present invention is resistant to dilation/contraction of the above-described portion.

In a preferable embodiment, the synthetic tissue or complex of the present invention advantageously has biological integration.

In another preferable embodiment, the biological integration includes at least one of interconnection of extracellular matrices, electrical integration, and intracellular signal transduction.

In another preferable embodiment, the synthetic tissue or complex for reinforcement of the present invention is formed by culturing a cell in the presence of an ECM synthesis promoting agent.

In another embodiment, the synthetic tissue or complex for reinforcement of the present invention comprises a cell (autologous cell) derived from an animal to be treated (e.g., a human). More preferably, a synthetic tissue for reinforcement of the present invention comprises only a cell(s) (autologous cell) derived from an animal to be treated (e.g., a human) as a cell source.

Applications for the therapy utilizing the present invention include, for example: cartilage full thickness injury, cartilage partial injury; osteochondral injury; osteonecrosis; osteoarthritis; meniscus injury; ligament injury (chronic injury, degenerative tear, biological augmentation for reconstruction surgery, etc.); rotator cuff (particularly, chronic injury, degenerative tear, etc.); delayed union; nonunion; skeletal muscle repair/regeneration; cardiac muscle repair; (augmenting the repair of necrotic tissue by ischemic-heart disease) or the like.

(Therapy Using Replacement and Coverage)

In another aspect, the present invention provides a method for reinforcement of a portion of an animal organism. The method comprises the steps of: A) disposing a synthetic tissue or complex to replace or cover the portion; and B) holding the synthetic tissue or complex for a time sufficient to connect to the portion. Herein, to position a portion for replacement typically means to perform debridement or curettage of an affected portion as necessary, to position the synthetic tissue or complex of the present invention on the lesion, and to allow it to stand so as to promote replacement. An objective of such replacement is to fill cells. Techniques known in the art can be combined and used. The step of disposing the synthetic tissue to cover the portion can be carried out using a technique well known in the art. The sufficient time varies depending on a combination of the portion and the synthetic tissue, and can be easily determined as appropriate by those skilled in the art depending on the combination. Examples of such a time include, but are not limited to, 1 week, 2 weeks, 1 month, 2 months, 3 months, 6 months, 1 year, and the like. In the present invention, a synthetic tissue preferably comprises substantially only cell(s) and material(s) derived from the cell. Therefore, there is no particular material which needs to be extracted after operation. The lower limit of the sufficient time is not particularly important. In this case, it can be said that the longer the time, the more preferable the synthetic tissue. If the time is sufficiently extremely long, it can be said that reinforcement is substantially completed. Therefore, the time is not particularly limited. The synthetic tissue of the present invention is also characterized in that it is easily handled, is not destroyed during an actual treatment, and facilitates a surgery due to its self-supporting ability.

In another embodiment, in a reinforcement method of the present invention, the above-described portion preferably includes bag-shaped organs (e.g., hearts, livers, kidneys, etc.). In order to reinforce such a bag-shaped tissue, it is necessary to replace or cover the organ. A synthetic tissue resistant to applications for replacement or covering is first provided by the present invention. Therefore, the reinforcement method of the present invention is advantageous over conventional techniques.

Alternatively, the above-described portion may include a bone or cartilage. Examples of such portions include, but not limited to, meniscus, ligament, tendon, and the like. By the method of the present invention a disease, injury, or condition of a heart, bone, cartilage, ligament, tendon, or meniscus may be treated, prevented or reinforced.

Particularly, in the reinforcement method of the present invention, a synthetic tissue or complex of the present invention is resistant to dilation/contraction of the above-described portion. Examples of such dilation/contraction include, but are not limited to, the pulsation motion of a heart, the contraction of a muscle, and the like.

In another preferable embodiment, in the reinforcement method of the present invention, a synthetic tissue or complex of the present invention has biological integration (e.g., interconnection of extracellular matrices, electrical integration, intracellular signal transduction, etc.). The biological integration is preferably provided in all three dimensions.

In another preferable embodiment, the reinforcement method of the present invention further comprises culturing a cell in the presence of an ECM synthesis promoting agent to forma synthetic tissue or complex of the present invention. An implantation/regeneration technique using the method which comprises the step of culturing a cell in the presence of an ECM synthesis promoting agent cannot be provided by conventional techniques. The method provides a therapy for diseases (e.g., cartilage injury, intractable bone fracture, etc.), which cannot be achieved by conventional therapies.

In a preferable embodiment, in the reinforcement method of the present invention, the cell used in the synthetic tissue or complex of the present invention is derived from an animal to which the synthetic tissue is to be implanted (i.e., an autologous cell). By using an autologous cell, adverse side effects, such as immune rejection reactions or the like, can be avoided.

In another preferable embodiment, the portion is a heart.

Applications for the therapy utilizing the present invention include, for example: cartilage full thickness injury, cartilage partial injury; osteochondral injury; osteonecrosis; osteoarthritis; meniscus injury; ligament injury (chronic injury, degenerative tear, biological augmentation for reconstruction surgery, etc.); rotator cuff (particularly, chronic injury, degenerative tear, etc.); delayed union; nonunion; skeletal muscle repair/regeneration; cardiac muscle repair; (augmenting the repair of necrotic tissue by ischemic-heart disease) or the like.

For some organs, it is said that it is difficult to radically treat a specific disease, disorder, or condition thereof (e.g., refractory heart diseases). However, the present invention provides the above-described effect, thereby making possible a treatment which cannot be achieved by conventional techniques. It has been clarified that the present invention can be applied to radical therapy. Therefore, the present invention has usefulness which cannot be achieved by conventional medicaments.

Thus, the present invention provides a method for treating a portion of an organism of an animal, comprising: A) positioning the synthetic tissue or complex so as to cover the portion; and B) retaining the synthetic tissue for a time period which is sufficient for the condition of the portion of the organism to be improved. Such an improvement in the condition can be determined can be determined in accordance with the function of the portion to be treated. For example, when a heart should be treated, an improvement in the condition can be determined by checking a cardiac function (heartbeat, bloodstream, or the like). If a bone should be treated, an improvement in the condition can be determined by observing osteogensis by using roentgen, CT scan, or the like. In the case of a bone, an improvement in the condition can be determined by measuring its strength or by evaluating bone marrow and/or a bone substance by using MRI. If a cartilage or meniscus should be treated, a surface of a joint can be observed by an arthroscopy. Further, it is possible to determine an improvement in the condition by performing a biomechanical inspection under arthroscopy. It is also possible to determine an improvement in the condition by confirming a repairing condition by using MRI. Regarding ligament, it is possible to determine by confirming whether there is laxity by a joint stability inspection. Further, an improvement of the condition can be determined by confirming a continuousness of a tissue by an MRI. In the case of any tissue, it is possible to determine whether the condition is improved by performing a biopsy of the tissue and making a histological evaluation.

In a preferred embodiment the treatment treats, prevents, prognosis, or enhances a disease, injury, or condition of a heart, bone, cartilage, ligament, tendon, or meniscus. Preferably, the synthetic tissue or the complex has a self-supporting ability. For such a synthetic tissue, those skilled in the art can use a synthetic tissue of any form described above herein, and a variant thereof.

(Combined Therapy)

In another aspect, the present invention provides a regeneration therapy which uses a cytokine, such as BMP (e.g., BMP-2, BMP-4, BMP-7, etc.), TGF-β1, TGF-β, HGF, FGF, IGF, or the like, in combination with a synthetic tissue.

Some cytokines used in the present invention are already commercially available (e.g., BMP (Yamanouchi Pharmaceutical), bFGF2 (Kaken Pharmaceutical), TGF-β1 (for research only, HGF-101 from Toyo Boseki, etc.). However, these cytokines can be prepared by various methods and can be used in the present invention if they are purified to an extent which allows them to be used as a medicament. A certain cytokine can be obtained as follows: primary cultured cells or an established cell line capable of producing the cytokine is cultured; and the cytokine is separated from the culture supernatant or the like, followed by purification. Alternatively, a gene encoding the cytokine is incorporated into an appropriate vector by a genetic engineering technique; the vector is inserted into an appropriate host to transform the host; a recombinant cytokine of interest can be obtained from the supernatant of the transformed host culture (e.g., Nature, 342, 440(1989); Japanese Laid-Open Publication No. 5-111383; Biochem-Biophys. Res. Commun., 163, 967 (1989), etc.). The above-described host cell is not particularly limited and can be various host cells conventionally used in genetic engineering techniques, including, for example, *Escherichia coli*, yeast, animal cells, and the like. The thus-obtained cytokine may have one or more amino acid substitutions, deletions and/or additions in the amino acid sequence as long as it has substantially the same action as that of the naturally-occurring cytokine.

Examples of a method for introducing the cytokine into patients in the present invention include, but are not limited to, a Sendai virus (HVJ) liposome method with high safety and efficiency (Molecular Medicine, 30, 1440-1448(1993); Jikken Igaku (Experimental Medicine), 12, 1822-1826 (1994)), an electrical gene introduction method, a shotgun gene introduction method, a ultrasonic gene introduction method, and the like. In another preferable embodiment, the above-described cytokines can be administered in the form of proteins.

(Production Method of Synthetic Tissue Having Desired Thickness)

Another aspect of the present invention provides a method for producing a synthetic tissue or complex having a desired thickness. This method comprises: A) providing cells; B) positioning the cells in a container having the base area sufficient for accommodating the synthetic tissue or complex having the desired size, which contains an ECM synthesis promoting agent (e.g., ascorbic acids, TGF-μ1, TGF-β3, etc.); C) culturing the cells in the container with a cell culture medium including the ECM synthesis promoting agent for a time sufficient for forming the synthetic tissue or complex having the desired size to convert the cells into a synthetic tissue; and D) adjusting the thickness of the synthetic tissue to obtain a desired thickness by a physical stimulation or a chemical stimulation. Herein, the steps of providing the cells, positioning the cells, stimulating and converting into the tissue or complex are described with respect to the production method for the synthetic tissue or complex of the present invention in detail, and it is understood that any embodiment can be employed.

Next, examples of the physical or chemical stimulation to be used may include, but not limited to, use pipetting, use of actin interacting substance. Pipetting may be preferable because operation is easy and no harmful substance is produced. Alternatively, examples of the chemical stimulation to be used may include actin depolymerizing factors and actin polymerizing factor. Examples of such an actin depolymerizing factor may include ADF (actin depolymerizing factor), destrin, depactin, actophorin, cytochalasin, NGF (nerve growth factor) and the like. Examples of the actin polymerizing factor include LPA (lysophosphatidic acid), insulin, PDGFa, PDGFb, chemokine, and TGFb. The polymerization or depolymerization of actin can be observed by checking the activity to actin. It is possible to test any substance whether it has such an activity. It is understood that a substance which is tested as such and identified can be used for achieving the desired thickness in production of the synthetic tissue of the present invention. For example, in the present invention, the adjustment of the desired thickness can be achieved by adjusting the ratio between the actin depolymerizing factor and actin polymerizing factor.

(Composite Tissue)

Another aspect of the present invention also provides a tissue complex including an implantable synthetic tissue and another synthetic tissue. Herein, another tissue may either be a synthetic tissue included within the scope of the present invention, or a synthetic tissue out of the scope (i.e., conventional tissues). Conventional tissues (e.g., an artificial bone, microfibrous collagen medical device, etc.,) do not have a biological integrating ability or have a biological integrating ability which cannot stand the practical use. Thus, it was almost impossible to form such a tissue complex. It is understood that, according to the present invention, a cartilage can be combined to a bone for treatment. For the case of a cavity in a bone or the like, particularly, for the case of treatment of bone cartilage complex, by using a tissue complex of an artificial bone (e.g., hydroxyapatite construct such as NEO BONE, a microfibrous collagen medical device, etc.) and the synthetic tissue or complex of the present invention, it is possible to treat the bone by the artificial bone, and the cartilage on the bone by the synthetic tissue at the same time. It is understood that the synthetic tissue or complex of the present invention is combined to an artificial bone and used for treatment. Herein, the implantable synthetic tissue or complex of the present invention substantially comprises, for example, cells and substances derived from the cells, and more preferably, cells and extracellular matrix derived from the cells. The extracellular matrix as used herein is selected from the group consisting of collagen I, collagen III, vitronectin, and fibronectin.

As used herein, the term "tissue complex" refers to a tissue obtained by combining a synthetic tissue or complex of the present invention with another synthetic tissue (including a synthetic tissue or complex of the present invention). Such a tissue complex can be used for a treatment of a plurality of tissues. For example, such a tissue complex can be used for treatment of both cartilage and bone.

In the case there is a large defect of soft tissue (e.g., menisucus, etc.), the synthetic tissue of the present invention can be coupled to another synthetic tissue (microfibrous collagen medical device (e.g., CMI (Amgen, USA), Integran® (Nippon Zoki Pharmaceutical), hyaluronic acid gel, collagen gel, agarose gel, alginate gel, beads etc.) to promote biological integration between another synthetic tissue and an implantation cells.

Preferably, in the complex of the present invention, an implantable synthetic tissue and another synthetic tissue are biologically integrated. Such integration can be produced by culturing two tissues in contact. Such a biological integration is mediated by extracellular matrix.

Hereinafter, the present invention will be described by way of examples. Examples described below are provided only for illustrative purposes. Accordingly, the scope of the present invention is not limited except as by the appended claims.

EXAMPLES

In the examples below, animals were treated in accordance with rules defined by Osaka University (Japan) and were cared for in the spirit of animal protection.

Example 1

Synovial Cell

In this example, various synovial cells were used to produce a synthetic tissue as follows.

<Preparation of Cells>

Synovial cells were collected from a knee joint of a pig (LWD ternary hybrid, 2-3 months old upon removal of cells), followed by treatment with collagenase. The cells were cultured and subcultured in 10% FBS-DMEM medium (FBS was obtained from HyClone, DMEM was obtained from GIBCO). It has been reported that 10th passage synovial cells still have pluripotency. Although cells of 10 or less passages were used in this example, cells of more than 10 passages may be used depending on the application. Autotransplantation was performed for humans, where a sufficient number of cells were used and the cells were cultured for a short period of time so as to reduce the risk of infection or the like.

Considering these points, cells of various passages were used. Actually, primary culture cells, first passage cells, second passage cells, third passage cells, fourth passage cells, fifth passage cells, sixth passage cells, eighth passage cells, and tenth passage cells were used in experiments. These cells were used for synthetic tissues.

<Preparation of Synthetic Tissue>

Synovial cells ($4.0 \times 10^6$) were cultured in 2 ml of 10% FBS-DMEM medium in a 35-mm dish, a 60-mm dish, or 100-mm dish (BD Biosciences, culture dish and multiwell cell culture plate). In this case, ascorbic acid was added. The dishes, the ascorbic acid concentrations, and the cell concentration are described below.

Dishes: BD Biosciences, cell culture dishes and multiwell cell culture plates
Ascorbic acid 2-phosphate: 0 mM, 0.1 mM, 0.5 mM, 1 mM, 2 mM, and 5 mM
The number of cells: $5 \times 10^4$ cells/cm$^2$, $1 \times 10^5$ cells/cm$^2$, $2.5 \times 10^5$ cells/cm$^2$, $4.0 \times 10^5$ cells/cm$^2$, $5 \times 10^5$ cells/cm$^2$, $7.5 \times 10^5$ cells/cm$^2$, $1 \times 10^6$ cells/cm$^2$, $5 \times 10^6$ cells/cm$^2$, and $1 \times 10^7$ cells/cm$^2$ Medium was exchanged two times per week until the end of a predetermined culture period. At the end of the culture period, a cell sheet was detached from the dish by pipetting circumferentially around the dish using a 100 μl pipetteman. After detachment, the cell sheet was made as flat as possible by lightly shaking the dish. Thereafter, 1 ml of medium was added to completely suspend the cell sheet. The cell sheet was allowed to stand for two hours, resulting in the contraction of the cell sheet into a three-dimensional form. Thus, a synthetic tissue was obtained (FIG. 1).

<Hematoxylin-Eosin (HE) Staining>

The acceptance or vanishment of cells in a sheet was observed by HE staining. The procedure is described as follows. A sample is optionally deparaffinized (e.g., with pure ethanol), followed by washing with water. The sample is immersed in Omni's hematoxylin for 10 min. Thereafter, the sample is washed with running water, followed by color development with ammonia in water for 30 sec. Thereafter, the sample is washed with running water for 5 min and is stained with eosin hydrochloride solution for 2 min, followed by dehydration, clearing, and mounting.

(Various Extracellular Matrix Staining)
1. Make 5 μm thick sections from frozen block.
2. Sections are fixed in acetone at −20° C. for 5-10 mins. (Paraffin blocks should be deparaffinized and rehydrated).
3. Endogenous peroxide activity is blocked in 0.3% $H_2O_2$ in methanol for 20 mins at RT.
   (1 ml 30% $H_2O_2$+99 ml methanol)
4. Wash with PBS (3×5 mins).
5. Incubate with primary monoclonal antibody (mouse or rabbit antibody against each extracellular matrix protein) in a moist chamber at 4° C. for overnight (1 μl antibody+200 μl PBS per slide).
6. Next day wash with PBS (3×5 mins).
7. Apply anti mouse and anti rabbit no. 1 Biotynalated link for 30 mins-1 hrs at RT.
   (apply about 3 drops directly on slide).
8. Wash with PBS (3×5 mins).
9. Apply about 3 drops directly Streptavidin HRP no. 2 for LSAB. 10-15 mins.
10. Wash with PBS (3×5 mins).
11. Apply DAB (5 ml DAB+5 μl $H_2O_2$).
12. Observe under microscope for brownish colour.
13. Dip in water for 5 mins.
14. Apply HE for 30 sec-1 min.
15. Wash several times.
16. Ion exchange water wash 1 time.
17. 80% ethanol wash for 1 min.
18. 90% ethanol wash for 1 min.
19. 100% ethanol wash for 1 min (3 times).
20. Xylene wash for 1 min (3 times), Coverslip.
21. Examine color development.

Figure 2:
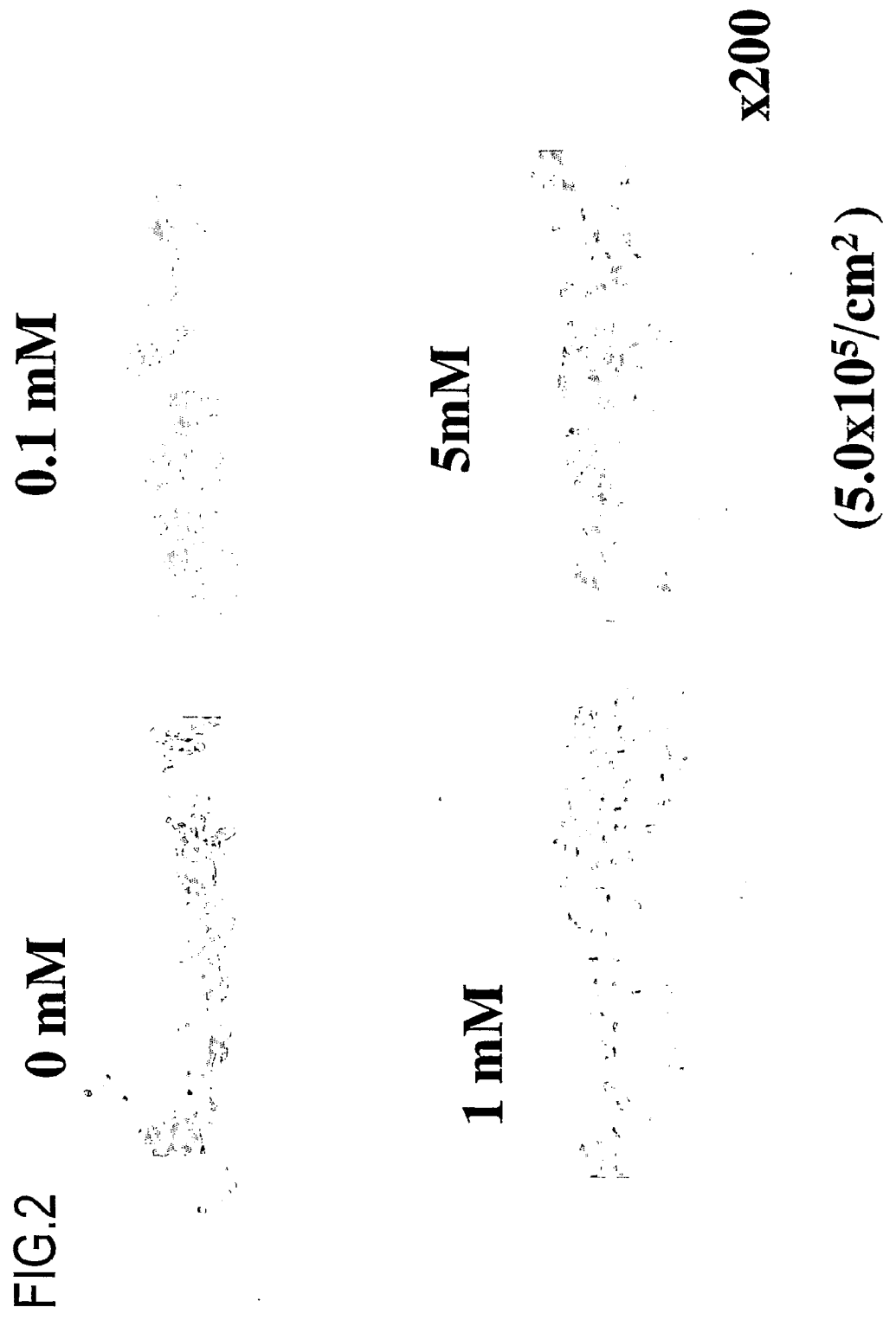
FIG. 2 shows high magnification histology of a synthetic tissue when ascorbic acid 2-phosphate has a concentration of 0 mM, 0.1 mM, 1 mM, and 5 mM. As can be seen, Eosin staining of the synthetic tissue is more intense when ascorbic acid 2-phosphate is added at a concentration of more than 0.1 mM.

An exemplary result is shown in FIG. 1. As shown in the right portion of FIG. 1, when ascorbic acid 2-phosphate was added as an ECM synthesis promoting agent, a contractile three-dimensional tissue of the cells was only slightly observed. On the other hand, by detaching the sheet-like cells from the base of the culture dish and allowing the cells to self organize, the cells were promoted to be layered and were accelerated into a three-dimensional structure, as shown in the left portion of FIG. 1. As shown in a left portion of FIG. 1, large tissue without a hole was also produced when synovial cells were used. This tissue was thick and its extracellular matrix was rich as shown in a right portion of FIG. 1. When ascorbic acid 2-phosphate was added at a concentration of 0.1 mM or more, the formation of an extracellular matrix was promoted (FIG. 2). FIG. 3 shows an enlarged view of a synthetic tissue on Day 3, 7, 14, and 21. As can be seen, after 3 days of culture, the tissue was already so rigid that it can be detached (FIG. 3). As the number of culture days is increased, the density of the extracellular matrix fluctuates and increases.

The tissue was detached from the base of the culture dish and self-contracted. The synthetic tissue was prepared in a sheet form. When the sheet was detached from the dish and was allowed to stand, the sheet self contracted into a three-dimensional structure. It is seen that a number of layers of cells exist in the tissue.

Next, various markers including extracellular matrix markers were stained.

Figure 4:
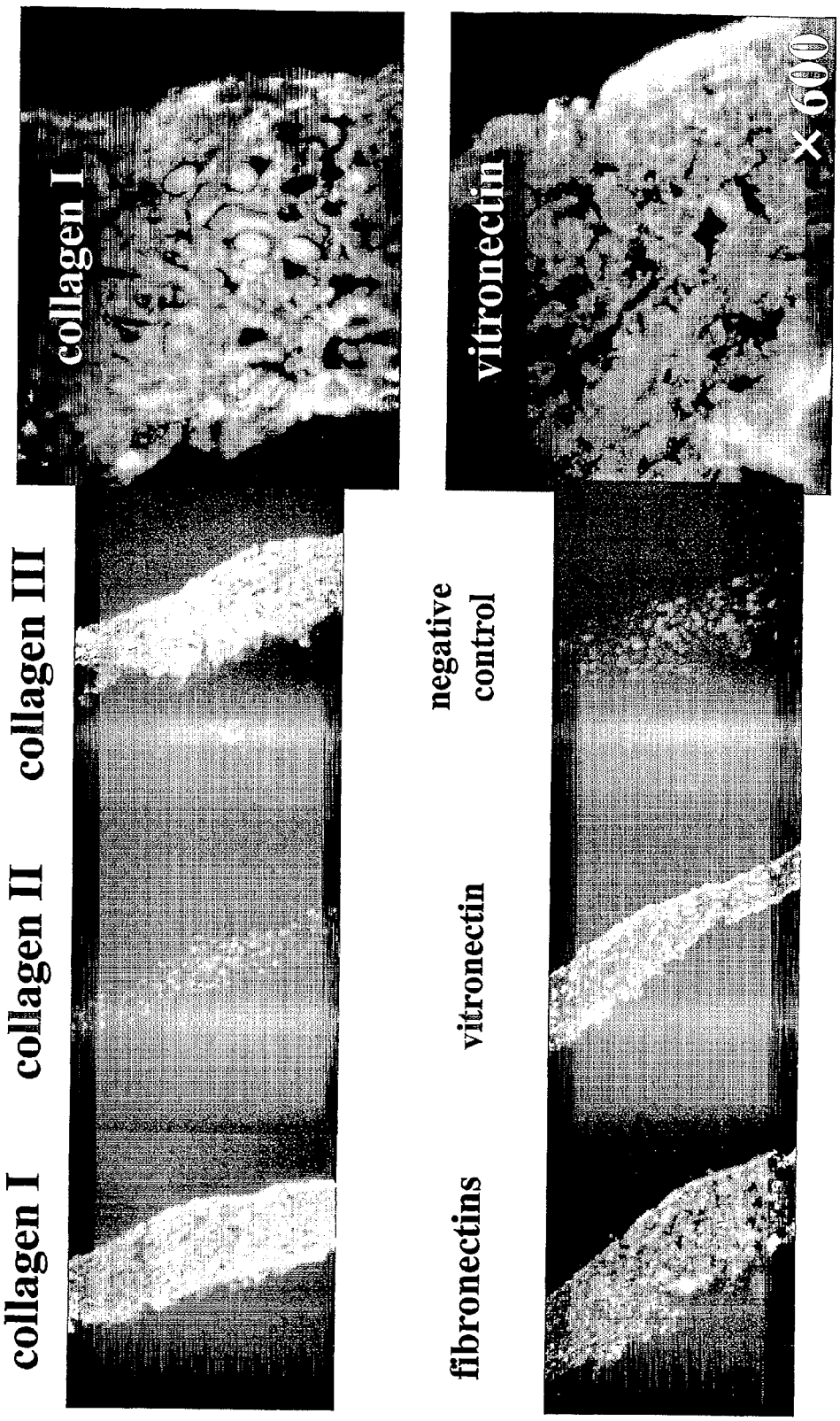
FIG. 4 shows an exemplary stained extracellular matrix in a synthetic tissue derived from synovial cells.

FIG. 4 shows the result of staining extracellular matrix. It can be seen that various extracellular matrix components (collagen I, II, III, fibronectin, vitronectin, etc.) existed. Immunostaining was conducted, so that collagen I and III were strongly stained while collagen II staining was limited to a portion. By being strongly magnified, it can be confirmed that collagen was stained at a site slightly away from the nuclei, i.e., collagen was a part of the extracellular matrix. On the other hand, fibronectin and vitronectin, which are believed to be important cell adhesion molecules. By being strongly magnified, it can be confirmed that fibronectin and vitronectin were stained at a region close to nulei unlike collagen, i.e., fibronectin and vitronectin existed around the cells.

These results demonstrated that cells of at least 3 to 8 passages are preferable for production of synthetic tissue.

Figure 6:
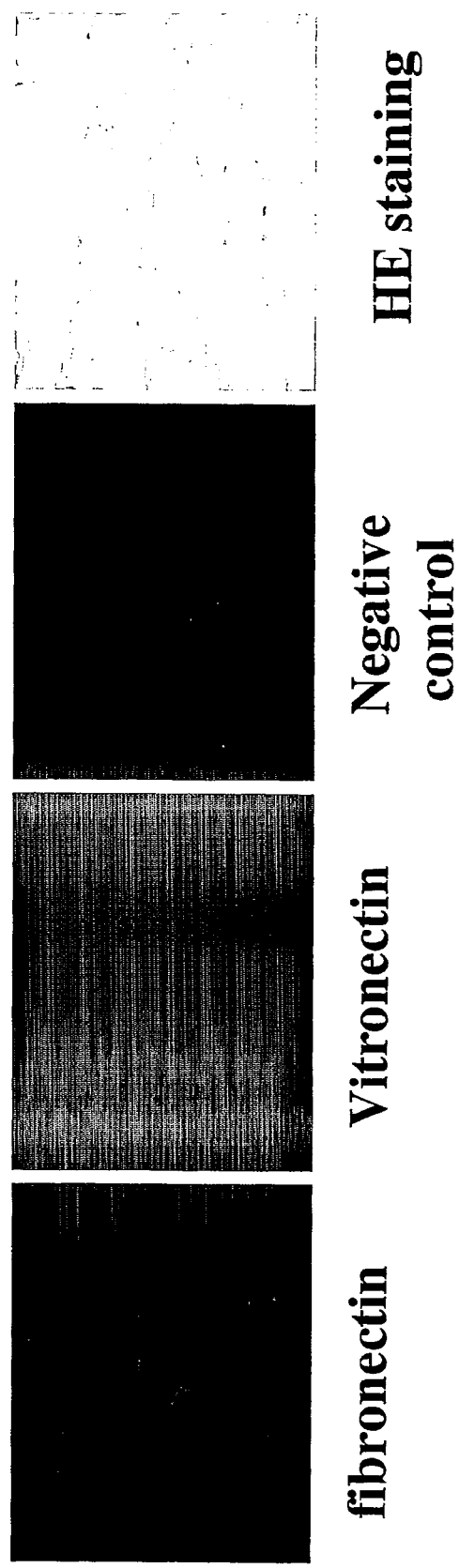
FIG. 6 shows exemplary histology of a commercially available stained collagen sponge as a control: From the left, staining of fibronectin, vitronectin, non-IgG-immune as a negative control and HE staining are shown.

For comparison, a nomal tissue and a collagen sponge (CMI, Amgen, USA) were stained. FIG. 5 shows the normal tissue (normal synovial membrane tissue, tendon tissue, cartilage tissue, skin, and meniscus tissue). FIG. 6 shows the stained collagen sponge, which was the comparative example. From the left, fibronectin, vitronectin, negative control, and HE staining are indicated. As can be seen, the conventional synthetic tissue was not stained with fibronectin or vitronectin. Therefore, the synthetic tissue of the present invention is different from conventional synthetic tissues. Existing collagen scaffolds do not contain fibronectin and vitronectin (adhesion agents). In view of this, the originality of the synthetic tissue of the present invention is clearly understood. No stain in found in the extracellular matrix. When the synthetic tissue of this example was compared with normal tissue, the synthetic tissue has a lower extracellular matrix density and had a structure different from normal tissue.

Further, when the synthetic tissue of the present invention was contacted with a filter paper in order to remove moisture from the tissues, the filter is adhered to the synthetic tissue, and it was difficult to manually detach the synthetic tissue of the present invention.

Figure 7:
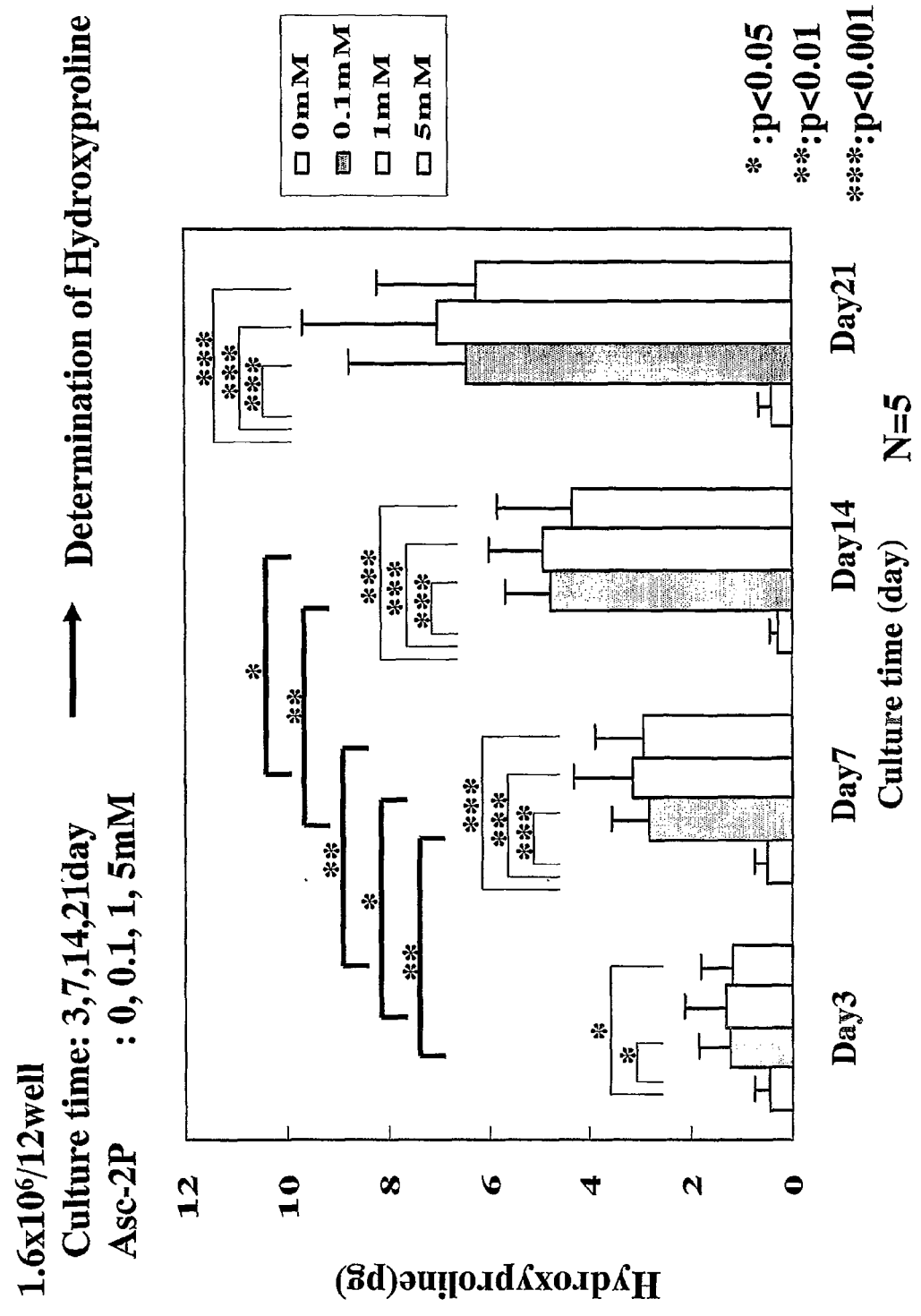
FIG. 7 shows the results of collagen content measurement. When 0.1 mM or more of ascorbic acid diphosphate is added, collagene content in the synthetic tissue of the present invention is significantly increased in any of the culture periods. However, substantially no difference among the concentrations of 0.1 mM, 1 mM and 5 mM were found.
Figure 8:
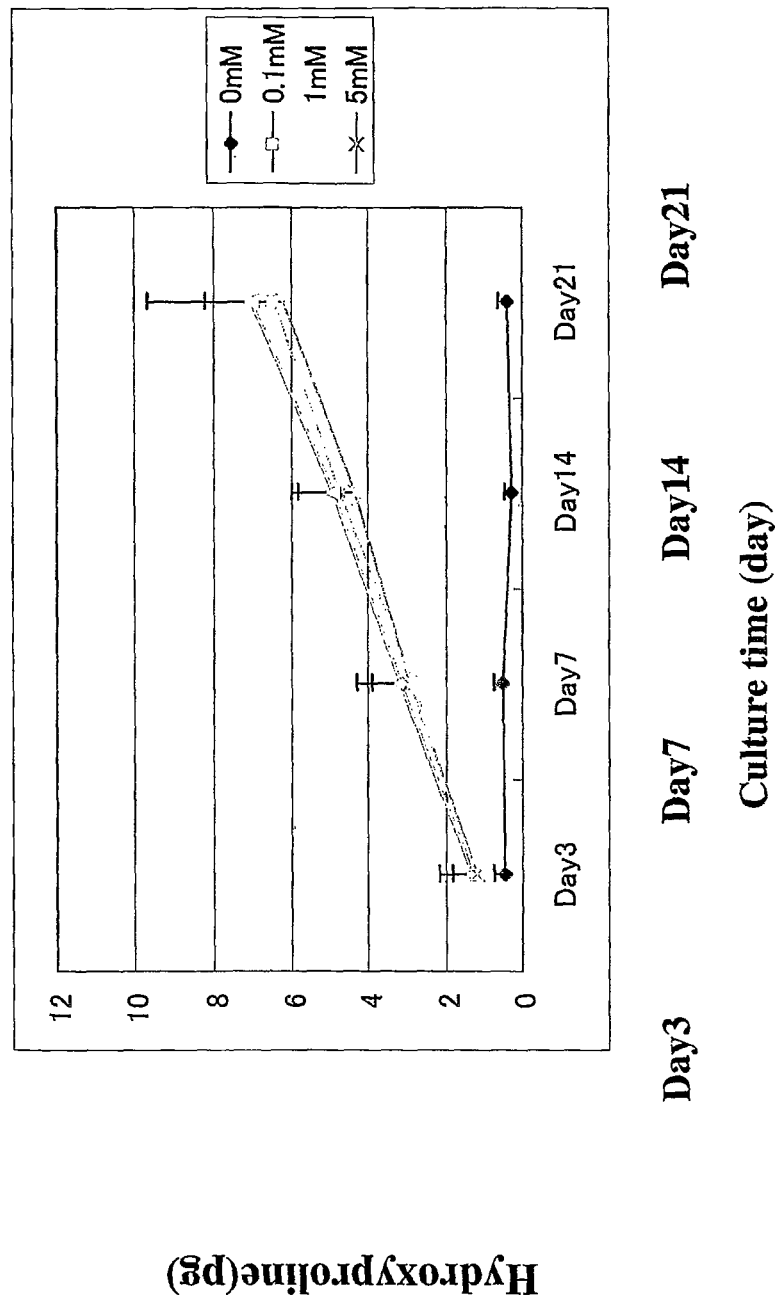
FIG. 8 shows the results of collagen content measurement. When 0.1 mM or more of ascorbic acid diphosphate is added, collagene content in the synthetic tissue of the present invention is significantly increased in any of the culture periods. However, substantially no difference among the concentrations of 0.1 mM, 1 mM and 5 mM were found.

In order to determine the collagen concentration, the collagen content was measured. The result is shown in FIGS. 7 and 8. As can be seen, the amount of hydroxyproline clearly indicates that when 0.1 mM or more ascorbic acid 2-phosphate was added, the production of collagen was significantly promoted. The amount of produced collagen is substantially proportional to the time period of culture (FIG. 8).

Example 2

Measurement of Collagen Production

Next, it was determined whether or not collagen (extracellular matrix) is sufficiently secreted after implantation of a synthetic tissue of the present invention. The following protocol was used.

<Method>

Culture periods: 3 days, 7 days, 14 days, and 21 days,

Concentrations of ascorbic acid 2-phosphate: 0 mM, 0.1 mM, 1 mM, and 5 mM

Under the above-described conditions, a synovial membrane-derived synthetic tissue was produced.

6 N HCl was added to culture medium for the synthetic tissue, followed by hydrolysis at 105° C. for 18 hours. The medium was oxidized with chloramine T. Thereafter, the synthetic tissue was subjected to color development using Ehrlich's Reagent Solution (2 g of p-dimethylamino-benz-aldehyde+3 ml of 60% perchloric acid; isopropanol was diluted at 3:13), followed by measurement of absorbance.

<Results>

1) The quantities of collagen produced was dependent on the ascorbic acid concentration in the following manner: 0 mM<<5 mM<1 mM≤0.1 mM (FIGS. 7 and 8).

2) it was demonstrated that the quantity of produced collogen is increased with an increase in the culture time period.

Example 3

Influences of the Size of a Dish, the Number of Cells, and the Number of Passages Next, influences of the size of a dish and the number of passages were investigated.

Figure 9:
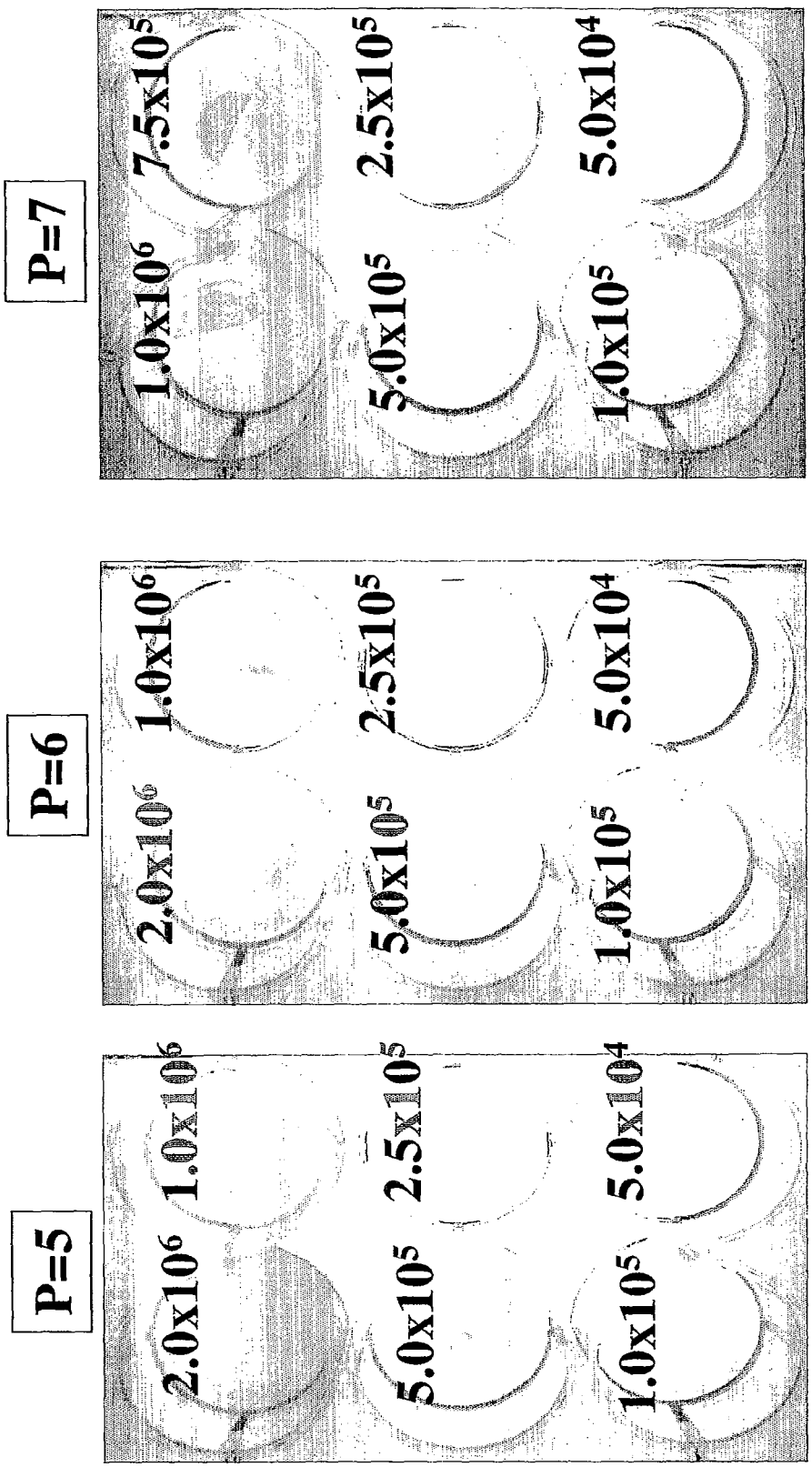
FIG. 9 shows a production of synthetic tissues using a different number of cells. P represents the number of passages. Numeral figures in the photograph indicate the number of cells per $cm^2$.

FIG. 9 shows the formation of synthetic tissues where the number of cells and the number of the passage were changed. A synthetic tissue was formed in all concentrations tested.

Figure 10:
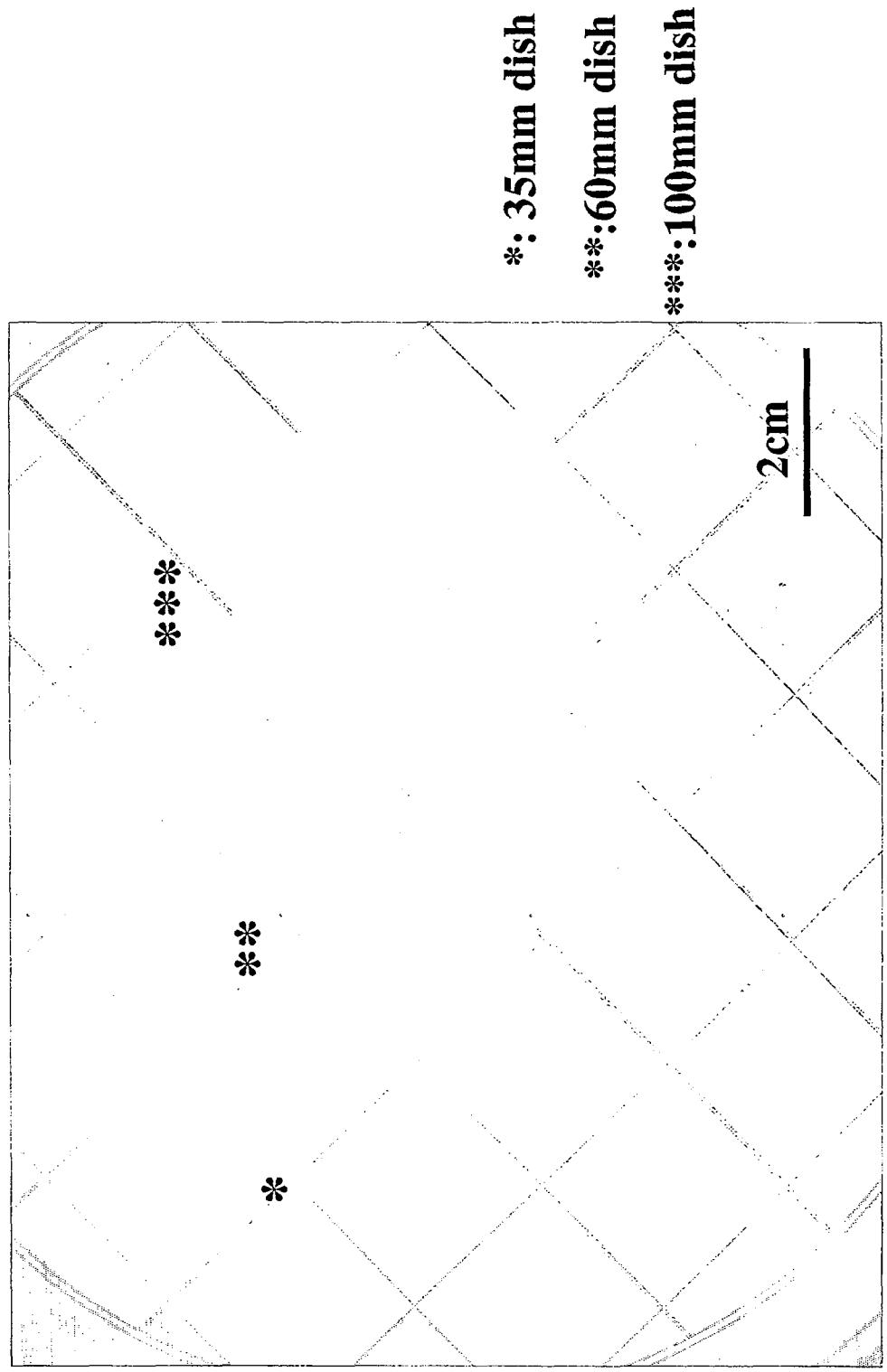
FIG. 10 shows a production of synthetic tissues using dishes with different sizes. * indicates culture in a 35-mm dish.  indicates culture in a 60-mm dish. * indicates culture in a 100-mm dish.

Under the conditions of the above-described Example 1, a similar experiment was conducted where the sizes of dishes were 35 mm, 65 mm, and 100 mm and the number of passages were 5 to 7 (FIG. 10).

The results are shown in FIGS. 9 and 10. FIG. 9 shows the states of synthetic tissues, where the number of passages was changed. FIG. 10 shows the states of synthetic tissues, where the size of a dish was changed. As can be seen from the figures, it was demonstrated that a synthetic tissue can be formed using any size of dish and any number of passages.

As shown in FIG. 9, basically, a greater number of cells may be preferable for the purpose of matrix production. However, when an excessive number of cells were provided, the cells produced an excessive level of contraction force, so that the cell sheet was detached on the day following the start of culture. Therefore, it was demonstrated that when a larger synthetic tissue is desired, it is preferable to dessimate cells at a relatively small concentration. Particularly, in order to control the strength or the like of a synthetic tissue, a relatively small cell concentration seems to be preferable. As can be seen from the figure, when the number of passages was five, the resultant cell sheet was spontaneously detached if the cell concentration was $5.0 \times 10^5/cm^2$, and was not spontaneously detached if the cell concentration was $2.5 \times 10^5/cm^2$. Also, when the number of passages was six or more, the resultant cell sheet was spontaneously detached if the cell concentration was $7.5 \times 10^5/cm^2$, and was not spontaneously detached if the cell concentration was $5.0 \times 10^5/cm^2$. Therefore, the production of a preferable synthetic tissue of the present invention seems to require a sufficient number of cells and a relatively great number of passages. Fourth passage cells were used to produce a trial synthetic tissue. It was spontaneously detached when the cell concentration was $40 \times 10^5/cm^2$. Thus, there seems to be a close relationship between the strength of a synthetic tissue and the number of passages. Various synthetic tissues can be produced, depending on the application. According to these results, cells capable of withstanding implantation seems to be obtained by culturing fifth passage cells at a concentration of $4.0 \times 10^5/cm^2$, however, the present invention seems not to be limited to this.

Similarly, the strength of tissues consisting of other cells is demonstrated to be able to be regulated by changing the cell concentration. Under the conditions described in Example 1, myoblasts can be used to produce a synthetic tissue and the influence of cell density on the strength of the synthetic tissue can be measured. Under the conditions described in Example 28, synovial cells can be used to produce a synthetic tissue and the influence of cell density on the strength of the synthetic tissue can be measured. Under the conditions described in Example 12, fat-derived cells can be used to produce a synthetic tissue and the influence of cell density on the strength of the synthetic tissue can be measured.

Example 4

Measurement of Mechanical Properties

In this example, cells ($4 \times 10^5$ cells/cm$^2$) were cultured in medium containing ascorbic acid 2-phosphate for three weeks. Following detachment at 48 hours, the mechanical properties of the tissue were investigated. The protocol will be described below.

The mechanical properties were examined by a tensile test.

Figure 11:
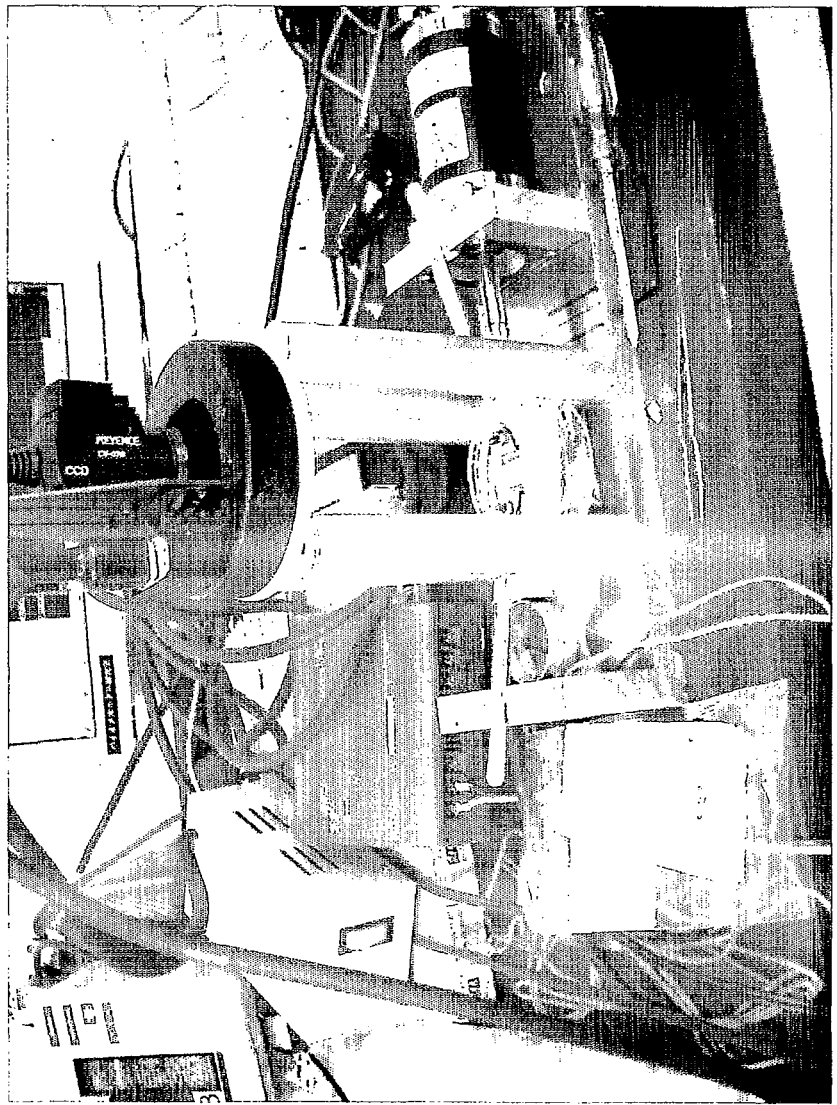
FIG. 11 shows an exemplary mechanical testing system for measuring mechanical properties.
Figure 12:
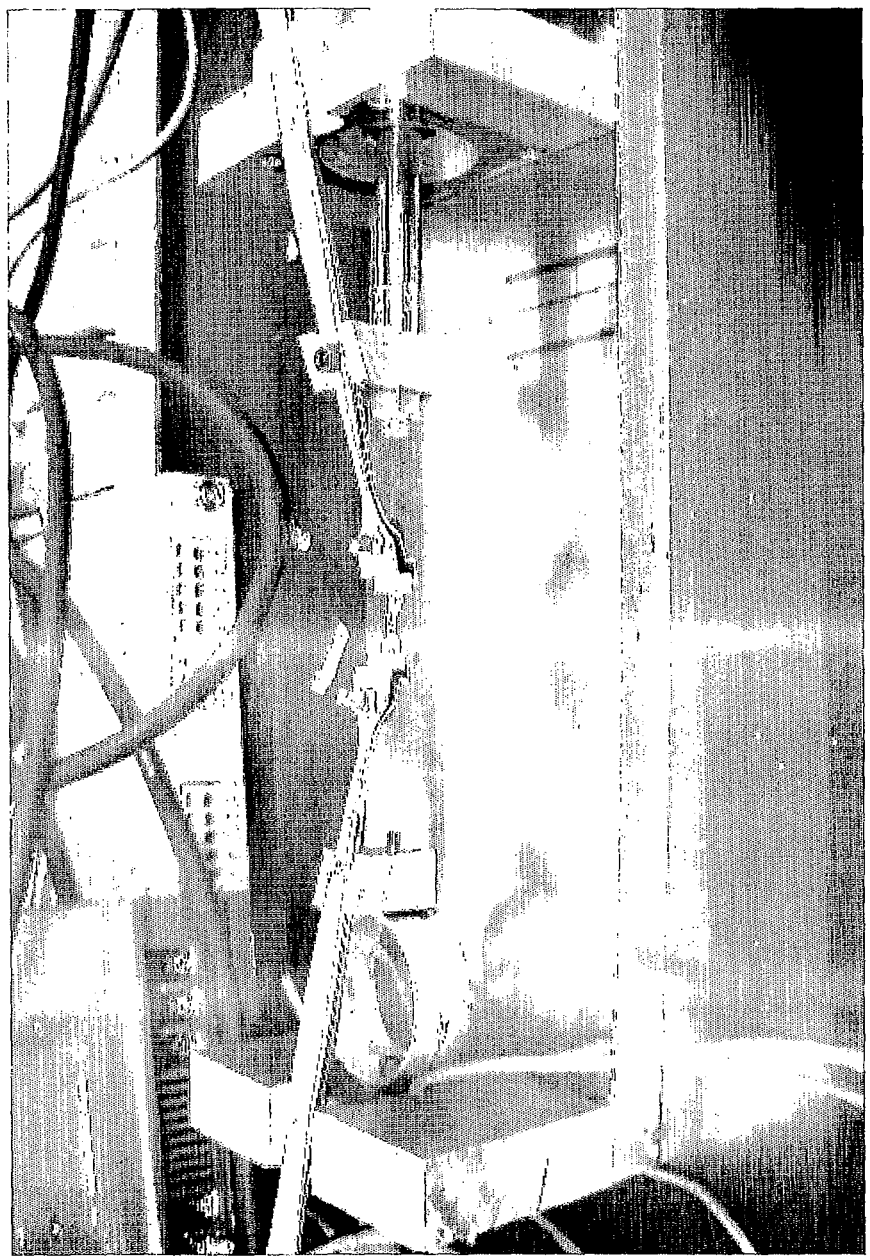
FIG. 12 shows a test piece holding portion of an apparatus for measuring mechanical properties.
Figure 13:
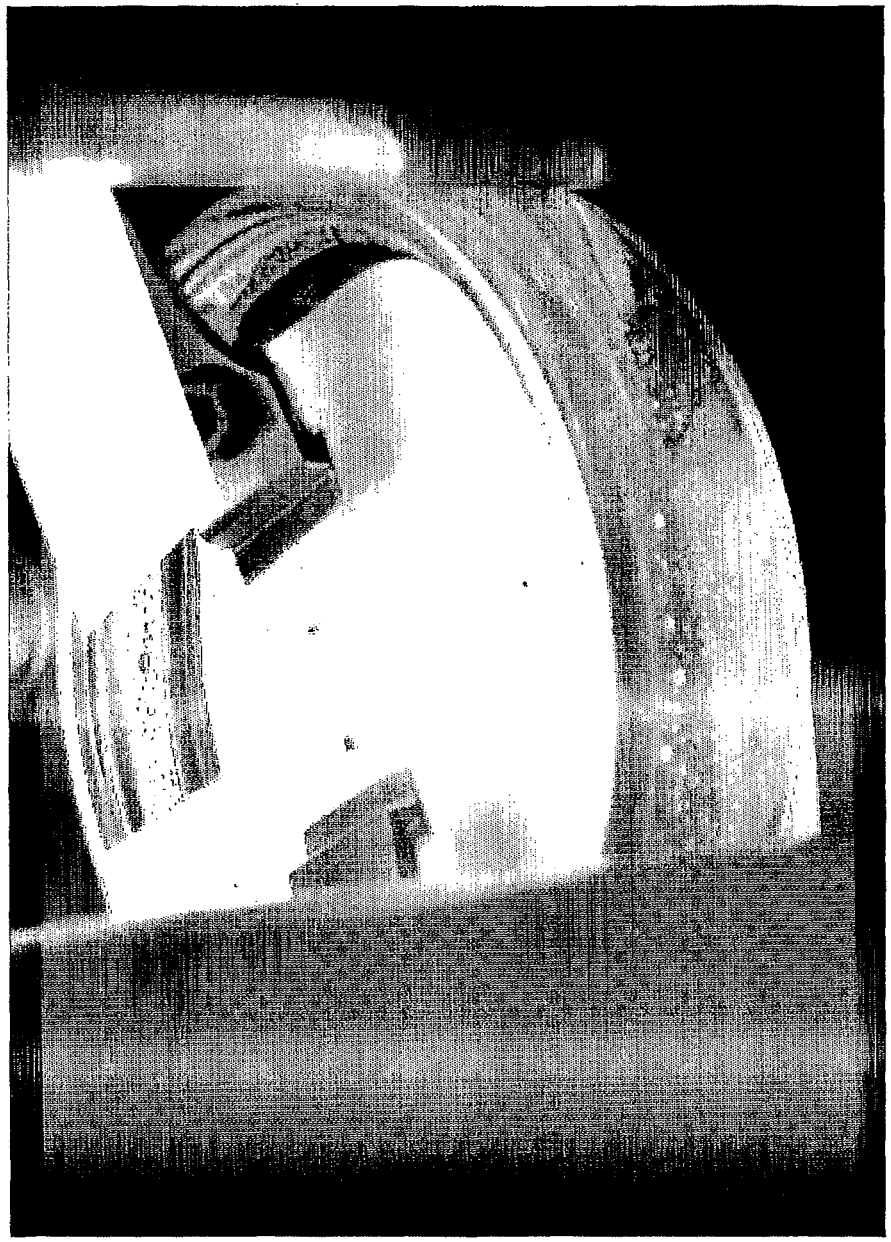
FIG. 13 shows an enlarged view of an apparatus for measuring mechanical properties. A test piece is provided with a marker.
Figure 14:
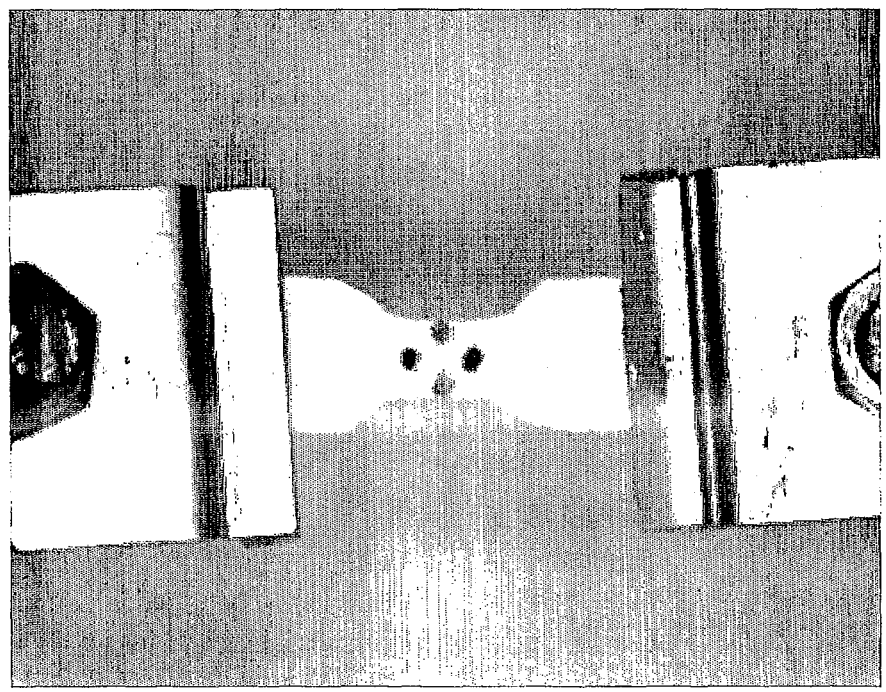
FIG. 14 shows an enlarged view of a test piece holding portion.
Figure 15:
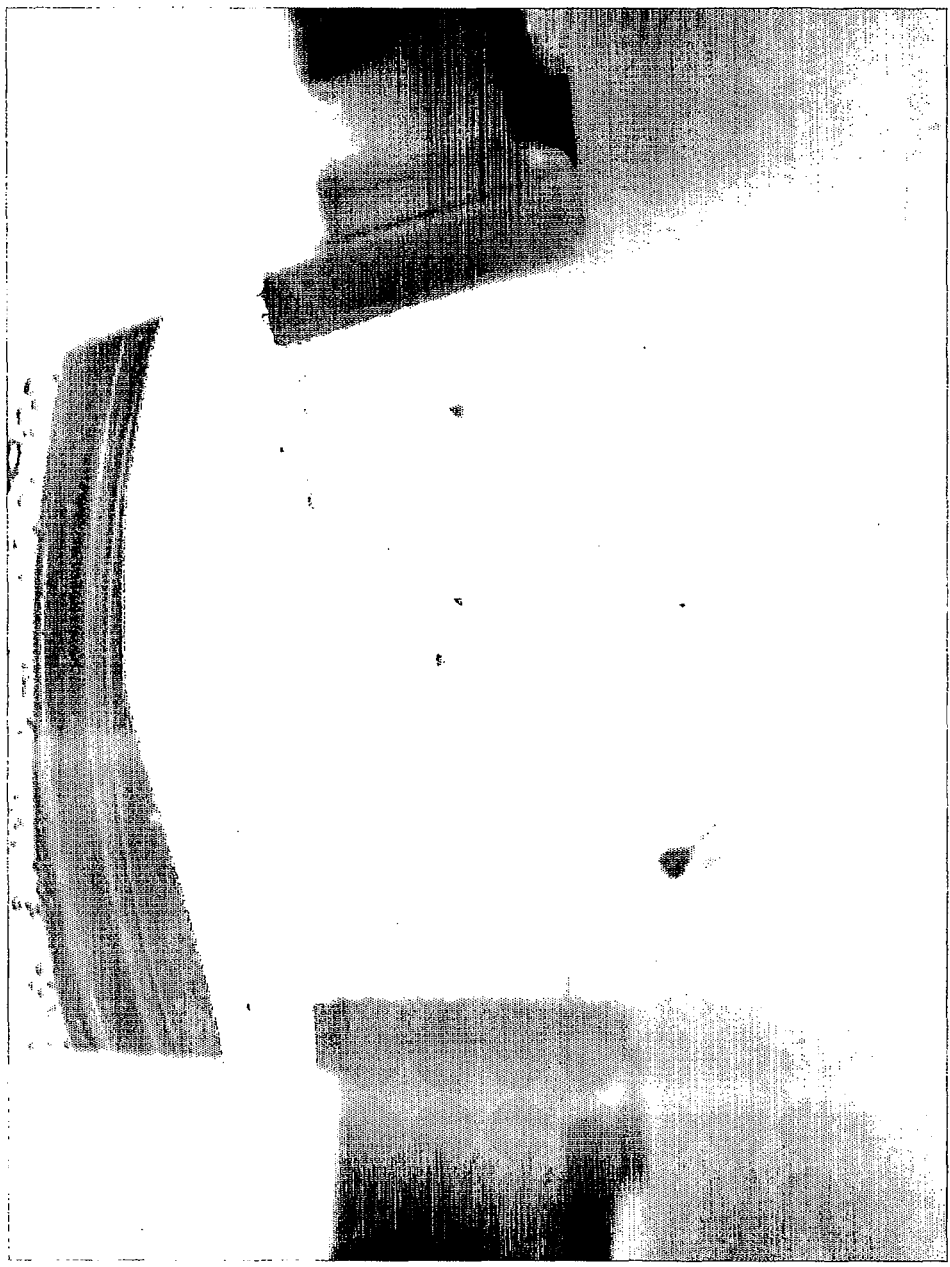
FIG. 15 shows a disrupted synthetic tissue after a tensile test.

FIGS. 11 and 12 show the outer appearance of a testing apparatus. FIG. 11 shows a test piece holding portion (an original piece is shown). As shown in FIG. 12, the opposite ends of a synthetic tissue were held by the test piece holding portion. A marker was attached to the synthetic tissue for ease of measurement. FIG. 13 shows the attachment of the marker. FIG. 14 shows an enlarged view of the test piece holding portion. FIG. 15 shows the state of the synthetic tissue after a tensile test.

A synthetic tissue was held as shown in the figures and a marker was attached to the synthetic tissue, followed by a tensile test. The maximum load was 1.89 N, and the Young's modulus was 19.2 Mega pascal. As a reference, the maximum load (tension) of cartilage is typically 0.7 and that of skin is 1.2. The Young's modulus of cartilage is 10 MPa and that of skin is 35 Mpa. Thus, it was demonstrated that the synthetic tissue of the present invention has substantially the same mechanical strength as that of skin, cartilage, or the like, and can resist surgical handling.

Figure 16:
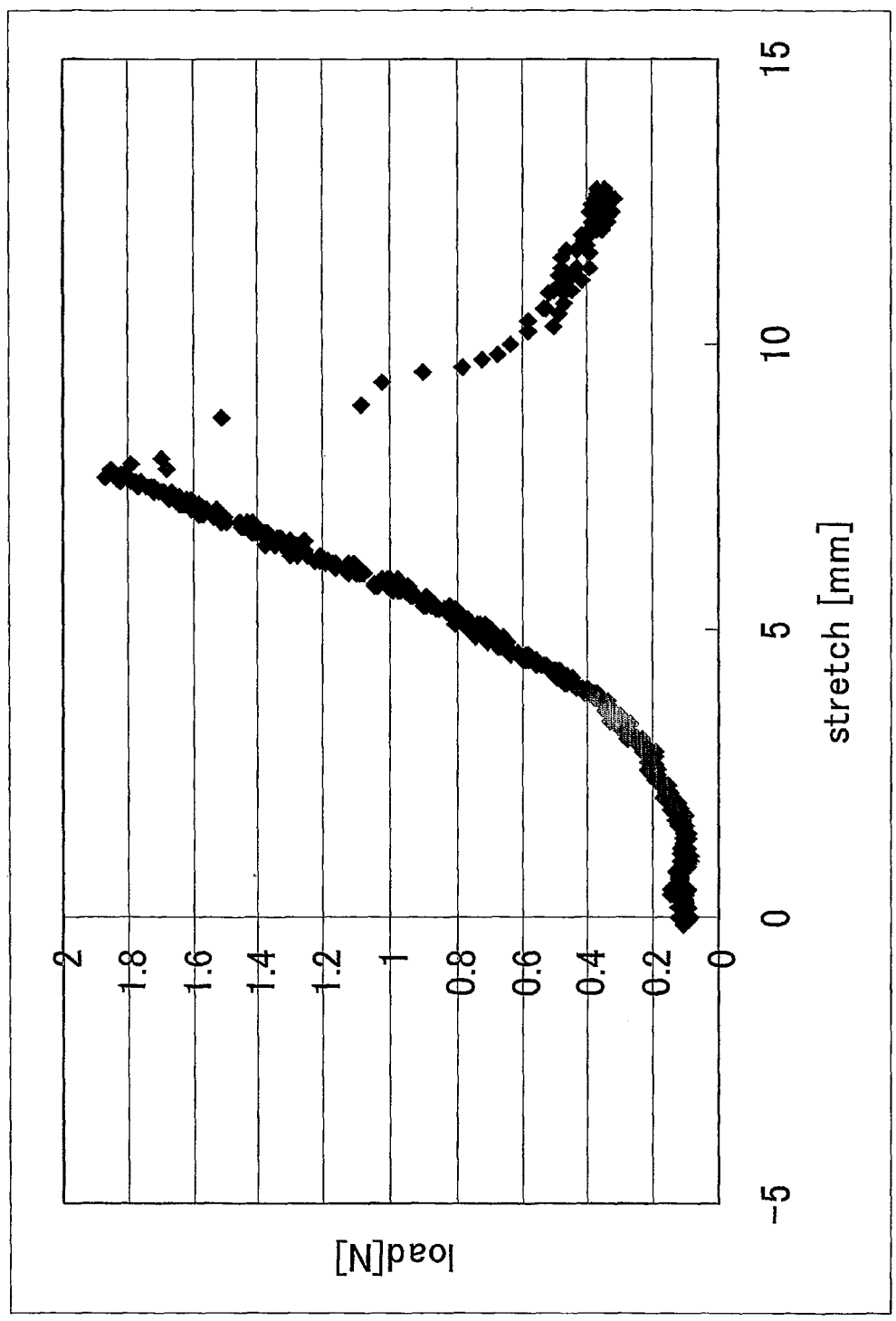
FIG. 16 shows the results (load-deformation curve) of a tensile test of a synthetic tissue (derived from synovium) of the present invention.
Figure 17:
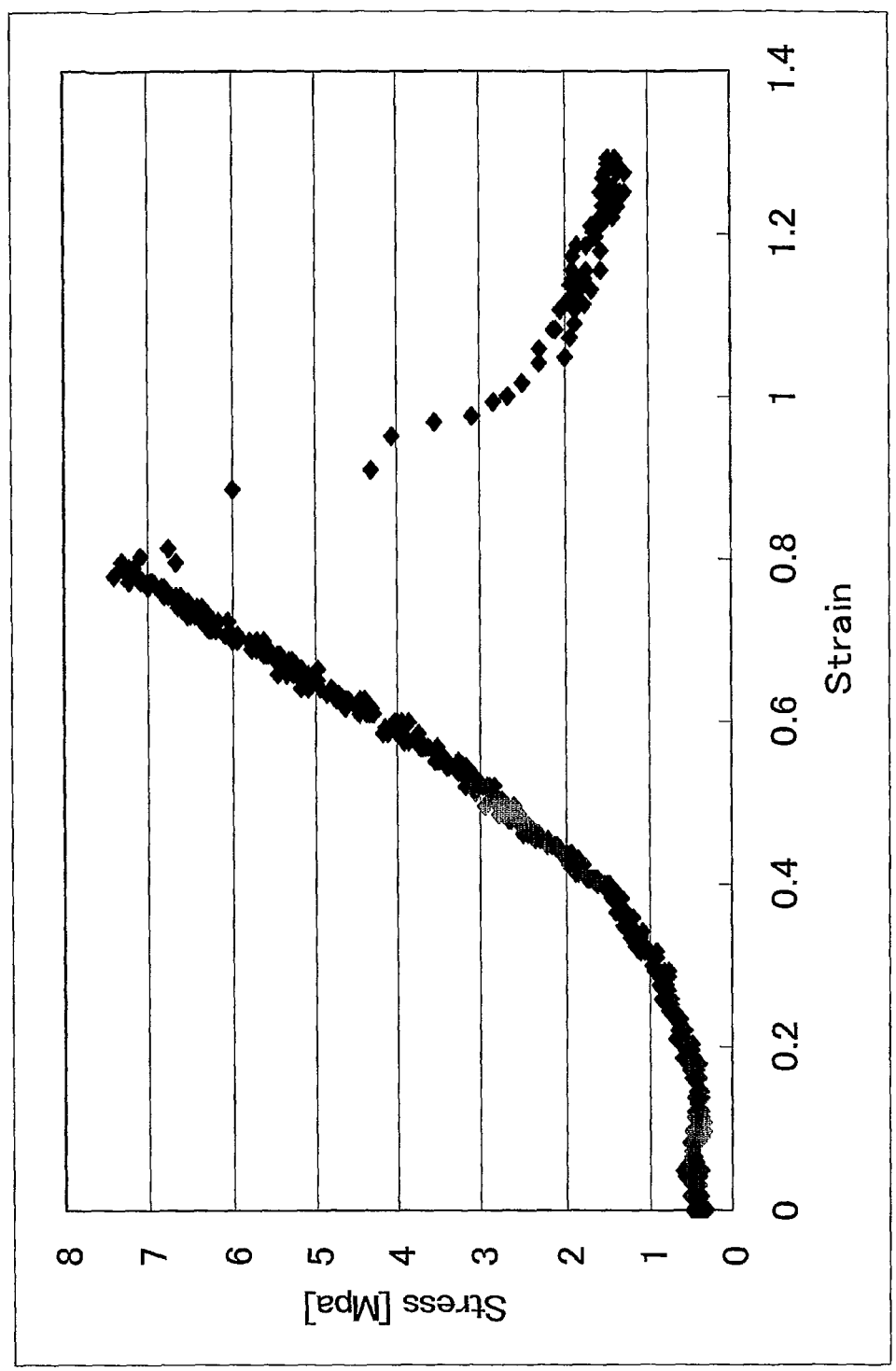
FIG. 17 shows the results (stress-strain curve) of a mechanical properties test of a synthetic tissue (derived from synovial membrane tissue) of the present invention.

The results of the experiment are shown in FIGS. 16 and 17. The results demonstrate that the maximum load was 1.89 N and 1.9 N, respectively. Young's modulus (tangent tensile modulus) was 19.2 MPa.

Example 5

Determination of Self-supporting Ability

Next, the self-supporting ability of a synthetic tissue of the present invention was tested. The synthetic tissue was held and tested using curved fine forceps A-11 (made of stainless steel; full length: 120 mm; curved: 20 mm, tip: 0.1 mm; manufactured by Natsume Seisakusho). It was determined by visual inspection whether or not the synthetic tissue has self-supporting ability. If the synthetic tissue was divided into a plurality of pieces, it was determined to lacking self-supporting ability. The same result was obtained when another forceps, e.g., curved fine forceps A-12-2 (made of stainless steel, full length: 100 mm; tip: 0.05 mm; manufactured by Natsume Seisakusho) were used by another experimenter performing the same experiment.

The self-supporting ability may be determined immediately after detaching a synthetic tissue off or after preserving a detached synthetic tissue.

None of the synthetic tissues comprising cardiomyocytes, myoblasts, and synovial cells, which are produced in the presence of a three-dimensional promoting agent comprising ascorbic acid as described in the above examples, had self-supporting ability. In contrast, it was already difficult to hold a synthetic tissue produced in the absence of such an agent with forceps upon detachment, so that lack of self-supporting ability was confirmed.

Therefore, 1) if a sheet is easily detached by circumferential pipetting; and 2) if the detached sheet is easily attached to a target site by lightly touching an edge thereof, the sheet spontaneously contracts to have sufficient strength.

Therefore, self-supporting ability is a property which was first obtained by the method of the present invention.

Example 6

Osteogenic Differentiation Induction

In this example, it was determined whether or not the synthetic tissue of the present invention works when osteogenesis was induced in the synthetic tissue.

It was confirmed that synovial cells can be cultured in osteogenesis induction medium (10% FBS-DMEM+0.1 µM dexamethasone, 10 mM beta glycerophosphate, 0.2 mM ascorbic acid 2-phosphate) from the beginning to produce a synthetic tissue.

Figure 18:
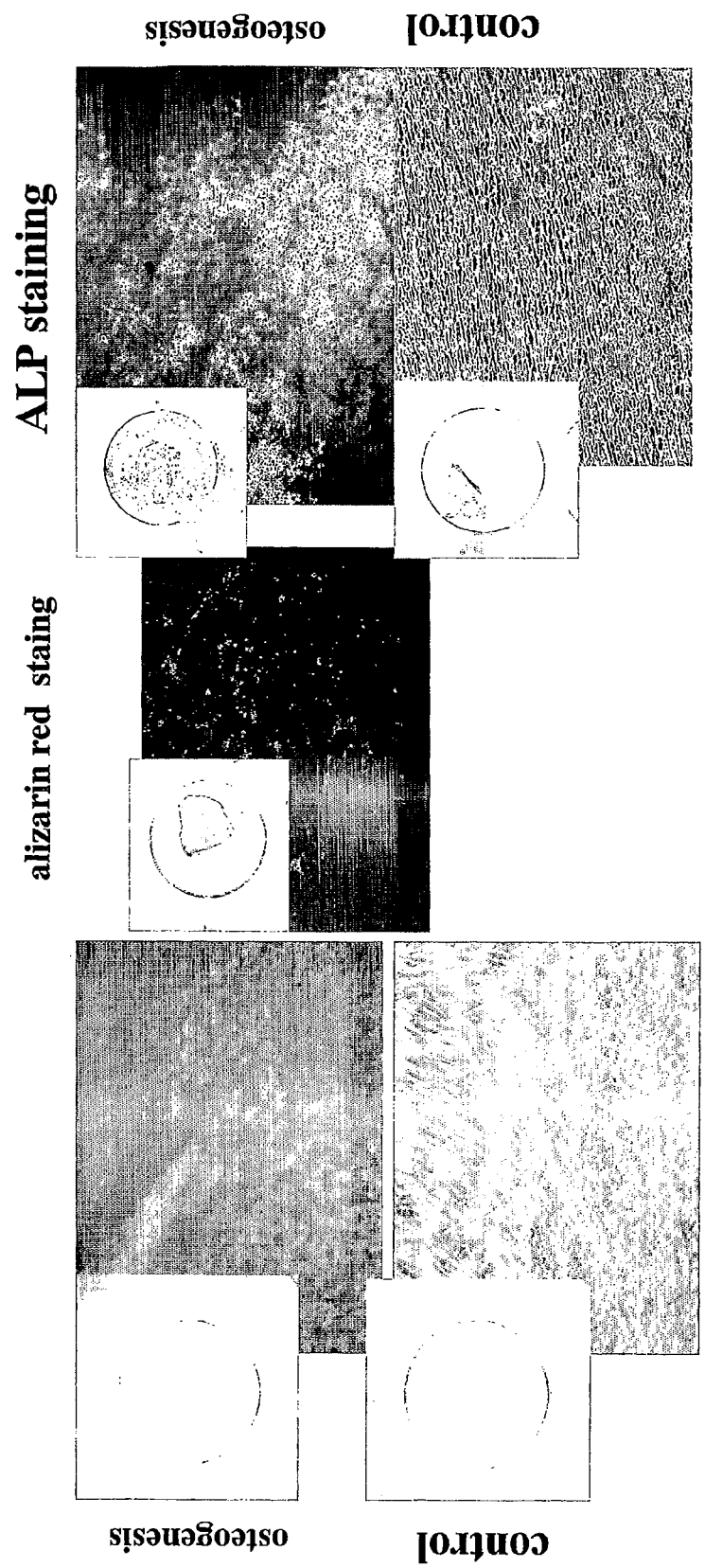
FIG. 18 shows an exemplary osteogenic induction experiment of the synthetic tissue of the present invention and the results. The upper half portion shows a scheme for osteogenesis induction. The induction was conducted in the presence of 0. μM dexamethasone, 10 mM β-glycerophosphate, and 50 μg/ml ascorbic acid 2-phosphate. The lower left portion shows a control. The middle left portion shows a synthetic tissue differentiated into a bone by osteogenic induction. The middle lane portion shows Alizarin Red staining. The lower right portion shows an ALP-stained control. The middle right portion shows positive ALP-staining in a synthetic tissue by osteogenic induction.

Also, it was confirmed that a synthetic tissue was produced without osteogenesis induction, and thereafter, the medium was exchanged with osteogenesis induction medium and the tissue was cultured, so that calcificated bone was generated in the synthetic tissue. The result is shown in FIG. 18.

Whereas a synthetic tissue without differentiation induction appears to be transparent, an ossificated synthetic tissue has a white colour. The synthetic tissue was strongly stained with Alizarin Red, and was also strongly stained by alkali phosphatase (ALP) staining as compared to the control. Thus, it was confirmed that the synthetic tissue of synovial cells is capable of osteogenesis.

Example 7

Chondrogenesis Induction

In this example, it was determined whether or not chondrogenesis induction can be used for the production method of the synthetic tissue of the present invention.

(Culture Conditions)

Cell density: $4 \times 10^4$ cells/cm$^2$

Conditions: $CO_2$ 5%, air 95%, 37° C.

These conditions and a chondrogenesis induction medium described below were used to produce a synthetic tissue.

Cartilage differentiation induction medium: DMEM (GIBCO), FBS (HyClone) 10%, ITS+Premix (insulin, transferrin, selenious acid) (BD Biosciences) 6.25 µg/ml, dexdmethasone (Sigma) $10^{-7}$ M, ascorbic acid (WAKO) 50 µg/ml, pyrubic acid (SIGMA) 100 µg/ml.

Figure 19:
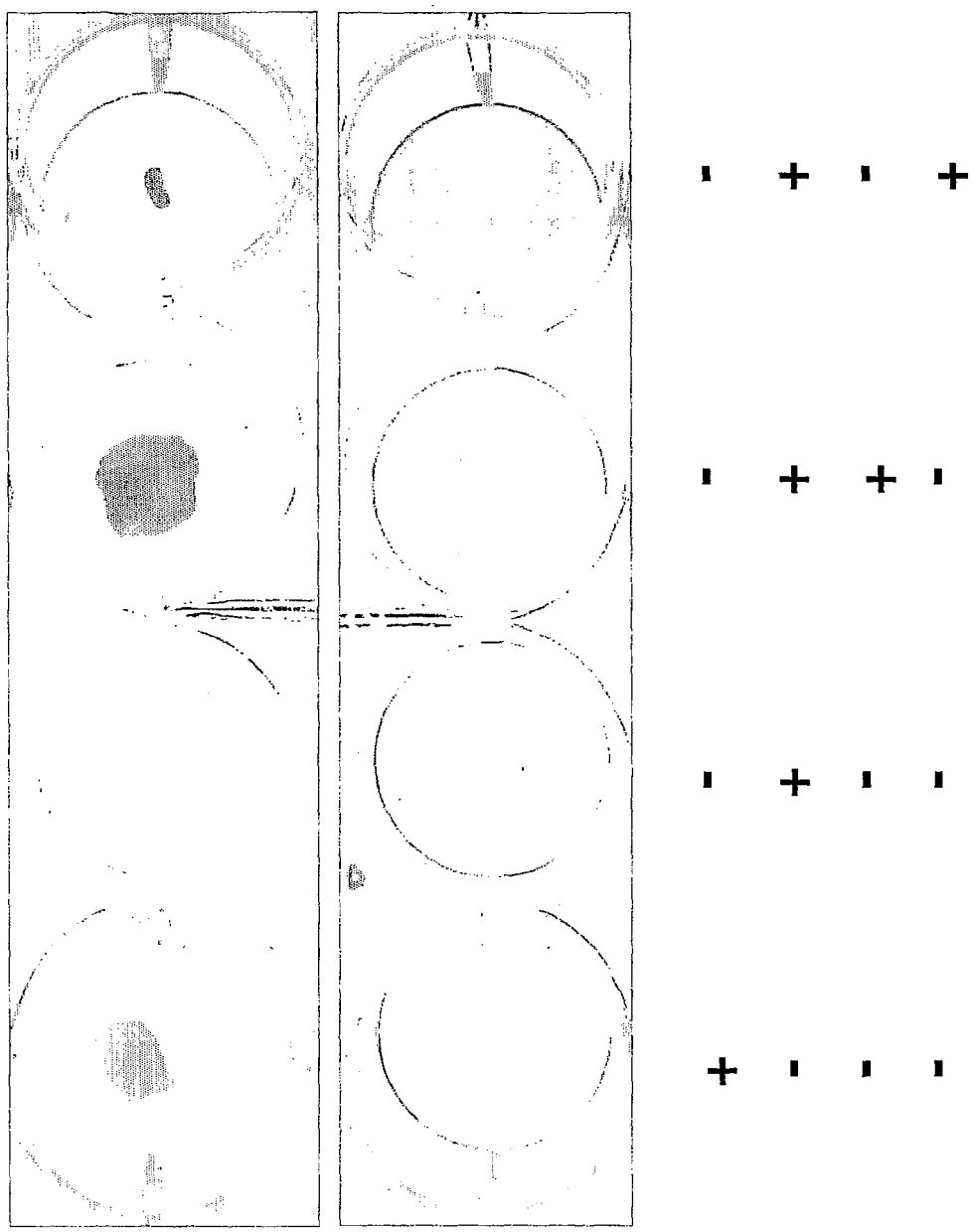
FIG. 19 shows the results of chondrogenic differentiation of a synthetic tissue of the present invention. This figure shows cultured synthetic tissues (A) and monolayer (B) using, from the leftmost, normal culture medium, chondrogenic medium, chondrogenic medium plus BPM-2 and chondrogenic medium plus TGF-β1, respectively. Note that A) synthetic tissues have more intense staining of Alcian blue than B) monolayer culture. Also, note that addition of TGF-β results in detachment of a synthetic tissue from the container without mechanical stimulation. (A) Most right lane.
Figure 20:
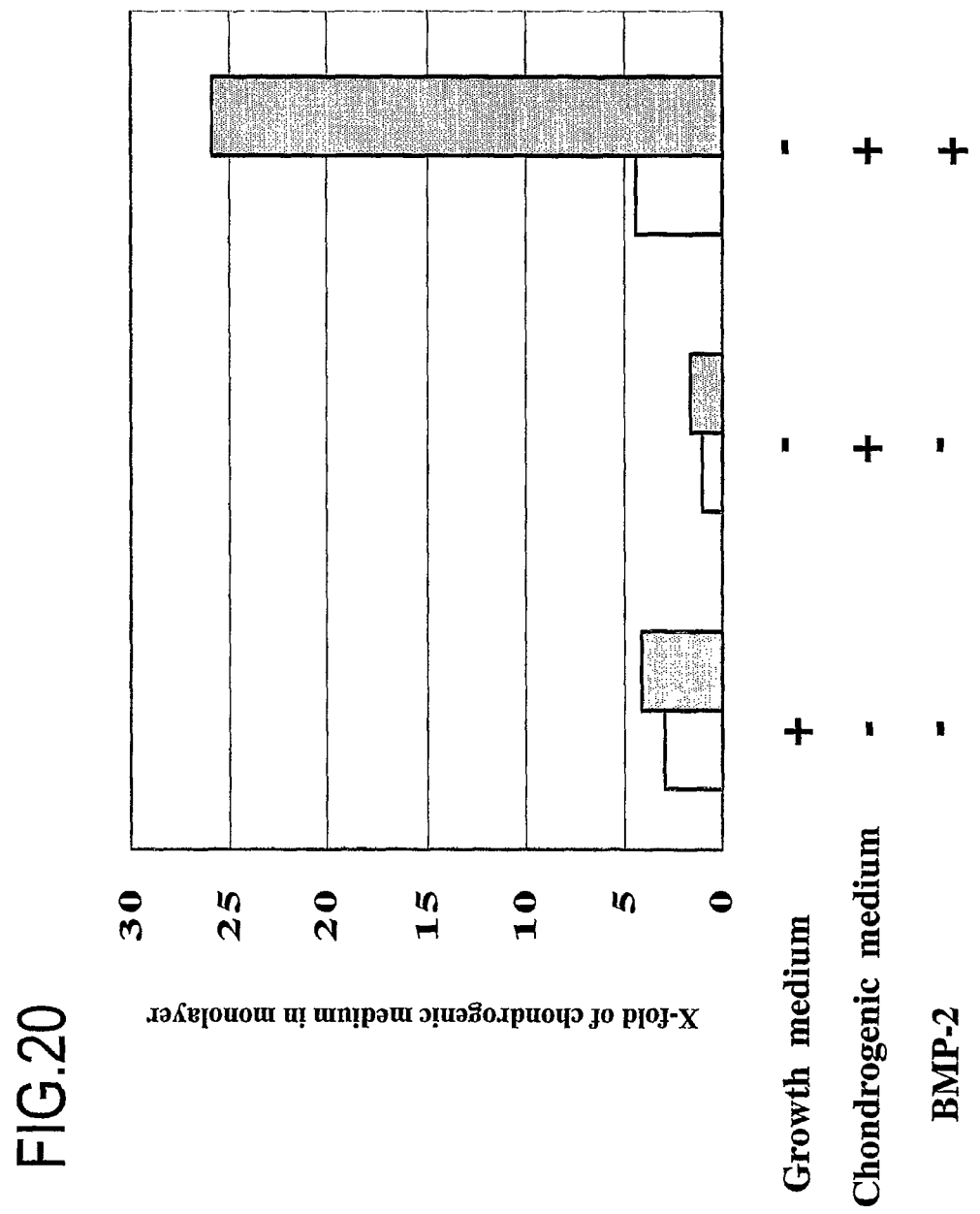
FIG. 20 shows semi-quantification of Alcian blue staining for comparison of a synthetic tissue of the present invention with a single cell sheet under chondrogenic stimulation as in FIGS. 19 and 39. The left (blue) shows a result of monolayer, and the right (red) shows a result of the synthetic tissue.

The results are shown in FIG. 19. The cells were induced into cartilage. From the left, a typical medium, a chondrogenesis induction medium, a chondrogenesis induction medium+BMP-2, and a chondrogenesis induction medium+TGF-b1 were used to culture a synthetic tissue. All of the tissues were stained blue with Alcian blue staining. It was confirmed that a cartilage-like matrix production was accelerated. Such an effect is significant for cells cultured in medium containing BMP-2. The result of quantification of staining ability is shown in FIG. 20.

Figure 21:
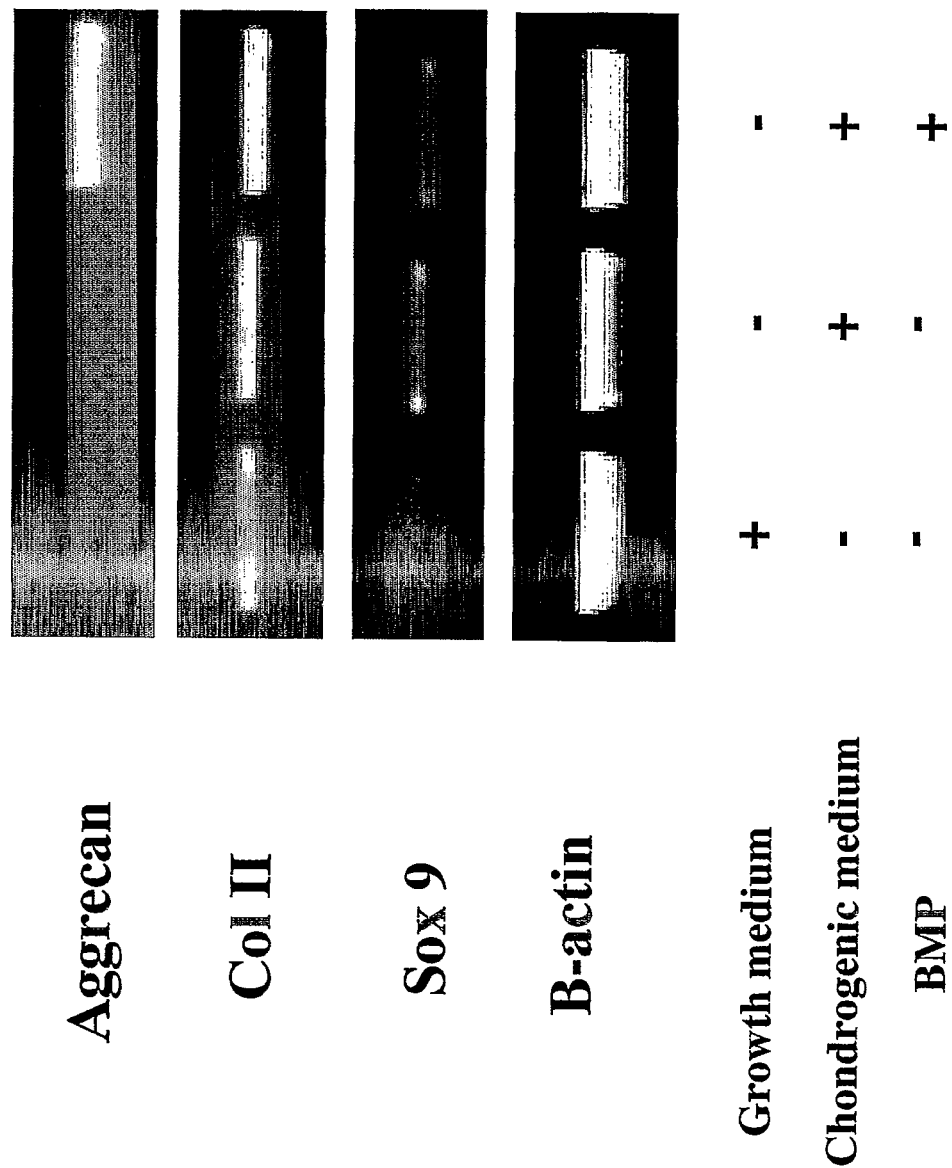
FIG. 21 shows the expression of various chondrogenic marker genes (aggrecan, Col II, Sox9, B-actin) under chondrogenic stimulation.
Figure 22:
FIG. 22 shows the comparison of the expression of chondrogenic marker genes within a synthetic tissue and a monolayer culture of synovial cells under chondrogenic stimulation as in FIGS. 19 and 21.

Expression of cartilage-associated genes (aggrecan, Col II, Sox9) in the synthetic tissue is shown in FIG. 21. When the synthetic tissue was transferred from the typical medium (leftmost column) to the chondrogenesis induction medium (middle column), expression of the Sox9 gene, which is a chondrogenesis marker, was increased. When the synthetic tissue was further cultured in the chondrogenesis induction medium+BMP-2, expression of the collagen II gene was also increased. Thus, stronger chondrogenesis could be confirmed. FIG. 22 shows the results of comparison of a chondrogenesis reaction between a monolayer culture synovial cell and a synovial cell in a three-dimensional synthetic tissue, when the same differentiation inducing stimulus was applied. When counted from the left, odd-numbered columns indicate monolayer culture, while even-numbered columns indicate three-dimensional synthetic tissue, where culture was performed under the same culture conditions. When the chondrogenesis induction medium or the chondrogenesis induction medium+BMP-2 was added as a stimulus, it was confirmed that the chondrogenesis marker gene was significantly expressed in the synthetic tissue. Thus, the three-dimensional synthetic tissue was confirmed to have strong chondrogenesis ability.

Example 8

Repair of a Pig Cartilage

Next, it was determined whether or not cartilage can be repaired. An allogenic synthetic tissue was used.

To determine the presence or absence of the adhesion capability of a synthetic tissue, an allogenic synthetic tissue was implanted onto a pig cartilage piece. The synthetic tissue was prepared under conditions where the number of cells was $4.0 \times 10^6$ cells/35-mm dish, the concentration of ascorbic acid was 1 mM, and the culture period was 7 to 14 days. A wound having a diameter of 6 mm was generated on the cartilage piece. An upper layer zone thereof was cut off from the cartilage piece using a scalpel. Chondroitinase ABC (1 U/ml) was added. The cartilage piece was allowed to react for 5 minutes. A synthetic tissue was sized to have a diameter of 6 mm and was implanted, followed by culture for 7 days. The synthetic tissue is closely attached to the attachment surface of the cartilage piece. Fibronectin aggregated on the attachment surface (FIG. 23).

Figure 24:
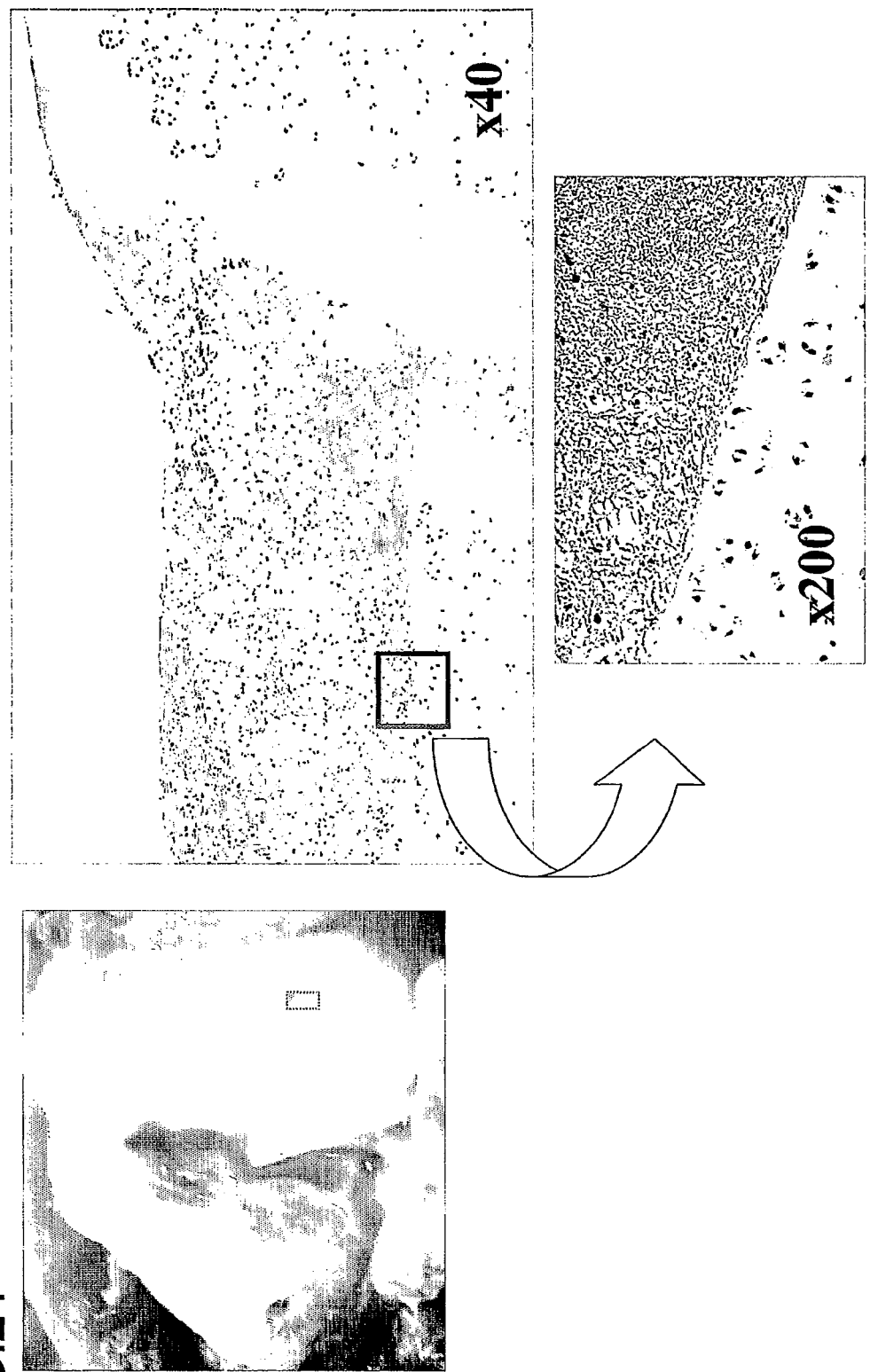
FIG. 24 shows an in vivo cartilage implantation experiment of the present invention and the 10 day results. A synthetic tissue is firmly adhered to a partial cartilage injury. The left shows a macroscopic view of the result. The upper right shows a histology (×40) and the lower right shows a histology at higher magnification (×200).
Figure 25:
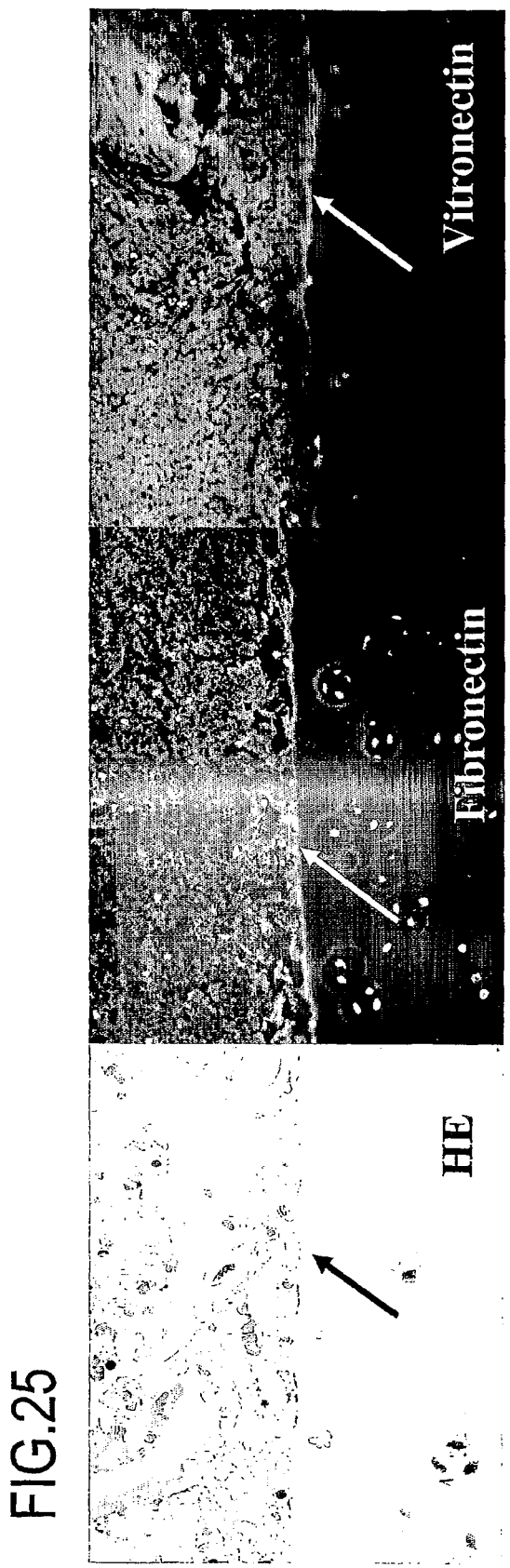
FIG. 25 shows the adhesion of a synthetic tissue of the present invention in a cartilage implantation experiment. The state on day 10 is shown. The left portion shows the result of HE staining, the middle portion shows the result of fibronectin staining, and the right portion shows the result of vitronectin staining.

Next, pig cartilage implantation was performed. As described above, a wound having a diameter of 6 mm was created in a medial femoral condyle. An upper layer zone thereof was cut off from the cartilage piece using a scalpel. Chondroitinase ABC (1 U/ml) was added. The cartilage piece was allowed to react for 5 minutes. A allogenic synthetic tissue was sized to have a diameter of 6 mm and was implanted, followed by culture for 7 days. The results are shown in FIG. 24. FIG. 25 shows a strongly enlarged view of a culture portion of a surface of the cartilage adhered to the synthetic tissue of FIG. 24. The left portion of FIG. 25 is a photograph showing the result of HE staining, the middle portion is a photograph showing the result of staining with anti-fibronectin antibodies, and the right portion is a photograph showing the result of staining with anti-vitronectin antibodies. As indicated by an arrow (the interface between the synthetic tissue and the cartilage tissue), it was demonstrated that the matrix of the synthetic tissue was directly attached to the cartilage matrix, but not via cells. It is shown that fibronectin and vitronectin were accumulated at the adhesion surface. Thus, the results suggest that these adhesion molecules are involved in adhesion between a synthetic tissue and a recipient tissue. Therefore, the present invention is also characterized in that the synthetic tissue is more effectively adhered to in vivo tissue than conventional synthetic tissues, or cells.

Figures 26, 27, 28:
FIG. 26 shows the 1-month result of an in vivo implantation experiment of the present invention. A synthetic tissue is integrated with adjacent cartilage tissue without inflammation. Further, a superficial portion of the synthetic tissue contained a number of fibroblast-like cells (FIG. 27), and a deep portion of the synthetic tissue contained a number of chondrocyte-like cells (FIG. 28), indicating the chondrogenesis of the synthetic tissue after the implantation at particularly deep portions.
FIG. 27 shows a superficial portion of a synthetic tissue at one month after implantation.
FIG. 28 shows a deep portion of a synthetic tissue at one month after implantation.
Figure 27:
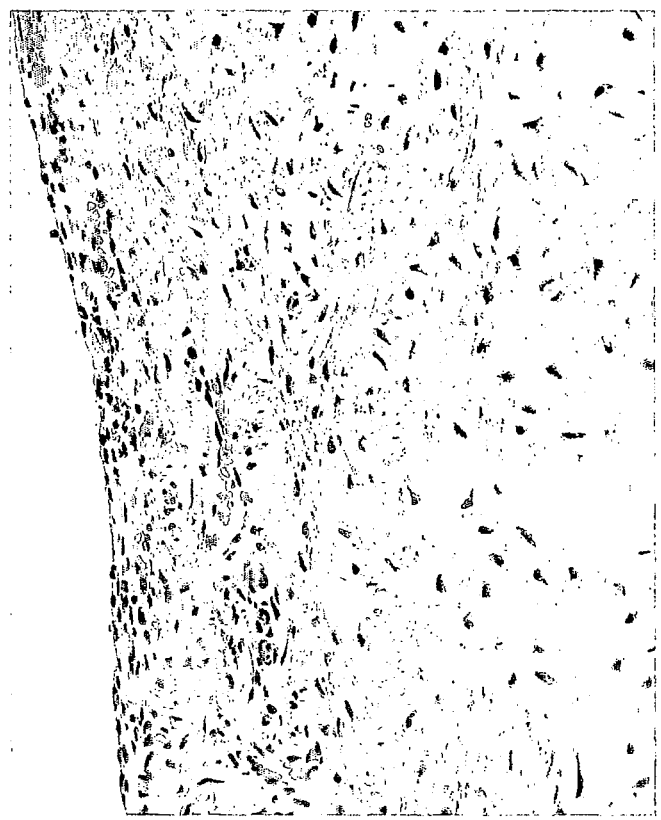
Figure 28:

Further, the tissue was examined after one month of implantation. The result is shown in FIG. 26. As can be seen, it is confirmed that the synthetic tissue was biologically integrated with the cartilage injury portion and was accepted without inflammation. The surface layer portion of the synthetic tissue was made mainly of fibroblast-like cells as shown in FIG. 27. On the other hand, a deeper layer portion of the synthetic tissue was made mainly of cartilage-like cells as shown in FIG. 28. Therefore, the implanted synthetic tissue had differentiated into cartilage-like tissue over time. No significant rejection was confirmed in any period of time, and rejection which is expected for allogenic implantation, was not observed.

Therefore, it was found that the allogenic synthetic tissue can be implanted without a side effect.

Example 9

Repair of a Pig Meniscus

Next, it was determined whether or not the synthetic tissue of the present invention is applicable to repair of meniscus.

As in the above-described Example 6, an allogenic synthetic tissue was prepared under conditions where the number of cells was $4.0 \times 10^6$ cells/35-mm dish, the concentration of ascorbic acid was 1 mM, and the culture period of time was 7 to 14 days. A portion having a diameter of 6.5 mm was removed from a meniscus (FIG. 29), and the synthetic tissue was implanted thereinto. The portion containing the implant was covered with a collagen sheet (Nipro) for protection until the synthetic tissue was accepted (FIG. 30). The pig was kept for one month. The protocol is described below.

(Anesthesia)

A pig 15 to 17 weeks old (LWD ternary hybrid) was intramuscularly injected via the dorsal portion of its neck with 20 mg/kg Ketaral+10 mg/kg Seractal. Thereafter, an infusion route was provided in the ear vein, and thereafter, the respiratory tract was secured using endotracheal intubation. Diprivan was continuously administered at a rate of 0.5 mg/kg/hr to maintain anesthesia. An antibiotic (Cefamezin, 1 g) was administered to prevent post-operational infection.

(Operation)

The animal was positioned and an operation portion was cleaned with a sterilized drape. A knee joint was accessed by medial para-patellar approach. After detecting the internal articular capsule, the middle portion at the medial collateral ligament (MCL) of the knee was defected. A cylinder-shaped cavity (diameter: 6.5 mm) was created using the mosaic plasty DP (Smith & Nephew) (FIG. 29). The cavity was filled with the synthetic tissue (FIG. 30), followed by the coverage with fascia. After hemostasis was confirmed, the incised internal collateral ligament was repaired, and the articular capsule, the subcutaneous tissue, and the epidermis were sutured. A cast was fixed to the knee joint in its incurvation position. The operation was ended.

(Evaluation Method)

Visual inspection and histological study were performed.

(Results)

Figure 31:
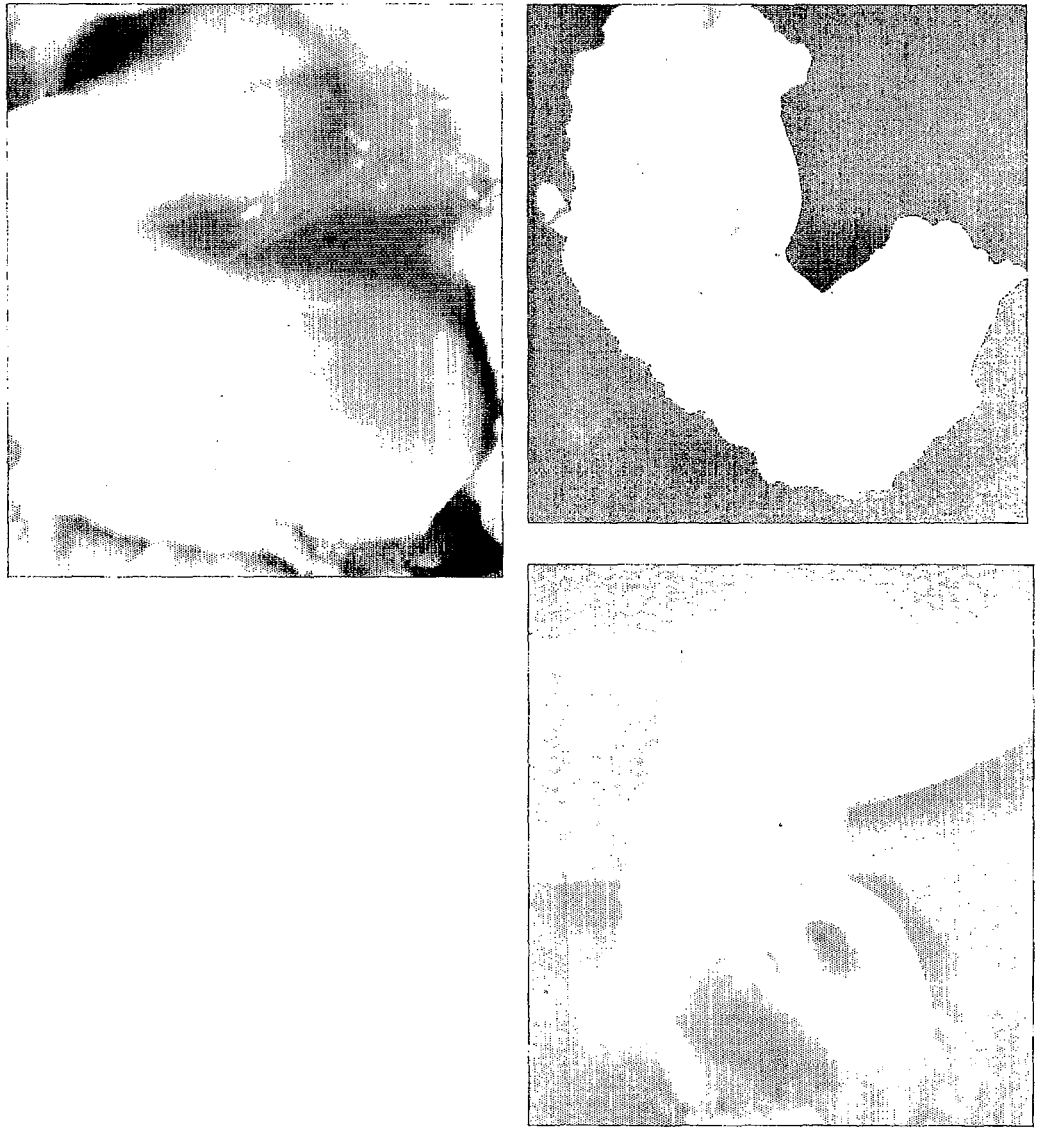
FIG. 31 shows the results of a meniscus repair experiment using a synthetic tissue of the present invention. A visual inspection four weeks after operation is shown. The upper portion shows a state of a cartilage. It is shown that substantially no degeneration or injury due to friction or the like was found on the corresponding chondral surface, i.e., the meniscal defect was recovered. The lower left and right portions show a repaired defect.
Figure 32:
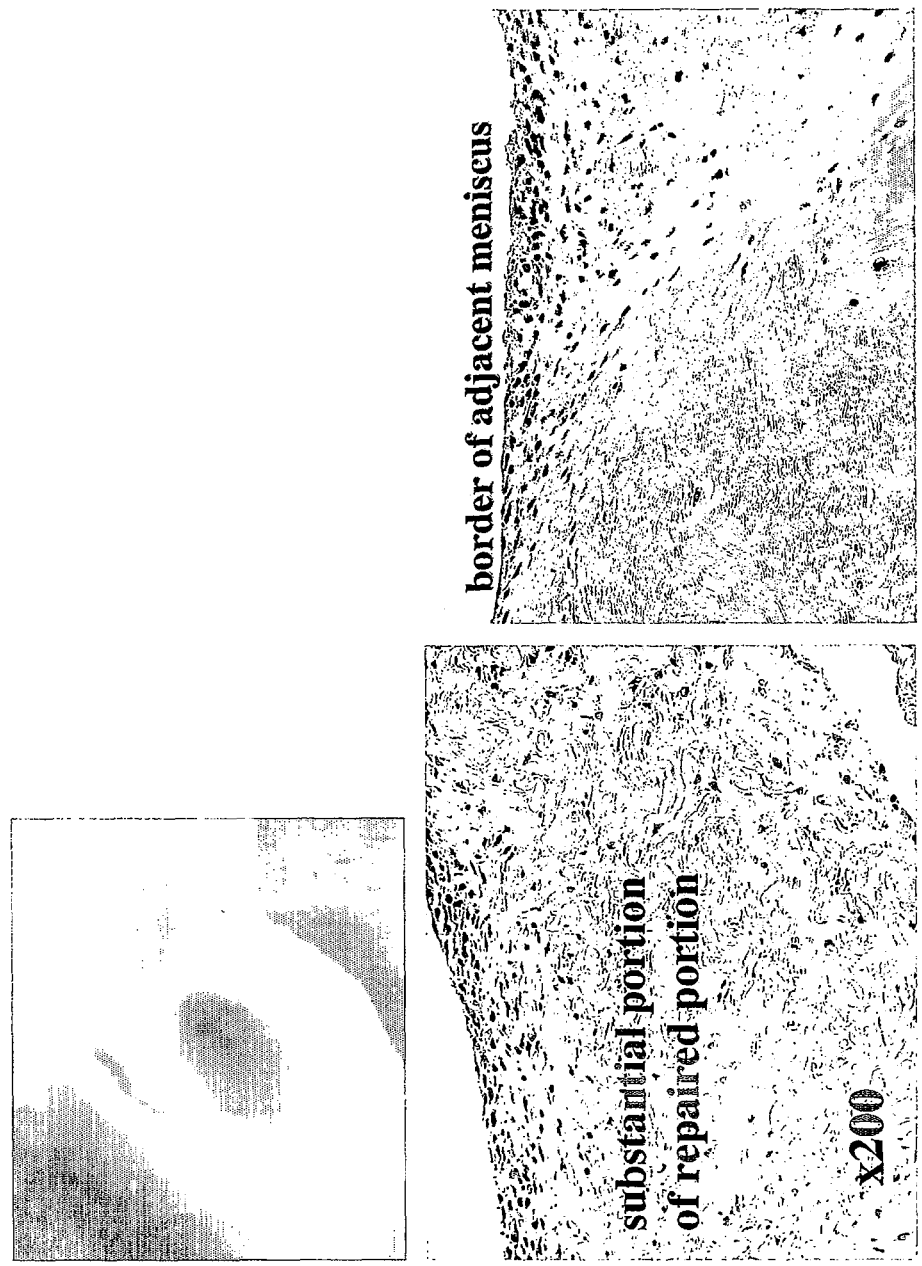
FIG. 32 shows the results of a meniscus repair experiment using a synthetic tissue of the present invention. The upper portion shows a macroscopic view. The lower left portion shows histology of a repaired tissue. The lower right portion shows histology of a border between the repaired tissue and its adjacent meniscus (magnification: ×200).

Four weeks after operation, the animals receiving the synthetic tissue was significantly repaired according to visual finding (FIG. 31) and histological finding (FIG. 32).

Remarkably, an eosin positive result was observed in the synthetic tissue four weeks after implantation. Also, the formation of a meniscus tissue-like matrix was observed and the biological integration of the synthetic tissue and its adjacent meniscus tissue was completed.

Example 10

Repair of Pig Tendon/Ligament Tissues

Tendon/ligament tissues were subjected to a repair operation. The state of the wound of a tendon/ligament tissue is confirmed. In this case, a portion of synovial cells are collected. The synovial cells are cultured. The cells are used to produce a synthetic tissue using a protocol as described in Example 1.

Next, by operation, the vicinity of the wound site of the tendon/ligament tissue is cut off to obtain a fresh portion, on which the above-described synthetic tissue is in turn placed. In this case, since the synthetic tissue has adhesion molecules, the synthetic tissue is adhered to the portion without suture. The protocol is described below.

(Anesthesia)

A pig 15 to 17 weeks old (LWD ternary hybrid) was intramuscularly injected via the dorsal portion of its neck with 20 mg/kg Ketaral+10 mg/kg Seractal. Thereafter, an infusion route was provided in the ear vein, and thereafter, the respiratory tract was secured using endotracheal intubation. Diprivan was continuously administered at a rate of 0.5 mg/kg/hr to maintain anesthesia. An antibiotic (Cefamezin, 1 g) was administered to prevent post-operational infection.

(Operation)

The animal was positioned and an operation portion was cleaned with a sterilized drape. A knee joint was accessed by medial para-patellar approach. After detecting the internal articular capsule, the middle portion of the capsule was dissected. The lower thighs were bent and laterally rotated, and were further pulled forward, so that the anterior horn portion of the internal meniscus was exposed. In this place, a cylinder-shaped cavity (diameter: 6.5 mm) was created using the mosaic plasty DP (Smith & Nephew). The cavity was filled with the synthetic tissue. In order to protect the synthetic tissue until it was accepted, the meniscus was wrapped with a collagen sheet (Nipro) which was fixed by suture. After hemostasis was confirmed, the incised internal collateral ligament was repaired, and the articular capsule, the subcutaneous tissue, and the epidermis were sutured. A cast was fixed to the knee joint in its incurvation position. The operation was ended.

(Evaluation Method)

Histological study was performed based on Frank's method (J. Orthop. Res., 13, 923-9, 1995).

(Results)

According to visual finding and histological finding 6 weeks after operation, the group filled with the synthetic tissue had significantly better healing quality.

Example 11

Repair of a Pig Bone

In this example, repair of bone is experimentally conducted. Using a protocol as described in Example 1, synovial cells are collected and cultured to produce a synthetic tissue.

Next, a sheet of this synthetic tissue is applied to a bone. The synthetic tissue is applied to an affected portion mainly by covering it over a cortical bone as well as a periosteum. As a result, it is demonstrated that the synthetic tissue comprising synovial cells is effective for repair of a bone. The protocol is described below.

(Anesthesia)

A pig 15 to 17 weeks old (LWD ternary hybrid) was intramuscularly injected via the dorsal portion of its neck with 20 mg/kg Ketaral+10 mg/kg seractal. Thereafter, an infusion route was provided in the ear vein, and thereafter, the respiratory tract was secured using endotracheal intubation. Diprivan was continuously administered at a rate of 0.5 mg/kg/hr to maintain anesthesia. An antibiotic (Cefamezin, 1 g) was administered to prevent post-operational infection.

(Operation)

The animal was positioned and an operation portion was cleaned with a sterilized drape. A second metatarsal bone was accessed from a longitudinal incised portion. The periosteum of the second metatarsal bone was ablated as much as possible so that the surface of the second metatarsal bone was exposed. A window of 1.5 cm (horizontal)×3 cm (vertical) was created on the surface of the second metatarsal bone using a chisel. The window was covered with the outstretched synthetic tissue. After confirming the attachment of the synthetic tissue, the the subcutaneous tissue and the epidermis were sutured. A cast is fixed to the lower thigh. The operation was ended.

(Evaluation Method)

Radiography, micro CT, and histology.

(Results)

Four weeks after operation, evaluation confirmed that osteogenesis was accelerated in the window portion for the group filled with the synthetic tissue.

Example 12

Pig Fat-derived Tissue

Next, cells derived from adipose tissue were used to produce a synthetic tissue.

A) Cells were Collected as Follows.

1) A specimen was removed from the fat-pad of a knee joint.

2) The specimen was washed with PBS.

3) The specimen was cut into as many pieces as possible using scissors.

4) 10 ml of collagenase (0.1%) was added to the specimen, followed by shaking for one hour in a water bath at 37° C.

5) An equal amount of DMEM (supplement with 10% FBS) was added, followed by filtration using a 70 µl filter (available from Millipore or the like).

6) Cells which passed through the filter and residues which remained on the filter were placed in a 25-cm$^2$ flask (available from Falcon or the like) containing 5 ml of DMEM supplemented with 10% FBS.

7) Cells attached to the bottom of the flask (including mesenchymal stem cells) were removed and subjected to the production of a synthetic tissue as follows.

B) Production of Synthetic Tissue

Figure 33:
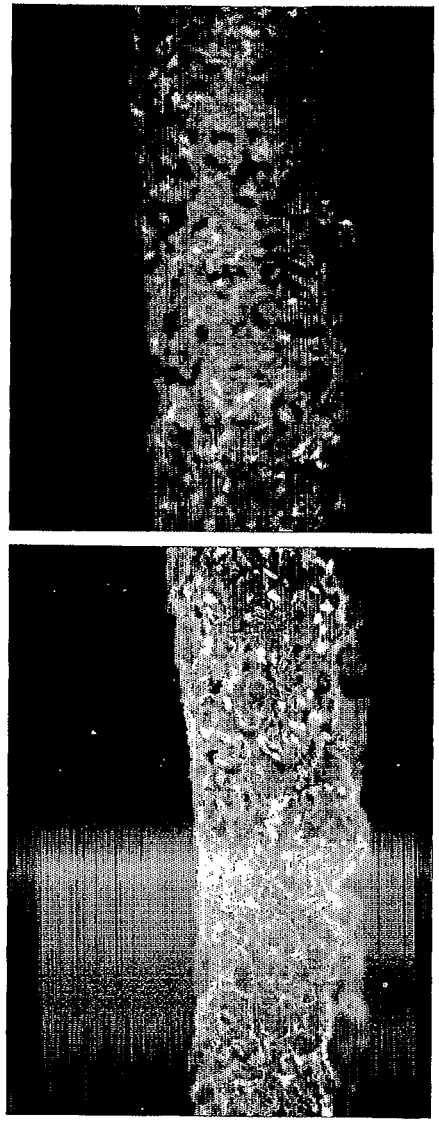
FIG. 33 shows an immunohistochemistry of a synthetic tissue derived from adipose tissue. From the left, H&E staining, fibronectin staining, and vitronectin staining.

Next, the above-described fat-derived cells were used to produce a synthetic tissue. The concentrations of ascorbic acid 2-phosphate were 0 mM (absent), 0.1 mM, 0.5 mM, 1.0 mM, and 5.0 mM. The synthetic tissue was produced in accordance with the above-described method which was used to produce synovial cells (Example 1). Cells were dessimated at an initial concentration of 5×10$^4$ cells/cm$^2$. The result is shown in FIG. 33. The cells were cultured for 14 days. A synthetic tissue was also formed from ah adipose tissue-derived cell and had as rich fibronectin and vitronectin as the synovial cell-derived synthetic tissue. Collagen I and III were similarly expressed richly.

C) Implantation Experiment

Next, the above-described synthetic tissue is subjected to an implantation experiment in Example 8 (cartilage repair) and in Example 9 (meniscus repair). As a result, it is demonstrated that a repairing capability is possessed by the fat-derived synthetic tissue as with a synovial cell-derived synthetic tissue.

Figure 34:
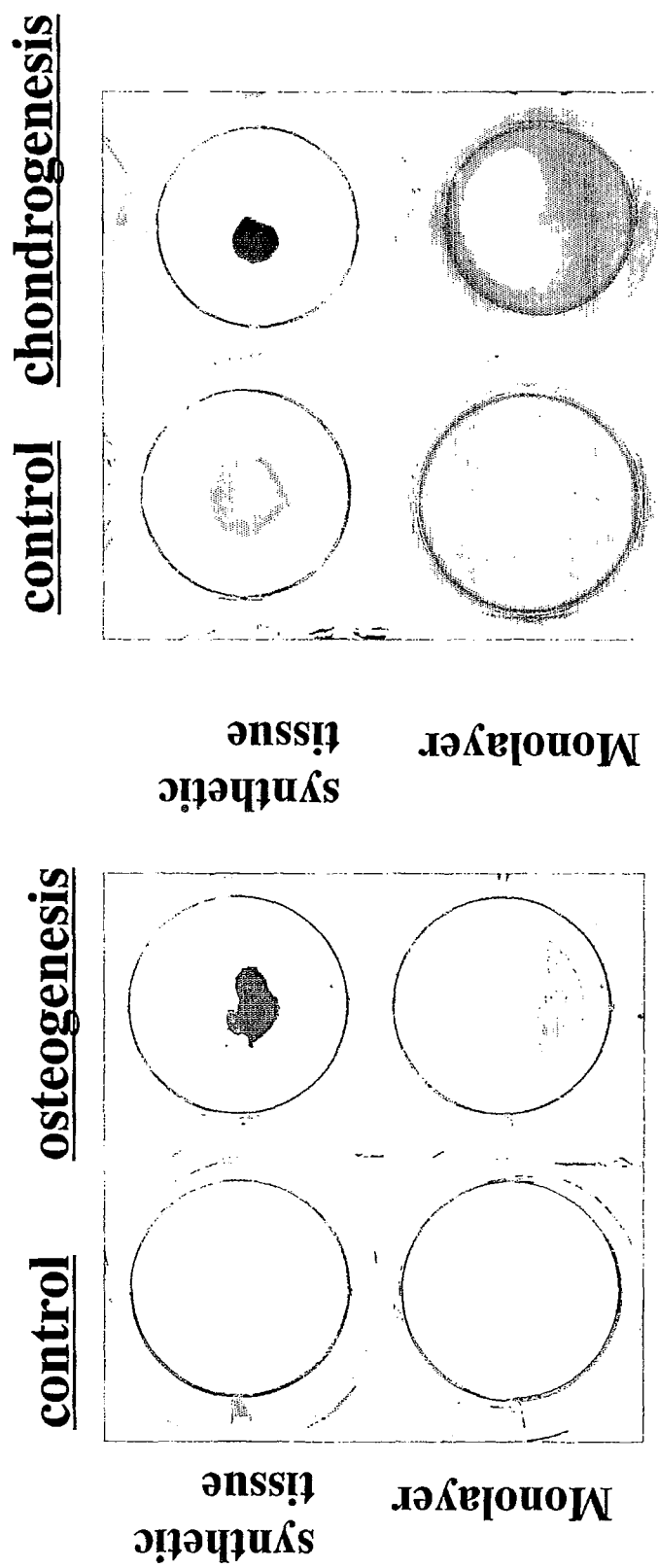
FIG. 34 shows the results of osteogenic or chondrogenic induction of a synthetic tissue derived from adipose tissue.

D) Differentiation Induction of a Fat-derived Synthetic Tissue into Bone/Cartilage The synthetic tissue of this example was induced to differentiate into a cartilage or a bone. The results are shown in FIG. 34. The left portion of the figure indicates the results of an osteogenesis experiment. The uppor portion indicates a synthetic tissue, while the lower portion indicates monolayer culture. The synthetic tissue had a positive reaction to Alizarin Red in an osteogenesis induction medium. Thus, osteogenesis was confirmed. The right portion indicates a chondrogenesis induction experiment. In this experiment, the synthetic tissue was differentiated with a stimulus due to chondrogenesis induction medium+BMP-2 into a cartilage-like tissue which was positive to Alcian blue. Thus, it was demonstrated that the fat-derived synthetic tissue also has the ability to differentiate into a bone and a cartilage as with a synovial cell-derived synthetic tissue.

Example 13

Versatility of Shape of Synthetic Tissue

In this example, a difference in function due to the shape of a synthetic tissue is measured. The synthetic tissue may be crumpled up and implanted into an affected portion instead of using a sheet of the synthetic tissue. Thereby, it is determined whether or not a tailor-made operation can be conducted, depending on the shape or the like of a wound portion.

In this example, it is investigated whether or not a synthetic tissue can be implanted when it is in the shape of a ball, a line, or a tube. The synthetic tissue is confirmed not to require suture, since it has an adhesion molecule.

Example 14

Treatment Using a Synovial Cell

In this example, a synovial cell is collected from a patient having an injured meniscus, and it is determined whether or not the synovial cell can be used to produce a synthetic tissue.

(Collection of a Human Synovial Cell)

A human patient, who has a clinical symptom is diagnosed by an imaging technique as having cartilage injury or meniscus injury, is subjected to arthroscopy under lumber anesthesia or general anesthesia. In this case, several milligrams of synovial membrane is collected. The collected synovial membrane is transferred to a 50-ml centrifuge tube (manufactured by Falcon) and washed with phosphate buffered saline (PBS). Thereafter, the sample is transferred to a 10-cm diameter culture dish (Falcon) and is cut into small pieces using a sterilized blade. Thereafter, 10 ml of 0.1% collagenase (Sigma) is added to the cut pieces in the dish. The dish is shaken in a constant temperature bath at 37° C. for 1 hour 30 minutes. To the solution, 10 ml of medium (DMEM, Gibco) containing self-serum previously collected or bovine serum (FBS) is added to inactivate the collagenase, followed by centrifugation at 1500 rpm for 5 minutes to pellet the cells. Thereafter, 5 ml of the serum-containing medium is added again. The culture medium is passed through a 70-μl filter (Falcon). The collected cells are transferred to a 25 cm$^2$ flask (Falcon), followed by culture in a $CO_2$ incubator at 37° C.

(Subculture of a Synovial Cell)

During primary culture, medium is exchanged two times every week. When cells become confluent, the cells are subcultured. For initial subculture, the medium is suctioned and thereafter the cells are washed with PBS. Trypsin-EDTA (Gibco) is added to the cells which are in turn allowed to stand for 5 minutes. Thereafter, the serum-containing medium is added and the resultant mixture was transferred to a 50-ml centrifuge tube (Falcon), followed by centrifugation at 1500 rpm for 5 minutes. Thereafter, 15 ml of the serum-containing medium is added to the pellet. The cells are placed in a 150-cm$^2$ culture dish (Falcon). Subsequent subculture is performed so that the cell ratio was 1:3. The same procedure is repeated up to 4 to 5 passages.

(Production of a Synthetic Tissue)

The synovial cell of 4 to 5 passages is treated with trypsin-EDTA. The synovial cells ($4.0 \times 10^6$) are dispersed in 2 ml of medium containing 0.2 mM ascorbic acid 2-phosphate on a 35-ml culture dish (Falcon), followed by culture in a $CO_2$ incubator at 37° C. for 7 days. As a result, a culture cell-extracellular matrix complex is formed. The complex is mechanically detached from the culture dish by pipetting the periphery thereof two or more hours before an implantation operation. After detachment, the culture cell-extracellular matrix complex contracts into a three-dimensional tissue having a diameter of about 15 mm and a thickness of about 0.1 mm.

Example 15

Production of a Synthetic Tissue from a Human Adipocyte

A collection-intended site (e.g., around a knee joint) from a patient under local anesthesia is resected. Several milligrams of adipocytes are collected from the site. The collected adipocytes were treated in a manner similar to that of the synovial cells. As a result, a three-dimensional synthetic tissue can be produced.

Example 16

Implantation of a Synthetic Tissue into a Joint Cartilage Injury Portion

The synthetic tissue produced in Example 14 or 15 is used for actual implantation. A human subject is subjected to lumbar anesthesia or general anesthesia. Thereafter, the inside of a joint is opened at minimum incision for arthroscopy. After detecting a cartilage injury portion, the size of the cartilage injury is measured. A circular portion of the cartilage is dissected from the bone-cartilage interface using the mosaic plasty harvesting system (Smith and Nephew) and a dental explorer, where the circular portion fully contains the injured cartilage. The synthetic tissue was implanted into the cavity in a portion of cartilage. The synthetic tissue is adhered to the base of the cavity several minutes after implantation. When an affected portion receives a high mechanical stress, the fixation of the synthetic tissue may be reinforced using fibrin glue (initial fixation is reinforced). The present invention is not limited to this. After fixation, the articular capsule, the subcutaneous tissue, and the skin are sutured collectively. After closing the incision site, the joint is fixed using a cast or an orthosis for 2 to 3 weeks. Thereafter, rehabilitation is started within a limited range of motion. When an affected portion is present in a weight-bearing joint (e.g., a knee, a ankle joint, etc.). A full load is able to be applied after 6 to 8 weeks.

As a result, symptoms are cured or ameliorated as follows: a reduction in joint pain when a load or an exercise is applied; elimination of joint effusion; recovery of a joint range of motion; recovery of muscle strength around the joint; prevention of osteoarthritis; and the like. Thus, it is observed that the synthetic tissue of the present invention has no significant side effects and improves the function of a repaired portion.

Example 17

Implantation into a Meniscus Injury Portion

In this example, the synthetic tissue, produced in Example 14 or 15 is actually implanted into a meniscus injury portion.

A meniscus injury portion is detected in a human subject under lumbar anesthesia or general anesthesia, using an arthroscope. A rupture portion of an injury meniscus is filled with the synthetic tissue. Thereafter, the injured meniscus and the synthetic tissue are sutured together. All surgical procedures are performed under an arthroscope. After surgery, a knee orthosis is used for 2 to 3 weeks. 15. Thereafter, rehabilitation is started within a limited range of motion. A full weight bearing is permitted after 5 to 6 weeks.

As a result, symptoms are cured or ameliorated as follows: a reduction in joint pain when a load or an exercise is applied to the knee joint; elimination of hydrarthrosis; recovery of a joint range of motion; recovery of muscle strength around the joint; recovery of activity; doing sports again; and the like. Thus, it is observed that the synthetic tissue of the present invention has no significant side effects and improves the function of a repaired portion.

Example 18

Implantation into an Achilles Tendon

The synthetic tissue produced in Example 14 or 15 is implanted into an Achilles tendon injury portion.

A human subject under lumbar anesthesia or general anesthesia is subjected to Achilles tendon by para-tendon approach. The portion of degenative tear is detected and then curetted. The synthetic tissue is implanted into the portion of degenerative tear. After implantation, conventional tendon repair is performed. In addition, the surface layer of the repaired portion is covered with the synthetic tissue, which is in turn sutured and fixed thereto. After closing the incision site, a cast is fixed to the lower limb for 4 weeks. A full weight bearing is permitted after 6 to 8 weeks.

As a result, symptoms are cured or ameliorated as follows: recovery of activity level (from walking to a sport level); a reduction in pain; and a decrease in possibility of re-rupture. Thus, it is observed that the synthetic tissue of the present invention has no significant side effects and improves the function of a repaired portion.

Example 19

Treatment of Intractable Pseudarthrosis

In this example, intractable pseudarthrosis is treated using the synthetic tissue produced in Example 14 or 15. A feature of intractable pseudarthrosis is that a periosteum, which is a source of supplying cells in a bone fracture therapy, is severely damaged and lost. Implantation of the synthetic tissue is considered to be appropriate in such a case.

A bone fracture portion is opened in a human subject under anesthesia. Thereafter, the bone fracture portion is curetted. After the remaining portion is fixed with a plate or an intramedullary nail, the injured periosteum is covered with the synthetic tissue. The synthetic tissue is sutured and fixed to adjacent periosteum tissue. After closing the incision site, the joint adjacent to the bone fracture portion is fixed with a cast for 3 to 4 weeks. In the case of a lower limb bone, full weight bearing is permitted after 6 to 8 weeks.

As a result, symptoms are cured or ameliorated as follows: elimination of pain; recovery of muscle strength around the joint; and recovery of an activity level. Thus, it is observed that the synthetic tissue of the present invention has no significant side effects and improves the function of a repaired portion.

Example 20

Implantation into a Rotator Cuff Injury Portion

In this example, a synthetic tissue is implanted into a rotator cuff injury portion. The synthetic tissue is produced as described in Example 1. Under general anesthesia, the rotator cuff injury portion is detected by transdeltoid approach.

After detecting the rotator cuff injury portion, the portion is curetted and is subjected to a typical rotator cuff repair operation. Thereafter, the surface layer of the repaired rotator cuff portion is covered with the synthetic tissue. After closing the incision site, the shoulder joint is fixed with an orthosis for 2 to 3 weeks. Thereafter, rehabilitation is started within a limited range of motion. After 6 weeks, full range of motion is permitted.

As a result, symptoms are cured or ameliorated as follows: remission of shoulder pain (particularly, night pain); recovery of a joint range of motion; recovery of muscle strength around the shoulder; and recovery of activity. Thus, it is observed that the synthetic tissue of the present invention has no significant side effects and improves the function of a repaired portion.

Example 21

Study on the Possibility of Cell Differentiation Induction Before and after Production of a Synthetic Tissue In this example, a synthetic tissue is produced using a human synovial cell.

Figure 35:
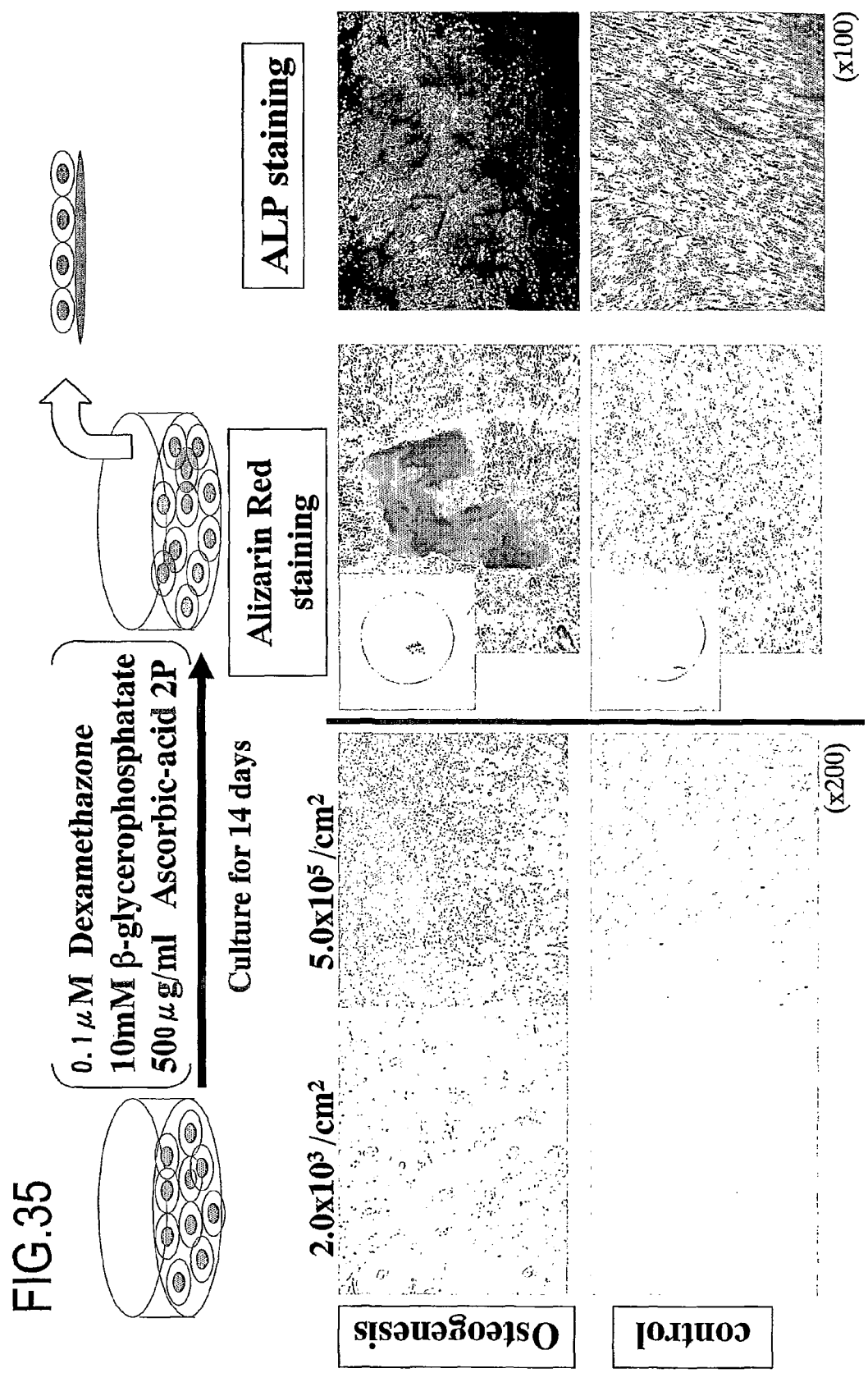
FIG. 35 shows the results of a synthetic tissue with osteogenic induction when dexamethasone and β-glycerophosphate were added in culture medium prior to a detachment procedure.
Figure 36:
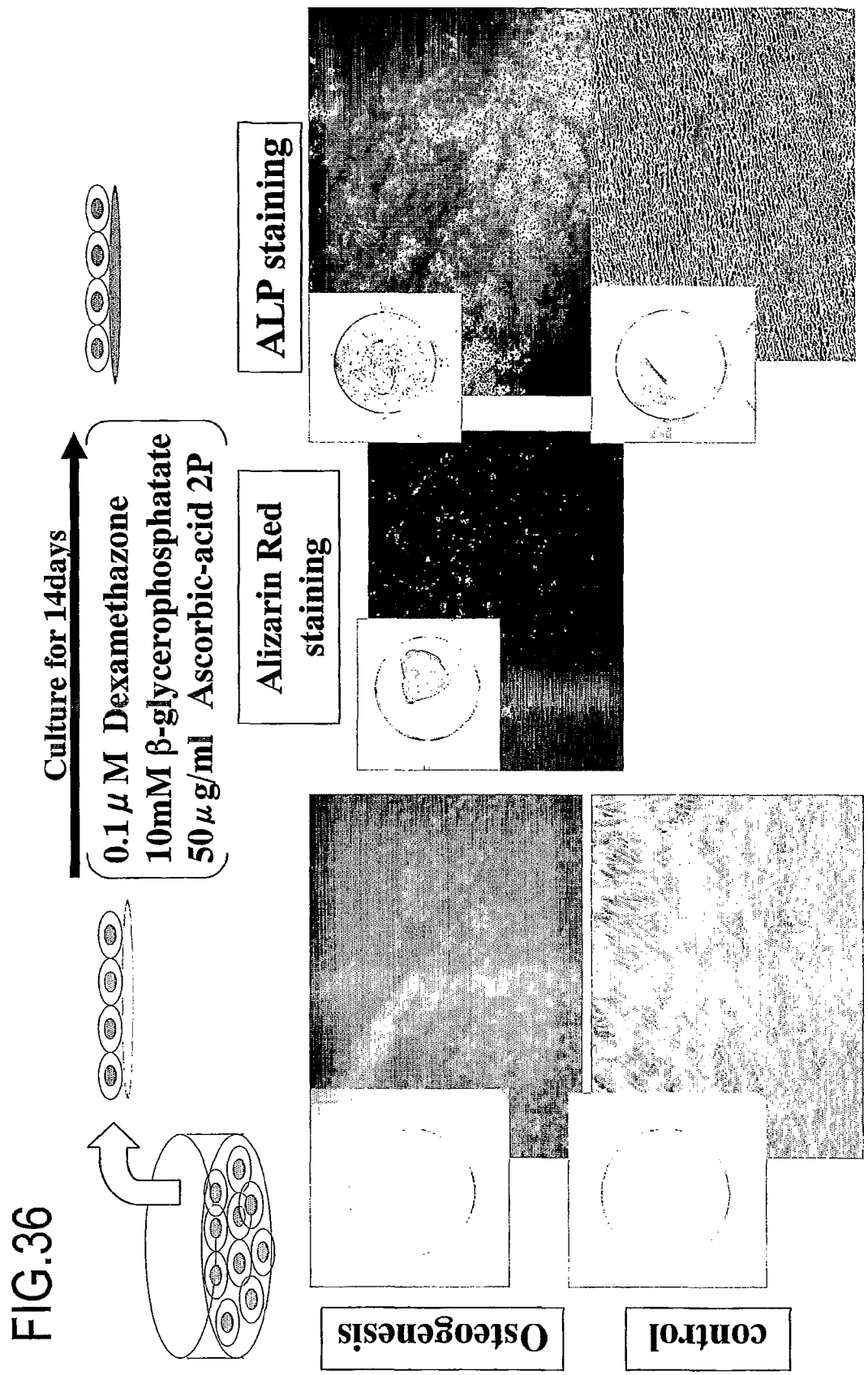
FIG. 36 shows the results of a synthetic tissue with osteogenic induction when dexamethasone and β-glycerophosphate were added in culture medium after a detachment procedure.

The production process of the synthetic tissue using a human synovial cell is shown in the upper portions of FIGS. 35 and 36. FIG. 35 shows production of a synthetic tissue after a human synovial cell is subjected to differentiation induction. FIG. 36 shows that a synthetic tissue is produced before the tissue is subjected to differentiation induction. The differentiation induction is performed by culturing a human synovial cell in DMEM medium containing 0.1 µM dexamethasone, 10 mM β-glycerophosphate, and 50 µg/ml ascorbic acid 2-phosphate for 14 days. The synthetic tissue is stained with Alzarin red and alkali phosphatase (ALP). The results of the staining are shown in the lower portions of FIGS. 35 and 36. As can be seen from FIG. 35, in either case, the synthetic tissue is produced and exhibits an osteogenic reaction positive to the Alzarin red and ALP staining. Therefore, it is demonstrated that the differentiation induction of a tissue can be performed either before or after production of a synthetic tissue.

Example 22

Study on Timing of Differentiation for Production of a Synthetic Tissue in the Case of Human Cells In this example, a synthetic tissue was produced using cells derived from adipose tissue.

A) the Cells were Collected as Follows.
1) A specimen was collected from a fat-pad of a knee joint.
2) The specimen was washed with PBS.
3) The specimen was cut into as many pieces as possible.

4) 10 ml of collagenase (0.1%) was added, followed by shaking in 37° C. water bath for one hour.

5) An equal amount of DMEM (supplemented with 10% FBS) was added. The resultant mixture was passed through a 70-μl filter (available from Millipore, etc.).

6) Cells passing through the filter and cells remaining on the filter were cultured in 25-cm² flask containing 5 ml of DMEM medium supplemented with 10% FBS.

7) The cells (including a mesenchymal stem cell) attached to the base of the flask were used to produce a synthetic tissue as follows.

B) Production of a Synthetic Tissue

Next, the fat-derived cells were used to produce a synthetic tissue. Ascorbic acid 2-phosphate was used at a concentration of 0 mM (absence), 0.1 mM, 0.5 mM, 1.0 mM, or 5.0 mM. The production was conducted in accordance with the method for producing a synthetic tissue from a synovial cells (Example 1). The cells were disseminated at an initial density of $5 \times 10^4$ cells/cm².

The cells were used to study the importance of the differentiation timing using the conditions as described in Example 21.

As a result, it was similarly demonstrated that the differentiation timing has no particular influence on the adipocyte-derived synthetic tissue of the present invention.

Example 23

Confirmation of Biological Integration

Figure 37:
FIG. 37 shows histology of biological integration of collagen gel containing synovial cells with cartilage after implantation. There is failure in integration observed (arrow).

It is known that conventional collagen gel does not always achieve biological integration after implantation. In this example, a conventional collagen gel (3% type I collagen, Koken, Tokyo, Japan) was used. Synovial cells ($1 \times 10^5$ cells/ml) were embedded in the gel. The resultant gel was implanted into a cavity in a portion of cartilage. As a result, as can be seen from FIG. 37, the integration between the collagen gel and its adjacent cartilage was insufficient, so that a crack was observed (arrow in FIG. 37).

Figure 38:
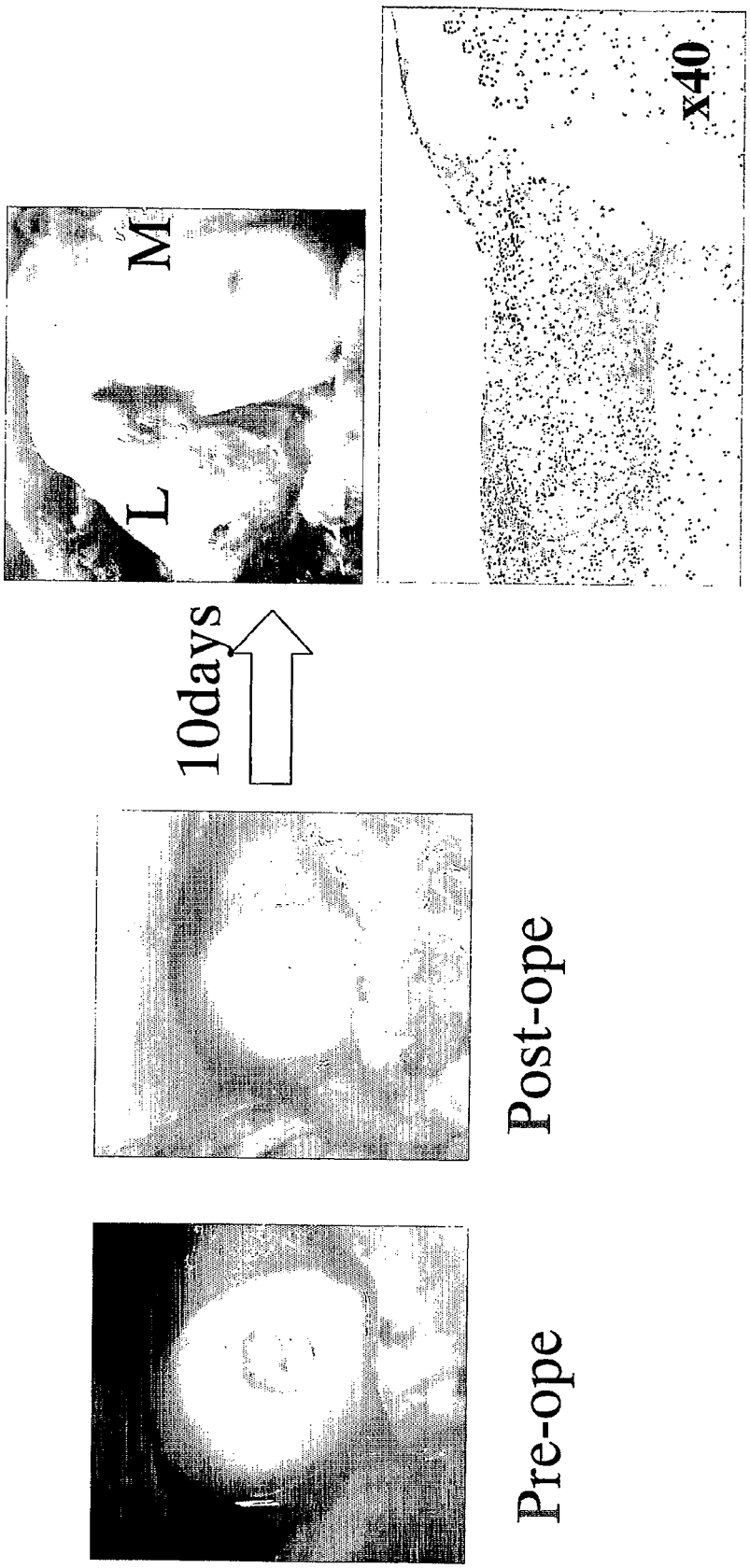
FIG. 38 shows biological integration after implantation to a chondral defect when a synthetic tissue of the present invention was used. The biological integration is completely established.

On the other hand, when a synthetic tissue of the present invention as produced in Example 1 is introduced into a pig, biological integration is histologically established as shown in FIG. 38.

Example 24

Study on Conditions for Detachment During Production of a Synthetic Tissue

In this example, it was determined whether or not chemical detachment can be used instead of physical detachment (mechanical detachment (e.g., pipetting, etc.)) during the production of the synthetic tissue of the present invention.

(Conditions for Culture)

Cell density: $4 \times 10^4$ cells/cm²

Conditions: $CO_2$ 5%, air 95%, 37° C.

Medium: DMEM/F12 (FBS 10%) supplemented with 10 ng/ml TGFβ1.

This medium was used to conduct culture under the conditions described in Examples 14 and 15 to produce a synthetic tissue.

When TGF-β was added, the monolayer culture cells could be more easily detached from the culture dish.

Medium: DMEM (GIBCO), FBS (HyClone) 10%, ITS+Premix (insulin, transferrin, selenious acid) (BD Biosciences) 6.25 μg/ml, dexamethasone (Sigma) $10^{-7}$ M, ascorbic acid (WAKO) 50 μg/ml, pyrubic acid (SIGMA) 100 μg/ml.

Figure 39:
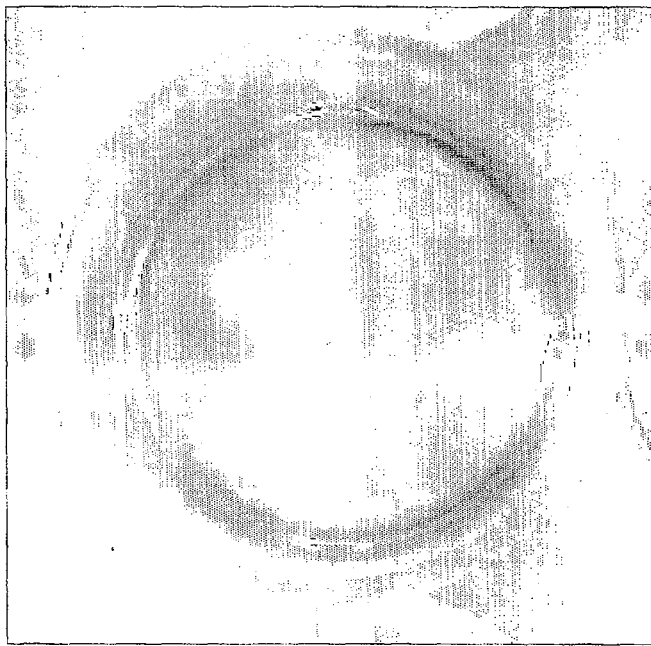
FIG. 39 shows the effect of TGF-β on the detachment of a synthetic tissue. Addition of TGF-β leads to active detachment of the synthetic tissue.

The results are shown in FIGS. 19 and 39. The rightmost column in FIG. 19 shows the case where TGF-β was added. In this case, cells were detached from a culture dish during monolayer culture. Therefore, a synthetic tissue could not be satisfactorily produced. FIG. 39 shows the result of a tissue which was detached without a physical stimulus when TGF-β was added in monolayer culture. These results indicate that TGF-β has the effect of detaching culture cells.

Example 25

Actin Regulatory Agent

Dihydrocytochalasin B and Y27632 (Yamanouchi Pharmaceutical), which are known to have an actin depolymerizing function, were used to study their influence on the contraction of a synthetic tissue.

Figure 40:
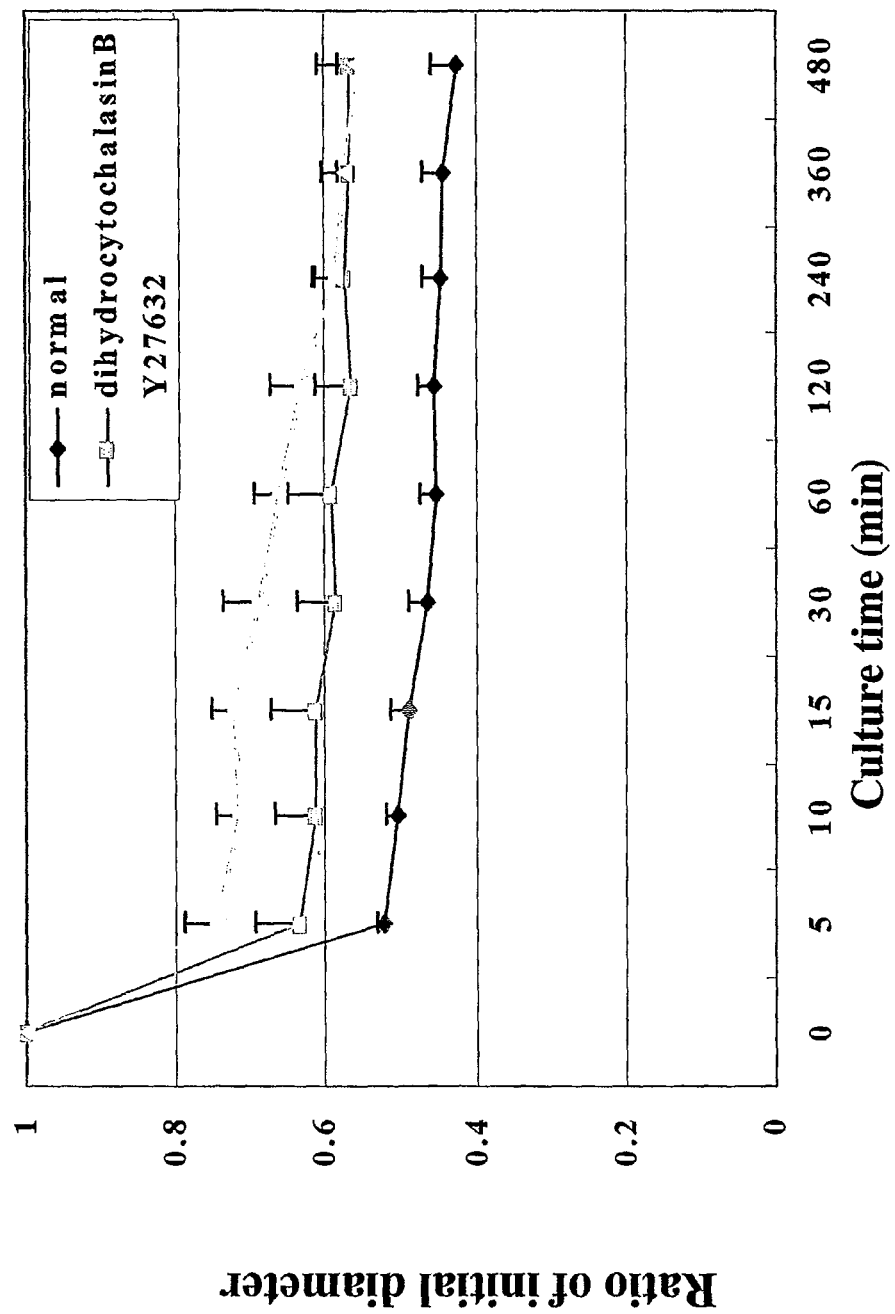
FIG. 40 shows a transition in contraction of a synthetic tissue of the present invention where dihydrochytochalasin or Y27632 was added or not. Data is shown in predetermined culture time intervals.

A synovium-derived synthetic tissue was produced by monolayer culture. The tissue was detached from a culture dish. The tissue was cultured in medium in the presence of dihydrocytochalasin B (3 μM) and Y27632 (10 μM). The transition of the radius of the tissue is shown every unit culture time in FIG. 40. As can be seen from the figure, contraction was inhibited by the addition of these actin depolymerizaing agents. Dihydrocytochalasin B and Y27632 are representative exemplary actin polymerization inhibitors. It will be understood by those skilled in the art that other actin polymerization inhibitors, such as cytochalasin D and the like, have a similar function.

Example 26

Production of an Artificial Bone/Cartilage Column as a Complex of a Synthetic Tissue and an Artificial Bone A 12-well culture dish was used to produce a synthetic tissue.

A column-like artificial bone (NEO BONE: MMT) having a diameter of 5 mm×6 mm was placed in a 96-well culture dish. The synthetic tissue was implanted onto the artificial bone. 100 μl of medium (DMEM, 10% FBS) was placed in each well of the dish, followed by culture for 2 hours. As a result, the synthetic tissue was attached to the artificial bone, thereby obtaining a tissue complex.

This complex was cultured in cartilage induction medium (DMEM, 10% FBS, ITS+Premix, sodium pyrubate, ascorbic acid 2-phosphate, 500 ng/ml BMP-2) for 14 days.

Figure 41:
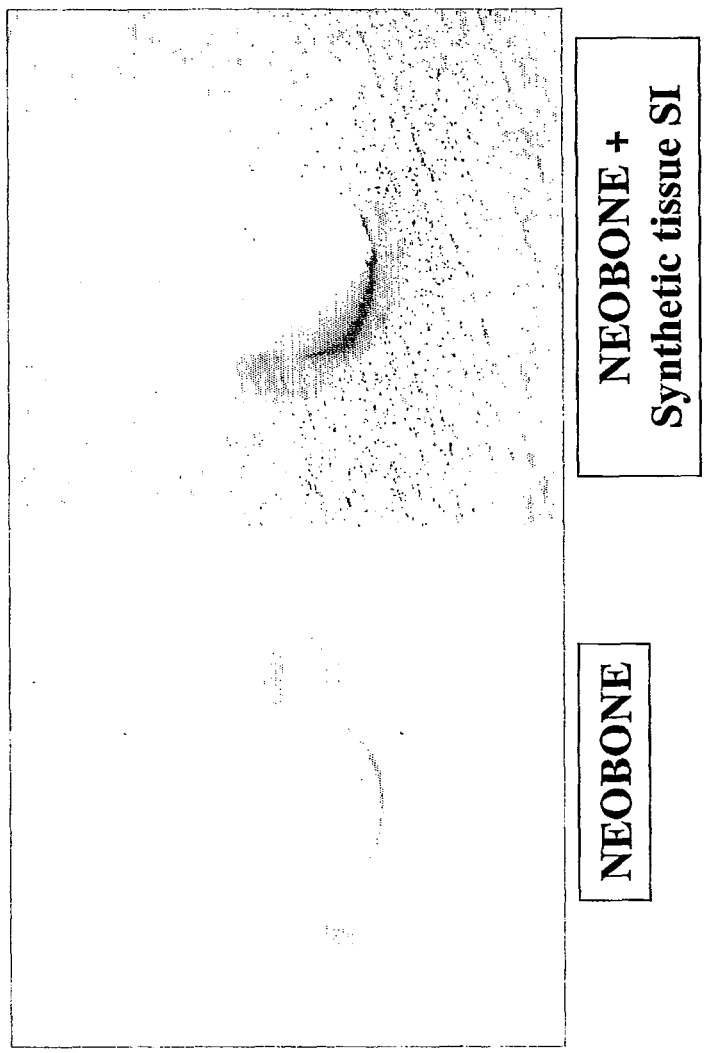
FIG. 41 shows a photograph indicating adhesion of a synthetic tissue of the present invention with an artificial bone after fourteen days of culture in chondrogenic medium.

The result is shown in FIG. 41.

As can be seen from FIG. 41, it is demonstrated that the synthetic tissue of the present invention was satisfactorily adhered to the other synthetic tissue (i.e., the artificial bone). Therefore, it will be understood that the synthetic tissue of the present invention can be combined with other synthetic tissues into a tissue complex.

Example 27

Figure 42:
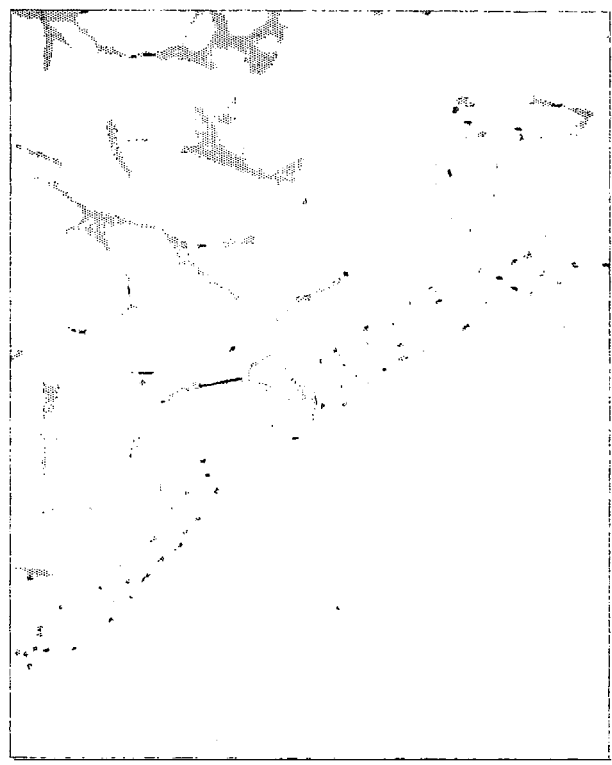
FIG. 42 shows histology of a synthetic tissue cultured on a collagen synthetic tissue (CMI collagen sponge, Amgen, USA), which is a microfibrous collagen medical device, for 7 days.

Composite Tissue Obtained by Attaching a Synthetic Tissue to a Collagen Scaffold In this example, a microfibrous collagen medical device (specifically, a collagen synthetic tissue (CMI (Collagen Meniscal Implant) collagen sponge, Amgen, USA)) was attached to a synthetic tissue instead of NEO BONE in Example 26. The result is shown in FIG. 42 (enlarged photograph). The synthetic tissue of the present invention is observed to be biologically integrated with the surface of the CMI. Thus, it was demonstrated that a microfibrous collagen medical device, which is a conventional synthetic tissue, can be combined with the synthetic tissue of the present invention to obtain a tissue complex.

Example 28

Production of a Synthetic Tissue Using a Myoblast

In this example, an influence of ascorbic acid or a derivative thereof on the production of a synthetic tissue when a myoblast was used, was studied. The synthetic tissue was produced as in Example 1.

After the myoblast was well grown, $5 \times 10^6$ myoblast cells were cultured to form a synthetic tissue. For culture, SkBM Basal Medium (Clonetics (Cambrex)) was used. Next, ascorbic acid 2-phosphate (0.5 mM), a magnesium salt of ascorbic acid 1-phosphate (0.1 mM), and L-ascorbic acid Na (0.1 mM) were added to the medium. After four days of culture, the tissue was detached. As a control, a synthetic tissue was produced in medium without ascorbic acids.

(Results)

Figure 43:
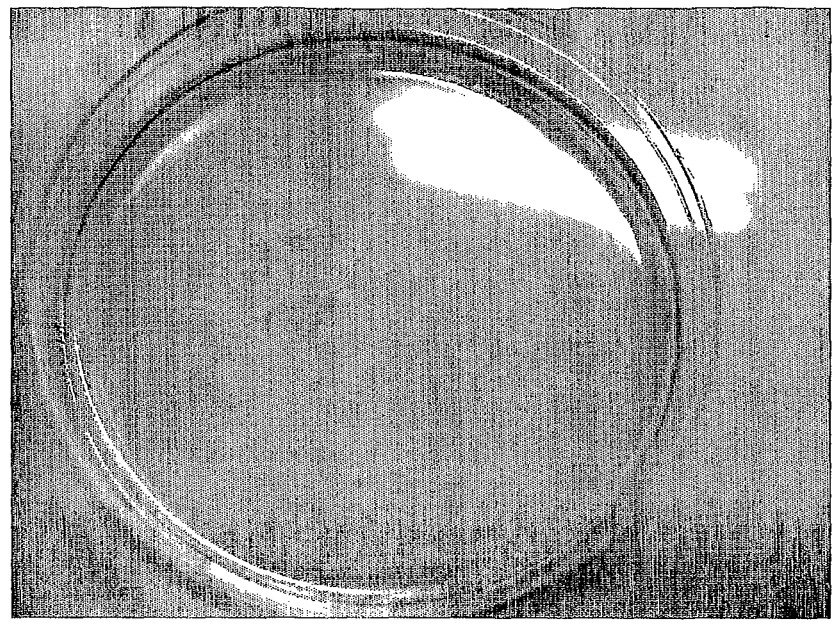
FIG. 43 shows a skeletal muscle-derived sheet developed by a synthetic tissue production method without ascorbic acid.
Figure 44:
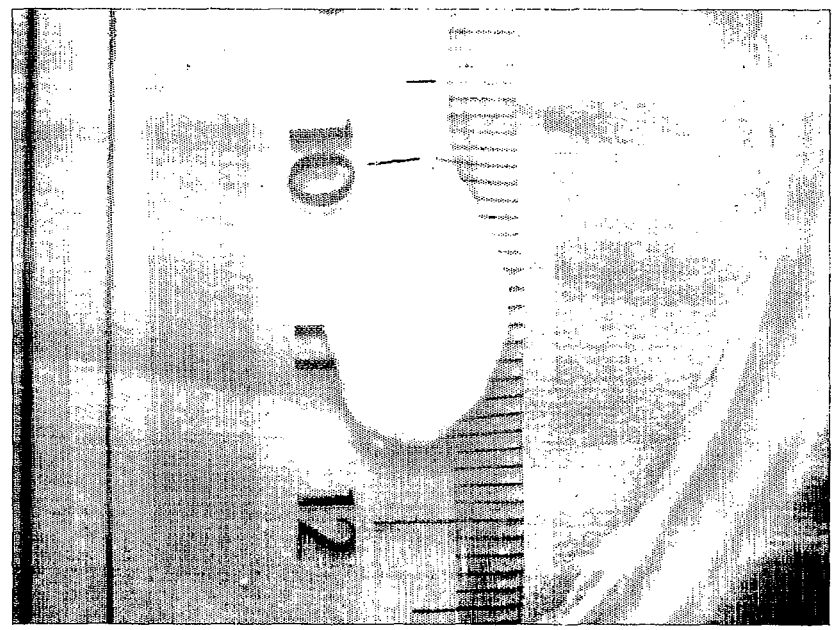
FIG. 44 shows a skeletal muscle-derived synthetic tissue developed by a synthetic tissue production method with ascorbic acid according to the present invention.
Figure 45:
FIG. 45 shows histology of the synthetic tissue as shown in FIG. 44 (HE staining).

When ascorbic acids were used, the synthetic tissue was easily detached as compared to when the ascorbic acid-free culture system was used. Also, in the ascorbic acid-free culture system, the tissue was cultured to about several millimeters. When the tissue exceeded such a level, a crack or the life occurred in the tissue so that the tissue did not grow satisfactorily. In addition, it was substantially difficult to detach the tissue. Thus, no implantable synthetic tissue was produced (FIG. 43) In contrast, the synthetic tissue of the present invention, which was cultured in medium containing ascorbic acids, was grown to a size which allows implantation, and was easily isolated (FIG. 44). Biological integration was investigated, so that extracellular matrices were highly interacted (FIG. 45).

Example 29

Effect of a Synthetic Tissue in the Presence of Ascorbic Acids

The synthetic tissue of Example 28, which was produced in the presence of ascorbic acids, was implanted into a dilated cardiomyopathy rat. In 28 rats, the left anterior descending (LAD) was ligated for two weeks to produce injured hearts. The synthetic tissue of the present invention was implanted into some of the injured hearts, while the synthetic tissue of the present invention was not implanted into the other injured hearts. As controls, rats without injury to their hearts were obtained.

The rats were anesthetized and operated. The heart function of the rats was monitored on Day 14 and 28 after surgery. A ultrasonic instrument (Sonos 5500) having an anular array converter operating at 12 MHz was used to perform endocardiography. Parasternal minor axis imaging and parasternal major axis imaging were performed in a B-imaging mode and an M-imaging mode. In addition to the anterior wall pressure, general parameters (e.g., left ventricular telediastolic diameter, left ventricular telesystolic diameter, internal diameter contraction rate, and ejection fraction) were measured.

Two and four weeks after implantation, the rats were sacrificed with an excessive amount of pentobarbital. The heart was dissected, fixed with 10% formalin, and embedded in paraffin. In a low temperature bath, the heart was cut along the longitudinal axis thereof from the base to the apex to prepare a series of sections having a thickness of 5 mm. Thereafter, the sections were treated for standard histology.

All of the rats with implants were completely cured, and survived for substantially the same period of time as normal rats. Therefore, it was demonstrated that the present invention can completely cure diseases, which are conventionally said to be intractable, in the presence of a specific ECM synthesis promoting agent.

Example 30

Combined Therapy

A combined therapy of the synthetic tissue produced in the examples and a gene therapy was performed. The combined therapy was intended to promote vascularization in a portion which a synthetic tissue was implanted; promotion of acceptance of an implanted synthetic tissue; and suppression of cell necrosis in a synthetic tissue.

(Methods)

A hemagglutinating virus of Japan (HVJ)-liposome complex was prepared in accordance with Kaneda Y., Iwai K., Uchida T., Increased expression of DNA co-introduced with nuclear protein in adult rat liver. Science, 1989; 243:375-378. The procedure will be briefly described below. A DNA solution (200 µl) was added, followed by shaking for 30 seconds. The solution was allowed to stand at 37° C. in a constant temperature bath for 30 seconds. This step was performed 8 times. Thereafter, ultrasonication was performed for 5 seconds, followed by shaking for 30 seconds. BSS (0.3 ml) was added, followed by shaking at 37° C. in a constant temperature bath. Inactivated HVJ was added. The mixture was placed on ice for 10 minutes. The mixture was then shaken at 37° C. in a constant temperature bath for one hour. A 60% sucrose solution (1 ml) and a 30% sucrose solution (6 ml) were layered in a centrifuge tube. A HVJ liposome solution was placed on top of the layered sucrose solution. Additional BSS was added to the tube. Centrifugation was performed at 62,800 g at 4° C. for 1.5 hours. A solution immediately above the 30% sucrose solution layer was recovered. The solution was preserved at 4° C. and was used for gene introduction.

About 0.2 ml of Sendai virus liposome-plasmid complex (including 15 µg of human HGF cDNA) was injected into a cardiac infarction region. For a control group, an empty vector was introduced into a heart muscle having infarction. The human HGF concentration of heart tissue was measured with an enzyme linked immunosolvent assay (ELISA) using an anti-human HGF monoclonal antibody (Institite of Immunology, Tokyo, Japan) (Ueda H., Sawa Y., Matsumoto K. et al., Gene Transfection of Hepatocyte Growth Factor Attenuates reperfusion Injury in the Heart, Ann. Thorac. Surg., 1999, 67:1726-1731). The synthetic tissue produced in Example 30 was used. The cardiac infarction models produced by ligating LAD were subjected to three different therapies: 1) a cell sheet group; 2) a gene therapy group; 3) a combined therapy group; and 4) a control group. Changes in heart function and cardiomuscular tissue were studied.

(Results)

For the synthetic tissue implanted group and the combined therapy group, the contractibility and expansibility of the heart were ameliorated. In addition, for the combined therapy group, it can be confirmed that vasculization was observed in the cardiac infarction portion, and the acceptance of implanted cells was improved.

(Conclusion)

By combining a synthetic tissue and a gene therapy, the decreased heart function ameliorating effect, the vasculization effect, and the cell protecting effect are obtained, so that a higher level of amelioration of the decreased heart function can be observed.

Although certain preferable embodiments have been described herein, it is not intended that such embodiments be construed as limitations on the scope of the invention except as set forth in the appended claims. Various other modifications and equivalents will be apparent to and can be readily made by those skilled in the art, after reading the description herein, without departing from the scope and spirit of this invention. All patents, published patent applications and publications cited herein are incorporated by reference as if set forth fully herein.

INDUSTRIAL APPLICABILITY

The present invention usefully provides a basic therapeutic method, technique, pharmaceutical agent, and medical device for diseases which are conventionally difficult to treat. Particularly, the present invention provides an epoch-making therapy and prevention because it promotes recovery to a substantially native state. The present invention also provides a pharmaceutical agent, cell, tissue, composition, system, kit, and the like, which are used for such an epoch-making therapy and prevention.

There is a demand for repair and regeneration of joint tissues, mainly including bones and cartilages which are targeted by the present invention. The number of bone fracture patients, which are targeted by bone regeneration, accounts for several hundreds of thousands per year. It is also said that there are 30 million potential patients having osteoarthritis which is targeted by the cartilage regenerative therapy. Thus, the potential market is huge. The present invention is also highly useful for peripheral industries. Acute competition has been started in the regenerative medical research on joint tissues, mainly including bone and cartilage. The synthetic tissue of the present invention is a safe and original material made of cells collected from an organism, such as a patient or the like, and is highly useful in view of the lack of side effects or the like.

What is claimed is:

1. A tissue complex comprising an implantable synthetic autograft or allograft tissue and another synthetic tissue which is different from the implantable autograft or allograft tissue,
wherein the implantable synthetic autograft or allograft tissue is substantially made of (i) cells that are autologous or allogeneic relative to the recipient and which thereby constitute the synthetic autograft or allograft tissue, said cells being selected from the group consisting of myoblasts, mesenchymal stem cells, adipocytes, synovial cells and bone marrow cells; and (ii) an extracellular matrix (ECM) derived from the cells constituting the synthetic autograft or allograft tissue, said extracellular matrix comprising fibronectin, collagen I, collagen III, and vitronectin,
wherein the synthetic autograft or allograft tissue is free of scaffolds and comprises multiple layers of said cells, and
wherein the implantable synthetic autograft or allograft tissue has integration ability with its surroundings when implanted and has sufficient strength to provide self-supporting ability.

2. The tissue complex of claim 1, wherein the fibronectin, collagen I, collagen III, and vitronectin are evenly distributed in the synthetic autograft or allograft tissue.

3. The tissue complex of claim 1, wherein the fibronectin, collagen I, collagen III, and vitronectin three-dimensionally wrap the cells.

4. The tissue complex of claim 1, wherein the extracellular matrix is integrated throughout the tissue.

5. The tissue complex of claim 1, wherein the implantable synthetic autograft or allograft tissue comprises 10 or more layers of said cells.

6. The tissue complex of claim 1, wherein the implantable synthetic autograft or allograft tissue has a thickness of at least 50 µm and is dimensioned so as to fit an injured site in a tissue or organ.

7. The tissue complex of claim 1, wherein the another synthetic tissue is an artificial bone.

8. The tissue complex of claim 7, wherein the artificial bone is made of hydroxyapatite.

9. The tissue complex of claim 1, wherein the another synthetic tissue is a microfibrous collagen medical device, a collagen gel, a hyaluronic acid gel, an agarose gel, an alginate gel or beads.

* * * * *